United States Patent
Ting et al.

(10) Patent No.: US 9,624,524 B2
(45) Date of Patent: Apr. 18, 2017

(54) IN VIVO PROTEOMIC MAPPING

(75) Inventors: Alice Y. Ting, Allston, MA (US);
Jeffrey Daniel Martell, Cambridge, MA (US); Hyun-Woo Rhee, Gulhwart (KR); Peng Zou, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/125,819

(22) PCT Filed: Jun. 15, 2012

(86) PCT No.: PCT/US2012/042817
§ 371 (c)(1),
(2), (4) Date: Feb. 18, 2014

(87) PCT Pub. No.: WO2012/174479
PCT Pub. Date: Dec. 20, 2012

(65) Prior Publication Data
US 2014/0186870 A1    Jul. 3, 2014

Related U.S. Application Data

(60) Provisional application No. 61/497,155, filed on Jun. 15, 2011.

(51) Int. Cl.
C12Q 1/28    (2006.01)
G01N 33/50   (2006.01)
G01N 33/68   (2006.01)

(52) U.S. Cl.
CPC ........... *C12Q 1/28* (2013.01); *G01N 33/5023* (2013.01); *G01N 33/6803* (2013.01); *G01N 2570/00* (2013.01)

(58) Field of Classification Search
None
See application file for complete search history.

(56) References Cited

U.S. PATENT DOCUMENTS

| | | | | |
|---|---|---|---|---|
| 6,280,961 | B1 * | 8/2001 | Kaplan | 435/7.2 |
| 6,335,173 | B1 * | 1/2002 | Kaplan | 435/7.2 |
| 7,172,877 | B2 * | 2/2007 | Ting | C12N 9/93 |
| | | | | 435/69.1 |

OTHER PUBLICATIONS

Tanke, Hans J; et al; "Fish and immunocytochemistry: towards visualising single target molecules in living cells" Current Opinions in Biotechnology; 16, 49-54, 2005.*

(Continued)

*Primary Examiner* — Renee Claytor
*Assistant Examiner* — David Berke-Schlessel
(74) *Attorney, Agent, or Firm* — Wolf, Greenfield & Sacks, P.C.

(57) ABSTRACT

The application discloses methods, materials, and compositions for the labeling of molecules, for example, proteins, in living cells or in subcellular compartments of living cells. In particular, the application relates to proteomic analysis methods; materials and compositions and means based on direct tagging of unknown proteins with tagging enzymes (such as biotin ligase or a peroxidase) within the vicinity of a tagging substrate (such as a tyramide) within living cells, with optional targeting to specific subcellular locations by expression of genetic constructs.

16 Claims, 183 Drawing Sheets

(56) References Cited

OTHER PUBLICATIONS

Clutter, Matthew R; et al; "Tyramide Signal Amplification for Analysis of Kinase Activity by Intracellular Flow Cytometry" Cytometry: Part A, 77A, 1020-1031, 2010.*
Mishima, Tsuneko; et al; "Intracellular labeling of single cortical astrocytes in vivo" Journal of Neuroscience Methods, 166, 32-40, 2007.*
van de Corput, Mariette PC; et al; "Fluorescence in situ hybridization using horseradish peroxidase-labeled oligodeoxynucleotides and tyramide signal amplification for sensitive DNA and mRNA detection" Histochemistry and Cell Biology, 110, 431-437, 1998.*
Pernthaler, Annelie; Amann, Rudolf; "Simultaneous Fluorescence In Situ Hybridization of mRNA and rRNA in Environmental Bacteria" Applied and Environmental Microbiology, 70, 5426-5433, 2004.*
Fernandez-Suarez, Marta; et al; "Protein-Protein Interaction Detection in Vitro and in Cells by Proximity Biotinylation" Journal of the American Chemical Society, 130, 9251-9253, 2008.*
Verma, Mukesh; et al; "Proteomic analysis of cancer-cell mitochondria" Nature Reviews, 4, 789-795, 2003.*
Choi-Rhee et al., Promiscuous protein biotinylation by *Escherichia coli* biotin protein ligase. Protein Sci. Nov. 2004;13(11):3043-50. Epub Sep. 30, 2004.
Roux et al., A promiscuous biotin ligase fusion protein identifies proximal and interacting proteins in mammalian cells. J Cell Biol. Mar. 19, 2012;196(6):801-10. doi: 10.1083/jcb.201112098. Epub Mar. 12, 2012.
Van Tine et al., Localization of HuC (ELAVL3) to chromosome 19p13.2 by fluorescence in situ hybridization utilizing a novel tyramide labeling technique. Genomics. Nov. 1, 1998;53(3):296-9.
Aebersold et al., Mass spectrometry-based proteomics. Nature. Mar. 13, 2003;422(6928):198-207.
Bai et al., Synaptosome proteomics. Subcell Biochem. 2007;43:77-98.
Baughman et al., Integrative genomics identifies MCU as an essential component of the mitochondrial calcium uniporter. Nature. Jun. 19, 2011;476(7360):341-5. doi: 10.1038/nature10234.
Becer et al., Click chemistry beyond metal-catalyzed cycloaddition. Angew Chem Int Ed Engl. 2009;48(27):4900-8. doi:10.1002/anie.200900755.
Beck et al., Fluorophore-assisted light inactivation: a high-throughput tool for direct target validation of proteins. Proteomics. Mar. 2002;2(3):247-55.
Brunner et al., Proteomics of regulated secretory organelles. Mass Spectrom Rev. Sep.-Oct. 2009;28(5):844-67. doi: 10.1002/mas.20211.
Chen et al., Molecular characterization of the endoplasmic reticulum: insights from proteomic studies. Proteomics. Nov. 2010;10(22):4040-52. doi: 10.1002/pmic.201000234. Epub Nov. 2, 2010.
Chudakov et al., Fluorescent proteins and their applications in imaging living cells and tissues. Physiol Rev. Jul. 2010;90(3):1103-63. doi: 10.1152/physrev.00038.2009.
Connolly et al., Transport into and out of the Golgi complex studied by transfecting cells with cDNAs encoding horseradish peroxidase. J Cell Biol. Nov. 1994;127(3):641-52.
Cusick et al., Interactome: gateway into systems biology. Hum Mol Genet. Oct. 15, 2005;14 Spec No. 2:R171-81. Epub Sep. 14, 2005.
Fancy et al., Chemistry for the analysis of protein-protein interactions: rapid and efficient cross-linking triggered by long wavelength light. Proc Natl Acad Sci U S A. May 25, 1999;96(11):6020-4. Erratum in: Proc Natl Acad Sci U S A Feb. 1, 2000;97(3):1317.
Forner et al., Quantitative proteomic comparison of rat mitochondria from muscle, heart, and liver. Mol Cell Proteomics. Apr. 2006;5(4):608-19. Epub Jan. 14, 2006.
Friedman et al., ER tubules mark sites of mitochondrial division. Science. Oct. 21, 2011;334(6054):358-62. doi: 10.1126/science.1207385. Epub Sep. 1, 2011.
Gilchrist et al., Quantitative proteomics analysis of the secretory pathway. Cell. Dec. 15, 2006;127(6):1265-81.
Kim et al., mGRASP enables mapping mammalian synaptic connectivity with light microscopy. Nat Methods. Dec. 4, 2011;9(1):96-102. doi: 10.1038/nmeth.1784.
Kolb et al., Click Chemistry: Diverse Chemical Function from a Few Good Reactions. Angew Chem Int Ed Engl. Jun. 1, 2001;40(11):2004-2021.
Kornmann et al., ERMES-mediated ER-mitochondria contacts: molecular hubs for the regulation of mitochondrial biology. J Cell Sci. May 1, 2010;123(Pt 9):1389-93. doi: 10.1242/jcs.058636.
Kotani et al.,Biochemical visualization of cell surface molecular clustering in living cells. Proc Natl Acad Sci U S A. May 27, 2008;105(21):7405-9. doi: 10.1073/pnas.0710346105. Epub May 21, 2008.
Li et al., Inhibition of alpha-chymotrypsin with an enzyme-activated n-nitrosoamide: active-site labeling by the naphthylmethyl cation. Arch Biochem Biophys. Jun. 20, 1995;320(1):135-40.
Lipovsek et al., Selection of horseradish peroxidase variants with enhanced enantioselectivity by yeast surface display. Chem Biol. Oct. 2007;14(10):1176-85.
Liu et al., A systematic N-terminal peptide quantitative labeling strategy for differential proteomic analysis. Proteomics Clin Appl. Jul. 2010;4(6-7):633-43. doi: 10.1002/prca.200900065. Epub Mar. 9, 2010.
Mayer et al., Biotinyl-tyramide: a novel approach for electron microscopic immunocytochemistry. J Histochem Cytochem. Nov. 1997;45(11):1449-54.
Nguyen et al., A fast and efficient metal-mediated oxidation of isoniazid and identification of isoniazid-NAD(H) adducts. Chembiochem. Dec. 3, 2001;2(12):877-83.
Pagliarini et al., A mitochondrial protein compendium elucidates complex I disease biology. Cell. Jul. 11, 2008;134(1):112-23. doi: 10.1016/j.cell.2008.06.016.
Patterson et al., Mass spectrometric identification of proteins released from mitochondria undergoing permeability transition. Cell Death Differ. Feb. 2000;7(2):137-44.
Shacter, Quantification and significance of protein oxidation in biological samples. Drug Metab Rev. Aug.-Nov. 2000;32(3-4):307-26.
Shibata et al., Mechanisms determining the morphology of the peripheral ER. Cell. Nov. 24, 2010;143(5):774-88. doi: 10.1016/j.cell.2010.11.007.
Shu et al., a genetically encoded tag for correlated light and electron microscopy of intact cells, tissues, and organisms. PLoS Biol. Apr. 2011;9(4):e1001041. doi: 10.1371/journal.pbio.1001041. Epub Apr. 5, 2011.
Siddiqui et al., Synaptic organizing complexes. Curr Opin Neurobiol. Feb. 2011;21(1):132-43. doi: 10.1016/j.conb.2010.08.016. Epub Sep. 9, 2010.
Ting, Chemical reporters for probing the localization and function of proteins in living cells. BioBricks Foundation. SB 5.0 Fifth International Meeting on Synthetic Biology. 2011;46. Abstract.

* cited by examiner

Table 1. Summary of proteomics studies of ER protome

| Species | Tissue | Organelle | ER purification | Protein/peptide separation | MS | Proteins detected | Reference |
|---|---|---|---|---|---|---|---|
| Rat | Liver | ER | Differential centrifugation; sodium cholate wash | Proteins, 1-D and 2-D gels | MALDI-TOF MS | 60 (1-DE) 41 (2-DE) | [22] |
| Mouse | Liver | rER | Step sucrose gradient | Proteins, 2-D gels | MALDI-TOF MS, Tandem MS | 141 | [13] |
| Hamster | Liver | ER | Continuous iodixanol gradient | Proteins, 2-D gels | MALDI-Q-TQF MS | 34 a) | [32] |
| Mouse | Liver | ER fraction | Rate-zonal centrifugation on continuous sucrose gradient | Peptides, LC | linear ion-trap Fourier transform MS, Tandem MS | 229 | [16] |
| Rat | Liver | rER | Step sucrose gradient | Proteins, 1-D gels, LC | QTOF-2 MS, Tandem MS | 787 | [20] |
| Rat | Liver | sER | Step sucrose gradient | Proteins, 1-D gels, LC | QTOF-2 MS, Tandem MS | 998 | [20] |
| Bovine | Mammary gland | Microsomes | Differential centrifugation | Proteins, 1-D gels, LC | Tandem MS, LTQ | 703 | [36] |
| Mouse | Brain | Microsomes | Differential centrifugation | Peptides, 2-D-LC separation (SCX, rpHPLC) | Tandem MS, LTQ-FT | 1914 | [37] |
| Rat | Pancreas | rER | Step sucrose gradient | Peptides, iTRAQ, 2-D-LC separation (SCX, rpHPCL) | Tandem MS, MALDI-TOF/TOF | 469 | [12] |
| Canine | Pancreas | rER | Step sucrose gradient; carbonate wash | Proteins, SDS-PAGE, 2-D BAC/SDS-PAGE b) | nanoLC-MS/MS, | 258 | [19] |
| Chicken | Pre-B-cell | ER fraction | Continuous iodixanol density gradient | Peptides, iTRAQ, 2-D-LC separation (SCX, rpHPLC) | Tandem MS, QSTAR | 79 | [21] |
| Canine | Pancreas | rER | Step cucrose gradient; fractionation of RER membrane | Proteins, 2-D gels | Tandem MS, LCQdecaXP | 32 c) | [24] |

(From Williams et al. Proteomics 2010)

FIG. 4

Bergeron, *Cell Biology Lab Handbook*, 2006

Imaging to assess labeling specificity

Gel analysis of biotinylated proteins

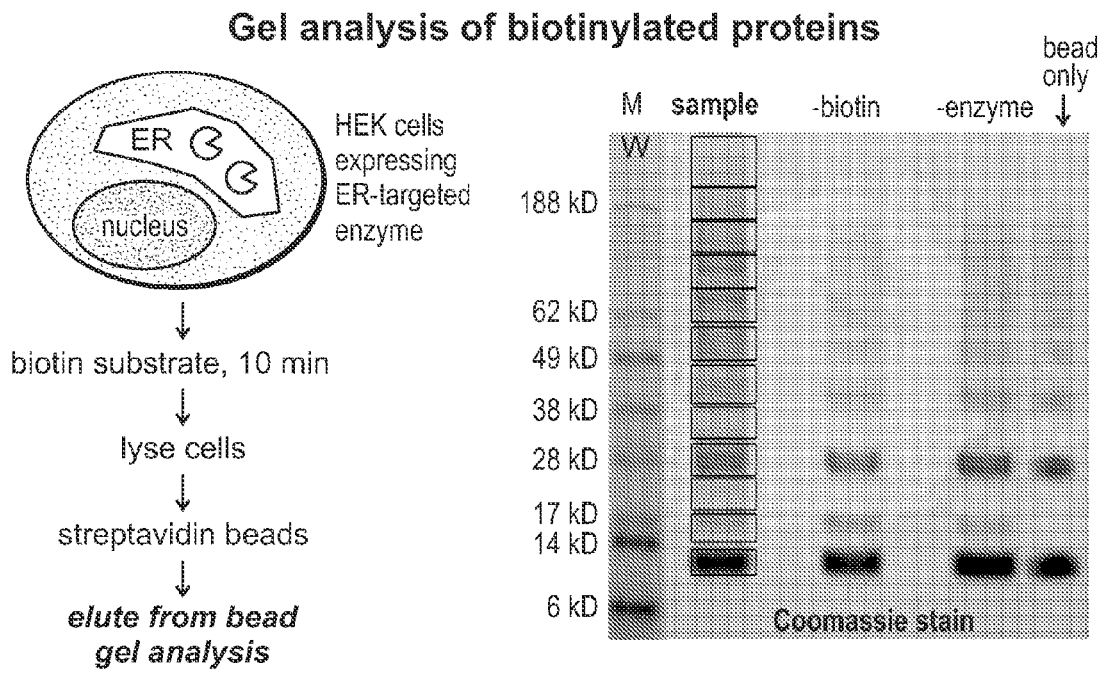

FIG. 10

Mass-spec analysis of biotinylated proteins

- LTQ-Orbitrap XL machine
- SILAC (stable isotope) labeling allows background subtraction from –enzyme control cells
- 13,928 unique peptides from 1565 distinct proteins detected
- 4 out of 4 naturally biotinylated proteins detected
- 279 proteins significantly enriched in +ER-enzyme cells compared to –ER-enzyme cells
= our ER proteome

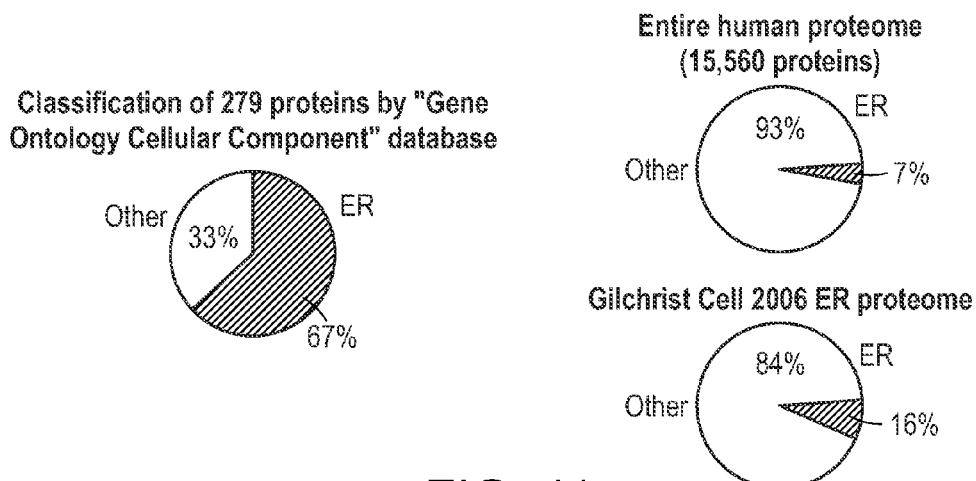

FIG. 11

Compare to Rapoport list of 25 ER membrane proteins

| Rank | Normalized spectral count | Protein Name |
|---|---|---|
| 1 | 0.36806 | Bap31 |
| 2 | 0.27825 | Calnexin |
| 3 | 0.22566 | Ribophorin II |
| 4 | 0.21252 | p180 |
| 5 | 0.21239 | Dad1 |
| 6 | 0.20629 | TRAPα |
| 7 | 0.19868 | TRAPδ |
| 8 | 0.16850 | Surfeit locus protein 4 |
| 9 | 0.16611 | Climp63 |
| 10 | 0.15909 | Uncharacerized XP_848469 |
| 11 | 0.14201 | TRAPγ |
| 12 | 0.13849 | Ribophorin I |
| 13 | 0.12395 | Sec61α |
| 14 | 0.12299 | Tram1 |
| 15 | 0.11667 | Signal peptidase complex subunit 3 |
| 16 | 0.11618 | TMED6 |
| 17 | 0.10780 | STT3 |
| 18 | 0.09735 | Sognal peptidase subunit 2 |
| 19 | 0.09375 | Sec61β |
| 20 | 0.09053 | VAPB |
| 21 | 0.08955 | Magt (OST3/OST6 family) |
| 22 | 0.08856 | SRP Receptor β |
| 23 | 0.08456 | Malectin |
| 24 | 0.08451 | PIS1 |
| 25 | 0.08377 | VAPA |

Table S1
Rapoport et al. *Cell* 2010

We observe 21/25 of Rapoport's confirmed ER membrane proteins in our ER dataset

FIG. 12

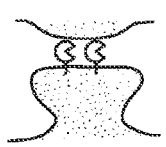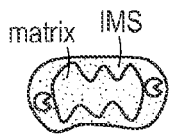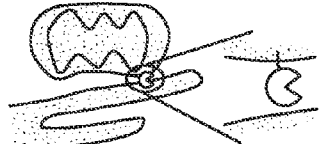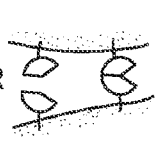
FIG. 21A  FIG. 21B  FIG. 21C
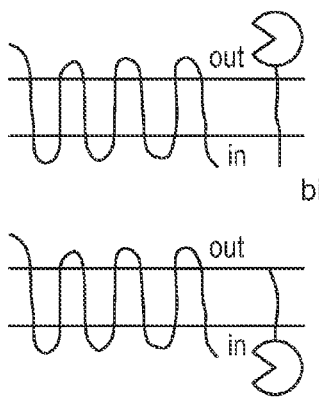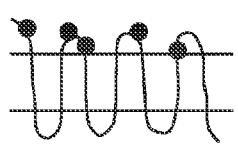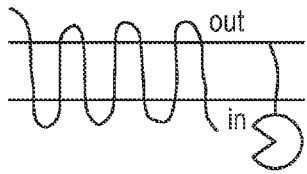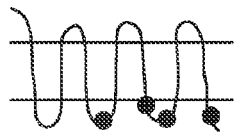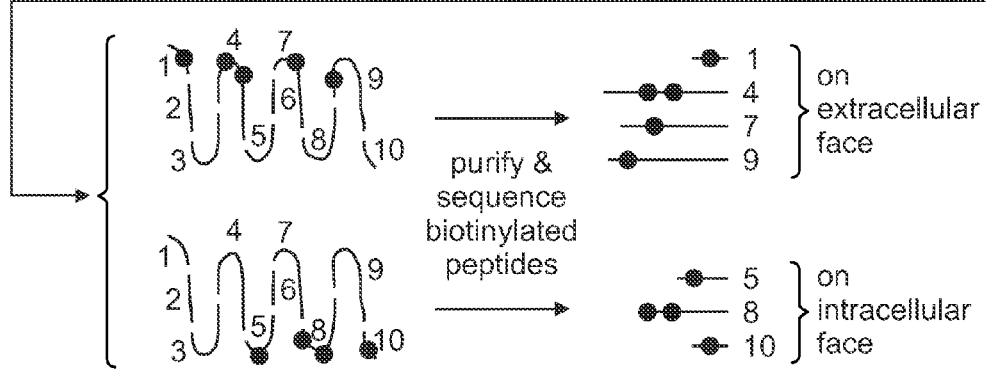
FIG. 22 i. aminoacyl-tRNA synthetases
ii. mitoribosomal proteins
iii. nucleoid-associated proteins
iv. amino acid metabolism enzymes
v. tricarboxylic acid cycle enzymes

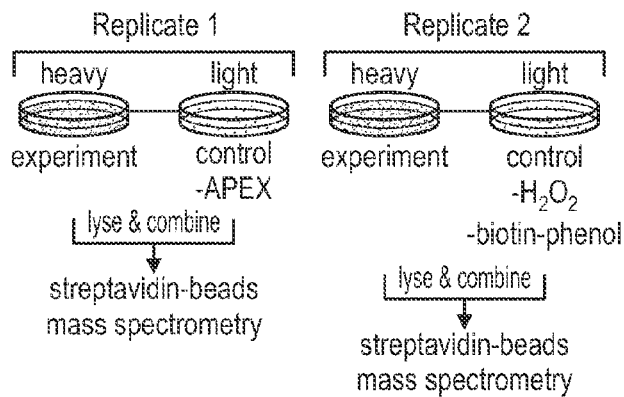
FIG. 28A
FIG. 28B
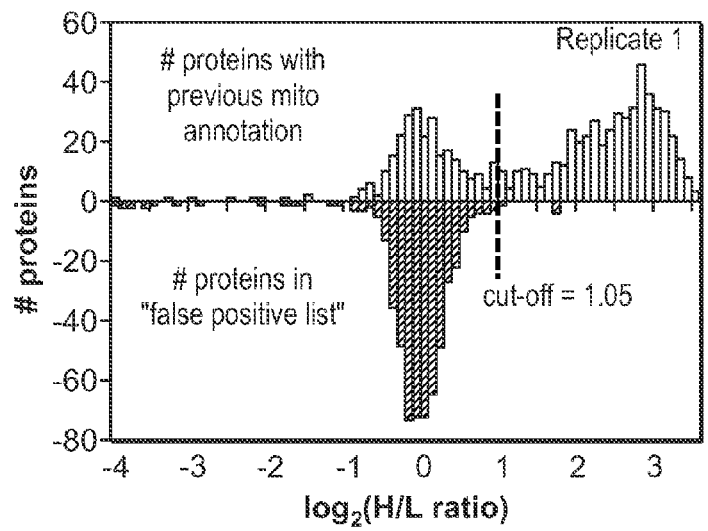
FIG. 28C
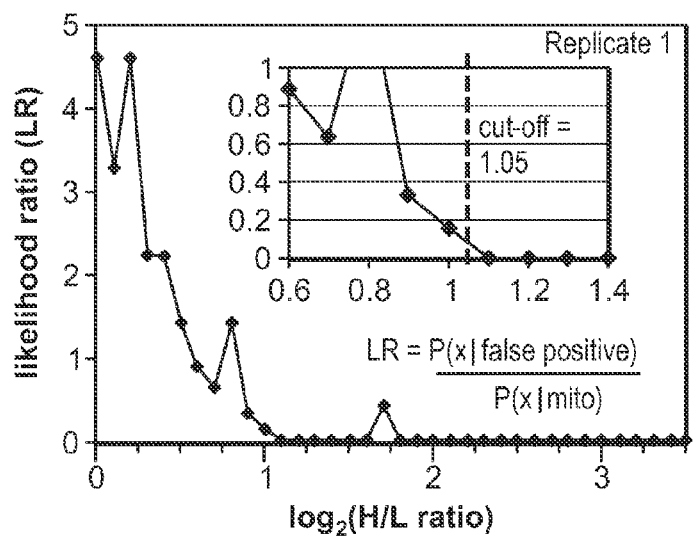
FIG. 28D

FIG. 29

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 3867 | Q6P4F2 | 112812 | Adrenodoxin-like protein, mitochondrial;Ferredoxin-1-like protein | FDX1L | mitochondrion \| mitochondrial matrix |
| 4737 | Q99757 | 25828 | Thioredoxin, mitochondrial;Thioredoxin-2 | TXN2;TXN2 | mitochondrion |
| 65 | A4D1V4;Q9BYC8 | 64983 | cDNA, FLJ93927, Homo sapiens mitochondrial ribosomal protein L32 (MRPL32), nuclear gene encoding mitochondrial protein, mRNA;Mitochondrial ribosomal protein L32, isoform CRA_d;39S ribosomal protein L32, mitochondrial | hCG_19886;MRPL32;lca g7,464;HSPC283 | mitochondrion \| ribosome \| mitochondrial ribosome \| large ribosomal subunit |
| 2535 | P23434 | 2653 | Glycine cleavage system H protein, mitochondrial | GCSH | mitochondrion \| glycine cleavage complex |
| 1571 | Q9NQ50;F8W5K5 | 64976 | 39S ribosomal protein L40, mitochondrial;Nuclear localization signal-containing protein deleted in velocardiofacial syndrome;Up-regulated in metastasis | MRPL40;NLVCF;URIM | mitochondrion \| ribosome \| mitochondrial ribosome \| nucleus |
| 5322 | Q9NZE8;D3YTC1;Q9NZE8-2 | 51318 | 39S ribosomal protein L35, mitochondrial;Putative uncharacterized protein MRPL35 | BM-007;MRPL35 | mitochondrion \| ribosome \| mitochondrial ribosome \| intracellular |
| 3626 | Q4U2R6 | 51258 | 39S ribosomal protein L51, mitochondrial;bMRP-64 | CDA09;HSPC241;MRP64;MRPL51 | mitochondrion \| ribosome \| mitochondrial large ribosomal subunit |
| 5125 | Q9HD34;F5H189;C9JRX8;C9JY28 | 57128 | LYR motif-containing protein 4;Putative uncharacterized protein LYRM4 | C6orf149;CGI-203;ISD11;LYRM4 | mitochondrion \| nucleus |
| 1537 | Q9S4A26;F8W7Q4;E9PH05 | 26355 | E2-induced gene 5 protein;Protein FAM162A | C3orf28;DC16;E2IG5;FAM162A;FWP001 | integral to membrane \| membrane |

FIG. 29 cont.

TABLE 1

Mitochondrial matrix proteome (495 proteins), ranked from most enriched to least enriched [H/L ratio from Rep1]

| id | Majority Protein IDs | Entrez | Protein Names | Gene Names | GO celloc |
|---|---|---|---|---|---|
| 4765 | Q9BQC6 | 78988 | Ribosomal protein 63, mitochondrial | MRP63 | mitochondrion | ribosome | mitochondrial ribosome |
| 2350 | P10109 | 2230 | Adrenal ferredoxin;Adrenodoxin, mitochondrial;Ferredoxin-1;Hepatoredoxin | ADX;FDX1 | mitochondrion | mitochondrial matrix |
| 5206 | Q9NUJ1;B7 Z6A8 | 55347 | Abhydrolase domain-containing protein 10, mitochondrial;cDNA FLJ50858, highly similar to Homo sapiens abhydrolase domain containing 10 (ABHD10), mRNA | ABHD10 | mitochondrion |
| 4204 | Q8N8R5 | 205327 | UPF0565 protein C2orf69 | C2orf69 | extracellular region |
| 5093 | Q9HAV7;B4 DWV5 | 80273 | GrpE protein homolog 1, mitochondrial;HMGE;Mt-GrpE#1;GrpE protein homolog | GRPEL1;GRPEL1 | mitochondrion | mitochondrial matrix |
| 4940 | Q9GZT6;Q9 GZT6-2;B3KP87 | 60492 | Coiled-coil domain-containing protein 90B, mitochondrial;cDNA FLJ14410 fis, clone NT2NE2000195, highly similar to Homo sapiens MDS025 mRNA;Putative uncharacterized protein MDS025 | CCDC90B;CUA003;MDS0 11;MDS025;hCG_27349 | mitochondrion | integral to membrane | membrane |
| 2430 | P14927;B7Z 2R2;E5RJU0 | 7381 | Complex III subunit 7;Complex III subunit VII;Cytochrome b-c1 complex subunit 7;QP-C;Ubiquinol-cytochrome c reductase complex 14 kDa protein;cDNA FLJ52271, moderately similar to Ubiquinol-cytochrome c reductase complex 14 kDa protein (EC 1.10.2.2) | UQCRB;UQCRB | mitochondrial respiratory chain | mitochondrion | membrane |
| 3881 | Q6PI78 | 157378 | Transmembrane protein 65 | TMEM65 | integral to membrane | membrane |
| 4994 | Q9H2W6 | 26589 | 39S ribosomal protein L46, mitochondrial | C15orf4;IFCG2;MRPL46 | mitochondrion | ribosome | cellular_component |
| 4892 | Q9BYC9 | 55052 | 39S ribosomal protein L20, mitochondrial | MRPL20 | mitochondrion | ribosome | intracellular | mitochondrial large ribosomal subunit |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 1443 | Q9BYD6;F5H5L4;H0Y8N7 | 65008 | 39S ribosomal protein L1, mitochondrial | BM-022;MRPL1 | mitochondrion \| ribosome \| intracellular \| mitochondrial large ribosomal subunit \| large ribosomal subunit |
| 3869 | Q6P587;Q1AK40;Q6P587-2 | 81889 | Fumarylacetoacetate hydrolase domain-containing protein 1;YjsK-like protein;Fumarylacetoacetate hydrolase domain containing 1 | C16orf36;FAHD1;YISK;-A1 | mitochondrion |
| 3286 | Q13084;Q4TT38;A2IDC6;Q4TT37;A2IDC7 | 10573 | 39S ribosomal protein L28, mitochondrial;Melanoma-associated antigen recognized by T lymphocytes;Mitochondrial ribosomal protein L28 | MAAT1;MRPL28;297634.1-001;297634.1-010;297634.1-009;297634.1-011 | mitochondrion \| ribosome \| mitochondrial ribosome |
| 4002 | Q86SX6 | 51218 | Glutaredoxin-related protein 5, mitochondrial;Monothiol glutaredoxin-5 | C14orf87;GLRX5 | mitochondrion |
| 4750 | Q9BPW8 | 8508 | Protein NipSnap homolog 1 | NIPSNAP1 | mitochondrion \| mitochondrial inner membrane |
| 2336 | P09669 | 1345 | Cytochrome c oxidase polypeptide VIc;Cytochrome c oxidase subunit 6C | COX6C | mitochondrion \| integral to membrane \| mitochondrial inner membrane \| membrane |
| 4291 | Q8TCC3-2;Q8TCC3;Q8TCC3-3;B8ZZV5 | 51263 | 39S ribosomal protein L30, mitochondrial;Putative uncharacterized protein MRPL30 | HSPC249;MRPL28;MRPL30;RPML28 | mitochondrion \| ribosome \| intracellular |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 1384 | Q9NNW7;D3YTF9;F5H2M2;F5H2V0;Q9NNW7-2;E7ENA2;F5H1L4;D3YTF8;Q8NXNW7-3;F6WBI2;Q9NNW7-4 | 10587 | Selenoprotein Z;Thioredoxin reductase 2, mitochondrial;Thioredoxin reductase TR3;TR-beta;Putative uncharacterized protein TXNRD2 | KIAA1652;TXNR2;TXNRD2 | mitochondrion \| cytoplasm |
| 4894 | Q9BYD2;Q5SZR1 | 65005 | 39S ribosomal protein L9, mitochondrial;Mitochondrial ribosomal protein L9 | MRPL9;RP11-98D18.5-002 | mitochondrion \| ribosome \| mitochondrial ribosome \| intracellular |
| 5599 | Q9Y2R9 | 51081 | 28S ribosomal protein S7, mitochondrial;bMRP-27a | MRPS7 | cytosolic small ribosomal subunit \| mitochondrion \| ribosome \| intracellular |
| 2374 | P11182;Q5VVL7;F5H1F9 | 1629 | Branched-chain alpha-keto acid dehydrogenase complex component E2;Dihydrolipoamide acetyltransferase component of branched-chain alpha-keto acid dehydrogenase complex;Dihydrolipoamide branched chain transacylase;Dihydrolipoyllysine-residue (2-methylpropanoyl)transferase;Lipoamide acyltransferase component of branched-chain alpha-keto acid dehydrogenase complex, mitochondrial;Dihydrolipoamide branched chain transacylase E2 | BCATE2;DBT;RP11-305E17.3-002 | mitochondrial nucleoid \| mitochondrion \| mitochondrial alpha-ketoglutarate dehydrogenase complex |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4294 | Q8TCS8 | 87178 | 3'-5' RNA exonuclease OLD35;PNPase old-35;Polynucleotide phosphorylase 1;Polynucleotide phosphorylase-like protein;Polyribonucleotide nucleotidyltransferase 1, mitochondrial | PNPASE;PNPT1 | mitochondrion ¦ mitochondrial intermembrane space |
| 2725 | P42126;P42126-2 | 1632 | 3,2-trans-enoyl-CoA isomerase, mitochondrial;Delta(3),Delta(2)-enoyl-CoA isomerase;Dodecenoyl-CoA isomerase | DCI | mitochondrion ¦ mitochondrial inner membrane ¦ mitochondrial matrix |
| 3320 | Q13405;H0YDP7 | 7405 | 39S ribosomal protein L49, mitochondrial;Neighbor of FAU;Protein NOF1 | C11orf4;MRPL49;NOF1;OK/SW-cl.67 | mitochondrion ¦ ribosome ¦ intracellular ¦ cellular_component |
| 5340 | Q9P032 | 29078 | Hormone-regulated proliferation-associated protein of 20 kDa;NADH dehydrogenase [ubiquinone] 1 alpha subcomplex assembly factor 4 | C6orf66;HRPAP20;HSPC125;MYO13;NDUFAF4 | mitochondrion ¦ mitochondrial membrane |
| 2022 | O75208 | 57017 | Ubiquinone biosynthesis protein COQ9, mitochondrial | C16orf49;COQ9;HSPC326;PSEC0129 | mitochondrion |
| 4758 | Q9BQ48 | 64981 | 39S ribosomal protein L34, mitochondrial | MRPL34 | mitochondrion ¦ ribosome ¦ mitochondrial ¦ ribosome ¦ intracellular ¦ mitochondrial large ribosomal subunit |
| 4854 | Q9BV55;F8WDR2 | 55006 | Potential tRNA (adenine-N(1))-methyltransferase catalytic subunit TRMT61B | TRMT61B | 0 |
| 5528 | Q9UMS0;Q9UMS0-3;E9PAQ8;Q9UMS0-2;F8W9P7;C9J8Q1 | 27247 | HIRA-interacting protein 5;NFU1 iron-sulfur cluster scaffold homolog, mitochondrial;Putative uncharacterized protein NFU1 | CGI-33;HIRIP5;NFU1 | cytosol ¦ mitochondrion ¦ nucleus ¦ cytoplasm |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4111 | Q8IXM3 | 64975 | 39S ribosomal protein L27 homolog;39S ribosomal protein L41, mitochondrial;Bcl-2-interacting mitochondrial ribosomal protein L41;Cell proliferation-inducing gene 3 protein;MRP-L27 homolog | BMRP,MRPL27,MRPL41;PIG3;RPML27 | mitochondrion | ribonucleoprotein complex | ribosome | mitochondrial large ribosomal subunit |
| 4895 | Q9BYD3;Q9BYD3-2 | 51073 | 39S ribosomal protein L4, mitochondrial | C3ABP0091;CGI-28;MRPL4 | mitochondrion | ribosome | intracellular |
| 5327 | Q9NZJ6 | 51805 | 3,4-dihydroxy-5-hexaprenylbenzoate methyltransferase;Dihydroxyhexaprenylbenzoate methyltransferase;Hexaprenyldihydroxybenzoate methyltransferase, mitochondrial | COQ3;UG0215E05 | mitochondrion | mitochondrial matrix |
| 2508 | P22033 | 4594 | Methylmalonyl-CoA isomerase;Methylmalonyl-CoA mutase, mitochondrial | MUT | mitochondrion | mitochondrial matrix |
| 2405 | P13073 | 1327 | Cytochrome c oxidase polypeptide IV;Cytochrome c oxidase subunit 4 isoform 1, mitochondrial;Cytochrome c oxidase subunit IV isoform 1 | COX4;COXAI1 | mitochondrion | mitochondrial inner membrane | nucleus | membrane |
| 2571 | P26440;B3KVI7;H0YLC3 | 3712 | Isovaleryl-CoA dehydrogenase, mitochondrial;cDNA FLJ16602 fis, clone TEST4007816, highly similar to Isovaleryl-CoA dehydrogenase, mitochondrial (EC 1.3.99.10);Isovaleryl Coenzyme A dehydrogenase, isoform CRA_b | IVD;hCG_38955 | mitochondrion | mitochondrial membrane | mitochondrial matrix |
| 3561 | Q16854;C9JFV8;Q16854-5;Q16854-3;Q16854-2;Q16854-4 | 1716 | Deoxyguanosine kinase, mitochondrial;Putative uncharacterized protein DGUOK | DGK;DGUOK | cytosol | mitochondrion | cytoplasm |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 2206 | P00505;E7E RW2 | 2806 | Aspartate aminotransferase, mitochondrial;Fatty acid-binding protein;Glutamate oxaloacetate transaminase 2;Plasma membrane-associated fatty acid-binding protein;Transaminase A | GOT2 | mitochondrion | mitochondrial inner membrane | plasma membrane | mitochondrial matrix |
| 2406 | P13196;B4D DG9 | 211 | 5-aminolevulinate synthase, nonspecific, mitochondrial;5-aminolevulinic acid synthase 1;Delta-ALA synthase 1;Delta-aminolevulinate synthase 1;cDNA FLJ53856, highly similar to 5-aminolevulinate synthase, nonspecific, mitochondrial [EC 2.3.1.37] | ALAS1;ALAS3;ALASH;CK /SW-cl.121 | mitochondrion | mitochondrial matrix |
| 5427 | Q9UGM6;B 7ZSX7 | 10352 | [Mt]TrpRS;Tryptophan -tRNA ligase;Tryptophanyl-tRNA synthetase, mitochondrial;cDNA FLJ50844, highly similar to Tryptophanyl-tRNA synthetase, mitochondrial [EC 6.1.1.2] | WARS2 | mitochondrion | mitochondrial matrix | cytoplasm |
| 2531 | P23368;Q9B WL6 | 4200 | Malic enzyme 2;NAD-dependent malic enzyme, mitochondrial;Malic enzyme | ME2;hCG_23687 | intracellular membrane-bounded organelle | mitochondrion | mitochondrial matrix |
| 2133 | O95202 | 3954 | LETM1 and EF-hand domain-containing protein 1, mitochondrial;Leucine zipper-EF-hand-containing transmembrane protein 1 | LETM1 | mitochondrion | integral to membrane | mitochondrial inner membrane | membrane |
| 3755 | Q5U5X0 | 90624 | LYR motif-containing protein 7 | C5orf31;LYRM7 | mitochondrion |
| 1222 | P30048;E9P H29 | 10935 | Antioxidant protein 1;HBC189;Peroxiredoxin-3;Protein MER5 homolog;Thioredoxin-dependent peroxide reductase, mitochondrial | AOP1,PRDX3 | mitochondrion | IkappaB kinase complex | early endosome | cytoplasm |
| 3149 | Q00059;A8 MRB2 | 7019 | Mitochondrial transcription factor 1;Transcription factor 6;Transcription factor 6-like 2;Transcription factor A, mitochondrial;Putative uncharacterized protein TFAM | TCF6;TCF6L2;TFAM | mitochondrial nucleoid | mitochondrion | nucleus | mitochondrial matrix |
| 5074 | Q9H9J2 | 65080 | 39S ribosomal protein L44, mitochondrial | MRPL44 | mitochondrion | ribosome | intracellular | cellular_component |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4578 | Q96HY7 | 55526 | Dehydrogenase E1 and transketolase domain-containing protein 1;Probable 2-oxoglutarate dehydrogenase E1 component DHKTD1, mitochondrial | DHTKD1;KIAA1630 | mitochondrion |
| 2697 | P38117;P38117-2 | 2109 | Electron transfer flavoprotein subunit beta | ETFB;FP585 | mitochondrion | mitochondrial matrix |
| 4468 | Q96A35 | 79590 | 39S ribosomal protein L24, mitochondrial | MRPL24 | mitochondrion | ribosome | intracellular |
| 2360 | P10606 | 1329 | Cytochrome c oxidase polypeptide Vb;Cytochrome c oxidase subunit 5B, mitochondrial | COX5B | mitochondrial envelope | mitochondrion | mitochondrial inner membrane | membrane |
| 3364 | Q13825;Q13825-2 | 549 | AU-specific RNA-binding enoyl-CoA hydratase;Methylglutaconyl-CoA hydratase, mitochondrial | AUH | mitochondrion |
| 2578 | P27144;D5DQ64 | 205 | Adenylate kinase 3-like;Adenylate kinase isoenzyme 4, mitochondrial;ATP-AMP transphosphorylase;HCG2031840, isoform CRA_c | AK3;AK3L1;AK3L2;AK4;hCG_2031340 | mitochondrion | mitochondrial matrix |
| 3250 | Q10713;B4DKL3 | 23203 | Alpha-MPP;Mitochondrial-processing peptidase subunit alpha;P-55;cDNA FLJ54899, highly similar to Mitochondrial-processing peptidase alpha subunit, mitochondrial (EC 3.4.24.64) | INPP5E;KIAA0123;MPPA ,PMPCA | mitochondrion | mitochondrial inner membrane | mitochondrial matrix |
| 3263 | Q12849;B3KP14;H0YAK1 ;H0Y8R1;F5H5I6;B3KPW0 | 2926 | G-rich sequence factor 1;cDNA FLJ30937 fis, clone FLJ32329 fis, clone PROST2004526, highly similar to G-rich sequence factor 1;cDNA BRAWH2014511, highly similar to G-rich sequence factor 1;cDNA FLJ38480 fis, clone FEBRA2022911, highly similar to G-rich sequence factor 1;cDNA FLJ39736 fis, clone SMINT2016313, highly similar to G-rich sequence factor 1;G-rich RNA sequence binding factor 1, isoform CRA_a | GRSF1;hCG_17800 | mitochondrion | cytoplasm |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4992 | Q9H2U2;Q9H2U2-2;E2QRM6;Q9H2U2-3;H0Y9D8;F8WDW9;D6R9G7 | 27068 | Inorganic pyrophosphatase 2, mitochondrial;Pyrophosphatase SID6-306;Pyrophosphate phospho-hydrolase 2 | HSPC124;PPA2 | mitochondrion | mitochondrial matrix | cytoplasm |
| 5577 | Q9Y276 | 617 | BCS1-like protein;Mitochondrial chaperone BCS1 | BCS1;BCS1L | mitochondrion | integral to membrane | mitochondrial inner membrane | membrane | mitochondrial respiratory chain complex III |
| 3966 | Q7Z2W9;B4DKI4;C9JPR2;F5H7V8 | 219927 | 39S ribosomal protein L21, mitochondrial;cDNA FLJ52689, highly similar to Homo sapiens mitochondrial ribosomal protein L21 (MRPL21), transcript variant 4, mRNA;Mitochondrial ribosomal protein L21, isoform CRA_a;Putative uncharacterized protein MRPL21 | MRPL21;hCG_27184 | mitochondrion | ribosome | intracellular |
| 4188 | Q8N5N7;B7Z358 | 54534 | 39S ribosomal protein L50, mitochondrial;cDNA FLJ52265, highly similar to Homo sapiens mitochondrial ribosomal protein L50 (MRPL50), mRNA | MRPL50 | mitochondrion | ribosome |
| 2955 | P56181-2 | 4731 | | | mitochondrion | respiratory chain | mitochondrial inner membrane | mitochondrial respiratory chain complex | membrane |

FIG. 29 cont.

TABLE 1
Mitochondrial matrix proteome (495 proteins), ranked from most enriched to least enriched (H/L ratio from Rep1)

| id | Majority Protein IDs | Entrez | Protein Names | Gene Names | GO cellloc |
|---|---|---|---|---|---|
| 416 | Q96GC5;B4DN34;F5H7O2;F5H8D0 | 51642 | 39S ribosomal protein L48, mitochondrial;cDNA FLJ60720, highly similar to Homo sapiens mitochondrial ribosomal protein L48 (MRPL48), transcript variant 1, mRNA | CGI-118;HSPC290;MRPL48 | mitochondrion ∣ ribosome ∣ intracellular |
| 3724 | Q5T653 | 51069 | 39S ribosomal protein L2, mitochondrial | CGI-22;MRPL2 | mitochondrion ∣ ribosome ∣ intracellular ∣ cytoplasm |
| 4153 | Q8N183;D6RA56 | 91942 | B17.2-like;Mimitin, mitochondrial;Myc-induced mitochondrial protein;NADH dehydrogenase [ubiquinone] 1 alpha subcomplex assembly factor 2;NDUFA12-like protein | NDUFA12L;NDUFAF2 | mitochondrion ∣ membrane |
| 4123 | Q8IYB8 | 6832 | ATP-dependent RNA helicase SUPV3L1, mitochondrial;Suppressor of var1 3-like protein 1 | SUPV3L1;SUV3 | mitochondrial nucleoid ∣ mitochondrion ∣ nucleus ∣ mitochondrial matrix |
| 5338 | Q9P015;E5RHF4 | 29088 | 39S ribosomal protein L15, mitochondrial | HSPC145;MRPL15 | mitochondrion ∣ ribosome ∣ large ribosomal subunit |
| 5641 | Q9Y307 | 51025 | Mitochondria-associated granulocyte macrophage CSF-signaling molecule;Mitochondrial import inner membrane translocase subunit Tim16 | CGI-136;MAGMAS;TIM16;TIMM16 | mitochondrion ∣ mitochondrial inner membrane ∣ membrane |
| 3713 | Q5T1C6;E9PU7;F6XC58 | 117145 | Carboxyl-terminal modulator protein;Thioesterase superfamily member 4 | CTMP;THEM4 | ruffle membrane ∣ mitochondrion ∣ plasma membrane ∣ cell projection ∣ cytoplasm |
| 2913 | P53370 | 11162 | Antisense basic fibroblast growth factor;Nucleoside diphosphate-linked moiety X motif 6;Protein GFG | FGF2AS;NUDT6 | mitochondrion ∣ nucleus ∣ cellular_component ∣ cytoplasm |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 1936 | O43766;D6RCP8;C9JCF6 | 11019 | Lipoate synthase;Lipoic acid synthase;Lipoyl synthase, mitochondria;Putative uncharacterized protein LIAS | HUSSY-01;LIAS;LIAS | mitochondrion \| nucleolus \| nucleus \| cytoplasm |
| 4938 | Q9GZT3;G3V2S9;G3V4X6;H0YH4Q;H0MW7 | 81892 | SRA stem-loop-interacting RNA-binding protein, mitochondrial | C14orf156;DC23;DC50;PD04872;SLIRP | mitochondrion \| nucleus |
| 5124 | Q9HD33;Q9HD33-2;Q9HD33-3 | 57129 | 39S ribosomal protein L47, mitochondrial;Nasopharyngeal carcinoma metastasis-related protein 1 | CGI-204;MRPL47;NCM1 | mitochondrion \| ribosome \| mitochondrial ribosome \| cellular_component |
| 2028 | O75323;C9JVI3 | 2631 | Glioblastoma-amplified sequence;Protein NipSnap homolog 2;Glioblastoma amplified sequence, isoform CRA_a;Putative uncharacterized protein GBAS | GBAS;NIPSNAP2;hCG_18231 | mitochondrion \| integral to plasma membrane \| membrane fraction |
| 4275 | Q8TAE8 | 90480 | CKII beta-associating protein;CR6-interacting factor 1;Growth arrest and DNA damage-inducible proteins-interacting protein 1;p53-responsive gene 6 protein;Papillomavirus L2-interacting nuclear protein 1 | GADD45GIP1;PLINP1;PRG6 | mitochondrion \| nucleus |
| 4537 | Q96EY8;F5H4Z7 | 326625 | Cob(I)alamin adenosyltransferase;Cob(I)yrinic acid a,c-diamide adenosyltransferase, mitochondrial;Methylmalonic aciduria type B protein | MMAB | mitochondrion |
| 1634 | Q86TS9;G3XCN9;A6NMQ8;G3V3U6 | 122704 | 39S ribosomal protein L52, mitochondrial;Mitochondrial ribosomal protein L52, isoform CRA_c;Putative uncharacterized protein MRPL52 | MRPL52;hCG_41985 | mitochondrion \| ribosome \| nucleus \| mitochondrial large ribosomal subunit |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 394 | O75390;B4DJV2 | 1431 | Citrate synthase, mitochondrial;Citrate synthase | CS | mitochondrion \| mitochondrial matrix |
| 1795 | O14548;H0YBD2;E5RIZ1 | 9167 | COX7a-related protein;Cytochrome c oxidase subunit 7A-related protein, mitochondrial;Cytochrome c oxidase subunit VIIa-related protein;EB1 | COX7A2L;COX7AR;COX7RP | mitochondrial respiratory chain \| mitochondrion \| membrane |
| 3749 | Q5TIU4;B3KR61;Q5TIEU4;2 | 79133 | Probable methyltransferase C20orf7, mitochondrial;cDNA FLJ33741 fis, clone BRAWH2018875, weakly similar to Protein At1g22800;HCG1811060, isoform CRA_c | C20orf7;hCG_1811060 | extrinsic to mitochondrial inner membrane \| mitochondrion \| membrane |
| 5202 | Q9NU23;G3V136;E5RG38;E5RJK7 | 57226 | LYR motif-containing protein 2 | LYRM2 | mitochondrion |
| 3118 | P78540 | 384 | Arginase-2, mitochondrial;Kidney-type arginase;Non-hepatic arginase;type II arginase | ARG2 | mitochondrion |
| 5180 | Q9NRX2;E9PKV2 | 63875 | 39S ribosomal protein L17, mitochondrial;LYST-interacting protein 2 | LIP2;MRPL17 | mitochondrion \| ribosome \| mitochondrial inner membrane \| intracellular |
| 4964 | Q9H0U6 | 29074 | 39S ribosomal protein L18, mitochondrial | HSPC071;MRPL18 | mitochondrion \| ribosome \| mitochondrial ribosome \| intracellular |
| 4876 | Q9BX68 | 84681 | HINT-3;Histidine triad nucleotide-binding protein 3, mitochondrial;HIT-17kDa;PKC-1-related HIT protein | HINT2 | mitochondrion |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celoc |
|---|---|---|---|---|---|
| 4230 | Q8NCN5;A8MT40;E7EMA7 | 55066 | Pyruvate dehydrogenase phosphatase regulatory subunit, mitochondrial;Putative uncharacterized protein ENSP00000381190 | KIAA1949;PDPR | mitochondrion \| mitochondrial matrix \| cytoplasm |
| 5419 | Q9UFN0 | 25934 | Protein NipSnap homolog 3A;Protein NipSnap homolog 4;Target for Salmonella secreted protein C | HSPC299;MIPSNAP3A;NIPSNAP4 | cytosol \| cytoplasm |
| 2689 | P36957;B7Z5W8;Q8N5W4 | 1743 | 2-oxoglutarate dehydrogenase complex component E2;Dihydrolipoamide succinyltransferase component of 2-oxoglutarate dehydrogenase complex;Dihydrolipoyllysine-residue succinyltransferase component of 2-oxoglutarate dehydrogenase complex, mitochondrial;E2K;cDNA FLJ55034, highly similar to Dihydrolipoyllysine-residue succinyltransferase component of 2-oxoglutarate dehydrogenase complex, mitochondrial (EC 2.3.1.61);Full-length cDNA 5-PRIME end of clone CS0DJ009YL13 of T cells (Jurkat cell line) of Homo sapiens (human) | DLST;DLTS | #N/A |
| 2871 | P51398;E7EM60;B4DP59 | 7818 | 28S ribosomal protein S29, mitochondrial;Death-associated protein 3;Ionizing radiation resistance conferring protein;cDNA FLJ57409, highly similar to Mitochondrial 28S ribosomal protein S29;Death associated protein 3, isoform CRA_d | DAP3;MRPS29;hCG_171 77 | mitochondrion \| small ribosomal subunit \| ribosome \| mitochondrial ribosome |
| 5134 | Q9NP92 | 10884 | 28S ribosomal protein S30, mitochondrial;Programmed cell death protein 9 | BM-047;MRPS30;PDCD9 | mitochondrion \| ribosome |
| 1796 | O14561 | 4706 | Acyl carrier protein, mitochondrial;CI-SDAP;NADH-ubiquinone oxidoreductase 9.6 kDa subunit | NDUFAB1 | mitochondrion \| respiratory chain \| mitochondrial membrane \| mitochondrial respiratory chain complex I \| mitochondrial matrix |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 3126 | P82673;P82673-2 | 60488 | 28S ribosomal protein S28, mitochondrial;28S ribosomal protein S35, mitochondrial | HDCMD11P;MDS023;MRPS28;MRPS35;PSEC0213 | mitochondrion \| ribosome \| mitochondrial small ribosomal subunit |
| 5443 | Q9UHN1 | 11232 | DNA polymerase gamma accessory 55 kDa subunit;DNA polymerase subunit gamma-2, mitochondrial;Mitochondrial DNA polymerase accessory subunit;MtPolB;PolG-beta | MTPOLB;POLG2 | mitochondrial nucleoid \| mitochondrion \| mitochondrial chromosome \| cytoplasm |
| 1930 | O43676;C9JKQ2 | 4709 | Complex I-B12;NADH dehydrogenase [ubiquinone] 1 beta subcomplex subunit 3;NADH-ubiquinone oxidoreductase B12 subunit;Putative uncharacterized protein NDUFB3 | NDUFB3 | mitochondrion \| respiratory chain \| integral to membrane \| mitochondrial inner membrane \| mitochondrial respiratory chain complex I \| membrane |
| 4512 | Q96V4B3;KN96 | 64978 | 39S ribosomal protein L38, mitochondrial;cDNA FLJ13996 fis, clone Y79AA1002211, highly similar to Homo sapiens mitochondrial ribosomal protein L38 (MRPL38), nuclear gene encoding mitochondrial protein, mRNA | HSPC262;MRPL38 | mitochondrion \| ribosome |
| 2738 | P42704 | 10128 | 130 kDa leucine-rich protein;GP130;Leucine-rich PPR motif-containing protein, mitochondrial | LRP130;LRPPRC | nucleoplasm \| condensed nuclear chromosome \| mitochondrion \| nuclear inner membrane \| perinuclear region of cytoplasm \| cytoplasm \| mitochondrial nucleoid \| nucleus \| cytoskeleton \| membrane \| nuclear outer membrane |
| 4536 | Q96EY7 | 55037 | Pentatricopeptide repeat-containing protein 3, mitochondrial;Transformation-related gene 15 protein | PTCD3;TRG15 | mitochondrion |
| 3394 | Q14197 | 3396 | Digestion substraction 1;Immature colon carcinoma transcript 1 protein;Peptidyl-tRNA hydrolase ICT1, mitochondrial | DS1;ICT1 | mitochondrion \| mitochondrial large ribosomal subunit |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 1074 | E7ETU7;H0Y 9G6;P09001 ;D6RCJ4;E9 PF06 | 11222 | 39S ribosomal protein L3, mitochondrial | MRL3;MRPL3;RPML3 | mitochondrion \| ribosome \| intracellular \| mitochondrial large ribosomal subunit |
| 2356 | P10515;E9P E14;H0YDD4 ;J5H7M3;E7 ESJ9 | 1737 | 70 kDa mitochondrial autoantigen of primary biliary cirrhosis;Dihydrolipoamide acetyltransferase component of pyruvate dehydrogenase complex;Dihydrolipoyllysine-residue acetyltransferase component of pyruvate dehydrogenase complex, mitochondrial;M2 antigen complex 70 kDa subunit;Pyruvate dehydrogenase complex component E2 | DLAT;DLTA | mitochondrion \| mitochondrial pyruvate dehydrogenase complex |
| 3125 | P82664 | 55173 | 28S ribosomal protein S10, mitochondrial | MRPS10;MSTP040 | mitochondrion \| ribosome \| intracellular |
| 2047 | O75489 | 4722 | NADH dehydrogenase [ubiquinone] iron-sulfur protein 3, mitochondrial;NADH-ubiquinone oxidoreductase 30 kDa subunit | NDUFS3 | mitochondrion \| respiratory chain \| mitochondrial inner membrane \| mitochondrial membrane \| mitochondrial respiratory chain complex I \| membrane |
| 316 | Q6YP21;B3K Q13 | 56267 | Cysteine-S-conjugate beta-lyase 2;Kynurenine aminotransferase III;Kynurenine--glyoxylate transaminase;Kynurenine--oxoglutarate transaminase 3;Kynurenine--oxoglutarate transaminase III;cDNA FLJ32614 fis, clone STOMA2000121, highly similar to Homo sapiens kynurenine aminotransferase III (KAT3), transcript variant 2, mRNA | CCBL2;KAT3;RBMXL1 | mitochondrion |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 2379 | Q8T4U5;P1 1310-2;P11310;B 7729;L B4DJE 7 | 34 | Acyl-Coenzyme A dehydrogenase, C-4 to C-12 straight chain;Acyl-Coenzyme A dehydrogenase, C-4 to C-12 straight chain, isoform CRA_a;Medium-chain specific acyl-CoA dehydrogenase, mitochondrial;cDNA, FLJ76845, highly similar to Medium-chain specific acyl-CoA dehydrogenase, mitochondrial [EC 1.3.99.3];cDNA FLJ52595, highly similar to Medium-chain specific acyl-CoA dehydrogenase, mitochondrial [EC 1.3.99.3] | ACADM;hCG_22915;RP4-662C21.1-002 | mitochondrion \| mitochondrial matrix |
| 4411 | Q92665 | 10240 | 28S ribosomal protein S31, mitochondrial;imogen 38 | IMOGN38;MRPS31 | mitochondrion \| ribosome |
| 1397 | G3V1M7;F5 H2A9;P4974 8;P49748-2;F5GYP4 | 37 | Very long-chain specific acyl-CoA dehydrogenase, mitochondrial | ACADVL;VLCAD | mitochondrial nucleoid \| mitochondrion \| mitochondrial inner membrane \| membrane |
| 4893 | Q9BYD1;E5 RJJ7 | 28998 | 39S ribosomal protein L13, mitochondrial | MRPL13 | mitochondrion \| ribosome \| intracellular \| mitochondrial large ribosomal subunit |
| 5349 | Q9P0M9;D6 RAN8 | 51264 | 39S ribosomal protein L27, mitochondrial | HSPC250;MRPL27 | mitochondrion \| ribosome \| intracellular \| mitochondrial large ribosomal subunit |
| 3619 | Q4G0N4;Q4 G0N4-2;B7Z8V7;Q 4G0N4-3 | 133686 | UPF0465 protein C5orf33;cDNA FLJ58577 | C5orf33 | mitochondrion |
| 4361 | Q8WW59;B 4DUC9 | 283377 | SPRY domain-containing protein 4;cDNA FLJ53756, highly similar to SPRY domain-containing protein 4 | SPRYD4 | mitochondrion \| nucleus |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO cellloc |
|---|---|---|---|---|---|
| 325 | O15382;B3K SI3;O15382-2 | 587 | Branched-chain-amino-acid aminotransferase, mitochondrial;Placental protein 18;Branched-chain-amino-acid aminotransferase | BCAT2;BCATM;BCT2;EC A40 | mitochondrion \| nucleus \| cytoplasm |
| 1593 | Q96E29;Q9 6E29-2;Q3V130;E 5RIK9;E5RIY 4 | 51001 | mTERF domain-containing protein 1, mitochondrial | CGI-12;MTERFD1 | mitochondrion \| nucleus |
| 4974 | Q9H1K1;Q9 H1K1-2;B3KQ30;B 4DNC9;F5H 5N2;B1P7G 3 | 23479 | iron-sulfur cluster assembly enzyme ISCU, mitochondrial;NifU-like N-terminal domain-containing protein;NifU-like protein;cDNA FLJ32689 fis, clone TEST12000207, highly similar to NifU-like N-terminal domain-containing protein, mitochondrial;cDNA FLJ51237, highly similar to NifU-like N-terminal domain-containing protein, mitochondrial;ISCU;ISCU | ISCU;NIFUN | cytosol \| mitochondrion \| nucleus \| cytoplasm |
| 4097 | Q8IWL3;B0 QYH2 | 150274 | DnaJ homolog subfamily C member 20;Hsc20;Iron-sulfur cluster co-chaperone protein HscB, mitochondrial;HscB iron-sulfur cluster co-chaperone homolog (E. coli);J-type co-chaperone homolog HSC20, isoform CRA_c;Putative uncharacterized protein HSCB | DNAJC20;HSC20;HSCB;h CG_40981;RP3-366L4.2;RP3-366L4.3-003 | mitochondrion |
| 600 | P38646;B7Z 4V2;F5H3L8 | 3313 | 75 kDa glucose-regulated protein;Heat shock 70 kDa protein 9;Mortalin;Peptide-binding protein 74;Stress-70 protein, mitochondrial;cDNA FLJ51907, highly similar to Stress-70 protein, mitochondrial | GRP75;HSPA9;HSPA9B | mitochondrial nucleoid \| mitochondrion \| cell surface \| cytoplasm |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 3559 | Q16836-2;Q16836;E9PF18 | 3033 | Hydroxyacyl-coenzyme A dehydrogenase, mitochondrial;Medium and short-chain L-3-hydroxyacyl-coenzyme A dehydrogenase;Short-chain 3-hydroxyacyl-CoA dehydrogenase | HAD;HADH;HADHSC;SC HAD | mitochondrion | mitochondrial matrix | cytoplasm |
| 3552 | Q16718;Q5H9R2;B9WA S3;C9IZN5 | 4698 | Complex I subunit B13;Complex I-13kD-B;NADH dehydrogenase [ubiquinone] 1 alpha subcomplex subunit 5;NADH-ubiquinone oxidoreductase 13 kDa-B subunit;Putative uncharacterized protein DKFZp781K1356;Putative uncharacterized protein NDUFA5 | NDUFA5;DKFZp781K135 6 | mitochondrion | respiratory chain | mitochondrial inner membrane | mitochondrial respiratory chain complex I | membrane |
| 47 | A4D154;Q9 6EH3 | 115416 | cDNA FLJ45842 fis, clone NT0NG2005468;cDNA, FLJ92099;Chromosome 7 open reading frame 30;Uncharacterized protein C7orf30 | C7orf30;hCG_37983;tca g7.1243 | 0 |
| 1931 | O43678;Q6 RJD6 | 4695 | Complex I-B8;NADH dehydrogenase [ubiquinone] 1 alpha subcomplex subunit 2;NADH-ubiquinone oxidoreductase B8 subunit | NDUFA2 | mitochondrion | respiratory chain | mitochondrial inner membrane | mitochondrial membrane | mitochondrial respiratory chain complex I | membrane |
| 2506 | P21912 | 6390 | Iron-sulfur subunit of complex II;Succinate dehydrogenase [ubiquinone] iron-sulfur subunit, mitochondrial | SDH;SDH1;SDHB | mitochondrial respiratory chain complex II | mitochondrion | mitochondrial inner membrane | membrane | membrane |
| 2124 | O95139;Q5 VIT2 | 4712 | Complex I-B17;NADH dehydrogenase [ubiquinone] 1 beta subcomplex subunit 6;NADH dehydrogenase (ubiquinone) 1 beta subunit;NADH dehydrogenase (Ubiquinone) 1 beta subcomplex, 6, 17kDa;NADH dehydrogenase (ubiquinone) 1 beta subcomplex, 6, 17kDa, isoform CRA_b | NDUFB6;hCG_30272;RP 11-205M20.6-002 | mitochondrion | respiratory chain | integral to membrane | mitochondrial inner membrane | mitochondrial membrane | mitochondrial inner membrane | mitochondrial respiratory chain complex I | membrane |

FIG. 29 cont.

TABLE 1

Mitochondrial matrix proteome (495 proteins), ranked from most enriched to least enriched (H/L ratio from Rep.1)

| id | Majority Protein IDs | Entrez | Protein Names | Gene Names | GO celloc |
|---|---|---|---|---|---|
| 2812 | P49406 | 9801 | 39S ribosomal protein L15, mitochondrial;39S ribosomal protein L19, mitochondrial | KIAA0104;MRPL15;MRPL19 | nuclear membrane \| mitochondrion \| ribosome \| nucleus \| intracellular |
| 3542 | Q16540;A8MVK1;A8MVT4;A6NUD9;A6NGQ5 | 6150 | 39S ribosomal protein L23, mitochondrial;L23 mitochondrial-related protein;Ribosomal protein L23-like;Putative uncharacterized protein MRPL23 | L23MRP;MRPL23;RPL23L | mitochondrion \| ribosome \| intracellular \| mitochondrial large ribosomal subunit |
| 5271 | Q9NX14-2;Q9NX14 | 54539 | Complex I-ESSS;NADH dehydrogenase [ubiquinone] 1 beta subcomplex subunit 11, mitochondrial;NADH-ubiquinone oxidoreductase ESSS subunit;Neuronal protein 17.3 | NDUFB11;UNQ111;PRO1064 | mitochondrion \| respiratory chain \| integral to membrane \| mitochondrial inner membrane \| mitochondrial respiratory chain complex I \| membrane |
| 5458 | Q9UII2;Q9UII2-2;Q9UII2-3 | 93974 | ATPase inhibitor, mitochondrial;Inhibitor of F(1)F(o)-ATPase | ATPI;ATPIF1 | mitochondrion \| cell surface \| mitochondrial proton-transporting ATP synthase complex |
| 2270 | P05091;57E UE5;F8VVX5;F8W0A9 | 217 | Aldehyde dehydrogenase, mitochondrial;ALDH class 2;ALDH-E2;ALDHI | ALDH2;ALDM | mitochondrion \| mitochondrial matrix |
| 4524 | Q96EL2;A6NI76 | 64951 | 28S ribosomal protein S24, mitochondrial;bMRP-47;Putative uncharacterized protein MRPS24 | HSPC335;MRPS24 | mitochondrion \| ribosome \| mitochondrial large ribosomal subunit \| mitochondrial small ribosomal subunit |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5260 | Q9NWU1;Q9NWU1-2;C9JQQ2 | 54995 | 3-oxoacyl-[acyl-carrier-protein] synthase, mitochondrial;Beta-ketoacyl-ACP synthase;Putative uncharacterized protein OXSM | OXSM | mitochondrion |
| 2083 | O75947;O75947-2;F5H608 | 10476 | ATP synthase subunit d, mitochondrial | ATP5H;Myq032 | mitochondrion | mitochondrial inner membrane | membrane | mitochondrial proton-transporting ATP synthase complex | mitochondrial proton-transporting ATP synthase complex, coupling factor F(o) |
| 3996 | Q7Z7F7-2;Q7Z7F7 | 128308 | 39S ribosomal protein L55, mitochondrial | MRPL55;UNQ5835/PRO19675 | mitochondrion | ribosome | mitochondrial large ribosomal subunit |
| 4586 | Q96DA6;C9JBV1;F2Z3A7;G5E6V2 | 131118 | DnaJ homolog subfamily C member 19;Mitochondrial import inner membrane translocase subunit TIM14;DnaJ (Hsp40) homolog, subfamily C, member 19, isoform CRA_a;Putative uncharacterized protein DNAJC19 | DNAJC19;TIM14;TIMM14;hCG_17532 | mitochondrion | integral to membrane | mitochondrial inner membrane | membrane |
| 621 | P34897;P34897-2;Q8N1A9;B4D1V4;H0YZ0 | 6472 | Glycine hydroxymethyltransferase;Serine hydroxymethyltransferase;cDNA FLJ58565, highly similar to Serine hydroxymethyltransferase, mitochondrial (EC 2.1.2.1);Serine hydroxymethyltransferase 2 [Mitochondrial], isoform CRA_h | SHMT2;hCG_41231 | mitochondrial nucleoid | mitochondrion | mitochondrial matrix |
| 52 | A4D1U3;Q04837;E7EUY5;C9K0U8 | 6742 | cDNA, FLJ93S04, Homo sapiens single-stranded DNA binding protein 1 (SSBP1), mRNA;Single-stranded DNA binding protein 1;Single-stranded DNA binding protein 1, isoform CRA_a;PWP1-interacting protein 17;Single-stranded DNA-binding protein, mitochondrial;Putative uncharacterized protein SSBP1 | hCG_2014251,SSBP1,tcag7.401,SSBP | mitochondrial nucleoid | mitochondrion |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 2634 | P31937;Q5J Z22 | 11112 | 3-hydroxyisobutyrate dehydrogenase, mitochondrial;3-hydroxyisobutyrate dehydrogenase;3-hydroxyisobutyrate dehydrogenase, isoform CRA_a;cDNA, FLJ96784, Homo sapiens 3-hydroxyisobutyrate dehydrogenase (HIBADH), mRNA;NS5ATP1 | HIBADH;hCG_39034;NS5ATP1;tcag7.211 | mitochondrion \| mitochondrial matrix |
| 3547 | Q16595;C9J AX1 | 2395 | Frataxin intermediate form;Frataxin(56-210);Frataxin(81-210);Frataxin, mitochondrial;Friedreich ataxia protein;Putative uncharacterized protein FXN | FRDA;FXN;X25 | cytosol \| mitochondrion \| mitochondrial matrix \| cytoplasm |
| 3719 | Q5T4A0;G5 EA38 | 200205 | Putative transferase C1orf69, mitochondrial | C1orf69 | mitochondrion \| cytoplasm |
| 1349 | Q9Y3B8;F5 GYG5;H0YG R4;Q9Y3B8-2;H0YG54;H 0YG83;F5GX 07;H0YH58 | 25996 | Oligoribonuclease, mitochondrial;RNA exonuclease 2 homolog;Small fragment nuclease | CGI-114;REXO2;SFN;SMFN | mitochondrion \| nucleus \| intracellular |
| 2616 | P30405;H0Y 548;Q2KD8 7 | 10105 | Cyclophilin F;Peptidyl-prolyl cis-trans isomerase F, mitochondrial;Rotamase F;Peptidyl-prolyl cis-trans isomerase | CYP3;PPIF;hCG_22611 | mitochondrion \| mitochondrial inner membrane \| mitochondrial matrix \| membrane fraction |
| 4793 | Q9BH5 | 81932 | Haloacid dehalogenase-like hydrolase domain-containing protein 3 | C9orf158;HDHD3 | mitochondrion |
| 2608 | P30042;P30 042-2 | 8209 | ES1 protein homolog, mitochondrial;Protein GT335;Protein KNP-I | C21orf33;HES1;KNP | mitochondrion |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 2532 | P23378 | 2731 | Glycine cleavage system P protein;Glycine decarboxylase;Glycine dehydrogenase [decarboxylating], mitochondrial | GCSP;GLDC | mitochondrion |
| 5230 | Q9NVH6-8;Q9NVH6-;Q9NVH6-7;Q9NVH6-5;Q9NVH6-6;Q9NVH6-3;Q9NVH6-2;Q9NVH6-4 | 55217 | Epsilon-trimethyllysine 2-oxoglutarate dioxygenase;Epsilon-trimethyllysine hydroxylase;TML hydroxylase;TML-alpha-ketoglutarate dioxygenase;Trimethyllysine dioxygenase, mitochondrial | TMLH;TMLHE | mitochondrion | mitochondrial matrix |
| 2095 | O75380;D6RBT3 | 4726 | Complex I-13kD-A;NADH dehydrogenase [ubiquinone] iron-sulfur protein 6, mitochondrial;NADH-ubiquinone oxidoreductase 13 kDa-A subunit | NDUFS6 | mitochondrion | respiratory chain | mitochondrial inner membrane | mitochondrial respiratory chain complex I | membrane |
| 4905 | Q9BZE1;E9PB99 | 51253 | 39S ribosomal protein L2, mitochondrial;39S ribosomal protein L37, mitochondrial | HSPC235;MRPL2;MRPL37;RPML2 | mitochondrion | ribosome | mitochondrial ribosome |
| 5122 | Q9HD23;B4DQL2;Q9HDQ3-;2;F5GWH3 | 57380 | Magnesium transporter MRS2 homolog, mitochondrial;MRS2-like protein;cDNA FLJ52725, highly similar to Magnesium transporter MRS2, mitochondrial | HPT;MRS2;MRS2L | mitochondrion | integral to membrane | mitochondrial inner membrane | membrane |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 820 | Q9NP80;C9J ZH4,Q9NP80-2;C9JN30 | 50640 | Calcium-independent phospholipase A2-gamma;Intracellular membrane-associated calcium-independent phospholipase A2 gamma;iPLA2-2;Patatin-like phospholipase domain-containing protein 8;PNPLA-gamma;Intracellular membrane-associated calcium-independent phospholipase A2 gamma, isoform CRA_b;Putative uncharacterized protein PNPLA8 | BM-043;iPLA22;iPLA2G iLA8;hCG_17116;iPLA2(G AMMA) | Golgi apparatus \| endoplasmic reticulum \| intracellular \| Golgi membrane \| perinuclear region of cytoplasm \| cytoplasm \| integral to membrane \| peroxisomal membrane \| endoplasmic reticulum membrane \| membrane \| membrane fraction |
| 280 | P35914,B1A KL3;B4DUP 4;F5GY19 | 3155 | 3-hydroxy-3-methylglutarate-CoA lyase;Hydroxymethylglutaryl-CoA lyase, mitochondrial;3-hydroxymethyl-3-methylglutaryl-Coenzyme A lyase;3-hydroxymethyl-3-methylglutaryl-Coenzyme A lyase (Hydroxymethylglutaricaciduria), isoform CRA_b;cDNA FLJ16378 fis, clone TKIDN2016399, highly similar to Hydroxymethylglutaryl-CoA lyase, mitochondrial [EC 4.1.3.4];cDNA FLJ53101, highly similar to Hydroxymethylglutaryl-CoA lyase, mitochondrial [EC 4.1.3.4] | HMGCL;hCG_37683;RP5-886K2.8-001 | mitochondrion \| mitochondrial inner membrane \| mitochondrial matrix |
| 5739 | Q9Y6M9;E9 PH64,E9PF4 9;E7EWZ0 | 4715 | Complex I-B22;LYR motif-containing protein 3;NADH dehydrogenase [ubiquinone] 1 beta subcomplex subunit 9;NADH-ubiquinone oxidoreductase B22 subunit | LYRM3;NDUFB9;UQCR2 2 | mitochondrion \| respiratory chain \| mitochondrial inner membrane \| mitochondrial respiratory chain complex I \| membrane |
| 793 | O75414;C9J QB1,C9J9V6 | 10201 | Inhibitor of p53-induced apoptosis-alpha;nm23-H6;Nucleoside diphosphate kinase 6;Nucleoside diphosphate kinase | NME6 | mitochondrion |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 14 | A2A274;Q9 9798;F5H2A 5;B4DW08; B4DEC3 | 50 | Aconitase 2, mitochondrial;Aconitate hydratase, mitochondrial;Citrate hydro-lyase;cDNA FLJ50886, highly similar to Aconitate hydratase, mitochondrial(EC 4.2.1.3);cDNA FLJ60429, highly similar to Aconitate hydratase, mitochondrial (EC 4.2.1.3) | ACO2;RP3-347H13.8-002 | mitochondrion \| nucleus |
| 2713 | P40926;E9P DB2;G3XAL 0 | 4191 | Malate dehydrogenase, mitochondrial | MDH2 | mitochondrion \| mitochondrial inner membrane \| mitochondrial matrix |
| 2131 | O95182 | 4701 | Complex I-B14.5a;NADH dehydrogenase [ubiquinone] 1 alpha subcomplex subunit 7;NADH-ubiquinone oxidoreductase subunit B14.5a | NDUFA7 | mitochondrion \| respiratory chain \| mitochondrial inner membrane \| mitochondrial respiratory chain complex I \| membrane |
| 4473 | Q96AB3-2;Q96AB3;Q 96AB3-3 | 79763 | Isochorismatase domain-containing protein 2, mitochondrial | ISOC2 | mitochondrion \| nucleus \| cytoplasm |
| 1139 | O00330;E9P B14 | 8050 | Dihydrolipoamide dehydrogenase-binding protein of pyruvate dehydrogenase complex;E3-binding protein;Lipoyl-containing pyruvate dehydrogenase complex component X;proX;Pyruvate dehydrogenase protein X component, mitochondrial | PDHX;PDX1 | mitochondrion \| mitochondrial matrix |
| 5451 | Q9UI09;F8V RD8 | 55967 | 13 kDa differentiation-associated protein;Complex I-B17.2;NADH dehydrogenase [ubiquinone] 1 alpha subcomplex subunit 12;NADH-ubiquinone oxidoreductase subunit B17.2 | DAP13;NDUFA12 | mitochondrion \| respiratory chain \| mitochondrial inner membrane \| mitochondrial respiratory chain complex I \| membrane |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4769 | Q9BQP7;Q5QPE8;Q5QPE7 | 92667 | Uncharacterized protein C20orf72;Chromosome 20 open reading frame 72 | C20orf72;RP11-504H3.1-003 | mitochondrion |
| 2596 | P28331;B4DUC1;E7ENF3;B4DPG1;B4DJ81 | 4719 | Complex I-75kD;NADH-ubiquinone oxidoreductase 75 kDa subunit, mitochondrial;cDNA FLJ53201, highly similar to NADH-ubiquinone oxidoreductase 75 kDa subunit, mitochondrial [EC 1.6.5.3];cDNA FLJ55879, highly similar to NADH-ubiquinone oxidoreductase 75 kDa subunit, mitochondrial [EC 1.6.5.3];cDNA FLJ60586, highly similar to NADH-ubiquinone oxidoreductase 75 kDa subunit, mitochondrial [EC 1.6.5.3] | NDUFS1 | mitochondrion \| respiratory chain \| mitochondrial inner membrane \| mitochondrial respiratory chain complex I \| membrane \| mitochondrial intermembrane space |
| 5106 | Q9HC36 | 55178 | RNA methyltransferase-like protein 1 | HC90;RNMTL1 | mitochondrion |
| 1061 | E7ESL0;Q9NWU5;A6NGJ8;Q9NWU5-2 | 29093 | 39S ribosomal protein L25, mitochondrial;39S ribosomal protein L22 (MRPL22), transcript variant 1, mRNA;Putative uncharacterized protein MRPL22 | HSPC158;MRPL22;MRPL25;RPML25 | mitochondrion \| ribosome \| intracellular \| large ribosomal subunit |
| 4015 | Q86U28 | 122961 | HESB-like domain-containing protein 1;Iron-sulfur cluster assembly 2 homolog, mitochondrial | HBLD1;ISCA2 | mitochondrion |
| 3671 | Q5JRX3;Q5JRX3-2;E9PDX6;C9JSL2;E9PDX7;E7ES23 | 10531 | Pitrilysin metalloproteinase 1;Presequence protease, mitochondrial;Putative uncharacterized protein PITRM1 | KIAA1104;MP1;PITRM1 | mitochondrion \| nucleus \| mitochondrial matrix |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4774 | Q93BH2 | 84311 | 39S ribosomal protein L45, mitochondrial | MRPL45 | mitochondrion \| ribosome \| mitochondrial inner membrane presequence translocase complex |
| 4838 | Q9BV79;Q9BV79-2 | 51102 | Nuclear receptor-binding factor 1;Trans-2-enoyl-CoA reductase, mitochondrial | CGI-63;MECR;NBRF1 | mitochondrion |
| 2496 | P20674 | 9377 | Cytochrome c oxidase polypeptide Va;Cytochrome c oxidase subunit 5A, mitochondrial | COX5A | mitochondrion \| mitochondrial inner membrane \| membrane |
| 2882 | P51649;G5E9A9;F5H32B;C9J8Q5 | 7915 | Aldehyde dehydrogenase family 5 member A1;NAD(+)-dependent succinic semialdehyde dehydrogenase;Succinate-semialdehyde dehydrogenase, mitochondrial;Putative uncharacterized protein ALDH5A1 | ALDH5A1;SSADH | mitochondrion \| soluble fraction |
| 5643 | Q9Y3D9 | 51649 | 28S ribosomal protein S23, mitochondrial | CGI-138;HSPC329;MRPS23 | mitochondrion \| ribosome |
| 3019 | P61604;B8ZZL8 | 3336 | 10 kDa chaperonin;10 kDa heat shock protein, mitochondrial;Chaperonin 10;Early-pregnancy factor;Heat shock 10kDa protein 1 (Chaperonin 10), isoform CRA_b;Putative uncharacterized protein HSPE1 | HSPE1;hCG_21429 | mitochondrion \| mitochondrial matrix \| cytoplasm |
| 3176 | Q02218;E9PCR7;E9PD72;Q02218-2;F5H801;E9PFG7 | 4967 | 2-oxoglutarate dehydrogenase complex component E1;2-oxoglutarate dehydrogenase, mitochondrial;Alpha-ketoglutarate dehydrogenase | OGDH | mitochondrion \| mitochondrial membrane \| mitochondrial matrix |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 2462 | P17568 | 4713 | Cell adhesion protein SQM1;Complex I-B18;NADH dehydrogenase [ubiquinone] 1 beta subcomplex subunit 7;NADH-ubiquinone oxidoreductase B18 subunit | NDUFB7 | mitochondrion ǀ respiratory chain ǀ mitochondrial inner membrane ǀ mitochondrial respiratory chain complex I ǀ membrane |
| 2199 | P00390;P00390-2;C3KIL8;C8KIL9;C8KIM0 | 2936 | Glutathione reductase, mitochondrial;Glutathion reductase delta8 alternative splicing variant;Glutathion reductase delta9 alternative splicing varian;Glutathion reductase delta8+9 alternative splicing variant | GLUR;GRD1;GSR | cytosol ǀ mitochondrion ǀ soluble fraction ǀ external side of plasma membrane ǀ cytoplasm |
| 1354 | P00367;F5GYQ4,F8WA2 0;B4DGN5;B3XV55;P49448 | 2746 | Glutamate dehydrogenase 1, mitochondrial;cDNA FLJ55203, highly similar to Glutamate dehydrogenase 1, mitochondrial (EC 1.4.1.3);cDNA FLJ16138 fis, clone BRALZ2017531, highly similar to Glutamate dehydrogenase 1, mitochondrial (EC 1.4.1.3);Glutamate dehydrogenase 1, isoform CRA_a;Glutamate dehydrogenase 2, mitochondrial | GLUD;GLUD1;hCG_1993 805;GLUD2;GLUDP1 | mitochondrion ǀ mitochondrial matrix ǀ cytoplasm |
| 3121 | P80404 | 18 | (S)-3-amino-2-methylpropionate transaminase;4-aminobutyrate aminotransferase;Gamma-amino-N-butyrate transaminase;L-AIBAT | ABAT;GA3A | 4-aminobutyrate transaminase complex ǀ synaptosome ǀ mitochondrion ǀ mitochondrial matrix |
| 3279 | Q13011 | 1891 | Delta(3,5)-Delta(2,4)-dienoyl-CoA isomerase, mitochondrial | ECH1 | mitochondrion ǀ peroxisome |
| 4146 | Q8NOX4;Q8NOX4-2;B4DU60 | 171425 | Citrate lyase subunit beta-like protein, mitochondrial;cDNA FLJ51306, highly similar to Homo sapiens citrate lyase beta like (CLYBL), transcript variant 2, mRNA | CLB;CLYBL | citrate lyase complex ǀ mitochondrion |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 921 | D6R9J0;Q9BRQ6;D6RIB4;H0Y922 | 84303 | Coiled-coil-helix-coiled-coil-helix domain-containing protein 6 | CHCHD6 | 0 |
| 2541 | P23786 | 1376 | Carnitine O-palmitoyltransferase 2, mitochondrial;Carnitine palmitoyltransferase ii | CPT1;CPT2 | mitochondrion | mitochondrial inner membrane | membrane |
| 1472 | Q8NE22;F5H713 | 133383 | Uncharacterized protein C5orf35 | C5orf35 | 0 |
| 5238 | Q9NVS2;Q9NVS2-2;Q5QPA5;Q5QPA4 | 55168 | 28S ribosomal protein S18-3, mitochondrial;28S ribosomal protein S18a, mitochondrial;Mitochondrial ribosomal protein S18A;cDNA FLJ52919, highly similar to 28S ribosomal protein S18a, mitochondrial;Mitochondrial ribosomal protein S18A, isoform CRA_b | MRPS18A;RP1-261G23.2;hCG_19012;RP1-261G23.2-001 | mitochondrion | ribosome | intracellular | mitochondrial small ribosomal subunit |
| 4241 | Q8NE62 | 55349 | Choline dehydrogenase, mitochondrial | CHDH | mitochondrion | mitochondrial inner membrane |
| 2104 | O94925 | 2744 | Glutaminase kidney isoform, mitochondrial;K-glutaminase;L-glutamine amidohydrolase | GLS;GLS1;KIAA0838 | mitochondrion |
| 4573 | Q96HJ9 | 154791 | UPF0362 protein C7orf55 | C7orf55;HSPC268 | mitochondrion |
| 5302 | Q9NYK5-2;Q9NYK5;C9J6J7 | 54148 | 39S ribosomal protein L39, mitochondrial;39S ribosomal protein L5, mitochondrial;Putative uncharacterized protein MRPL39 | C2orf92;MRPL39;MRPL5;MSTP003;PRED22;RP MI5 | mitochondrion | ribosome | mitochondrial ribosome |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4358 | Q8WWV3;Q8WWV3-2;C3V1R2;Q8WWV3-3 | 84816 | NOGO-interacting mitochondrial protein;Reticulon-4-interacting protein 1, mitochondrial | NIMP;RTN4IP1 | mitochondrion |
| 4740 | Q99797 | 4285 | Mitochondrial intermediate peptidase | MIP;MIPEP | mitochondrion \| mitochondrial matrix |
| 1893 | O43181;H0Y9M8 | 4724 | Complex I-18 kDa;Complex I-AQDQ;NADH dehydrogenase [ubiquinone] iron-sulfur protein 4, mitochondrial;NADH-ubiquinone oxidoreductase 18 kDa subunit | NDUFS4 | mitochondrion \| mitochondrial inner membrane \| mitochondrial respiratory chain complex I \| membrane |
| 2090 | O76031;Q9H0T2;H0YN08 | 10845 | ATP-dependent Clp protease ATP-binding subunit clpX-like, mitochondrial;Putative uncharacterized protein DKFZp586J151 | CLPX;DKFZp586J151 | mitochondrial nucleoid \| mitochondrion \| mitochondrial endopeptidase Clp complex \| mitochondrial inner membrane |
| 1652 | P82650;G5E9V5;G5E9W7 | 56945 | 28S ribosomal protein S22, mitochondrial | C3orf5;GK002;MRPS22;RPMS22 | mitochondrion \| ribosome \| mitochondrial ribosome \| mitochondrial small ribosomal subunit |
| 2130 | O95169;Q5W14;G5W143;E9PQ68;E9PME4 | 4714 | Complex I-ASHI;NADH dehydrogenase [ubiquinone] 1 beta subcomplex subunit 8, mitochondrial;NADH-ubiquinone oxidoreductase ASHI subunit;NADH dehydrogenase (Ubiquinone) 1 beta subcomplex, 8, 19kDa;NADH dehydrogenase (Ubiquinone) 1 beta subcomplex, 8, 19kDa, isoform CRA_a;cDNA FLJ52503, highly similar to NADH dehydrogenase [ubiquinone] 1 beta subcomplex subunit 8, mitochondrial [EC 1.6.5.3] [EC 1.6.99.3] (NADH-ubiquinone oxidoreductase ASHI subunit) [Complex I-ASHI] (CI-ASHI) | NDUFB8;hCG_24658;RP11-411B6.5-006;RP1-411B6.5-003 | mitochondrion \| respiratory chain \| integral to membrane \| endoplasmic reticulum \| mitochondrial inner membrane \| mitochondrial respiratory chain complex I \| membrane |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 2613 | P30084 | 1892 | Enoyl-CoA hydratase 1;Enoyl-CoA hydratase, mitochondrial;Short-chain enoyl-CoA hydratase | ECHS1 | mitochondrion | mitochondrial matrix |
| 2342 | P0C7P0 | 284106 | CDGSH iron sulfur domain-containing protein 3, mitochondrial;MitoNEET-related protein 2 | CISD3 | mitochondrion |
| 2025 | O75306;Q7Z912 | 4720 | Complex I-49kD;NADH dehydrogenase [ubiquinone] iron-sulfur protein 2, mitochondrial;NADH-ubiquinone oxidoreductase 49 kDa subunit;cDNA, FL78876, highly similar to NADH-ubiquinone oxidoreductase 49 kDa subunit, mitochondrial; [EC 1.6.5.3] | NDUFS2 | mitochondrion | respiratory chain | mitochondrial inner membrane | mitochondrial respiratory chain complex I | membrane |
| 2716 | P40939 | 3030 | 78 kDa gastrin-binding protein;Long chain 3-hydroxyacyl-CoA dehydrogenase;Long-chain enoyl-CoA hydratase;TP-alpha;Trifunctional enzyme subunit alpha, mitochondrial | HADH;HADHA | mitochondrial nucleoid | mitochondrion | mitochondrial inner membrane | fatty acid beta-oxidation multienzyme complex | mitochondrial matrix |
| 5639 | Q9Y3D3;B4E032;A6ND22 | 51021 | 28S ribosomal protein S16, mitochondrial;cDNA FLJ58442, highly similar to 28S ribosomal protein S16, mitochondrial (S16mt);Putative uncharacterized protein MRPS16 | CGI-132;MRPS16;RPMS16 | mitochondrion | ribosome | intracellular | mitochondrial small ribosomal subunit |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5722 | Q9Y676;Q5STN0;B4DFG6 | 28973 | 28S ribosomal protein S18-2, mitochondrial;28S ribosomal protein S18b, mitochondrial;Mitochondrial ribosomal protein S18B;Putative uncharacterized protein ENSP00000365691;cDNA FLJ54285, highly similar to 28S ribosomal protein S18a, mitochondrial | C6orf14;HSPC183;MRPS18B;PTD017;DADB-129D20.6-003;DAMA-178G23.8-003;DAMC-83F13.5-003;DAQB-47P19.5-003;DASS-182C6.3-003;XXbac-BCX48F10.3-003;XXbac-BPG249D20.2-003 | mitochondrion \| ribosome \| intracellular \| mitochondrial small ribosomal subunit |
| 57 | C9JR26;A4D1N4;Q9NX63;F8WAR4;G3V1K1 | 54927 | Putative uncharacterized protein CHCHD3;Coiled-coil-helix-coiled-coil-helix domain containing 3;Coiled-coil-helix-coiled-coil-helix domain containing 3, isoform CRA_d;Coiled-coil-helix-coiled-coil-helix domain-containing protein 3, mitochondrial | CHCHD3;hCG_2014841;tcag7.1158 | mitochondrion |
| 4739 | Q99766;Q8WXQ4 | 27109 | ATP synthase subunit s, mitochondrial;ATP synthase-coupling factor B;Mitochondrial ATP synthase regulatory component factor B;ATP synthase coupling factor B-like 1 | ATP5S;ATPW | proton-transporting ATP synthase complex, coupling factor F(o) \| mitochondrion \| mitochondrial inner membrane \| membrane |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 3531 | Q16134;C9J T69 | 2110 | Electron transfer flavoprotein-ubiquinone oxidoreductase, mitochondrial;Electron-transferring-flavoprotein dehydrogenase;Putative uncharacterized protein ETFDH | ETFDH | mitochondrion | mitochondrial inner membrane | mitochondrial membrane | membrane | integral to mitochondrial inner membrane |
| 84 | A6NCI0;Q9Y 6G3 | 28977 | Mitochondrial ribosomal protein L42, isoform CRA_e;Putative uncharacterized protein MRPL42;28S ribosomal protein S32, mitochondrial;39S ribosomal protein L31, mitochondrial;39S ribosomal protein L42, mitochondrial | hCG_1647154;MRPL42; HSPC204;MRPL31;MRPS 32;PTD007;RPML31 | mitochondrion | ribosome | mitochondrial small ribosomal subunit |
| 4530 | Q96ER9;Q9 6ER9-2 | 79714 | Coiled-coil domain-containing protein 51 | CCDC51 | mitochondrion | integral to membrane | membrane |
| 1724 | H0YIV9;O43 716;F8VRU3 | 283459 | GatC-like protein;Protein 15E1.2 | 15E1.2;GATC | mitochondrion | cellular_component |
| 4733 | Q99714;Q9 9714-2;Q5H9Z8 | 3028 | 17-beta-hydroxysteroid dehydrogenase 10;3-hydroxy-2-methylbutyryl-CoA dehydrogenase;3-hydroxyacyl-CoA dehydrogenase type II;3-hydroxyacyl-CoA dehydrogenase type-2;Endoplasmic reticulum-associated amyloid beta-peptide-binding protein;Mitochondrial ribonuclease P protein 2;Short-chain type dehydrogenase/reductase XH98G2;Type II HADH;Hydroxysteroid (17-beta) dehydrogenase 10 | ERAB;HADH2;HSD17B10; MRPP2;SCHAD;XH98G2; RP3-339A18.2-004 | mitochondrion | plasma membrane | cytoplasm |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5203 | Q9NUB1;Q9NUB1-2;78W7Y1;Q6ZV30;F5H6F4;E9PC79 | 84532 | Acetate--CoA ligase 2;Acetyl-coenzyme A synthetase 2, mitochondrial;Acyl-CoA synthetase short-chain family member 1;cDNA FLJ43068 fis, clone BRTHA3008778, moderately similar to Acetyl-coenzyme A synthetase [EC 6.2.1.1] | ACAS2L;ACSS1;KIAA1846 | mitochondrion \| mitochondrial matrix |
| 2412 | P13804;54DT43;H0Y1LU7;H0YWX6;H0YVK49;H0YKF0;H0YL12 | 2108 | Electron transfer flavoprotein subunit alpha, mitochondrial;cDNA FLJ60859, highly similar to Electron transfer flavoprotein subunit alpha, mitochondrial | ETFA | mitochondrion \| mitochondrial matrix |
| 4065 | Q86YH6;84DKU5;Q86YH6-2 | 57107 | Candidate tumor suppressor protein;Decaprenyl pyrophosphate synthase subunit 2;Decaprenyl-diphosphate synthase subunit 2;cDNA FLJ56514, highly similar to Decaprenyl-diphosphate synthase subunit 2 [EC 2.5.1.-] | C6orf210;DLP1;PDSS2 | mitochondrion |
| 2624 | P31040;C9PB15;D6RFM5;S9PEF8 | 6389 | Flavoprotein subunit of complex II;Succinate dehydrogenase [ubiquinone] flavoprotein subunit, mitochondrial | SDH2;SDH4;SDHF | mitochondrial respiratory chain complex II \| mitochondrion \| mitochondrial inner membrane \| membrane |
| 5345 | Q9P0J1 | 54704 | Pyruvate dehydrogenase [acetyl-transferring]]-phosphatase 1, mitochondrial;Protein phosphatase 2C;Pyruvate dehydrogenase phosphatase catalytic subunit 1 | PDP;PDP1;PPM2C | mitochondrion \| protein serine/threonine phosphatase complex \| mitochondrial matrix |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4987 | Q9H2K0 | 219402 | Translation initiation factor IF-3, mitochondrial | DC38;MTIF3 | mitochondrion |
| 2547 | P24539;Q5QNZ2 | 515 | ATP synthase subunit b, mitochondrial;ATP synthase, H+ transporting, mitochondrial F0 complex, subunit B1 | ATP5F1;RP11-532M11.5 005 | mitochondrion | mitochondrial inner membrane | membrane | mitochondrial matrix | mitochondrial proton-transporting ATP synthase complex | mitochondrial proton-transporting ATP synthase complex, coupling factor F(o) |
| 1286 | O75964;E9PN17 | 10632 | ATP synthase subunit g, mitochondrial | ATP5L | mitochondrion | mitochondrial inner membrane | membrane | mitochondrial proton-transporting ATP synthase complex | mitochondrial proton-transporting ATP synthase complex, coupling factor F(o) |
| 4903 | Q9BYT8;F8W713;E9PCB6;H0YAK4 | 57486 | Angiotensin-binding protein;Microsomal endopeptidase;Mitochondrial oligopeptidase M;Neurolysin, mitochondrial;Neurotensin endopeptidase | AGTBP;KIAA1226;NLN | mitochondrion | mitochondrial intermembrane space | cytoplasm |
| 4385 | Q93506 | 7923 | 17-beta-hydroxysteroid dehydrogenase 8;3-oxoacyl-[acyl-carrier-protein] reductase;Estradiol 17-beta-dehydrogenase 8;Protein Ke6;Really interesting new gene 2 protein;Testosterone 17-beta-dehydrogenase 8 | FABGL;HKE6;HSD17B8;RING2 | mitochondrial envelope | mitochondrion | plasma membrane | mitochondrial matrix | membrane fraction |
| 764 | C9J119;P82930 | 65993 | Putative uncharacterized protein MRPS34;28S ribosomal protein S34, mitochondrial | MRPS34 | mitochondrion | ribosome |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 1016 | E7EPT4,P19404 | 4729 | NADH dehydrogenase [ubiquinone] flavoprotein 2, mitochondrial;NADH-ubiquinone oxidoreductase 24 kDa subunit | NDUFV2 | mitochondrion \| respiratory chain \| mitochondrial inner membrane \| mitochondrial respiratory chain complex I \| membrane |
| 3124 | P82663;B4DFJ5;E7EPW2,B4DQG6 | 64432 | 28S ribosomal protein S25, mitochondrial;cDNA FLJ59193, highly similar to Mitochondrial 28S ribosomal protein S25;cDNA FLJ54123, moderately similar to Mitochondrial 28S ribosomal protein S25 | MRPS25;RPMS25 | mitochondrion \| ribosome \| mitochondrial small ribosomal subunit |
| 4781 | Q9BRT2,Q5TAQ0 | 84300 | Breast cancer-associated protein SGA-81M;Uncharacterized protein C6orf125;OTTHUMP00000016217 | C6orf125;RP11-6B20.2-002 | mitochondrion |
| 3706 | Q5SXM8,Q5SXM7 | 728499 | DNL-type zinc finger protein;Chromosome 9 open reading frame 151 | C9orf151,DNL2;RP11-413M3.2-002 | mitochondrion |
| 4583 | Q96I99;Q96I99-2;E9PDQ8;F5H4S7;H0Y852 | 8801 | GTP-specific succinyl-CoA synthetase subunit beta;Succinyl-CoA ligase [GDP-forming] subunit beta, mitochondrial;Succinyl-CoA synthetase beta-G chain | SUCLG2 | mitochondrion |
| 5596 | Q9Y2R0 | 28958 | Coiled-coil domain-containing protein 56 | CCDC56;HSPC009 | mitochondrion \| integral to membrane \| membrane |

FIG. 29 cont.

TABLE 1

Mitochondrial matrix proteome (495 proteins), ranked from most enriched to least enriched (H/L ratio from Rep.1)

| id | Majority Protein IDs | Entrez | Protein Names | Gene Names | GO celloc |
|---|---|---|---|---|---|
| 5107 | Q9HC38;Q9HC38-2;E7EMY5;B7Z403 | 51031 | Glyoxalase domain-containing protein 4;cDNA FLJ55095 | C17orf25;CGI-150;GLOD4;MyO27 | mitochondrion |
| 3675 | Q5JTZ9 | 57505 | Alanine--tRNA ligase;Alanyl-tRNA synthetase-like;Probable alanyl-tRNA synthetase, mitochondrial | AARS2;AARSL;KIAA1270 | mitochondrion ¦ mitochondrial matrix ¦ cytoplasm |
| 3133 | P82933 | 64965 | 28S ribosomal protein S9, mitochondrial | MRPS9;RPMS9 | mitochondrion ¦ ribosome ¦ intracellular ¦ mitochondrial small ribosomal subunit |
| 1750 | O00217;E9PPW7;E9PKH6;F8W9K7;E9PN51 | 4728 | Complex I-23kD;NADH dehydrogenase [ubiquinone] iron-sulfur protein 8, mitochondrial;NADH-ubiquinone oxidoreductase 23 kDa subunit;TYKY subunit | NDUFS8 | mitochondrion ¦ respiratory chain ¦ mitochondrial respiratory chain complex I ¦ membrane |
| 4901 | Q9BYN8 | 64949 | 28S ribosomal protein S26, mitochondrial | C20orf193;MRPS26;RPMS13 | mitochondrion ¦ ribosome ¦ mitochondrial small ribosomal subunit |
| 4864 | Q9BW91;Q9BW91-2;D6RAW2 | 53343 | Adenosine diphosphoribose pyrophosphatase;ADP-ribose diphosphatase;ADP-ribose phosphohydrolase;ADP-ribose pyrophosphatase, mitochondrial;Nucleoside diphosphate-linked moiety X motif 9 | NUDT10;NUDT9;PSEC0099;UNQ3012;PRO9771 | mitochondrion ¦ intracellular |
| 5191 | Q9NSE4;F6SBX2 | 55699 | Isoleucine--tRNA ligase;Isoleucyl-tRNA synthetase, mitochondrial | IARS2 | mitochondrion ¦ mitochondrial matrix ¦ cytoplasm |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 2024 | O75251;C9JKS5;F5GX41;B3KRN2;F5H5N1 | 374291 | Complex I-20kD;NADH dehydrogenase [ubiquinone] iron-sulfur protein 7, mitochondrial;NADH-ubiquinone oxidoreductase 20 kDa subunit;PSST subunit;Putative uncharacterized protein NDUFS7;cDNA FLJ34304 fis, clone FEBRA2007880, highly similar to NADH-ubiquinone oxidoreductase 20 kDa subunit, mitochondrial (EC 1.6.5.3) | NDUFS7 | mitochondrion \| respiratory chain \| mitochondrial respiratory chain complex I |
| 4941 | Q9GZT8;Q9GZT8-2;Q6X735;Q6X734;E7EXA3 | 60491 | Amyotrophic lateral sclerosis 2 chromosomal region candidate gene 1 protein;NIF3-like protein 1;NIF3L1 isoform beta;NIF3L1 isoform gamma | ALS2CR1;MDS015;My018;NIF3L1 | mitochondrion \| cytoplasm |
| 3830 | Q5I8O7;Q6L8Q7-2;F6T1Q0 | 201626 | 2,5-phosphodiesterase 12 | PDE12 | mitochondrion |
| 2904 | P82758;H0YB34;H0YBX3;E5RI71 | 10247 | 14.5 kDa translational inhibitor protein;Ribonuclease UK114;UK114 antigen homolog | HRSP12;PSP | mitochondrion \| nucleus \| cytoplasm |
| 4561 | Q96GW9;B4DVV7 | 92935 | Methionine—tRNA ligase 2;Methionyl-tRNA synthetase, mitochondrial;Mitochondrial methionine--tRNA ligase;cDNA FLJ51339, highly similar to Methionyl-tRNA synthetase, mitochondrial (EC 6.1.1.10) | MARS2 | mitochondrion \| mitochondrial matrix \| cytoplasm |
| 4534 | Q96EY1;Q96EY1-2 | 9093 | DnaJ homolog subfamily A member 3, mitochondrial;DnaJ protein Tid-1;Hepatocellular carcinoma-associated antigen 57;Tumorous imaginal discs protein Tid56 homolog | DNAJA3;HCA57;TID1 | mitochondrion \| kappaB kinase complex \| cytoplasm \| mitochondrial nucleoid \| cytosol \| actin filament \| nucleus \| mitochondrial matrix \| I-kappaB/NF-kappaB complex |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 3557 | Q16795 | 4704 | Complex I-39kD;NADH dehydrogenase [ubiquinone] 1 alpha subcomplex subunit 9, mitochondrial;NADH-ubiquinone oxidoreductase 39 kDa subunit | NDUFA9;NDUFS2L | mitochondrion | respiratory chain | mitochondrial inner membrane | mitochondrial membrane | mitochondrial respiratory chain complex | mitochondrial matrix |
| 2962 | P56556 | 4706 | Complex I-B14;LYR motif-containing protein 6;NADH dehydrogenase [ubiquinone] 1 alpha subcomplex subunit 6;NADH-ubiquinone oxidoreductase B14 subunit | LYRM6;NADHB14;NDUFA6 | mitochondrion | respiratory chain | mitochondrial inner membrane | mitochondrial membrane | mitochondrial respiratory chain complex | membrane |
| 2550 | P24752 | 38 | Acetoacetyl-CoA thiolase;Acetyl-CoA acetyltransferase, mitochondrial;T2 | ACAT;ACAT1;MAT | mitochondrion | mitochondrial inner membrane | mitochondrial matrix |
| 2365 | P10809 | 3329 | 60 kDa chaperonin;60 kDa heat shock protein, mitochondrial;Chaperonin 60;Heat shock protein 60;HuCHA60;Mitochondrial matrix protein P1;P60 lymphocyte protein | HSP60;HSPD1 | mitochondrion | stored secretory granule | cyclin-dependent protein kinase activating kinase holoenzyme complex | mitochondrial inner membrane | plasma membrane part | early endosome | cytoplasm | cytosol | coated pit | extracellular space | coated vesicle | lipopolysaccharide receptor complex | cell surface | mitochondrial matrix |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 1590 | P49821;Q3V015;P49821-2;B4DE93;E7ETQ4 | 4723 | Complex I-51kD;NADH dehydrogenase [ubiquinone] flavoprotein 1, mitochondrial;NADH dehydrogenase flavoprotein 1;NADH-ubiquinone oxidoreductase 51 kDa subunit;cDNA FLJ57949, highly similar to NADH-ubiquinone oxidoreductase 51 kDa subunit, mitochondrial (EC 1.6.5.3);cDNA FLJ79021, highly similar to NADH-ubiquinone oxidoreductase 51 kDa subunit, mitochondrial (EC 1.6.5.3) | NDUFV1;UQCR1 | mitochondrion \| respiratory chain \| mitochondrial inner membrane \| mitochondrial respiratory chain complex I membrane |
| 3128 | P82909 | 92259 | 28S ribosomal protein S36, mitochondrial | DC47;MRPS36 | mitochondrion \| ribosome \| mitochondrial small ribosomal subunit |
| 4145 | Q8N0V3;Q8N0V3-2 | 79863 | Putative ribosome-binding factor A, mitochondrial | C18orf22 | mitochondrion |
| 1087 | Q7L592;E7EUC3;Q91527;Q7L592-2;C9J236 | 55471 | Protein midA homolog, mitochondrial;Putative uncharacterized protein C2orf56 | C2orf56;PRO1853 | mitochondrion |
| 5601 | Q9Y2S7 | 26073 | 38 kDa DNA polymerase delta interaction protein;Polymerase delta-interacting protein 2 | HSPC017;PDIP38;POLD4;POLDIP2 | mitochondrial nucleoid \| mitochondrion \| nucleus |
| 3893 | Q6UB35 | 25902 | Formyltetrahydrofolate synthetase;Monofunctional C1-tetrahydrofolate synthase, mitochondrial | FTHFSDC1;MTHFD1L | mitochondrion |
| 518 | Q9NVS9;B4E1D7;B4E0V0;B4E1S2 | 55163 | Pyridoxamine-phosphate oxidase;Pyridoxine-5-phosphate oxidase;cDNA FLJ59601, highly similar to Pyridoxine-5-phosphate oxidase (EC 1.4.3.5);cDNA FLJ59109, highly similar to Pyridoxine-5-phosphate oxidase (EC 1.4.3.5);cDNA FLJ59599, highly similar to Pyridoxine-5-phosphate oxidase (EC 1.4.3.5) | PNPO | 0 |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5509 | Q9ULD0;Q9ULD0-2;Q9ULD0-3 | 55753 | 2-oxoglutarate dehydrogenase complex component E1-like;2-oxoglutarate dehydrogenase-like, mitochondrial;Alpha-ketoglutarate dehydrogenase-like | KIAA1290;OGDHL | mitochondrion \| mitochondrial matrix |
| 4231 | Q8NCW5;Q8NCW5-2;Q5T3I4 | 128240 | Apolipoprotein A-I-binding protein;YjeF N-terminal domain-containing protein 1;Apolipoprotein A-I binding protein | AIBP;APOA1BP;YJEFN1;RP11-284F21.3-004 | mitochondrion \| extracellular region |
| 2806 | P49247;Q53R32 | 22934 | Phosphoribioisomerase;Ribose-5-phosphate Isomerase;Putative uncharacterized protein RPIA | RPI;RPIA | cytosol \| intracellular |
| 3941 | Q7L0Y3;C9JVB6 | 54831 | HBV pre-S2 trans-regulated protein 2;Mitochondrial ribonuclease P protein 1;Renal carcinoma antigen NY-REN-49;RNA (guanine-9-)-methyltransferase domain-containing protein;Putative uncharacterized protein RG9MTD1 | MRPP1;RG9MTD1 | mitochondrion |
| 2109 | O94903;H0YBB9;E5RG7;F7ERFX7 | 11212 | Proline synthase co-transcribed bacterial homolog protein | PROSC | mitochondrion \| intracellular \| cytoplasm |
| 1127 | E9PAL9;Q9H857-2;Q9H857;C9JHZ6;Q9H857-3;Q9H857-4 | 64943 | 5-nucleotidase domain-containing protein 2;Putative uncharacterized protein NT5DC2 | NT5DC2 | 0 |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 453 | B4DRT2;Q9 2S52;G5EA0 6;D6RH20 | 23107 | cDNA FLJ54536, highly similar to Mitochondrial 28S ribosomal protein S27;28S ribosomal protein S27, mitochondrial | KIAA0264;MRPS27 | mitochondrion \| ribosome |
| 2188 | O96000;Q9 6I16 | 4716 | Complex I-PDSW;NADH dehydrogenase [ubiquinone] 1 beta subcomplex subunit 10;NADH-ubiquinone oxidoreductase PDSW subunit;NADH dehydrogenase (ubiquinone) 1 beta subcomplex, 10, 22kDa, isoform CRA_a;NDUFB10 protein | NDUFB10;hCG_42700 | mitochondrion \| respiratory chain \| mitochondrial inner membrane \| mitochondrial respiratory chain complex I \| membrane |
| 3842 | Q6NWY1;Q6 NWY12 | 26275 | 3-hydroxyisobutyryl-CoA hydrolase, mitochondrial;3-hydroxyisobutyryl-coenzyme A hydrolase | HIBCH | mitochondrion \| mitochondrial matrix |
| 5682 | Q9Y512 | 25813 | Sorting and assembly machinery component 50 homolog;Transformation-related gene 3 protein | CGI-51;SAMM50;TRG3 | mitochondrial outer membrane \| mitochondrial sorting and assembly machinery complex \| integral to membrane of membrane fraction \| mitochondrion \| outer membrane \| integral to membrane \| cytoplasm |
| 1993 | O60783 | 63931 | 28S ribosomal protein S14, mitochondrial | MRPS14 | mitochondrion \| ribosome \| mitochondrial ribosome \| intracellular |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO cellex |
|---|---|---|---|---|---|
| 3743 | Q5TC12;A8MRA7;B7Z771;G3HOYE;N4;B7Z7D6;H0YD21 | 64756 | ATP synthase mitochondrial F1 complex assembly factor 1;ATP11 homolog;Putative uncharacterized protein ATPAF1;cDNA FLJ52027, highly similar to Homo sapiens ATP synthase mitochondrial F1 complex assembly factor 1 (ATPAF1), mRNA;cDNA FLJ50725, highly similar to Homo sapiens ATP synthase mitochondrial F1 complex assembly factor 1 (ATPAF1), mRNA | ATP11;ATPAF1 | mitochondrion |
| 1303 | P22392;Q4TT34;Q00746;E9PDC0;H0Y6N0;A2IDD0 | 4833 | Nucleoside diphosphate kinase;nm23-H4;Nucleoside diphosphate kinase D;Nucleoside diphosphate kinase, mitochondrial | NME4;Z97634.4-011;NM23D;hCG_19855 12;Z97634.4-002 | mitochondrion | mitochondrial intermembrane space |
| 1611 | G3V325;A4D273;D7S1 27 | 100526740 | cDNA FLJ76276, highly similar to Homo sapiens pentatricopeptide repeat domain 1 (PTCD1), mRNA;Pentatricopeptide repeat domain 1;Pentatricopeptide repeat-containing protein 1 | hCG_2023422;PTCD1;tc ag7.1151;KIAA0632 | #N/A |
| 5133 | Q9NP81;B4DE10;E7EX8 7 | 54938 | Serine--tRNA ligase;SerRSmt;Seryl-tRNA synthetase, mitochondrial;Seryl-tRNA(Ser/Sec) synthetase;cDNA FLJ58521, highly similar to Seryl-tRNA synthetase, mitochondrial (EC 6.1.1.11) | SARS2;SARSM | mitochondrion | mitochondrial matrix | cytoplasm |
| 4273 | Q8TAA5 | 134266 | GrpE protein homolog 2, mitochondrial;Mt-GrpE#2 | GRPEL2 | mitochondrion | mitochondrial inner membrane | mitochondrial matrix |
| 1928 | O43615 | 10469 | Mitochondrial import inner membrane translocase subunit TIM44 | MIMT44;TIM44;TIMM44 | mitochondrion | membrane | mitochondrial matrix | mitochondrial inner membrane | presequence translocase complex |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5150 | Q9NQH7;Q9NQH7-4;Q9NQH7-2 | 63929 | Aminopeptidase P3;Probable Xaa-Pro aminopeptidase 3 | XPNPEP3 | mitochondrion |
| 2848 | P50336;B4DY76 | 5498 | Protoporphyrinogen oxidase;cDNA FLJ57666, highly similar to Protoporphyrinogen oxidase (EC 1.3.3.4) | PPOX | intrinsic to mitochondrial inner membrane \| mitochondrion \| mitochondrial membrane \| membrane \| mitochondrial intermembrane space |
| 2309 | P07954;P07954-2 | 2271 | Fumarate hydratase, mitochondrial | FH | mitochondrion \| tricarboxylic acid cycle enzyme complex \| mitochondrial matrix \| cytoplasm |
| 338 | P04179;B3KUX2;F5GY25;F5H4R2;B4DL20;F5H3C5;B4E3K9;G8JL2 | 6648 | Superoxide dismutase [Mn], mitochondrial;Superoxide dismutase | SOD2 | mitochondrion \| mitochondrial inner membrane \| soluble fraction \| mitochondrial matrix \| cytoplasm |
| 765 | Q5T2R2;C9J9J;Q5T2R2-3;Q5T2R2-2 | 23590 | Decaprenyl pyrophosphate synthase subunit 1;Decaprenyl-diphosphate synthase subunit 1;Trans-prenyltransferase;Putative uncharacterized protein PDSS1 | DPS1;PDSS1;TPRT | mitochondrion |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 2247 | P03915 | 4540 | NADH dehydrogenase subunit 5;NADH-ubiquinone oxidoreductase chain 5 | MTND5;MT-ND5;NADH5;ND5 | synaptosome \| mitochondrion \| respiratory chain \| integral to membrane \| mitochondrial inner membrane \| mitochondrial respiratory chain complex I \| membrane |
| 5083 | Q9HA77 | 79587 | Cysteine--tRNA ligase;Probable cysteinyl-tRNA synthetase, mitochondrial | CARS2;OK/SW-cl.10 | mitochondrion \| mitochondrial matrix \| cytoplasm |
| 5232 | Q9NVI7-2;Q9NVI7;H0Y2W2;G3V1I6 | 55210 | ATPase family AAA domain-containing protein 3A | ATAD3A | 0 |
| 3607 | Q3SY69;Q3SY69-3 | 160428 | Aldehyde dehydrogenase family 1 member L2;Probable 10-formyltetrahydrofolate dehydrogenase ALDH1L2 | ALDH1L2 | mitochondrion \| cytoplasm |
| 3970 | Q72Z3D6-2;Q72Z3D6;Q72Z3D6-3;Q72Z3D6-4;H0YB09;Q72Z3D6-5;G8JLP2;H0YB62 | 80017 | UPF0317 protein C14orf159, mitochondrial | C14orf159;UNQ2439;PRO5000 | mitochondrion |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 3857 | Q6P1X6;H0YF29;Q6P1X6-2 | 414919 | UPF0598 protein C8orf82 | C8orf82 | mitochondrion |
| 2417 | P13995;Q72Q650;S8ZZU9;B9A062;B4DY35 | 10797 | Bifunctional methylenetetrahydrofolate dehydrogenase/cyclohydrolase, mitochondrial;Methenyltetrahydrofolate cyclohydrolase;NAD-dependent methylenetetrahydrofolate dehydrogenase;cDNA FLJ52745, highly similar to Bifunctional methylenetetrahydrofolate dehydrogenase/cyclohydrolase, mitochondrial;Methylenetetrahydrofolate dehydrogenase (NADP+ dependent) 2, methenyltetrahydrofolate cyclohydrolase;Methylenetetrahydrofolate dehydrogenase (NADP+ dependent) 2, methenyltetrahydrofolate cyclohydrolase, isoform CRA_b;Putative uncharacterized protein MTHFD2;cDNA FLJ55007, highly similar to Bifunctional methylenetetrahydrofolate dehydrogenase/cyclohydrolase, mitochondrial | MTHFD2;NMDMC;hCG_40734 | mitochondrion |
| 2846 | P50213;H0YL72;P50213-2;H0YMU3;H0YLL6 | 3419 | Isocitrate dehydrogenase [NAD] subunit alpha, mitochondrial;Isocitric dehydrogenase subunit alpha;NAD(+)-specific ICDH subunit alpha | IDH3A | mitochondrion |
| 130 | Q969Y2-2;A6NG5;Q969Y2;Q969Y2-3 | 84705 | Putative uncharacterized protein FASTKD1;GTP-binding protein 3;Mitochondrial GTP-binding protein 1;RNA modification GTPase GTPBP3, mitochondrial | FASTKD1;GTPBP3;MTGP1 | mitochondrion | intracellular |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 2785 | P47985;P0C7P4 | 7386 | Complex III subunit 5;Complex III subunit IX;Cytochrome b-c1 complex subunit 11;Cytochrome b-c1 complex subunit 5;Cytochrome b-c1 complex subunit Rieske, mitochondrial;Rieske iron-sulfur protein;Ubiquinol-cytochrome c reductase 8 kDa protein;Ubiquinol-cytochrome c reductase iron-sulfur subunit;Putative cytochrome b-c1 complex subunit Rieske-like protein 1 | UQCRFS1;UQCRFSL1 | mitochondrion | respiratory chain | integral to membrane | mitochondrial inner membrane | membrane | mitochondrial respiratory chain complex III |
| 2316 | P08574 | 1537 | Complex III subunit 4;Complex III subunit IV;Cytochrome a-c1 complex subunit 4;Cytochrome c1, heme protein, mitochondrial;Ubiquinol-cytochrome-c reductase complex cytochrome c1 subunit | CYC1 | mitochondrion | respiratory chain | integral to membrane | mitochondrial inner membrane | membrane |
| 2609 | P30044;P30044-2;A6NG06;A6NC19 | 25824 | Alu corepressor 1;Antioxidant enzyme B166;Liver tissue 2D-page spot 71B;Peroxiredoxin V;Peroxiredoxin-5, mitochondrial;Peroxisomal antioxidant enzyme;PLP;Thioredoxin peroxidase PMP20;Thioredoxin reductase;Px type V;Putative uncharacterized protein PRDX5 | ACR1;PRDX5;SB10 | mitochondrion | cytosolic part | peroxisome | cytoplasm |
| 4624 | Q96LL9;F5H840 | 84277 | DnaJ homolog subfamily C member 30;Williams-Beuren syndrome chromosomal region 18 protein | DNAJC30;WBSCR18 | mitochondrion |
| 3132 | P82932 | 64968 | 28S ribosomal protein S6, mitochondrial | C21orf101;MRPS6;RPMS6 | mitochondrion | small ribosomal subunit | ribosome |
| 1260 | Q9NTG7;E9PNS8;E9PK80;E9PM75;B0;E9PM75;B7Z5U6 | 23410 | NAD-dependent deacetylase sirtuin-3, mitochondrial;SIR2-like protein 3;cDNA FLJ54618, highly similar to NAD-dependent deacetylase sirtuin-3, mitochondrial (EC 3.5.1.-) | SIR2L3;SIRT3 | mitochondrion | membrane | mitochondrial matrix | cytoplasm |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5638 | Q9Y3D2;A6NCQ5;H0YE51 | 2292 | Methionine-R-sulfoxide reductase B2, mitochondrial;Methionine sulfoxide reductase B2, isoform CRA_a;Methionine-R-sulfoxide reductase B2 variant 1;Putative uncharacterized protein MSRB2 | CBS-1;CGI-131;MSRB;MSRB2;hCG_23087 | mitochondrion |
| 5049 | Q9H727;A6NHH0 | 80142 | Microsomal prostaglandin E synthase 2;Prostaglandin E synthase 2;Prostaglandin E synthase 2 truncated form;Prostaglandin E synthase 2, isoform CRA_c;Putative uncharacterized protein PTGES2 | C9orf15;PGES2;PTGES2;hCG_1785478 | mitochondrion | Golgi apparatus | Golgi membrane | perinuclear region of cytoplasm | cytoplasm | cytosol | integral to membrane | nucleus | membrane |
| 2246 | P03905;Q9Y1 | 4538 | NADH dehydrogenase subunit 4;NADH-ubiquinone oxidoreductase chain 4 | MTND4;MT-ND4;NADH4;ND4 | mitochondrion | respiratory chain | integral to membrane | mitochondrial membrane | mitochondrial respiratory chain complex | membrane |
| 1690 | H0Y886;Q43674;E7EWP0;Q561V6 | 4711 | Complex I-SGDH;NADH dehydrogenase [ubiquinone] 1 beta subcomplex subunit 5, mitochondrial;NADH dehydrogenase (ubiquinone) 1 beta subcomplex, 5, 16kDa, isoform CRA_h;NDUFB5 protein | NDUFB5;hCG_1787208 | mitochondrion | respiratory chain | integral to membrane | mitochondrial inner membrane | mitochondrial respiratory chain complex | membrane |
| 2633 | P31930 | 7384 | Complex III subunit 1;Core protein 1;Cytochrome b-c1 complex subunit 1, mitochondrial;Ubiquinol-cytochrome-c reductase complex core protein 1 | UQCRC1 | mitochondrial respiratory chain | mitochondrion | membrane | mitochondrial respiratory chain complex III |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 1418 | Q5VTE6;F5H476;Q5VT E6-2;B7Z9T0 | 90806 | Protein angel homolog 2;cDNA FLJ50631, highly similar to Homo sapiens angel homolog 2 (Drosophila) (ANGEL2), mRNA | ANGEL2;KIAA0759L | 0 |
| 4053 | Q66X76;Q8 6X76-3;Q86X76-4;Q86X76-2;B1AQP4 | 4817 | Nitrilase homolog 1;Nitrilase 1 | NIT1;RP11-544M22.11-002 | mitochondrion \| cytoplasm |
| 3615 | Q49AM1 | 80298 | Mitochondrial transcription termination factor-like protein;mTERF domain-containing protein 3, mitochondrial | MTERFD3 | mitochondrion |
| 349 | P36776;B3K XS5;F5GZ27 | 9361 | Lon protease homolog, mitochondrial;Lon protease-like protein;LONH5;Mitochondrial ATP-dependent protease Lon;Serine protease 15;ion protease homolog | LONP1;PRSS15 | mitochondrial nucleoid \| mitochondrion \| mitochondrial matrix |
| 3992 | Q76EM4;B4 DFP7;C9JMJ 7;B4DXG5 | 130916 | mTERF domain-containing protein 2;cDNA FLJ59868, highly similar to Homo sapiens MTERF domain containing 2 (MTERFD2), mRNA;Putative uncharacterized protein MTERFD2;cDNA FLJ54914, highly similar to Homo sapiens MTERF domain containing 2 (MTERFD2), mRNA | HSPC096;MTERFD2 | 0 |
| 4128 | Q8NYQ7 | 79896 | Threonine synthase-like 1 | THNSL1 | cellular_component |
| 2058 | O75616;O7 5616-2 | 26284 | Conserved ERA-like GTPase;ERA-W;GTP-binding protein era homolog | ERAL1;HERA | intracellular \| cellular_component |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO cell loc |
|---|---|---|---|---|---|
| 366 | B4DFQ6;Q9 6CM8;B4DH T5;E9PF16; B4DJF5 | 80221 | cDNA FLJ51819, weakly similar to Long-chain-fatty-acid--CoA ligase (EC 6.2.1.3);Acyl-CoA synthetase family member 2, mitochondrial;cDNA FLJ54351, weakly similar to Long-chain-fatty-acid--CoA ligase (EC 6.2.1.3);cDNA FLJ50687, weakly similar to Long-chain-fatty-acid--CoA ligase (EC 6.2.1.3) | ACSF2;UNQ493/PRO100 9 | mitochondrion |
| 4028 | Q95UT6;Q8 6UT6-2 | 79671 | Caterpillar protein 11.3;NLR family member X1;Nucleotide-binding oligomerization domain protein 26;Nucleotide-binding oligomerization domain protein 5;Nucleotide-binding oligomerization domain protein 9 | NLRX1;NOD26;NOD5;N OD9 | mitochondrial outer membrane \| mitochondrion \| membrane |
| 2800 | P48735;B4D FL2;B4DSZ5; H0YL11 | 3418 | ICD-M;IDP;Isocitrate dehydrogenase [NADP], mitochondrial;NADP(+)-specific ICDH;Oxalosuccinate decarboxylase;cDNA FLJ50469, highly similar to Isocitrate dehydrogenase;cDNA FLJ79287, highly similar to Isocitrate dehydrogenase;cDNA FLJ50654, highly similar to Isocitrate dehydrogenase | IDH2 | mitochondrion |
| 3178 | Q02252 | 4329 | Aldehyde dehydrogenase family 6 member A1;Methylmalonate-semialdehyde dehydrogenase [acylating], mitochondrial | ALDH6A1;MMSDH | mitochondrion |
| 1597 | O75027-2;O75027;G 3V1J3;B4DG L8;G3XAC4 | 22 | ATP-binding cassette sub-family B member 7, mitochondrial;ATP-binding cassette transporter 7;cDNA FLJ53391, highly similar to ATP-binding cassette sub-family B member 7, mitochondrial | ABC7;ABCB7 | mitochondrion \| integral to membrane \| mitochondrial inner membrane \| membrane |
| 4503 | Q96D53;Q9 6D53-2 | 79934 | Uncharacterized aarF domain-containing protein kinase 4 | ADCK4 | mitochondrion \| integral to membrane \| membrane |

FIG. 29 cont.

TABLE 1
Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4253 | Q8NFF5;Q8NFF5-2;Q3MFF5-3;Q5T196;Q8NFF5-5 | 80308 | FAD pyrophosphorylase;FAD synthase;FAD synthase region;FAD synthase region;Flavin adenine dinucleotide adenylyltransferase;Molybdenum cofactor biosynthesis protein-like region;FAD1 flavin adenine dinucleotide synthetase homolog (S. cerevisiae);Fad1, flavin adenine dinucleotide synthetase, homolog (Yeast), isoform CRA_e | FLAD1;PP591;hCG_2001 9;RP11-307C12.7-004 | cytosol |
| 4557 | Q96GK7;Q6P2I3 | 51011 | Fumarylacetoacetate hydrolase domain-containing protein 2A;Fumarylacetoacetate hydrolase domain-containing protein 2B | CGI-105;FAHD2A;FAHD2B | 0 |
| 4761 | Q9BQ69 | 28992 | MACRO domain-containing protein 1;Protein LRP16 | LRP16;MACROD1 | mitochondrion |
| 5623 | Q9Y375;H0YL22;H0YNB7;H0YNN4 | 51103 | Complex I intermediate-associated protein 30, mitochondrial;NADH dehydrogenase [ubiquinone] 1 alpha subcomplex assembly factor 1 | CGI-65;CIA30;NDUFAF1 | mitochondrion | mitochondrial respiratory chain complex I |
| 4515 | Q96E11;Q96E11-3;Q96E11-8;Q96E11-2 | 92399 | Ribosome-recycling factor, mitochondrial;Ribosome-releasing factor, mitochondrial | MRRF | mitochondrion |
| 428 | Q99551;B4DPR9 | 7978 | Mitochondrial transcription termination factor 1;Transcription termination factor, mitochondrial;cDNA FLJ51270, highly similar to Transcription termination factor, mitochondrial | MTERF | mitochondrial nucleoid | mitochondrion |
| 5022 | Q9H5Q4 | 64216 | Dimethyladenosine transferase 2, mitochondrial;Hepatitis C virus NS5A-transactivated protein 5;Mitochondrial 12S rRNA dimethylase 2;Mitochondrial transcription factor B2;S-adenosylmethionine-6-N, N-adenosyl(rRNA) dimethyltransferase 2 | NS5ATP5;TFB2M | mitochondrial nucleoid | mitochondrial matrix |

FIG. 29 cont.

TABLE 1
Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5279 | Q9NXA8;Q9NXA8-2;Q9NXA8-3;Q9NXA8-4 | 23408 | NAD-dependent deacetylase sirtuin-5;SIR2-like protein 5 | SIR2L5;SIRT5 | mitochondrion \| mitochondrial matrix \| mitochondrial intermembrane space |
| 5726 | Q9Y697;Q9Y697-2;F5GYK5;B4DNL7;F2Z2E7 | 9054 | Cysteine desulfurase, mitochondrial;cDNA FLJ60737, highly similar to Cysteine desulfurase, mitochondrial (EC 2.8.1.7) | HUSSY-08;NFS1;NIFS | cytosol \| mitochondrion \| nucleus \| mitochondrial matrix \| cytoplasm |
| 4455 | Q96PG6;E7ES89;E7ES11 | 116447 | DNA topoisomerase I, mitochondrial | TOP1MT | mitochondrial nucleoid \| mitochondrion \| chromosome |
| 3621 | Q4G176;F5H5A1;F5H7S5;F5H362 | 197322 | Acyl-CoA synthetase family member 3, mitochondrial | ACSF3;PSEC0197 | mitochondrion |
| 2254 | P04181;Q68CS0 | 4942 | Ornithine aminotransferase, hepatic form;Ornithine aminotransferase, mitochondrial;Ornithine aminotransferase, renal form;Ornithine delta-aminotransferase;Ornithine--oxo-acid aminotransferase;cDNA FLJ78880, highly similar to Ornithine aminotransferase, mitochondrial (EC 2.6.1.13);cDNA, FLJ78846, highly similar to Ornithine aminotransferase, mitochondrial (EC 2.6.1.13);Putative uncharacterized protein DKFZp781A11155 | OAT;DKFZp781A11155 | mitochondrion \| mitochondrial matrix \| cytoplasm |

FIG. 29 cont.

TABLE 1

Mitochondrial matrix proteome (495 proteins), ranked from most enriched to least enriched [H/L ratio from Rep1]

| id | Majority Protein IDs | Entrez | Protein Names | Gene Names | GO celloc |
|---|---|---|---|---|---|
| 2560 | P25705;A8K092 | 498 | ATP synthase subunit alpha, mitochondrial;ATP synthase subunit alpha | ATP5A;ATP5A1;ATP5AL2 | mitochondrion \| mitochondrial inner membrane \| plasma membrane \| mitochondrial matrix \| mitochondrial proton-transporting ATP synthase complex \| mitochondrial proton-transporting ATP synthase complex, catalytic core F(1) |
| | | | ATPM | | 0 |
| 4661 | Q96QE5 | 79736 | UPF0629 protein C17orf42 | C17orf42 | |
| 3892 | Q6UB28 | 254042 | Methionine aminopeptidase 1D, mitochondrial | MAP1D | mitochondrion |
| 2527 | P22830;P22830-2;P22830 | 2235 | Ferrochelatase, mitochondrial;Heme synthase;Protoheme ferro-lyase | FECH | mitochondrion \| mitochondrial inner membrane \| membrane \| mitochondrial matrix |
| 1447 | F5H5P2;P12694;B4DP47;F5GXU9 | 593 | 2-oxoisovalerate dehydrogenase subunit alpha, mitochondrial;Branched-chain alpha-keto acid dehydrogenase E1 component alpha chain;cDNA FLJ55733, highly similar to 2-oxoisovalerate dehydrogenase alpha subunit, mitochondrial (EC 1.2.4.4) | BCKDHA | mitochondrion \| mitochondrial matrix \| mitochondrial alpha-ketoglutarate dehydrogenase complex |
| 1767 | O00411;E9PDE7 | 5442 | DNA-directed RNA polymerase, mitochondrial | POLRMT | mitochondrial nucleoid \| mitochondrion |
| 2762 | P46199;F5H3R4 | 4528 | Translation initiation factor IF-2, mitochondrial | MTIF2 | mitochondrion \| intracellular |
| 4525 | Q96EL3 | 116540 | 39S ribosomal protein L53, mitochondrial | MRPL53 | mitochondrion \| ribosome |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4089 | Q8IVS2 | 27349 | [Acyl-carrier-protein] malonyltransferase;Malonyl-CoA-acyl carrier protein transacylase, mitochondrial;Mitochondrial malonyltransferase | MCAT;MT | mitochondrion |
| 4960 | Q9H0R6;Q9H0R6-2 | 55278 | Glutaminyl-tRNA synthase-like protein 1;Glutamyl-tRNA(Gln) amidotransferase subunit A homolog | QRSL1 | 0 |
| 1424 | P09622;F5H4I0;E9PEX6;B4DT69;B4DHG0 | 1738 | Dihydrolipoamide dehydrogenase;Dihydrolipoyl dehydrogenase, mitochondrial;Glycine cleavage system L protein;Dihydrolipoyl dehydrogenase;cDNA FLJ50515, highly similar to Dihydrolipoyl dehydrogenase, mitochondrial (EC 1.8.1.4) | DLD;GCSL;LAD;PHE3 | oxoglutarate dehydrogenase complex \| mitochondrion \| flagellum \| pyruvate dehydrogenase complex \| acrosomal matrix \| mitochondrial matrix \| cytoplasm |
| 4143 | Q9NQU4;B4DMG7;Q8NOU4-3;C9JFI0 | 222234 | Protein FAM185A;cDNA FLJ55811;Putative uncharacterized protein FAM185A | FAM185A | 0 |
| 1358 | F5GYX8;F5H4W7;Q9NW81;E9PDC6 | 55101 | ATP synthase subunit s-like protein | ATP5SL | 0 |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5318 | Q9NZB8;Q9NZB8-8;Q9NZB8-2;Q9NZB8-7;Q9NZB8-5;Q9NZB8-6;Q9NZB8-3;F7ERN7;Q9NZB8-4 | 4337 | Cell migration-inducing gene 11 protein;Molybdenum cofactor biosynthesis protein 1;Molybdenum cofactor biosynthesis protein A;Molybdenum cofactor biosynthesis protein C;Molybdenum cofactor synthesis-step 1 protein A-B | MIG11;MOCS1 | molybdopterin synthase complex \| nucleus |
| 4280 | Q8TB22-2;Q8TB22-Q8TB22-3;Q8TB22-4 | 64847 | Spermatogenesis-associated protein 20;Sperm-specific protein 411 | SPATA20 | extracellular region |
| 3230 | Q08257-A6NW60;A6NP24;C9JH92;Q5HYE7 | 1429 | NADPH:quinone reductase;Quinone oxidoreductase;Zeta-crystallin;Putative uncharacterized protein CRYZ;Crystallin, zeta (Quinone reductase), isoform CRA_a;Putative uncharacterized protein DKFZp686C16101 | CRYZ;DKFZp686C16101;hCG_21668 | cytosol \| soluble fraction \| cytoplasm |
| 2739 | P42765 | 10449 | 3-ketoacyl-CoA thiolase, mitochondrial;Acetyl-CoA acyltransferase;Beta-ketothiolase;Mitochondrial 3-oxoacyl-CoA thiolase;T1 | ACAA2 | mitochondrion \| mitochondrial inner membrane |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5460 | Q9UIJ7;E7E T30;Q9H4C0 | 50808 | Adenylate kinase 3;Adenylate kinase 3 alpha-like 1;GTP:AMP phosphotransferase mitochondrial;Adenylate kinase 3, isoform CRA_b;cDNA FLJ40886 fis, clone UTERU2000663, highly similar to GTP:AMP phosphotransferase mitochondrial (EC 2.7.4.10);GTP:AMP phosphotransferase | AK3;AK3L1;AK6;AK3L2;h CG_2011468;RP11-6J24.4-001 | mitochondrion | mitochondrial matrix |
| 4270 | Q8N4J7 | 160760 | Protein phosphatase PTC7 homolog;T-cell activation protein phosphatase 2C;T-cell activation protein phosphatase 2C-like | PPTC7;TA-PP2C | mitochondrion |
| 3205 | Q05932;Q0 5932-4;Q05932-2;Q5JU23;Q 5JU20;Q5JU 21 | 2356 | Folylpoly-gamma-glutamate synthetase;Folylpolyglutamate synthase, mitochondrial;Tetrahydrofolyl polyglutamate synthase;Folylpolyglutamate synthase | FPGS;RP11-228B15.1-017;RP11-228B15.1-020;RP11-228B15.1-001 | cytosol | mitochondrion | cytoplasm |
| 2040 | O75439;G3 V0F4;E7ERZ 4;B3KQ85 | 9512 | Beta-MPP;Mitochondrial-processing peptidase subunit beta;P-52;cDNA FLJ33094 fis, clone TRACH2000703, highly similar to Mitochondrial-processing peptidase subunit beta, mitochondrial (EC 3.4.24.64) | MPPB;PMPCB | mitochondrion | mitochondrial matrix |
| 1849 | O15091;O1 5091-2;O15091-4 | 9692 | Mitochondrial ribonuclease P protein 3 | KIAA0391;MRPP3 | mitochondrion |
| 5476 | Q9UJZ1;B4E 1K7 | 30968 | EPB72-like protein 2;Stomatin-like protein 2;cDNA FLJ61039, highly similar to Stomatin-like protein 2 | HSPC108;SLP2;STOML2 | mitochondrion | mitochondrial inner membrane | cytoskeleton | membrane | cytoplasm |

FIG. 29 cont.

TABLE 1
Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 136 | A6NJ78 | 196074 | Methyltransferase 5 domain-containing protein 1;Probable S-adenosyl-L-methionine-dependent methyltransferase METTSD1 | METTSD1 | 0 |
| 3471 | Q15119;D6RDN9 | 5164 | Pyruvate dehydrogenase [lipoamide]] kinase isozyme 2, mitochondrial;Pyruvate dehydrogenase kinase isoform 2 | PDK2 | mitochondrion \| nucleolus \| nucleus \| mitochondrial matrix |
| 3554 | Q16762;E7ENO5 | 7263 | Rhodanese;Thiosulfate sulfurtransferase | TST | mitochondrion \| mitochondrial inner membrane \| plasma membrane \| mitochondrial matrix |
| 2060 | O75891;E9PBX3 | 10840 | 10-formyltetrahydrofolate dehydrogenase;Aldehyde dehydrogenase family 1 member L1 | ALDH1L1;FTHFD | mitochondrion \| cytoplasm |
| 2285 | P06576;F8VPV9;H0YH81;F8W079 | 506 | ATP synthase subunit beta, mitochondrial | ATP5B;ATPMB;ATPSB | mitochondrial nucleoid \| mitochondrion \| mitochondrial proton-transporting ATP synthase, catalytic core \| mitochondrial membrane \| plasma membrane \| cell surface \| mitochondrial matrix \| mitochondrial proton-transporting ATP synthase complex |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 2787 | P48047 | 539 | ATP synthase subunit O, mitochondrial;Oligomycin sensitivity conferral protein | ATP5O;ATPO | proton-transporting ATP synthase complex, catalytic core F(1) \| mitochondrion \| mitochondrial inner membrane \| plasma membrane \| mitochondrial proton-transporting ATP synthase complex |
| 4030 | Q86Y78;Q8 6UY8-2 | 515595 | 5-nucleotidase domain-containing protein 3;GRP94-neighboring nucleotidase | GNN;NT5DC3;TU12B1-TY | cytosol \| mitochondrion |
| 2952 | P55809;E9P DW2 | 5019 | 3-oxoacid-CoA transferase 1;Somatic-type succinyl-CoA:3-oxoacid-CoA transferase;Succinyl-CoA:3-ketoacid-coenzyme A transferase 1, mitochondrial | OXCT;OXCT1;SCOT | mitochondrion \| mitochondrial matrix |
| 2180 | O95822 | 23417 | Malonyl-CoA decarboxylase, mitochondrial | MLYCD | cytosol \| mitochondrion \| peroxisome \| cytoplasm |
| 4674 | Q96RR1;Q9 6RR1-2;Q96RR1-3 | 56652 | Progressive external ophthalmoplegia 1 protein;T7 gp4-like protein with intramitochondrial nucleoid localization;T7-like mitochondrial DNA helicase;Twinkle protein, mitochondrial | C10orf2;PEO1 | mitochondrial nucleoid \| mitochondrion |
| 32 | A3KMH1;A3 KMH1-3;E2QRD0 | 23078 | Uncharacterized protein KIAA0564 | KIAA0564 | extracellular region |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 42 | A4D0W4;Q9 UDR5;F8WA H4;F8WE53 | 10157 | Aminoadipate-semialdehyde synthase;Aminoadipate-semialdehyde synthase, isoform CRA_a;Alpha-aminoadipic semialdehyde synthase, mitochondrial;LKR/SDH;Lysine ketoglutarate reductase;Saccharopine dehydrogenase | AASS;hCG_33410;tcag7. 61 | mitochondrion |
| 2611 | P30049 | 513 | ATP synthase subunit delta, mitochondrial;F-ATPase delta subunit | ATP5D | mitochondrion \| mitochondrial inner membrane \| membrane \| mitochondrial matrix \| mitochondrial proton-transporting ATP synthase complex \| mitochondrial proton-transporting ATP synthase complex, catalytic core F(1) |
| 2926 | P54098 | 5428 | DNA polymerase subunit gamma-1;Mitochondrial DNA polymerase catalytic subunit;PolG-alpha | MDP1;POLG;POLG1;POL GA | mitochondrial nucleoid \| gamma DNA polymerase complex \| mitochondrion |
| 117 | A6NGI4;Q7 Z7H8 | 124995 | cDNA FLJ45232 fis, clone BRCAN2021718, highly similar to Homo sapiens mitochondrial ribosomal protein L10 (MRPL10), mRNA;Mitochondrial ribosomal protein L10, isoform CRA_b;Putative uncharacterized protein MRPL10;39S ribosomal protein L10, mitochondrial;39S ribosomal protein L8, mitochondrial | hCG_29363;MRPL10;MR PL8;RPML8 | mitochondrion \| ribonucleoprotein complex \| ribosome \| intracellular \| mitochondrial large ribosomal subunit |
| 2605 | P30038;B4D GE4;D2D4A 3 | 8659 | Aldehyde dehydrogenase family 4 member A1;Delta-1-pyrroline-5-carboxylate dehydrogenase, mitochondrial;cDNA FLJ54479, highly similar to Delta-1-pyrroline-5-carboxylate dehydrogenase, mitochondrial (EC 1.5.1.12);Mitochondrial aldehyde dehydrogenase 4 family member A1 transcript variant ALDH4A1_v6 | ALDH4;ALDH4A1;P5CDH | mitochondrion \| mitochondrial matrix |
| 237 | A8MXV4 | 390916 | Nucleoside diphosphate-linked moiety X motif 19, mitochondrial | NUDT19 | mitochondrion \| peroxisome |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4271 | Q8N160;Q5T7A4;Q8N160-3;Q5T7A2;Q8N160-4;B4DED1;E7EV28 | 56997 | aarF domain-containing protein kinase 3;Chaperone activity of bc1 complex-like, mitochondrial;Chaperone, ABC1 activity of bc1 complex homolog (S. pombe);cDNA FLJ33175 fis, clone ADRGL2002392, highly similar to Chaperone-activity of bc1 complex-like, mitochondrial;cDNA FLJ53505, highly similar to Chaperone-activity of bc1 complex-like, mitochondrial | ADCK3;CABC1;PP265;RP5-1087E8.1-002;RP5-1087E8.1-003 | mitochondrion |
| 510 | E7ERL9;B4E0K6;E7ER01;F5GX40;F8W0W3;Q55T30;F8W0F9;F8VWW3;F5H823;F8VZ59 | 57176 | cDNA FLJ56191, highly similar to Homo sapiens valyl-tRNA synthetase-like (VARSL), mRNA;Valine--tRNA ligase;Valyl-tRNA synthetase, mitochondrial;Valyl-tRNA synthetase-like | KIAA1885;VARS2;VARS2L;VARSL | mitochondrion | cytoplasm |
| 4865 | Q9BW92;Q9H9V2;E7EVR9;Q5T5E9 | 80222 | Threonine--tRNA ligase;Threonyl-tRNA synthetase, mitochondrial;Threonyl-tRNA synthetase-like 1;cDNA FLJ12528 fis, clone NT2RM4000155, moderately similar to THREONYL-TRNA SYNTHETASE, CYTOPLASMIC [EC 6.1.1.3];Threonyl-tRNA synthetase 2, mitochondrial (Putative);Threonyl-tRNA synthetase-like 1, isoform CRA_b | TARS2;TARSL1;hCG_1999130;RP11-54A4.9-010;RP11-54A4.9-012 | mitochondrion | mitochondrial matrix | cytoplasm |
| 3645 | Q53R41;Q53R41-2 | 79675 | FAST kinase domain-containing protein 1 | FASTKD1;KIAA1800 | 0 |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 3622 | Q4J6C6;Q4J6C6-4;Q4J6C6-3;Q4J6C6-2 | 9581 | Prolyl endopeptidase-like;Prolylendopeptidase-like | KIAA0436;PREPL | cytosol \| cytoplasm |
| 4827 | Q9BUE6 | 81689 | HESB-like domain-containing protein 2;Iron sulfur assembly protein IscA;Iron-sulfur cluster assembly 1 homolog, mitochondrial | GK004;HBLD2;ISCA1 | mitochondrion |
| 3445 | Q14C27;Q6RAR6 | 79072 | FAST kinase domain-containing protein 3 | FASTKD3 | 0 |
| 4226 | Q6NC60 | 84273 | Uncharacterized protein C4orf14 | C4orf14 | mitochondrion \| mitochondrial inner membrane \| intracellular |
| 2622 | P30837 | 219 | Aldehyde dehydrogenase 5;Aldehyde dehydrogenase family 1 member B1;Aldehyde dehydrogenase X, mitochondrial | ALDH1B1;ALDH5;ALDHX | mitochondrion \| mitochondrial matrix |
| 2144 | O95363 | 10667 | Phenylalanine--tRNA ligase;Phenylalanyl-tRNA synthetase, mitochondrial | FARS1;FARS2;HSPC320 | mitochondrion \| soluble fraction \| mitochondrial matrix \| cytoplasm |
| 2744 | P43155;P43155-2;C9JBD1;P43155-3 | 1384 | Carnitine acetyltransferase;Carnitine O-acetyltransferase;Putative uncharacterized protein CRAT | CAT1;CRAT | mitochondrion \| endoplasmic reticulum \| mitochondrial inner membrane \| peroxisome \| membrane |
| 3847 | Q6P161 | 116541395 | 39S ribosomal protein L54, mitochondrial | MRPL54 | mitochondrion \| ribosome |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5678 | Q9Y4W6;Q8TA92 | 10939 | AFG3-like protein 2;Paraplegin-like protein;Similar to AFG3 ATPase family gene 3-like 2 (Yeast) | AFG3L2 | mitochondrion | integral to membrane | mitochondrial inner membrane | membrane |
| 4581 | Q96I51;F5H6C7;F5GX55 | 81554 | RCC1-like G exchanging factor-like protein;Williams-Beuren syndrome chromosomal region 16 protein | WBSCR16 | mitochondrion | cellular_component |
| 2444 | P16219;E9PE82 | 35 | Butyryl-CoA dehydrogenase;Short-chain specific acyl-CoA dehydrogenase, mitochondrial | ACADS | mitochondrion | mitochondrial matrix |
| 3950 | Q7L3T8 | 25973 | Probable prolyl-tRNA synthetase, mitochondrial;Proline--tRNA ligase | PARS2 | mitochondrion | mitochondrial matrix | cytoplasm |
| 2161 | O95571 | 23474 | Ethylmalonic encephalopathy protein 1;Hepatoma subtracted clone one protein;Protein ETHE1, mitochondrial | ETHE1;HSCO | mitochondrion | nucleus | mitochondrial matrix | cytoplasm |
| 1919 | O43488;C9J5L3 | 8574 | AFB1 aldehyde reductase 1;Aflatoxin B1 aldehyde reductase member 2;Aldoketoreductase 7;Succinic semialdehyde reductase;Putative uncharacterized protein AKR7A2 | AFAR;AFAR1;AKR7;AKR7A2 | Golgi apparatus | cytoplasm |
| 4763 | Q9BQ95;Q9BQ95-2 | 51295 | Evolutionarily conserved signaling intermediate in Toll pathway, mitochondrial;Protein SITPEC | ECSIT | mitochondrion | transcription factor complex | nucleus | cytoplasm |
| 5311 | Q9NYY8;Q9NYY8-2 | 22868 | FAST kinase domain-containing protein 2 | FASTKD2;KIAA0971 | mitochondrion |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4671 | Q96RP9;Q9 6RP9-2;C9IZQ1;F8 WAU4 | 85476 | Elongation factor G 1, mitochondrial;Elongation factor G, mitochondrial;Elongation factor G1;Putative uncharacterized protein GFM1 | EFG;EFG1;GFM;GFM1 | mitochondrion \| intracellular |
| 3624 | Q9HAC7-3;Q9HAC7;Q4KMW8;Q 9HAC7-2;H0Y4N1;B 7Z568 | 79783 | Caib/baiF CoA-transferase family protein C7orf10;Dermal papilla-derived protein 13;C7orf10 protein;cDNA FLJ53872 | C7orf10;DERP13 | 0 |
| 1715 | H0YGP4;P3 1327;P3132 7-2 | 1373 | Carbamoyl-phosphate synthase [ammonia], mitochondrial;Carbamoyl-phosphate synthetase I | CPS1 | mitochondrial nucleoid \| mitochondrion \| mitochondrial inner membrane \| protein complex \| mitochondrial matrix \| cytoplasm |
| 3334 | Q13472;Q1 3472-2;B4DX80 | 7156 | DNA topoisomerase 3-alpha;DNA topoisomerase III alpha;DNA topoisomerase | TOP3;TOP3A | PML body \| chromosome \| nucleus |
| 633 | P21953;B7Z 6B0 | 594 | 2-oxoisovalerate dehydrogenase subunit beta, mitochondrial;Branched-chain alpha-keto acid dehydrogenase E1 component beta chain;cDNA, FLJ79444, highly similar to 2-oxoisovalerate dehydrogenase subunit beta, mitochondrial (EC 1.2.4.4) | BCKDHB | mitochondrion \| mitochondrial matrix \| mitochondrial alpha-ketoglutarate dehydrogenase complex |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 1481 | Q12931;F5H897 | 10131 | Heat shock protein 75 kDa, mitochondrial;TNFR-associated protein 1;Tumor necrosis factor type 1 receptor-associated protein | HSP75;TRAP1 | mitochondrion \| cellular_component |
| 3470 | Q15118;E9PD65;B7Z7N6;B7Z207 | 5163 | Pyruvate dehydrogenase [lipoamide] kinase isozyme 1, mitochondrial;Pyruvate dehydrogenase (lipoamide) kinase isoform 1;cDNA FLJ51565, highly similar to Pyruvate dehydrogenase (lipoamide) kinase isozyme 1 [EC 2.7.11.2];cDNA FLJ51566, highly similar to Pyruvate dehydrogenase (lipoamide) kinase isozyme 1 [EC 2.7.11.2] | PDK1 | mitochondrion \| mitochondrial matrix |
| 4149 | Q8N0Z8 | 126789 | tRNA pseudouridine synthase-like 1;tRNA pseudouridylate synthase-like 1;tRNA-uridine isomerase-like 1 | PUS1L | 0 |
| 4477 | Q96AQ8 | 63931 | Coiled-coil domain-containing protein 90A, mitochondrial | C6orf79;CCDC90A | mitochondrion \| integral to membrane \| membrane |
| 4062 | Q86Y79;C9JZZ1 | 138428 | Probable peptidyl-tRNA hydrolase;Putative uncharacterized protein PTRH1 | C9orf115;PTRH1 | mitochondrion |
| 4301 | Q8TD30;Q8TD30-2 | 84706 | Alanine aminotransferase 2;Glutamate pyruvate transaminase 2;Glutamic--alanine transaminase 2;Glutamic-pyruvic transaminase 2 | AAT2;ALT2;GPT2 | mitochondrion |
| 4261 | Q8NFV4;Q8NFV4-4 | 83451 | Abhydrolase domain-containing protein 11;Williams-Beuren syndrome chromosomal region 21 protein | ABHD11;PP1226;WBSCR21 | cellular_component |
| 4436 | Q92947;B4DK85;Q929 47-2;B4DQF2 | 2639 | Glutaryl-CoA dehydrogenase, mitochondrial;cDNA FLJ59559, highly similar to Glutaryl-CoA dehydrogenase, mitochondrial [EC 1.3.99.7];cDNA FLJ59556, highly similar to Glutaryl-CoA dehydrogenase, mitochondrial [EC 1.3.99.7] | GCDH | mitochondrion \| mitochondrial inner membrane \| mitochondrial matrix |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 3880 | Q6P148 | 55157 | Aspartate--tRNA ligase;Aspartyl-tRNA synthetase, mitochondrial | DARS2 | mitochondrion \| mitochondrial matrix \| cytoplasm |
| 5401 | Q9UBQ7;Q5T946 | 9380 | Glyoxylate reductase/hydroxypyruvate reductase | GLXR;GRHPR;MSTP035;RP11-397D12.2-004 | cytoplasm |
| 4166 | Q8N3R3;Q8N3R3-4 | 285343 | Uncharacterized protein C3orf23 | C3orf23 | mitochondrion |
| 1945 | O43837;O43837-2 | 3420 | Isocitrate dehydrogenase [NAD] subunit beta, mitochondrial;Isocitrate dehydrogenase [NAD] subunit beta;NAD(+)-specific ICDH subunit beta | IDH3B | mitochondrion |
| 4180 | Q8N4T8;Q8N4T8-2;H0Y962 | 84869 | 3-oxoacyl-[acyl-carrier-protein] reductase;Carbonyl reductase family member 4;Quinone reductase CBR4 | CBR4 | mitochondrion \| mitochondrial matrix |
| 2061 | O75648;O75648-4 | 55687 | Mitochondrial tRNA-specific 2-thiouridylase 1;MTO2 homolog | MTU1;TRMT1;TRMU | mitochondrion \| cytoplasm |
| 2185 | O95900;B7Z7G5 | 26995 | Probable tRNA pseudouridine synthase 2;cDNA FLJ32131, highly similar to Homo sapiens TruB pseudouridine (psi) synthase homolog 2 (TRUB2), mRNA | TRUB2 | 0 |
| 4792 | Q9BSH4 | 51204 | Coiled-coil domain-containing protein 44;Translational activator of cytochrome c oxidase 1;Translational activator of mitochondrially-encoded cytochrome c oxidase I | CCDC44;PRO0477;TACO1 | mitochondrion |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5224 | Q9NVA1;B1AKV3;Q9NVA1-2;B1AKV5;B1AKV6;B1AKV2;Q9NVA1-3;B77ZC6 | 55245 | Basic FGF-repressed Zic-binding protein;Ubiquinol-cytochrome c reductase complex chaperone CBP3 homolog;Ubiquinol-cytochrome c reductase complex chaperone, CBP3 homolog (Yeast);cDNA FLJ55209, highly similar to Basic FGF-repressed Zic-binding protein;cDNA FLJ58847, highly similar to Basic FGF-repressed Zic-binding protein;cDNA FLJ59833, highly similar to Basic FGF-repressed Zic-binding protein | BZFB;C20orf44;UQCC;RP4-614O4.7-003;RP4-614O4.7-018;RP4-614O4.7-007;RP4-614O4.7-005 | cytoplasmic membrane-bounded vesicle |
| 2296 | P07203 | 2876 | Cellular glutathione peroxidase;Glutathione peroxidase 1 | GPX1 | cytosol \| mitochondrion \| cytoplasm |
| 4881 | Q9BXR0;B4DFM7 | 81890 | Guanine insertion enzyme;Queuine tRNA-ribosyltransferase;tRNA-guanine transglycosylase;cDNA FLJ52927, highly similar to Queuine tRNA-ribosyltransferase (EC 2.4.2.29) | QTRT1;TGT;TGUT | mitochondrion \| ribosome \| nucleus \| cytoplasm |
| 3912 | Q6YN16;Q6YN16-2;B4E136 | 84263 | Hydroxysteroid dehydrogenase-like protein 2;cDNA FLJ61200, highly similar to Homo sapiens hydroxysteroid dehydrogenase like 2 (HSDL2), mRNA | C9orf99;HSDL2 | mitochondrion \| peroxisome |
| 3736 | Q5T9A4;Q5T9A4-3 | 83858 | ATPase family AAA domain-containing protein 3B | ATAD3B;KIAA1273 | 0 |
| 3888 | Q6PML9 | 10463 | Human embryonic lung protein;Solute carrier family 30 member 9;Zinc transporter 9 | C4orf1;HUEL;SLC30A9 | integral to membrane \| cytoskeleton \| nucleus \| membrane |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4825 | Q9BUB7;Q9BUB7-2 | 54968 | Transmembrane protein 70, mitochondrial | TMEM70 | integral to mitochondrial membrane \| mitochondrion \| integral to membrane \| mitochondrial membrane \| membrane |
| 2597 | P28838;P28838-2 | 51056 | Cytosol aminopeptidase;Leucine aminopeptidase;Peptidase S;Proline aminopeptidase;Prolyl aminopeptidase | LAP3;LAPEP;PEPS | mitochondrion \| intracellular \| cytoplasm |
| 3686 | Q5HYK3;F8VVX6;B4DP72;F8VP53;F8VVW7 | 84274 | Ubiquinone biosynthesis methyltransferase COQ5, mitochondrial;cDNA FLJ55122, highly similar to Ubiquinone biosynthesis methyltransferase COQ5, mitochondrial (EC 2.1.1.-) | COQ5 | mitochondrion |
| 5012 | Q9H4K7;Q5JX0 | 26164 | GTP-binding protein 5;Protein obg homolog 1;GTP binding protein 5 (Putative) | GTPBP5;OBGH1;RP5-1005F21.5-001 | mitochondrion \| intracellular |
| 4459 | Q96RS9;Q96RS9-3;Q96RS9-2;F5H687;Q96RS9-4;Q96RS9-5 | 84340 | Elongation factor G 2, mitochondrial;Elongation factor G2;Ribosome-releasing factor 2, mitochondrial | EFG2;GFM2;MSTP027 | mitochondrion |
| 5614 | Q9Y2Z4;H0YHS6 | 51067 | Tyrosine--tRNA ligase;Tyrosyl-tRNA synthetase, mitochondrial | CGI-04;YARS2 | mitochondrion \| mitochondrial matrix \| cytoplasm |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 3325 | Q13423;E9P CX7 | 23530 | NAD(P) transhydrogenase, mitochondrial;Nicotinamide nucleotide transhydrogenase;Pyridine nucleotide transhydrogenase | NNT | mitochondrial respiratory chain \| mitochondrion \| integral to membrane \| mitochondrial inner membrane \| membrane |
| 4171 | Q8N442 | 60558 | GTP-binding protein GUF1 homolog | GUF1 | mitochondrion |
| 374 | Q96CB9;B4 DHA4 | 387338 | NOL1/NOP2/Sun domain family member 4;Putative methyltransferase NSUN4;cDNA FL60253, highly similar to Homo sapiens NOL1/NOP2/Sun domain family, member 4 (NSUN4), mRNA;HCG2031650, isoform CRA_f | NSUN4;hCG_2031650 | 0 |
| 5491 | Q9UKU7;B7 Z5N4;Q6Z WP6;F5H2N 4;B7Z7F1 | 27034 | Activator-recruited cofactor 42 kDa component;Acyl-CoA dehydrogenase family member 8;Isobutyryl-CoA dehydrogenase, mitochondrial;cDNA FL55244, highly similar to Acyl-CoA dehydrogenase family member 8, mitochondrial (EC 1.3.99.-);Acyl-Coenzyme A dehydrogenase family, member 8, isoform CRA_a;cDNA FLJ90159 fis, clone HEMBB1002465, weakly similar to ACYL-COA DEHYDROGENASE (EC 1.3.99.-);cDNA FLJ50096, highly similar to Acyl-CoA dehydrogenase family member 8, mitochondrial | ACAD8;ARC42;IBD;hCG_37259 | mitochondrion |
| 1607 | G3V5T0;G3 V257;G3V4T 6;Q43708;A 6NED0;Q43 708-2 | 2954 | Glutathione S-transferase zeta 1;GSTZ1-1;Maleylacetoacetate isomerase;Glutathione transferase zeta 1 (Maleylacetoacetate isomerase), isoform CRA_b;Putative uncharacterized protein GSTZ1 | GSTZ1;MAAI;hCG_2226 5 | cytosol \| mitochondrion \| nucleus \| cytoplasm |
| 3955 | Q7L8L6 | 60493 | FAST kinase domain-containing protein 5 | FASTKD5;KIAA1792 | 0 |
| 3712 | Q5T160 | 57038 | Arginine-tRNA ligase;Arginyl-tRNA synthetase-like;Probable arginyl-tRNA synthetase, mitochondrial | RARS2;RARSL | mitochondrion \| mitochondrial matrix \| cytoplasm |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO cellloc |
|---|---|---|---|---|---|
| 3218 | Q07021 | 708 | Complement component 1 Q subcomponent-binding protein, mitochondrial;GC1q-R protein;glycoprotein gC1qBP;Hyaluronan-binding protein 1;Mitochondrial matrix protein p32;p33 | C1QBP;GC1QBP;HABP1;SF2P32 | mitochondrion \| plasma membrane \| nucleus \| membrane \| mitochondrial matrix |
| 2684 | P36551 | 1371 | Coproporphyrinogen-III oxidase, mitochondrial | CPO;CPOX;CPX | mitochondrion \| mitochondrial intermembrane space \| cytoplasm |
| 3455 | Q15031;E9PHM2 | 23395 | Leucine--tRNA ligase;Probable leucyl-tRNA synthetase, mitochondrial | KIAA0028;LARS2 | mitochondrion \| mitochondrial matrix \| cytoplasm |
| 3850 | Q6P1L8 | 64928 | 39S ribosomal protein L14, mitochondrial;39S ribosomal protein L32, mitochondrial | MRPL14;MRPL32;RPML32 | mitochondrion \| ribosome \| intracellular |
| 5052 | Q9H845;F8W4N8;H0Y8Z9 | 28976 | Acyl-CoA dehydrogenase family member 9, mitochondrial | ACAD9 | mitochondrion |
| 3867 | Q5JPH6 | 124454 | Glutamate--tRNA ligase;Probable glutamyl-tRNA synthetase, mitochondrial | EARS2;KIAA1970 | mitochondrion \| mitochondrial matrix \| cytoplasm |
| 4883 | Q9BXW7;Q9BXW7-2 | 27440 | Cat eye syndrome critical region protein 5 | CECR5 | mitochondrion |
| 4345 | Q8WV93;H0Y5F4 | 246269 | Lactation elevated protein 1 | AFG1L;LACE1 | mitochondrion |
| 1239 | E9PH62;Q9BT17;E7EVK2 | 92170 | GTP-binding protein 7;Mitochondrial GTPase 1 | GTPBP7;MTG1 | mitochondrion \| intracellular |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 1584 | F8WEC0;Q9H3L0 | 27249 | Methylmalonic aciduria and homocystinuria type D protein, mitochondrial | C2orf25;CL25022;HSPC161;MMADHC;MyG11 | mitochondrion |
| 5242 | Q9NWV4 | 55149 | mtPAP;PAP-associated domain-containing protein 1;Poly(A) RNA polymerase, mitochondrial;Polynucleotide adenylyltransferase;Terminal uridylyltransferase 1 | MTPAP;PAPD1 | mitochondrion \| cytoplasm |
| 5101 | Q9HBH1 | 64146 | Peptide deformylase, mitochondrial;Polypeptide deformylase | PDF;PDF1A | mitochondrion |
| 4804 | Q9BT30 | 84266 | Alkylated DNA repair protein alkB homolog 7;Probable alpha-ketoglutarate-dependent dioxygenase ABH7;Spermatogenesis cell proliferation-related protein;Spermatogenesis-associated protein 11 | ABH7;ALKBH7;SPATA11;UNQ6002;PRO34564 | mitochondrion \| extracellular region \| nucleus \| cytoplasm |
| 4344 | Q8WV74;Q8WV74-2 | 254552 | Nucleoside diphosphate-linked moiety X motif 8, mitochondrial | NUDT8 | mitochondrion |
| 2753 | P45954;B4DQ51 | 36 | 2-methyl branched chain acyl-CoA dehydrogenase;2-methylbutyryl-coenzyme A dehydrogenase;Short/branched chain specific acyl-CoA dehydrogenase, mitochondrial;cDNA FLJ57418, highly similar to Short/branched chain specific acyl-CoAdehydrogenase, mitochondrial (EC 1.3.99.-) | ACADSB | mitochondrion \| mitochondrial matrix |
| 4997 | Q9H3H1;Q9H3H1-4;Q9H3H1-5;Q5QPK7;Q9H3H1-2 | 54802 | hGRO1;Isopentenyl-diphosphate:tRNA isopentenyltransferase;tRNA dimethylallyltransferase, mitochondrial;tRNA isopentenyltransferase 1 | IPT;MOD5;TRIT1;RP1-118J21.3-003 | mitochondrion \| cellular_component \| cytoplasm |
| 585 | Q9Y229;B7Z3K8;G3XA86;Q86U30;G3V564 | 51004 | Ubiquinone biosynthesis monooxygenase COQ6;cDNA FLJ50973, highly similar to Ubiquinone biosynthesis monooxygenase COQ6 (EC 1.14.13.-);Coenzyme Q6 homolog, monooxygenase (Yeast), isoform CRA_c;Full-length cDNA clone CS0DM001YP16 of Fetal liver of Homo sapiens (human) | CGI-10;COQ6;hCG_21715 | mitochondrion |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 4464 | Q96920;C9J VY2;Q96920-2 | 9238 | Cell cycle progression restoration protein 2;FAST kinase domain-containing protein 4;Protein TBRG4;Transforming growth factor beta regulator 4;Putative uncharacterized protein TBRG4 | CPR2;FASTKD4;KIAA094 8;TBRG4 | 0 |
| 2814 | P49419;P49 419-2;E7EPT3;F8 V502;P49419-3 | 501 | Aldehyde dehydrogenase family 7 member A1;Alpha-aminoadipic semialdehyde dehydrogenase;Antiquitin-1;Betaine aldehyde dehydrogenase;Delta1-piperideine-6-carboxylate dehydrogenase | ALDH7A1;ATQ1 | cytosol | mitochondrion | nucleus | cellular_component | cytoplasm |
| 3472 | Q15120 | 5165 | Pyruvate dehydrogenase [lipoamide]] kinase isozyme 3, mitochondrial;Pyruvate dehydrogenase kinase isoform 3 | PDK3 | mitochondrion | mitochondrial matrix |
| 3978 | Q72G4;Q7 Z4G4-2;F2Z2Q4;Q 72G4-3 | 60487 | tRNA guanosine-2-O-methyltransferase TRM11 homolog | C6orf75;MDS024;TRMT 11 | 0 |

FIG. 29 cont.

TABLE 1

Mitochondrial matrix proteome (495 proteins), ranked from most enriched to least enriched [H/L ratio from Rep1]

| id | Majority Protein IDs | Entrez | Protein Names | Gene Names | GO celloc |
|---|---|---|---|---|---|
| 297 | B1ANH1;B1ANG9;B1ANH0;B1ANH2;B1ANH6;Q16774;F5GX L9;B1ANH5;E9PEG7;B1ANH3 | 2987 | Guanylate kinase 1;GMP kinase;Guanylate kinase | GUK1;RP11-520H14.2-010;RP11-520H14.2-027;RP11-520H14.2-003;RP11-520H14.2-018;RP11-520H14.2-023;GMK;RP11-520H14.2-030;RP11-520H14.2-019 | 0 |
| 1330 | Q9P2R7;Q9P2R7-2;F5GXC8;F5H5G8;Q5T9Q5;F5H5Q7 | 8803 | ATP-specific succinyl-CoA synthetase subunit beta;Renal carcinoma antigen NY-REN-39;Succinyl-CoA ligase [ADP-forming] subunit beta, mitochondrial;Succinyl-CoA synthetase beta-A chain;Succinate-CoA ligase, ADP-forming, beta subunit | SUCLA2;RP11-528D24.2-010 | mitochondrion |
| 5613 | Q9Y2Z2-6;Q9Y2Z2-4;Q9Y2Z2;Q9Y2Z2-5;Q9Y2Z2-2 | 25821 | Protein MTO1 homolog, mitochondrial | CGI-02;MTO1 | mitochondrion |
| 165 | A6NNL5 | 145853 | Uncharacterized protein C15orf61 | C15orf61 | extracellular region |

FIG. 29 cont.

TABLE 1

Mitochondrial matrix proteome (465 proteins), ranked from most enriched to least enriched (H/L ratio from Rep1)

| id | Majority Protein IDs | Entrez | Protein Names | Gene Names | GO celloc |
|---|---|---|---|---|---|
| 4759 | Q9BQ52;E9PG10;G5E9D5;B4DPL9;E7ES68;Q9B0Q52-3 | 60528 | ElaC homolog protein 2;Heredity prostate cancer protein 2;Ribonuclease Z 2;tRNA 3 endonuclease 2;tRNase Z 2;Zinc phosphodiesterase ELAC protein 2;cDNA FLJ59369, highly similar to Zinc phosphodiesterase ELAC protein 2 (EC 3.1.26.11) | ELAC2;HPC2 | mitochondrion \| nucleus |
| 3827 | G3XAJ0;Q6QN1;Q6QN1-2;F8W119 | 80724 | Acyl-CoA dehydrogenase family member 10 | ACAD10 | 0 |
| 3845 | Q6P087;Q6P087-2;C9JM75 | 285367 | RNA pseudouridylate synthase domain-containing protein 3;Putative uncharacterized protein RPUSD3 | RPUSD3 | 0 |
| 4172 | Q8N465;F6XUM0;G5E9E8;B4E316;Q8N465-2;B5MCV2 | 728294 | D-2-hydroxyglutarate dehydrogenase, mitochondrial;cDNA FLJ61087, highly similar to D-2-hydroxyglutarate dehydrogenase, mitochondrial (EC 1.1.99.-);Putative uncharacterized protein D2HGDH | D2HGD;D2HGDH | mitochondrion |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 2876 | P51553;E9PDD5;G5E9Q7;E7EQB8;E9PCL6;E9PF84 | 3421 | Isocitrate dehydrogenase [NAD] subunit gamma, mitochondrial;Isocitric dehydrogenase subunit gamma;NAD(+)-specific ICDH subunit gamma | IDH3G | mitochondrion \| nucleolus \| nucleus |
| 5024 | Q9H649 | 63899 | NOL1/NOP2/Sun domain family member 3;Putative methyltransferase NSUN3 | MSTP077,NSUN3;UG0651E06 | 0 |
| 2078 | O75879;D6REA0;D6RDU9 | 5188 | Cytochrome oxidase assembly factor PET112 homolog;Probable glutamyl-tRNA(Gln) amidotransferase subunit B, mitochondrial | HSPC199;PET112;PET112L | mitochondrion |
| 2555 | P25325;E7ERL2;E7ENL2;B1AH49 | 4357 | 3-mercaptopyruvate sulfurtransferase;Mercaptopyruvate sulfurtransferase | MPST;TST2;LL22NC01-14GD10.4-005 | mitochondrion \| cytoplasm |
| 5138 | Q9NPE2 | 51335 | Mesenchymal stem cell protein DSC92;Neugrin;Neurite outgrowth-associated protein;Spinal cord-derived protein FI58G | FIS8G;HT020;NGRN | nucleus |
| 3856 | Q6P152;Q9GMB5 | 285315 | Uncharacterized protein C3orf33;cDNA FLJ31139 fis, clone iMR3220011185;Chromosome 3 open reading frame 33, isoform CRA_b | C3orf33;MSTP052;hCG_27946 | integral to membrane \| membrane |
| 2054 | O75370;B4DG01 | 9617 | Peptide chain release factor 1, mitochondrial;cDNA FLJ5831, highly similar to Peptide chain release factor 1, mitochondrial | MTRF1 | mitochondrion \| cytoplasm |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5373 | Q9P2J9 | 57546 | Pyruvate dehydrogenase [acetyl-transferring]]-phosphatase 2, mitochondrial;Pyruvate dehydrogenase phosphatase catalytic subunit 2 | KIAA1348;PDP2 | mitochondrion | protein serine/threonine phosphatase complex | mitochondrial matrix |
| 3985 | Q7Z4W1 | 51181 | Carbonyl reductase II;Dicarbonyl/L-xylulose reductase;Kidney dicarbonyl reductase;L-xylulose reductase;Sperm surface protein P34H | DCXR | brush border | membrane | microvillus |
| 3596 | Q3KQZ1;Q3KQZ1-2;Q3KQZ1-3;Q3KQZ1-4 | 399512 | Solute carrier family 25 member 35 | SLC25A35 | mitochondrion | integral to membrane | mitochondrial inner membrane | membrane |
| 5009 | Q9H4B0;Q9H4B0-2;Q9H4B0-3;F5RGZ1 | 64172 | O-sialoglycoprotein endopeptidase-like protein 1;Probable O-sialoglycoprotein endopeptidase 2 | OSGEPL1 | mitochondrion |
| 2525 | P22695 | 7385 | Complex III subunit 2;Core protein 2;Cytochrome b-c1 complex subunit 2, mitochondrial;Ubiquinol-cytochrome-c reductase complex core protein 2 | UQCRC2 | mitochondrion | respiratory chain | mitochondrial inner membrane | nucleus | membrane | mitochondrial respiratory chain complex III |

FIG. 29 cont.

TABLE 1

Mitochondrial matrix proteome (495 proteins), ranked from most enriched to least enriched (H/L ratio from Rep1.)

| id | Majority Protein IDs | Entrez | Protein Names | Gene Names | GO celloc |
|---|---|---|---|---|---|
| 2315 | P08559;A5YVE9;B77Z3T7;B77Z3X5 | 5160 | PDHE1-A type I;Pyruvate dehydrogenase E1 component subunit alpha, somatic form, mitochondrial;cDNA FLJ59461, highly similar to Pyruvate dehydrogenase E1 component alpha subunit, somatic form, mitochondrial (EC 1.2.4.1);Mitochondrial PDHA1;cDNA FLJ54787, highly similar to Pyruvate dehydrogenase E1 component alpha subunit, somatic form, mitochondrial (EC 1.2.4.1);cDNA FLJ52314, highly similar to Pyruvate dehydrogenase E1 component alpha subunit, somatic form, mitochondrial (EC 1.2.4.1) | PDHA1;PHE1A | mitochondrion | mitochondrial matrix |
| 1070 | E7ETE0;Q9H825;B5ME25;Q9H825-2;C9JE69 | 79828 | Methyltransferase-like protein 8;Putative uncharacterized protein METTL8 | METTL8 | nucleus | cytoplasm |
| 2804 | P49189;B40XY7 | 223 | 4-trimethylaminobutyraldehyde dehydrogenase;Aldehyde dehydrogenase E3 isozyme;Aldehyde dehydrogenase family 9 member A1;Gamma-aminobutyraldehyde dehydrogenase;R-aminobutyraldehyde dehydrogenase;cDNA FLJ51658, highly similar to 4-trimethylaminobutyraldehyde dehydrogenase (EC 1.2.1.47);cDNA FLJ61765, highly similar to 4-trimethylaminobutyraldehyde dehydrogenase(EC 1.2.1.47) | ALDH4;ALDH7;ALDH9;AL DH9A1 | microtubule cytoskeleton | cytosol | mitochondrion | nucleus | cytoplasm |
| 1821 | O14874;A8MV43;Q96G95;E9PFL3 | 10295 | [3-methyl-2-oxobutanoate dehydrogenase [lipoamide]] kinase, mitochondrial;Branched-chain alpha-ketoacid dehydrogenase kinase;Branched chain ketoacid dehydrogenase kinase, isoform CRA_c;Putative uncharacterized protein BCKDK;BCKDK protein;Branched chain ketoacid dehydrogenase kinase, isoform CRA_a | BCKDK;hCG_21145 | mitochondrion | mitochondrial matrix | mitochondrial alpha-ketoglutarate dehydrogenase complex |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 3466 | Q15070;Q15070-2;E7EVY0 | 5018 | Hsa;Mitochondrial inner membrane protein OXA1L;OXA1Hs;Oxidase assembly 1-like protein | OXA1L | integral to mitochondrial membrane \| mitochondrial respiratory chain \| mitochondrion \| integral to membrane \| protein complex. \| membrane |
| 2048 | O75521;O75521-2;E7EVJ0 | 10455 | Delta(3),delta(2)-enoyl-CoA isomerase;Diazepam-binding inhibitor-related protein 1;Dodecenoyl-CoA isomerase;DRS-1;Hepatocellular carcinoma-associated antigen 88;Peroxisomal 3,2-trans-enoyl-CoA isomerase;Renal carcinoma antigen NY-REN-1 | DRS1;HCA88;PECI | intracellular membrane-bounded organelle \| mitochondrion \| peroxisomal matrix \| peroxisome |
| 1021 | B4DHX5;E7EQL1;P22570;P22570-2;B7Z7G2;G3V9F2 | 2232 | cDNA FLJ53329, highly similar to NADPH:adrenodoxin oxidoreductase, mitochondrial (EC 1.18.1.2);Ferredoxin--NADP(+) reductase;NADPH:adrenodoxin oxidoreductase, mitochondrial;cDNA FLJ54567, highly similar to NADPH:adrenodoxin oxidoreductase, mitochondrial (EC 1.18.1.2) | ADXR;FDXR | mitochondrion \| mitochondrial matrix |
| 4510 | Q96DP5 | 123263 | Methionyl-tRNA formyltransferase, mitochondrial | FMT;FMT1;MTFMT | mitochondrion |
| 4352 | Q8WVM0 | 51106 | Dimethyladenosine transferase 1, mitochondrial;Mitochondrial 12S rRNA dimethylase 1;Mitochondrial transcription factor B1;S-adenosylmethionine-6-N, N-adenosyl(rRNA) dimethyltransferase 1 | CGI-75;TFB1M | mitochondrial nucleoid \| mitochondrion |
| 2751 | P43897;P43897-2;P43897-3;B8ZW6R3;C9JT21 | 10102 | Elongation factor Ts, mitochondrial;Elongation factor Ts | TSFM | mitochondrion \| nucleus \| intracellular |
| 3357 | Q13686 | 8846 | Alkylated DNA repair protein alkB homolog 1;Alpha-ketoglutarate-dependent dioxygenase ABH1;DNA lyase ABH1 | ABH;ABH1;ALKBH;ALKBH1 | mitochondrion \| nucleus |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO cellloc |
|---|---|---|---|---|---|
| 3556 | Q16775;Q16775-2 | 3029 | Glyoxalase III;Hydroxyacylglutathione hydrolase, mitochondrial | GLO2;HAGH;HAGH1 | mitochondrion \| mitochondrial matrix \| cytoplasm |
| 3553 | Q16740 | 8192 | Endopeptidase Clp;Putative ATP-dependent Clp protease proteolytic subunit, mitochondrial | CLPP | mitochondrion \| mitochondrial matrix |
| 1455 | F5H620;Q96HP4 | 92106 | Oxidoreductase NAD-binding domain-containing protein 1 | OXNAD1 | mitochondrion |
| 1943 | O43824;H0Y2S1 | 8225 | Pseudoautosomal GTP-binding protein-like;Putative GTP-binding protein 6 | GTPBP6;PGPL | intracellular |
| 238 | O75880;A8MY34 | 6341 | Protein SCO1 homolog, mitochondrial;Putative uncharacterized protein SCO1 | SCO1;SCOD1 | mitochondrion \| mitochondrial inner membrane |
| 2978 | P58557;P58557-2 | 54059 | Putative metalloprotease C21orf57 | C21orf57 | mitochondrion |
| 2327 | P09417;B3KW71;D6RGG7;B7Z415 | 5860 | Dihydropteridine reductase;HDHPR;Quinoid dihydropteridine reductase;cDNA FLJ42391 fis, clone 3NB692002806, highly similar to Dihydropteridine reductase [EC 1.5.1.34];Quinoid dihydropteridine reductase, isoform CRA_e;cDNA FLJ55000, highly similar to Dihydropteridine reductase [EC 1.5.1.34];Quinoid dihydropteridine reductase, isoform CRA_c | DHPR;QDPR;hCG_39606 | mitochondrion \| cytoplasm |
| 1662 | Q9Y606;Q9Y606-2;G8JLB3;F5H1S9 | 80324 | tRNA pseudouridine synthase A;tRNA pseudouridylate synthase I;tRNA-uridine isomerase I | PP8985;PUS1 | mitochondrion \| transcription factor complex \| nucleolus \| nucleus |
| 5084 | Q9HA92 | 55316 | Oxygen-independent coproporphyrinogen-III oxidase-like protein RSAD1;Radical S-adenosyl methionine domain-containing protein 1, mitochondrial | RSAD1 | mitochondrion \| cytoplasm |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 1282 | Q96CM3;E9PML2 | 84881 | RNA pseudouridylate synthase domain-containing protein 4 | RPUSD4 | mitochondrion |
| 2819 | P49590;B4DDY8;C9JV49;C9JW95;E9PG66;C9JH18;E9PD50;F5HHF0;B4DQ57 | 23438 | Histidine--tRNA ligase;Histidine--tRNA ligase-like;Probable histidyl-tRNA synthetase, mitochondrial;cDNA FLJ50406, highly similar to Histidyl-tRNA synthetase homolog (EC 6.1.1.21);Histidyl-tRNA synthetase-like, isoform CRA_a;Putative uncharacterized protein HARS2;cDNA FLJ50611, highly similar to Histidyl-tRNA synthetase homolog (EC 6.1.1.21) | HARS2;HARSL;HARSR;H03;HCG_1982406 | mitochondrion | mitochondrial matrix | cytoplasm |
| 5076 | Q9H9P8;C9JVN9;Q9H9P8-2 | 79944 | Duranin;L-2-hydroxyglutarate dehydrogenase, mitochondrial;Putative uncharacterized protein L2HGDH | C14orf160;L2HGDH | mitochondrion | integral to membrane | integral to mitochondrial inner membrane |
| 5145 | Q9NPL8;C9JU35 | 51100 | Protein MS-14;Transmembrane protein C3orf1;Putative uncharacterized protein C3orf1 | C3orf1;UNQ247;PRO284 | mitochondrion | integral to membrane | mitochondrial inner membrane | membrane |
| 2201 | P00403 | 4513 | Cytochrome c oxidase polypeptide II;Cytochrome c oxidase subunit 2 | COII;COXII;MTCO2;MT-CO2 | mitochondrion | respiratory chain | integral to membrane | mitochondrial inner membrane | membrane |
| 3285 | Q13057-2;Q13057 | 80347 | Bifunctional coenzyme A synthase;Dephospho-CoA kinase;Dephospho-CoA pyrophosphorylase;Dephosphocoenzyme A kinase;NBP;Pantetheine-phosphate adenylyltransferase;Phosphopantetheine adenylyltransferase;POV-2 | COASY;PSEC0106 | cellular_component | cytoplasm |

FIG. 29 cont.

TABLE 1
Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 5207 | Q9NUL7 | 55794 | Mitochondrial DEAD box protein 28;Probable ATP-dependent RNA helicase DDX28 | DDX28;MDDX28 | mitochondrial nucleoid \| mitochondrion \| nucleus |
| 2813 | P49411 | 7284 | Elongation factor Tu, mitochondrial;P43 | TUFM | mitochondrial nucleoid \| mitochondrion \| intracellular |
| 5170 | Q9NRK6 | 23456 | ATP-binding cassette sub-family B member 10, mitochondrial;ATP-binding cassette transporter 10;Mitochondrial ATP-binding cassette 2 | ABCB10 | integral to mitochondrial membrane \| mitochondrion \| integral to membrane \| mitochondrial inner membrane \| membrane |
| 2003 | O60930 | 246243 | Ribonuclease H type II;Ribonuclease H1 | RNASEH1;RNH1 | mitochondrion \| nucleus \| cytoplasm |
| 4334 | Q9WUK0;Q8WUK0-2 | 114971 | Phosphoinositide lipid phosphatase;Protein-tyrosine phosphatase mitochondrial 1;PTEN-like phosphatase | MOSP-PLIP;PNAS-129;PTPMT1 | mitochondrion \| mitochondria inner membrane \| membrane |
| 2426 | P14735 | 3416 | Abeta-degrading protease;Insulin protease;insulin-degrading enzyme;Insulysin | IDE | cytosol \| mitochondrion \| extracellular space \| peroxisomal matrix \| peroxisome \| nucleus \| soluble fraction \| cytosolic proteasome complex \| cell surface \| cytoplasm |
| 51 | A4D1E9;A4D1E9-2;C9JNL1;C9J8R7 | 85865 | GTP-binding protein 10;Protein obg homolog 2;Putative uncharacterized protein GTPBP10 | GTPBP10;OBGH2;UG075;1c10 | mitochondrion \| nucleolus \| nucleus \| intracellular |

FIG. 29 cont.

TABLE 1

Mitochondrial matrix proteome (495 proteins), ranked from most enriched to least enriched (H/L ratio from Rep1)

| id | Majority Protein IDs | Entrez | Protein Names | Gene Names | GO celloc |
|---|---|---|---|---|---|
| 609 | Q16698;B77 688;E5RFV2;E5RIG7;E5RJD2 | 1666 | 2,4-dienoyl-CoA reductase [NADPH];2,4-dienoyl-CoA reductase, mitochondrial;cDNA FLJ50204, highly similar to 2,4-dienoyl-CoA reductase, mitochondrial [EC 1.3.1.34] | DECR;DECR1 | mitochondrion |
| 3179 | Q02338;E9P CG9;C9K0G 7;C9KQ90;C 9JM78 | 622 | 3-hydroxybutyrate dehydrogenase;D-beta-hydroxybutyrate dehydrogenase, mitochondrial;Putative uncharacterized protein BDH1 | BDH;BDH1 | mitochondrion ∣ mitochondrial inner membrane ∣ mitochondrial matrix |
| 5625 | Q9Y399;Q5 T8A0 | 51116 | 28S ribosomal protein S2, mitochondrial;Mitochondrial ribosomal protein S2 | CGI-91;MRPS2;RP11-426A6.2-007 | mitochondrion ∣ small ribosomal subunit ∣ ribosome ∣ intracellular |
| 998 | E7ENH9;P53 396;P53396-2;B4E3P0 | 47 | ATP-citrate (pro-S)-lyase;ATP-citrate synthase;Citrate cleavage enzyme;cDNA FLJ55447, highly similar to ATP-citrate synthase [EC 2.3.3.8] | ACLY | cytosol ∣ citrate lyase complex ∣ cytoplasm |
| 4493 | Q96C36;E7E U59;E7EU0 8 | 29920 | Pyrroline-5-carboxylate reductase 2 | PYCR2 | 0 |
| 3127 | P82675 | 64969 | 28S ribosomal protein S5, mitochondrial | MRPS5 | mitochondrion ∣ ribosome ∣ intracellular |
| 2513 | P22234;P22 234-2;B9PB31;D 6RFG2 | 10606 | AIR carboxylase;Multifunctional protein ADE2;Phosphoribosylaminoimidazole carboxylase;Phosphoribosylaminoimidazole-succinocarboxamide synthase;SAICAR synthetase | ADE2;AIRC;PAICS;AIS | 0 |

FIG. 30

TABLE 2

Mitochondrial orphans (31 proteins), ranked from most enriched to least enriched (H/L ratio from Rep1)

| id | Majority Protein IDs | Entrez | Protein Names | Gene Names | GO celloc |
|---|---|---|---|---|---|
| 4204 | Q8N8R5 | 205327 | UPF0565 protein C2orf69 | C2orf69 | extracellular region 0 |
| 4654 | Q9BV55;F8WDR2 | 55006 | Potential tRNA (adenine-N(1)-)-methyltransferase catalytic subunit TRMT61B | TRMT61B | 0 |
| 1472 | Q8N2E2;F5H713 | 133383 | Uncharacterized protein C5orf35 | C5orf35 | 0 |
| 518 | Q9NVS9;B4E1D7;B4E0V0;B4E152 | 55163 | Pyridoxamine-phosphate oxidase;Pyridoxine-5-phosphate oxidase;cDNA FLJ59601, highly similar to Pyridoxine-5-phosphate oxidase (EC 1.4.3.5);cDNA FLJ59109, highly similar to Pyridoxine-5-phosphate oxidase (EC 1.4.3.5);cDNA FLJ59599, highly similar to Pyridoxine-5-phosphate oxidase (EC 1.4.3.5) | PNPO | 0 |
| 2805 | P49247;Q53R32 | 22934 | Phosphoriboisomerase;Ribose-5-phosphate isomerase;Putative uncharacterized protein RPIA | RPI;RPIA | cytosol \| intracellular |
| 1227 | E9PAL9;Q9H857-2;Q9H857;C9JTZ6;Q9H857-3;Q5T196;Q8NFF5-4 | 64943 | 5-nucleotidase domain-containing protein 2;Putative uncharacterized protein NT5DC2 | NT5DC2 | 0 |
| 1418 | Q5VTE6;F5H476;Q5VTE6-2;B72ST0 | 90806 | Protein angel homolog 2;cDNA FLJ50631, highly similar to Homo sapiens angel homolog 2 (Drosophila) (ANGEL2), mRNA | ANGEL2;KIAA0759L | 0 |
| 4128 | Q8IYQ7 | 79896 | Threonine synthase-like 1 | THNSL1 | cellular_component |
| 4253 | Q8NFF5;Q8NFF5-2;Q8NFF5-3;Q5T196;Q8NFF5-5 | 80308 | FAD pyrophosphorylase;FAD synthase;FAD synthase region;Flavin adenine dinucleotide synthase;FMN adenylyltransferase;Molybdenum cofactor biosynthesis protein-like region;FAD1 flavin adenine dinucleotide synthetase homolog (S. cerevisiae);Fad1, flavin adenine dinucleotide synthetase, homolog (Yeast), isoform CRA_e | FLAD1;PP591;hCG_2001 9;RP11-307C12.7-004 | cytosol |
| 4143 | Q8N0U4;B4DMG7;Q8N0U4-3;C9JFL0 | 222234 | Protein FAM185A;cDNA FLJ55811;Putative uncharacterized protein FAM185A | FAM185A | 0 |

FIG. 30 cont.

TABLE 2

Mitochondrial orphans (31 proteins), ranked from most enriched to least enriched (H/L ratio from Rep1)

| id | Majority Protein IDs | Entrez | Protein Names | Gene Names | GO celloc |
|---|---|---|---|---|---|
| 5318 | Q9NZB8;Q9NZB8-8;Q9NZB8-2;Q9NZB8-7;Q9NZB8-5;Q9NZB8-6;Q9NZB8-3;E7ERN7;Q9NZB8-4 | 4337 | Cell migration-inducing gene 11 protein;Molybdenum cofactor biosynthesis protein 1;Molybdenum cofactor biosynthesis protein A;Molybdenum cofactor biosynthesis protein C;Molybdenum cofactor synthesis-step 1 protein A-B | MIG11;MOCS1 | molybdopterin synthase complex \| nucleus |
| 4280 | Q8TB22-2;Q8TB22;Q8TB22-3;Q8TB22-4 | 64847 | Spermatogenesis-associated protein 20;Sperm-specific protein 411 | SPATA20 | extracellular region |
| 3230 | Q08257;A6MN60;A6NP24;C9JH92;Q5HYE7 | 1429 | NADPH:quinone reductase;Quinone oxidoreductase;Zeta-crystallin;Putative uncharacterized protein CRYZ;Crystallin, zeta (Quinone reductase), isoform CRA_a;Putative uncharacterized protein DKFZp686C16101 | CRYZ;DKFZp686C16101;hCG_21668 | cytosol \| soluble fraction \| cytoplasm |
| 136 | A6NJ78 | 196074 | Methyltransferase 5 domain-containing protein 1;Probable S-adenosyl-L-methionine-dependent methyltransferase METT5D1 | METT5D1 | 0 |
| 3622 | Q4J6C5;Q4J6C6-4;Q4J6C6-3;Q4J6C6-2 | 9581 | Prolyl endopeptidase-like;Prolylendopeptidase-like | KIAA0435;PREPL | cytosol \| cytoplasm |
| 4149 | Q8NO28 | 126789 | tRNA pseudouridine synthase-like 1;tRNA pseudouridylate synthase-like 1;tRNA-uridine isomerase-like 1 | PUS1 | 0 |
| 5401 | Q9JBQ7;Q5T9A6 | 9380 | Glyoxylate reductase/hydroxypyruvate reductase | GLXR;GRHPR;MSTP035;R P11-397D12.2-004 | cytoplasm |
| 2185 | O95900;B7Z7G5 | 26995 | Probable tRNA pseudouridine synthase 2;cDNA FLJ52131, highly similar to Homo sapiens TruB pseudouridine (psi) synthase homolog 2 (TRUB2), mRNA | TRUB2 | 0 |

FIG. 30 cont.

TABLE 2

Mitochondrial orphans (31 proteins), ranked from most enriched to least enriched (H/L ratio from Rep1)

| id | Majority Protein IDs | Entrez | Protein Names | Gene Names | GO celloc |
|---|---|---|---|---|---|
| 3888 | Q6PML9 | 10463 | Human embryonic lung protein;Solute carrier family 30 member 9;Zinc transporter 9 | C4orf1;HUEL;SLC30A9 | integral to membrane \| cytoskeleton \| nucleus \| membrane 0 |
| 3978 | Q72464;Q72464-2;F2Z2Q4;Q72464-3 | 60487 | tRNA guanosine-2-O-methyltransferase TRM11 homolog | C6orf75;MDS024;TRMT11 | 0 |
| 297 | B1ANH1;B1ANG9;B1ANH0;B1ANH2;B1ANH6;Q16774;F5GXL9;B1AWH5;E9PEG7;B1ANH3 | 2987 | Guanylate kinase 1;GMP kinase;Guanylate kinase | GUK1;RP11-520H14.2-010;RP11-520H14.2-027;RP11-520H14.2-003;RP11-520H14.2-018;RP11-520H14.2-023;GMK;RP11-520H14.2-030;RP11-520H14.2-019 | |
| 165 | A6NNL5 | 145653 | Uncharacterized protein C15orf61 | C15orf61 | extracellular region |
| 3845 | Q6P087;Q6P087-2;C9JM75 | 285367 | RNA pseudouridylate synthase domain-containing protein 3;Putative uncharacterized protein RPUSD3 | RPUSD3 | 0 |
| 5024 | Q9H649 | 63899 | NOL1/NOP2/Sun domain family member 3;Putative methyltransferase NSUN3 | MSTP077;NSUN3;UG065 1E06 | 0 |
| 5138 | Q9NPE2 | 51335 | Mesenchymal stem cell protein DSC92;Neugrin;Neurite outgrowth-associated protein;Spinal cord-derived protein FI58G | FI58G;HT020;NGRN | nucleus |

FIG. 30 cont.

TABLE 2

Mitochondrial orphans (31 proteins), ranked from most enriched to least enriched (H/L ratio from Rep1)

| id | Majority Protein IDs | Entrez | Protein Names | Gene Names | GO celloc |
|---|---|---|---|---|---|
| 3856 | Q6P1S2;Q96NB5 | 285315 | Uncharacterized protein C3orf33;cDNA FLJ31139 fis, clone NKR32200185;Chromosome 3 open reading frame 33, isoform CRA_b | C3orf33;MSTP052;hCG_27946 | integral to membrane \| membrane |
| 3985 | Q724W1 | 51181 | Carbonyl reductase II;Dicarbonyl/L-xylulose reductase;Kidney dicarbonyl reductase;L-xylulose reductase;Sperm surface protein P34H | DCXR | brush border \| membrane \| microvillus |
| 1070 | E7ETE0;Q9H825;B5ME2 5;Q9H825-2;C9JE69 | 79828 | Methyltransferase-like protein 8;Putative uncharacterized protein METTL8 | METTL8 | nucleus \| cytoplasm |
| 1943 | O43824;H0Y2S1 | 8225 | Pseudoautosomal GTP-binding protein-like;Putative GTP-binding protein 6 | GTPBP6;PGPL | intracellular |
| 4493 | Q96C36;E7EUS9;E7EUD8 | 29920 | Pyrroline-5-carboxylate reductase 2 | PYCR2 | 0 |
| 2513 | P22234;P22234-2;E9PB51;D6RFG2 | 10606 | AIR carboxylase;Multifunctional protein ADE2;Phosphoribosylaminoimidazole carboxylase;Phosphoribosylaminoimidazole-succinocarboxamide synthase;SAICAR synthetase | ADE2;AIRC;PAICS;PAIS | 0 |

FIG. 31

TABLE 3

Biotinylated peptides detected (88 unique peptides, derived from 63 unique enriched proteins), grouped by protein

| id | Protein Group IDs | Individual protein group ID | Peptide ID | Length | Leading Proteins | Protein Names | Gene Names | Modified Sequence | GO cellcr |
|---|---|---|---|---|---|---|---|---|---|
| 36911 | 62 | 62 | 9908 | 8 | A0A3U3 | cDNA, FLJ35504, Homo sapiens single-stranded DNA binding protein 1 (SSBP1), mRNA;Single-stranded DNA-binding protein 1;Single-stranded DNA binding protein 1, isoform CRA_a;PWP1-interacting protein 17;Single-stranded DNA-binding protein, mitochondrial;Putative uncharacterized protein SSBP1 | hCG_2014231;SSBP1;tcag7_401;SSBP;SSBP1 | DVAVT(ph)QYMK_ | mitochondrial nucleoid \| mitochondrion |
| 36931 | 62 | 62 | 9906 | 8 | A0A3U3 | cDNA, FLJ35504, Homo sapiens single-stranded DNA binding protein 1 (SSBP1), mRNA;Single-stranded DNA-binding protein 1;Single-stranded DNA binding protein 1, isoform CRA_a;PWP1-interacting protein 17;Single-stranded DNA-binding protein, mitochondrial;Putative uncharacterized protein SSBP1 | hCG_2014231;SSBP1;tcag7_401;SSBP;SSBP1 | DVAYQY(ph)MK_ | mitochondrial nucleoid \| mitochondrion |
| 186336 | 62 | 62 | 49882 | 15 | A0A3U3 | cDNA, FLJ35504, Homo sapiens single-stranded DNA binding protein 1 (SSBP1), mRNA;Single-stranded DNA-binding protein 1;Single-stranded DNA binding protein 1, isoform CRA_a;PWP1-interacting protein 17;Single-stranded DNA-binding protein, mitochondrial;Putative uncharacterized protein SSBP1 | hCG_2014231;SSBP1;tcag7_401;SSBP;SSBP1 | SGDSEVY(ph)QGDVSQ_ | mitochondrial nucleoid \| mitochondrion |
| 250539 | 349 | 349 | 65520 | 8 | P36776 | Lon protease homolog, mitochondrial;Lon protease-like protein;LONHS;Mitochondrial ATP-dependent protease Lon;Serine protease 15;Lon protease homolog | LONP1;PRSS15 | Y(ph)LLQEQLK_ | mitochondrial nucleoid \| mitochondrion \| mitochondrial matrix |
| 23036 | 394 | 394 | 5895 | 8 | 075390 | Citrate synthase, mitochondrial;Citrate synthase | CS | AM(ox)AQGISR_ | mitochondrion \| mitochondrial matrix |
| 144336 | 394 | 394 | 38257 | 7 | 075390 | Citrate synthase, mitochondrial;Citrate synthase | CS | LVAQLVD(hl)K_ | mitochondrion \| mitochondrial matrix |
| 147812 | 600 | 600 | 39180 | 14 | P38646 | 75 kDa glucose-regulated protein;Heat shock 70 kDa protein 9;Mortalin;Peptide-binding protein 74;Stress-70 protein, mitochondrial;cDNA FLJ51907, highly similar to Stress-70 protein, mitochondrial | GRP75;HSPA9;HSPA9B | LV(ph)SPSQIGAPVLMK_ | mitochondrion \| mitochondrial nucleoid \| cell surface \| cytoplasm |
| 154712 | 600 | 600 | 40720 | 11 | P38646 | 75 kDa glucose-regulated protein;Heat shock 70 kDa protein 9;Mortalin;Peptide-binding protein 74;Stress-70 protein, mitochondrial;cDNA FLJ51907, highly similar to Stress-70 protein, mitochondrial | GRP75;HSPA9;HSPA9B | NAEK(hl)AEEDRR_ | mitochondrion \| mitochondrial nucleoid \| cell surface \| cytoplasm |
| 169449 | 600 | 600 | 44396 | 14 | P38646 | 75 kDa glucose-regulated protein;Heat shock 70 kDa protein 9;Mortalin;Peptide-binding protein 74;Stress-70 protein, mitochondrial;cDNA FLJ51907, highly similar to Stress-70 protein, mitochondrial | GRP75;HSPA9;HSPA9B | QAVTNPNNTFY(ph)ATK_ | mitochondrion \| mitochondrial nucleoid \| cell surface \| cytoplasm |
| 169453 | 600 | 600 | 44400 | 15 | P38646 | 75 kDa glucose-regulated protein;Heat shock 70 kDa protein 9;Mortalin;Peptide-binding protein 74;Stress-70 protein, mitochondrial;cDNA FLJ51907, highly similar to Stress-70 protein, mitochondrial | GRP75;HSPA9;HSPA9B | QAVTNPNNTFY(ph)ATK_R | mitochondrion \| mitochondrial nucleoid \| cell surface \| cytoplasm |

FIG. 31 cont.

TABLE 3

Biotinylated peptides detected (88 unique peptides, derived from 63 unique enriched proteins), grouped by protein

| id | Protein Group IDs | Individual protein group ID | Peptide ID | Length | Leading Proteins | Protein Names | Gene Names | Modified Sequence | GO cellc |
|---|---|---|---|---|---|---|---|---|---|
| 39935 | 764 | 764 | 9672 | 19 | C9J119 | Putative uncharacterized protein MRPS34, mitochondrial;28S ribosomal protein S34, mitochondrial | MRPS34;MRPS34 | DSQLYAVDV(bi)ETLTRP_TSGR | mitochondrion ; ribosome |
| 195592 | 1061 | 1061 | 51831 | 12 | E7ESX0 | 39S ribosomal protein L22, mitochondrial;28S ribosomal protein L25, mitochondrial;cDNA FLJ55304, highly similar to Homo sapiens mitochondrial ribosomal protein L22 (MRPL22), transcript variant 1, mRNA; Putative uncharacterized protein MRPL22 | HSPE1B;MRPL22;MRPL25;RPML25;MRPL22 | SNLY(bi)IASTSGR_ | mitochondrion ; ribosome | intracellular | large ribosomal subunit |
| 6175 | 1222 | 1222 | 1643 | 31 | P30048 | Antioxidant protein 1;HBC189;Peroxiredoxin III;Peroxiredoxin-3;Protein MER5 homolog;Thioredoxin-dependent peroxide reductase, mitochondrial | AOP1;PRDX3 | AFQH(bi)VETHGEVCPA_NVTPDSPTNK(bi)PAASK | mitochondrion ; IkappaB kinase complex | early endosome | cytoplasm |
| 119242 | 1286 | 1286 | 31171 | 9 | 073954 | ATP synthase subunit g, mitochondrial | ATP5L | LATFW(bi)IVAK_ | mitochondrion ; mitochondrial inner membrane | membrane | mitochondrial protein-transporting ATP synthase complex | mitochondrial protein-transporting ATP synthase complex, coupling factor F(o) |
| 10272 | 1354 | 1354 | 2702 | 23 | P00367 | Glutamate dehydrogenase 1, mitochondrial;cDNA FLJ55283, highly similar to Glutamate dehydrogenase 1, mitochondrial (EC 1.4.1.3);cDNA FLJ56138 fis, clone BRALZ2017531, highly similar to Glutamate dehydrogenase 1, mitochondrial (EC 1.4.1.3);Glutamate dehydrogenase 1, isoform CRA_a | GLUD;GLUD1;GLUD1;hCG_1993805 | AKPV(bi)EGSILEADCD(bi)I_PAASEK_ | mitochondrion ; mitochondrial matrix | cytoplasm |
| 46794 | 1481 | 1481 | 12567 | 11 | Q12931 | Heat shock protein 75 kDa, mitochondrial;TNFR-associated protein 1;Tumor necrosis factor type 1 receptor-associated protein | HSP75;TRAP1 | ELGSIVALY(bi)SR_ | mitochondrion ; cellular_component |
| 253221 | 1481 | 1481 | 66368 | 10 | Q12931 | Heat shock protein 75 kDa, mitochondrial;TNFR-associated protein 1;Tumor necrosis factor type 1 receptor-associated protein | HSP75;TRAP1 | Y(bi)VAQLQH(bi)KFR_ | mitochondrion ; cellular_component |

FIG. 31 cont.

TABLE 3

Biotinylated peptides detected (88 unique peptides, derived from 63 unique enriched proteins), grouped by protein

| id | Protein Group IDs | Individual protein group ID | Peptide ID | Length | Leading Proteins | Protein Names | Gene Names | Modified Sequence | GO cellc |
|---|---|---|---|---|---|---|---|---|---|
| 143859 | 1795 | 1795 | 38132 | | 131049549 | COX7a-related protein;Cytochrome c oxidase subunit 7A-related protein, mitochondrial;Cytochrome c oxidase subunit VIIa-related protein;B1 | COX7A2L;COX7AR;COX7 RP | LTSDSTVPDY(b)(h)AGK_ | mitochondrial respiratory chain | mitochondrion | membrane |
| 234751 | 1796 | 1796 | 61190 | | 61018561 | Acyl carrier protein, mitochondria;CI-SDAP;NADH-ubiquinone oxidoreductase 9.6 kDa subunit | NDUFAB1 | VLY(b)(h)LK_ | mitochondrion | respiratory chain | mitochondrial membrane | mitochondrial respiratory chain complex I | mitochondrial matrix |
| 245508 | 1931 | 1931 | 64552 | | 21043678 | Complex I-B8;NADH dehydrogenase [ubiquinone] 1 alpha subcomplex subunit 2;NADH-ubiquinone oxidoreductase B8 subunit | NDUFA2 | Y(b)IAFCQETAVPLANVFS_ ACQVTR_ | mitochondrion | respiratory chain | mitochondrial inner membrane | mitochondrial membrane | mitochondrial respiratory chain complex I | membrane |
| 26964 | 2047 | 2047 | 7897 | | 111075489 | Complex I-30kD;NADH dehydrogenase [ubiquinone] iron-sulfur protein 3, mitochondrial;NADH-ubiquinone oxidoreductase 30 kDa subunit | NDUFS3 | DRPLGST(b)NELR_ | mitochondrion | respiratory chain | mitochondrial inner membrane | mitochondrial membrane | mitochondrial respiratory chain complex I | membrane |
| 110594 | 2047 | 2047 | 26797 | | 151075489 | Complex I-30kD;NADH dehydrogenase [ubiquinone] iron-sulfur protein 3, mitochondrial;NADH-ubiquinone oxidoreductase 30 kDa subunit | NDUFS3 | KFT(b)IASPVVEAFPV(b)(h)R_ | mitochondrion | respiratory chain | mitochondrial inner membrane | mitochondrial membrane |
| 6491 | 2254 | 2254 | 1721 | | 151041431 | Ornithine aminotransferase, hepatic form;Ornithine aminotransferase, mitochondrial;Ornithine aminotransferase, renal form;Ornithine delta aminotransferase;Ornithine—oxo-acid aminotransferase | OAT | APHWVGEYEEF(b)(h)TR_ | mitochondrion | mitochondrial matrix | cytoplasm |

FIG. 31 cont.

TABLE 3

Biotinylated peptides detected (88 unique peptides, derived from 63 unique enriched proteins), grouped by protein

| id | Protein Group IDs | Individual protein in group ID | Peptide ID | Length | Leading Proteins | Protein Names | Gene Names | Modified Sequence | GO cellc |
|---|---|---|---|---|---|---|---|---|---|
| 84861 | 2285 | 2309 | 21561 | 19 | P06576 | ATP synthase subunit beta, mitochondrial | ATP5B;ATP5MB;ATP5B | _AIAELGIYPAVDPLDS TSR_ | mitochondrial nucleoid \| mitochondrion \| mitochondrial proton-transporting ATP synthase, catalytic core \| mitochondrial membrane \| plasma membrane \| cell surface \| mitochondrial matrix \| mitochondrial proton-transporting ATP synthase complex |
| 93243 | 2309 | 2309 | 24555 | 10 | P07954 | Fumarate hydratase, mitochondrial | FH | _EM(ox)DITFGELK_ | mitochondrion \| tricarboxylic acid cycle enzyme complex \| mitochondrial matrix \| cytoplasm |
| 74276 | 2350 | 2350 | 19663 | 11 | P10606 | Cytochrome c oxidase polypeptide Vb, Cytochrome c oxidase subunit 5B, mitochondrial | COX5B | _GLDPY(ph)NVLAPK_ | mitochondrial envelope \| mitochondrion \| mitochondrial inner membrane \| membrane |
| 111213 | 2350 | 2350 | 28966 | 12 | P10606 | Cytochrome c oxidase polypeptide Vb, Cytochrome c oxidase subunit 5B, mitochondrial | COX5B | _KGLDPY(ph)NVLAPK_ | mitochondrial envelope \| mitochondrion \| mitochondrial inner membrane \| membrane |
| 103494 | 2355 | 2365 | 26925 | 19 | P10809 | 60 kDa chaperonin;60 kDa heat shock protein, mitochondrial;Chaperonin 60;Heat shock protein 65;HuCHA60;Mitochondrial matrix protein P1;P60 lymphocyte protein | HSP60;HSPD1 | _IQEIIEQLDVTTSEF(ph)EK_ | mitochondrion \| stored secretory granule \| cyclin-dependent protein kinase activating kinase holoenzyme complex \| mitochondrial inner membrane \| plasma membrane part \| early endosome \| cytoplasm \| cytosol \| coated pit \| extracellular space \| coated vesicle \| lipopolysaccharide receptor complex \| cell surface \| mitochondrial matrix |

FIG. 31 cont.

TABLE 3
Biotinylated peptides detected (88 unique peptides, derived from 63 unique enriched proteins), grouped by protein

| id | Protein Group IDs | Individual protein group ID | Peptide ID | Length | Leading Proteins | Protein Names | Gene Names | Modified Sequence | GO celloc |
|---|---|---|---|---|---|---|---|---|---|
| 103513 | 2365 | 2365 | 269626 | 23 | P10809 | 60 kDa chaperonin;60 kDa heat shock protein, mitochondrial;Chaperonin 60;Heat shock protein 60;HuCHA60;Mitochondrial matrix protein P1;P60 lymphocyte protein | HSP60;HSPD1 | AQIIEQLDVTTSEY(ph)EK_ | mitochondrion ǀ stored secretory granule ǀ cyclin-dependent protein kinase activating kinase holoenzyme complex ǀ mitochondrial inner membrane ǀ plasma membrane part ǀ early endosome ǀ cytoplasm ǀ cytosol ǀ coated pit ǀ extracellular space ǀ coated vesicle ǀ lipopolysaccharide receptor complex ǀ cell surface ǀ mitochondrial matrix |
| 180996 | 2365 | 2365 | 43701 | 20 | P10809 | 60 kDa chaperonin;60 kDa heat shock protein, mitochondrial;Chaperonin 60;Heat shock protein 60;HuCHA60;Mitochondrial matrix protein P1;P60 lymphocyte protein | HSP60;HSPD1 | BIQEIIEQLDVTTSEY(ph)E K_ | mitochondrion ǀ stored secretory granule ǀ cyclin-dependent protein kinase activating kinase holoenzyme complex ǀ mitochondrial inner membrane ǀ plasma membrane part ǀ early endosome ǀ cytoplasm ǀ cytosol ǀ coated pit ǀ extracellular space ǀ coated vesicle ǀ lipopolysaccharide receptor complex ǀ cell surface ǀ mitochondrial matrix |
| 134822 | 2412 | 2412 | 35532 | 17 | P13804 | Electron transfer flavoprotein subunit alpha, mitochondrial;cDNA FLJ50659, highly similar to Electron transfer flavoprotein subunit alpha, mitochondrial | ETFA | LLY(ph)DLADQLHAAVG_ASR_ | mitochondrion ǀ mitochondrial matrix |
| 220737 | 2412 | 2412 | 55373 | 12 | P13804 | Electron transfer flavoprotein subunit alpha, mitochondrial;cDNA FLJ50659, highly similar to Electron transfer flavoprotein subunit alpha, mitochondrial | ETFA | TIY(ph)AGNHALCTVK_ | mitochondrion ǀ mitochondrial matrix |

FIG. 31 cont.

TABLE 3

Biotinylated peptides detected (88 unique peptides, derived from 63 unique enriched proteins), grouped by protein

| id | Protein Group IDs | individual protein group ID | Peptide ID | Length | Leading Proteins | Protein Names | Gene Names | Modified Sequence | GO cellloc |
|---|---|---|---|---|---|---|---|---|---|
| 137439 | 2525 | 2525 | 36234 | 18 | P22695 | Complex III subunit 2;Core protein II;Cytochrome b-c1 complex subunit 2, mitochondrial;Ubiquinol-cytochrome-c reductase complex core protein 2 | UQCRC2 | _LPNGLVHASLENVK(bi)SPV_ SR_ | mitochondrion ǀ respiratory chain ǀ mitochondrial inner membrane ǀ nucleus ǀ membrane ǀ mitochondrial respiratory chain complex III |
| 239678 | 2525 | 2525 | 62724 | 18 | P22695 | Complex III subunit 2;Core protein II;Cytochrome b-c1 complex subunit 2, mitochondrial;Ubiquinol-cytochrome-c reductase complex core protein 2 | UQCRC2 | _VTSEELHV(bi)FVQNHFT SAR_ | mitochondrion ǀ respiratory chain ǀ mitochondrial inner membrane ǀ nucleus ǀ membrane ǀ mitochondrial respiratory chain complex III |
| 185161 | 2535 | 2535 | 48892 | 10 | P23434 | Glycine cleavage system H protein, mitochondrial | GCSH | _SCV(bi)HEDGWFLK_ | mitochondrion ǀ glycine cleavage complex |
| 29599 | 2550 | 2550 | 7675 | 9 | P24752 | Acetoacetyl-CoA thiolase;Acetyl-CoA acetyltransferase, mitochondrial;T2 | ACAT,ACAT1,MAT | _DGLTDV(bi)INK_ | mitochondrion ǀ mitochondrial inner membrane ǀ mitochondrial matrix |
| 80073 | 2550 | 2550 | 21260 | 16 | P24752 | Acetoacetyl-CoA thiolase;Acetyl-CoA acetyltransferase, mitochondrial;T2 | ACAT,ACAT1,MAT | _GSTPV(bi)GCVK.EDLNK_ | mitochondrion ǀ mitochondrial inner membrane ǀ mitochondrial matrix |
| 83124 | 2560 | 2560 | 21988 | 10 | P25705 | ATP synthase subunit alpha, mitochondrial;ATP synthase subunit alpha | ATP5A,ATP5A1,ATP5A_2,ATPM | _GV(bi)LDKLEPSK_ | mitochondrion ǀ mitochondrial inner membrane ǀ plasma membrane ǀ mitochondrial matrix ǀ mitochondrial proton-transporting ATP synthase complex ǀ mitochondrial proton-transporting ATP synthase complex, catalytic core F(1) |

FIG. 31 cont.

TABLE 3

Biotinylated peptides detected (88 unique peptides, derived from 63 unique enriched proteins), grouped by protein

| id | Protein Group IDs | Individual protein group ID | Peptide ID | Length | Leading Proteins | Protein Names | Gene Names | Modified Sequence | GO celloc |
|---|---|---|---|---|---|---|---|---|---|
| 122315 | 2560 | 2560 | 32022 | 7 | P25705 | ATP synthase subunit alpha, mitochondrial;ATP synthase subunit alpha | ATP5A;ATP5A1;ATP5AL2;ATPM | LELAQY(bi)R_ | mitochondrion \| mitochondrial inner membrane \| plasma membrane \| mitochondrial matrix \| mitochondrial proton-transporting ATP synthase complex \| mitochondrial proton-transporting ATP synthase complex, catalytic core F(1) |
| 75244 | 2596 | 2596 | 20896 | 14 | P28331 | Complex I: 75kD;NADH-ubiquinone oxidoreductase 75 kDa subunit, mitochondrial;cDNA FLJ53204, highly similar to NADH-ubiquinone oxidoreductase 75 kDa subunit, mitochondrial (EC 1.6.5.3);cDNA FLJ56979, highly similar to NADH-ubiquinone oxidoreductase 75 kDa subunit, mitochondrial (EC 1.6.5.3);cDNA FLJ56586, highly similar to NADH-ubiquinone oxidoreductase 75 kDa subunit, mitochondrial (EC 1.6.5.3) | NDUFS1 | GLLTVY(bi)TSWEDALSR_ | mitochondrion \| respiratory chain \| mitochondrial inner membrane \| mitochondrial respiratory chain complex I \| membrane \| mitochondrial intermembrane space |
| 147335 | 2597 | 2597 | 39041 | 12 | P28838 | Cytosol aminopeptidase;Leucine aminopeptidase 3;Leucyl aminopeptidase;Peptidase S;Proline aminopeptidase;Prolyl aminopeptidase | LAP3;LAPEP;PEPS | LV(bi)GSGIVGEAWGK_ | mitochondrion \| intracellular \| cytoplasm |
| 61403 | 2608 | 2608 | 21178 | 26 | P30042 | ES1 protein homolog, mitochondrial;Protein GT335;Protein KNP-I | C21orf33;HES1;KNP1 | GNEVTVGHEQEEGGKW PY(bi)AGTACAIK_ | mitochondrion |
| 232139 | 2622 | 2622 | 60615 | 10 | P30837 | Aldehyde dehydrogenase 5;Aldehyde dehydrogenase family 1 member B1;Aldehyde dehydrogenase X, mitochondrial;cDNA FLJ51239, highly similar to Aldehyde dehydrogenase X, mitochondrial (EC 1.2.1.3) | ALDH1B1;ALDH5;ALDHX | VLGY(bi)HLGLQK_ | mitochondrion \| mitochondrial matrix |
| 86383 | 2633 | 2633 | 22797 | 21 | P31930 | Complex III subunit 1;Core protein I;Cytochrome b-c1 complex subunit 1, mitochondrial;Ubiquinol-cytochrome-c reductase complex core protein 1 | UQCRC1 | HLGGPWYN(bi)HJACLAV IP7LPCR_ | mitochondrion \| mitochondrial respiratory chain \| mitochondrial respiratory chain complex |
| 229003 | 2697 | 2697 | 59618 | 7 | P38117 | Electron transfer flavoprotein subunit beta | ETFB;FP585 | VIGY(bi)HAVK_ | mitochondrion \| mitochondrial matrix |
| 245930 | 2697 | 2697 | 64430 | 9 | P38117 | Electron transfer flavoprotein subunit beta | ETFB;FP585 | Y(bi)AI1PNIMAK_ | mitochondrion \| mitochondrial matrix |

FIG. 31 cont.

TABLE 3
Biotinylated peptides detected (88 unique peptides, derived from 63 unique enriched proteins) grouped by protein

| id | Protein group IDs | individual protein group ID | Peptide ID | Length | Leading Proteins | Protein Names | Gene Names | Modified Sequence | GO celloc |
|---|---|---|---|---|---|---|---|---|---|
| 83143 | 2713 | 2713 | 21990 | 13 | P40926 | Malate dehydrogenase, mitochondrial | MDH2 | GYLDLLGPELPLCLK_ | mitochondrion \| mitochondrial inner membrane \| mitochondrial matrix |
| 85513 | 2713 | 2713 | 22524 | 8 | P40926 | Malate dehydrogenase, mitochondrial | MDH2 | HGVY(bi)NMAK_ | mitochondrion \| mitochondrial inner membrane \| mitochondrial matrix |
| 194187 | 2725 | 2725 | 51313 | 8 | P42126 | 3,2-trans-enoyl-CoA isomerase, mitochondrial;Delta(3),Delta(2)-enoyl-CoA isomerase;Dodecenoyl-CoA isomerase | DCI | SLQMY(bi)LER_ | mitochondrion \| mitochondrial inner membrane \| mitochondrial matrix |
| 146315 | 2787 | 2787 | 38686 | 14 | P48047 | ATP synthase subunit O, mitochondrial;Oligomycin sensitivity conferral protein | ATP5O;ATPO | EVRPPQVY(bi)HGEGR_ | proton-transporting ATP synthase complex, catalytic core F(1) \| mitochondrion \| mitochondrial inner membrane \| plasma membrane \| mitochondrial proton-transporting ATP synthase complex |
| 221315 | 2787 | 2787 | 58619 | 11 | P48047 | ATP synthase subunit O, mitochondrial;Oligomycin sensitivity conferral protein | ATP5O;ATPO | VAASVLAPY(bi)WK_ | proton-transporting ATP synthase complex, catalytic core F(1) \| mitochondrion \| mitochondrial inner membrane \| plasma membrane \| mitochondrial proton-transporting ATP synthase complex |
| 32031 | 2813 | 2813 | 6577 | 19 | P49411 | Elongation factor Tu, mitochondrial;P43 | TUFM | DLERPFLLPVEAVY(bi)SV PGR_ | mitochondrial nucleoid \| mitochondrion \| intracellular |
| 130507 | 2813 | 2813 | 34346 | 14 | P49411 | Elongation factor Tu, mitochondrial;P43 | TUFM | ELDAVDTY(bi)IPVPAR_ | mitochondrial nucleoid \| mitochondrion \| intracellular |

FIG. 31 cont.

TABLE 3

Biotinylated peptides detected (88 unique peptides, derived from 63 unique enriched proteins), grouped by protein

| id | Protein Group IDs | Individual protein group ID | Peptide ID | Length | Leading Proteins | Protein Names | Gene Names | Modified Sequence | GO cellcc |
|---|---|---|---|---|---|---|---|---|---|
| 161413 | 2955 | 2955 | 42203 | | 14|P56181-2 | | | _NLSDPSSY(bi)PPAVNK_ | mitochondrion \| respiratory chain \| mitochondrial inner membrane \| mitochondrial respiratory chain complex I \| membrane |
| 66410 | 2962 | 2962 | 17911 | | 7|P56556 | Complex I-B14.7;NADH dehydrogenase [ubiquinone] 1 alpha subcomplex subunit 6;NADH-ubiquinone oxidoreductase B14 subunit | LRRMC;NADHB14;NDUF A6 | _SY(bi)VGHDP_ | mitochondrion \| respiratory chain \| mitochondrial inner membrane \| mitochondrial respiratory chain complex I \| membrane |
| 28393 | 3019 | 3019 | 7792 | | 10|P61604 | 10 kDa chaperonin;10 kDa heat shock protein, mitochondrial;Chaperonin 10;Early-pregnancy factor;Heat shock 10kDa protein 1 (Chaperonin 10), isoform CRA_b;Putative uncharacterized protein HSPE1 | HSPE1;hCG_21429;HSPE 1 | _DGDKLGK(bi)HVD_ | mitochondrion \| mitochondrial matrix \| cytoplasm |
| 232602 | 3019 | 3019 | 60760 | | 10|P61604 | 10 kDa chaperonin;10 kDa heat shock protein, mitochondrial;Chaperonin 10;Early-pregnancy factor;Heat shock 10kDa protein 1;Heat shock 10kDa protein 1 (Chaperonin 10), isoform CRA_b | HSPE1;hCG_21429;HSPE 1 | _VLLPEY(bi)GGTK_ | mitochondrion \| mitochondrial matrix \| cytoplasm |
| 217537 | 3125 | 3125 | 56299 | | 15|P82664 | 28S ribosomal protein S10, mitochondrial | MRPS10;MSTP040 | _AVELSYEY(bi)HFAVLAAK_ | mitochondrion \| ribosome \| intracellular |
| 5379 | 3149 | 3149 | 1439 | | 12|Q00059 | Mitochondrial transcription factor 1;Transcription factor 6;Transcription factor 6-like 2;Transcription factor A, mitochondrial;Putative uncharacterized protein TFAM | TCF6;TCF6L2;TFAM;TFA M | _AEWQVY(bi)KEEISR_ | mitochondrial nucleoid \| mitochondrion \| nucleus \| mitochondrial matrix |
| 249024 | 3263 | 3263 | 65270 | | 11|Q13849 | G-rich sequence factor 1;cDNA FL36937 fis, clone PROST2004526, highly similar to G-rich sequence factor 1;cDNA FEBRA2007247, highly similar to G-rich sequence factor 1;cDNA FL38430 fis, clone FEBRA2012291, highly similar to G-rich sequence factor 1;cDNA FL32329 fis, clone BRAWH2014511, highly similar to G-rich sequence factor 1;cDNA FL39736 fis, clone SMINT2016313, highly similar to G-rich sequence factor 1;G-rich RNA sequence binding factor 1, isoform CRA_a | GRSF1;GRSF;hCG_1708 0 | _Y(bi)IELFLNSCPK_ | mitochondrion \| cytoplasm |

FIG. 31 cont.

TABLE 3

Biotinylated peptides detected (88 unique peptides, derived from 63 unique enriched proteins), grouped by protein

| id | Protein Group IDs | individual protein group ID | Peptide ID | Length | Leading Proteins | Protein Names | Gene Names | Modified Sequence | GO cellloc |
|---|---|---|---|---|---|---|---|---|---|
| 251819 | 3279 | 3279 | 65939 | 10 | Q13011 | Delta(3,5)-Delta(2,4)-dienoyl-CoA isomerase, mitochondrial | ECH1 | YL(bi)QETFNVER_ | mitochondrion ; peroxisome |
| 192892 | 3235 | 3235 | 90963 | 23 | Q13423 | NAD(P) transhydrogenase, mitochondrial;Nicotinamide nucleotide transhydrogenase;Pyridine nucleotide transhydrogenase | NNT | SLGAEPLEVDK(bi)ESGECQ GCY(bi)AK_ | mitochondrial respiratory chain ; mitochondrion ; integral to membrane ; mitochondrial inner membrane ; membrane |
| 9985 | 3470 | 3470 | 2615 | 11 | Q15118 | [Pyruvate dehydrogenase [lipoamide]] kinase isozyme 4, mitochondrial;Pyruvate dehydrogenase [lipoamide] kinase isozyme 1 (EC 2.7.11.2);Putative uncharacterized protein PDK1 | PDK1;PDK1 | _AI(Y(bi)DFTDTVYR_ | mitochondrion ; mitochondrial matrix |
| 116674 | 3567 | 3567 | 30525 | 9 | Q5JPH6 | Glutamate-tRNA ligase;Probable glutamyl-tRNA synthetase, mitochondrial | EARS2;KIAA1970 | KY(bi)AGSFILR_ | mitochondrion ; mitochondrial matrix ; cytoplasm |
| 102324 | 3941 | 3941 | 26652 | 8 | Q7L0Y3 | HBV pre-S2 trans-regulated protein 2;Mitochondrial ribonuclease P protein 1;Renal carcinoma antigen NY-REN-49;RNA (guanine-9-)-methyltransferase domain-containing protein 1;Putative uncharacterized protein RG9MTD1 | MRPP1;RG9MTD1;RG9 MTD1 | IPAVT(bi)PK_ | mitochondrion |
| 102352 | 3941 | 3941 | 26653 | 24 | Q7L0Y3 | HBV pre-S2 trans-regulated protein 2;Mitochondrial ribonuclease P protein 1;Renal carcinoma antigen NY-REN-49;RNA (guanine-9-)-methyltransferase domain-containing protein 1;Putative uncharacterized protein RG9MTD1 | MRPP1;RG9MTD1;RG9 MTD1 | IPAVT(bi)PK;MK(ESTPPASE ELELDK;WK_ | mitochondrion |
| 165300 | 3941 | 3941 | 43188 | 13 | Q7L0Y3 | HBV pre-S2 trans-regulated protein 2;Mitochondrial ribonuclease P protein 1;Renal carcinoma antigen NY-REN-49;RNA (guanine-9-)-methyltransferase domain-containing protein 1;Putative uncharacterized protein RG9MTD1 | MRPP1;RG9MTD1;RG9 MTD1 | NMDPFHV(bi)DFCNLK_ | mitochondrion |
| 110533 | 3996 | 3996 | 28776 | 15 | Q7Z2W9 | 39S ribosomal protein L55, mitochondrial | MRPL55;UNQ5825/PRO 19675 | KSY(bi)EQRLSDLHVER_ | mitochondrion ; ribosome ; mitochondrial large ribosomal subunit |

TABLE 3

Biotinylated peptides detected (88 unique peptides, derived from 63 unique enriched proteins), grouped by protein

| id | Protein Group IDs | individual protein group ID | Peptide ID | Length | Leading Proteins | Protein Names | Gene Names | Modified Sequence | GO celloc |
|---|---|---|---|---|---|---|---|---|---|
| 130033 | 4275 | 4275 | 36438 | 16 | Q8TAE8 | Cell beta-associating protein;CkB-interacting factor 1;Growth arrest and DNA damage-inducible proteins-interacting protein 1;p53-responsive gene 6 protein;Papillomavirus L2-interacting nuclear protein 1 | GADD45GIP1;PLINP1;PR G5 | LGAEAGELLGYTafbiQVD ip _ | mitochondrion ; nucleus |
| 147070 | 4294 | 4294 | 38951 | 15 | Q8TCS8 | 3'-5' RNA exonuclease OLD35;PNPase old-35;Polynucleotide phosphorylase 1;Polyribonucleotide nucleotidyltransferase 1, mitochondrial | PNPASE;PNPT1 | LYAVFTD(ph)q)EHCK(SR _ | mitochondrion ; mitochondrial intermembrane space |
| 30230 | 4536 | 4536 | 8060 | 20 | Q96EY7 | Pentatricopeptide repeat-containing protein 3, mitochondrial;Transformation-related gene 15 protein | PTCD3;TRG15 | DIAEPHPCLMPE(ph)PE PQK | mitochondrion |
| 93623 | 4740 | 4740 | 24663 | 11 | Q9Y6I7 | Mitochondrial intermediate peptidase | MIP;MIPEP | FFLY(b)P(bi)PNASQLK | mitochondrion ; mitochondrial matrix |
| 131796 | 4740 | 4740 | 34672 | 13 | Q9Y6I7 | Mitochondrial intermediate peptidase | MIP;MIPEP | LLGES(Ybi)AEQPAK | mitochondrion ; mitochondrial matrix |
| 83628 | 4750 | 4750 | 21835 | 14 | Q8BW88 | Protein NipSnap homolog 1 | NIPSNAP1 | GWDENVYY(ph)TVPLVR _ | mitochondrion ; mitochondrial inner membrane |
| 253462 | 4761 | 4761 | 66423 | 23 | Q8BD69 | MACRO domain-containing protein 1;Protein LRP16 | LRP16;MACROD1 | YHHTV(Gp)AY(b)GEPSA SQAAELR | mitochondrion |
| 77534 | 4865 | 4865 | 20701 | 15 | Q8W92 | Threonine–tRNA ligase;Threonyl-tRNA synthetase, mitochondrial;Threonyl-tRNA synthetase-like 1;cDNA FLJ2528 fis, clone MT2RM4000155, moderately similar to THREONYL-TRNA SYNTHETASE, CYTOPLASMIC (EC 6.1.1.3);Threonyl-tRNA synthetase 2, mitochondrial (Putative);Threonyl-tRNA synthetase-like 1, isoform CRA_b | TARS2,TARSL1;ACG_199 9130;RP11-54449-010;TARS2;TARSL1;RPL16 54449.012;TARS2 | GPSTE(ph)q)G-C(ph)DFLG _ K | mitochondrion ; mitochondrial matrix ; cytoplasm |
| 206277 | 5074 | 5074 | 53838 | 10 | Q9H4S2 | 39S ribosomal protein L44, mitochondrial | MRPL44 | TAPVNSCV(b)JK _ | mitochondrion ; ribosome ; intracellular ; cellular_component |
| 55998 | 5093 | 5093 | 15156 | 17 | Q9HAV7 | GrpE protein homolog 1, mitochondrial;HMGE;Mt-GrpEl;GrpE protein homolog | GRPEL1;GRPEL1 | FDP(Y)(bi)HEALPMPVE GK | mitochondrion ; mitochondrial matrix |

TABLE 3

Biotinylated peptides detected (88 unique peptides, derived from 63 unique enriched proteins), grouped by protein

| id | Protein Group IDs | individual protein group ID | Peptide ID | Length | Leading Proteins | Protein Names | Gene Names | Modified Sequence | GO cellc |
|---|---|---|---|---|---|---|---|---|---|
| 144572 | 5093 | 5093 | 38330 | 15 | Q96AV7 | GrpE protein homolog 1, mitochondrial;HMGE;Nk-GrpE#2;GrpE protein homolog | GRPEL1;GRPEL1 | LVEEAK(bi)DLGLQAFCK_ | mitochondrion ; mitochondrial matrix |
| 196247 | 5206 | 5206 | 51870 | 18 | Q9NUJ1 | Abhydrolase domain-containing protein 10, mitochondrial;Putative uncharacterized protein ABHD10 | ABHD10;ABHD10 | SPGIHFGVLS(bi)AAfxx_ jNGTK | mitochondrion |
| 253230 | 5206 | 5206 | 66096 | 15 | Q9NUJ1 | Abhydrolase domain-containing protein 10, mitochondrial;cDNA FLJ5RC58, highly similar to Homo sapiens abhydrolase domain containing 10 (ABHD10), mRNA | ABHD10 | YSEEGVK(bi)NVQYSFK_ | mitochondrion |
| 49962 | 5340 | 5340 | 13463 | 10 | Q9P032 | Hormone-regulated proliferation-associated protein of 28 kDa;NADH dehydrogenase [ubiquinone] 1 alpha subcomplex assembly factor 4 | C6orf66;HRPAP20;HSPC 125;M(ox)13;NDUFAF4 | EQISLY(bi)IPENK_ | mitochondrion ; mitochondrial membrane |
| 179715 | 5438 | 5438 | 47370 | 11 | Q9UII2 | ATPase inhibitor, mitochondrial;Inhibitor of F(1)H(+) ATPase | ATPIF1;ATPIF1 | REQAEEERY(bi)IR_ | mitochondrion ; cell surface ; mitochondrial proton-transporting ATP synthase complex |
| 253759 | 5476 | 5476 | 66479 | 6 | Q9UJZ1 | EPB72-like protein 2;Stomatin-like protein 2;cDNA FLJ61833, highly similar to Stomatin-like protein 2 | HSPC108;SLP2;STOML2 | V(bi)YQSLK_ | mitochondrion ; mitochondrial inner membrane ; cytoskeleton ; membrane ; cytoplasm |
| 114166 | 5599 | 5599 | 28927 | 14 | Q9Y289 | 28S ribosomal protein S7, mitochondrial;bMRP-27a | MRPS7 | KPVEELLTEEEKY(bi)IVR_ | cytosolic small ribosomal subunit ; mitochondrion ; ribosome ; intracellular |
| 202007 | 5641 | 5641 | 53224 | 11 | Q9Y3D7 | Mitochondria-associated granulocyte macrophage CSF-signaling molecule;Mitochondrial import inner membrane translocase subunit Tim16 | CGI-136;MAGMAS;TIM16;TI MM16 | SVGGSPY(bi)LQSK_ | mitochondrion ; mitochondrial inner membrane ; membrane |

FIG. 31 cont.

TABLE 3

Biotinylated peptides detected (83 unique peptides, derived from 63 unique enriched proteins), grouped by protein

| Protein Group IDs | Individual protein group ID | Peptide ID | Length | Leading Proteins | Protein Names | Gene Names | Modified Sequence | GO cellloc |
|---|---|---|---|---|---|---|---|---|
| 15926 | 5722 | 4197 | 231 | Q96EL6 | 28S ribosomal protein S18-3, mitochondrial;28S ribosomal protein S18b, mitochondrial;Mitochondrial ribosomal protein S18B;Putative uncharacterized protein FLJ90900;DKFZp686O35569;cDNA FLJ54255, highly similar to 28S ribosomal protein S18b, mitochondrial | C6orf14;HSPC183;MRPS 18B;PTD017;DAQB-129D20.6-003;DAMA-176G23.8-003;DAWC-83F13.5-003;DAQB-47P19.5-003;DASS-182C6.3-003;MRPS18B;XXbac-BCX495T10.3-003;XXbac-BPG249D20.2-003 | _APSEEDSLSSVPLSPV(ph)_ | mitochondrion | ribosome | intracellular | mitochondrial small ribosomal subunit |
| 5904 | 5739 | 1363 | 141 | Q9P0J0 | Complex I-B22; LYR motif-containing protein 3;NADH dehydrogenase [ubiquinone] 1 beta subcomplex subunit 3;NADH-ubiquinone oxidoreductase B22 subunit | LYRM3;MDUFB9;UQCR2 2 | _(ac)AFLASPVF(ph)ILTHQ_QK_ | mitochondrion | respiratory chain | mitochondrial inner membrane | mitochondrial respiratory chain complex I | membrane |

FIG. 32

TABLE 4
Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| aa-tRNA synthetase | Q5JTZ9 | 2.640822945 | 2.627174559 | Y | AARS2 | 57505 | alanyl-tRNA synthetase 2, mitochondrial | | Ann. Rev. Genomics Hum. Genet. (2008) 9:87-107 | Eric D. Green | | | | |
| aa-tRNA synthetase | Q9HA77 | 2.497398796 | 2.309320112 | Y | CARS2 | 79587 | cysteinyl-tRNA synthetase 2, mitochondrial | | Ann. Rev. Genomics Hum. Genet. (2008) 9:87-107 | Eric D. Green | | | | |
| aa-tRNA synthetase | Q9H917 | 2.015343695 | 1.999288053 | Y | DARS2 | 55157 | aspartyl-tRNA synthetase 2, mitochondrial | | Ann. Rev. Genomics Hum. Genet. (2008) 9:87-107 | Eric D. Green | | | | |
| aa-tRNA synthetase | Q5JPH6 | 1.910114496 | 1.861794492 | Y | EARS2 | 124454 | glutamyl-tRNA synthetase 2, mitochondrial | | Ann. Rev. Genomics Hum. Genet. (2008) 9:87-107 | Eric D. Green | | | | |
| aa-tRNA synthetase | O95363 | 2.132463619 | 1.876127003 | Y | FARS2 | 10667 | phenylalanyl-tRNA synthetase 2, mitochondrial | | Ann. Rev. Genomics Hum. Genet. (2008) 9:87-107 | Eric D. Green | | | | |
| aa-tRNA synthetase | P49590 | 1.428955173 | 2.314636695 | Y | HARS2 | 23438 | histidyl-tRNA synthetase 2, mitochondrial | | Ann. Rev. Genomics Hum. Genet. (2008) 9:87-107 | Eric D. Green | | | | |
| aa-tRNA synthetase | Q9NSE4 | 2.631692416 | 2.566402284 | Y | IARS2 | 55699 | isoleucyl-tRNA synthetase 2, mitochondrial | | Ann. Rev. Genomics Hum. Genet. (2008) 9:87-107 | Eric D. Green | | | | |

FIG. 32 cont.

TABLE 4

Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| aa-tRNA synthetase | Q15031 | 1.912083219 | 1.845775144 | Y | LARS2 | 23395 | leucyl-tRNA synthetase 2, mitochondrial | | Ann. Rev. Genomics Hum. Genet. (2008) 9-87/Green 107 | Eric D. | | | | |
| aa-tRNA synthetase | Q96GW9 | 2.618212064 | 2.553168412 | Y | MARS2 | 92935 | methionyl-tRNA synthetase 2, mitochondrial | | Ann. Rev. Genomics Hum. Genet. (2008) 9-87/Green 107 | Eric D. | | | | |
| aa-tRNA synthetase | G3V178 | - | - | Y | NARS2 | 79731 | asparaginyl-tRNA synthetase 2, mitochondrial | | Ann. Rev. Genomics Hum. Genet. (2008) 9-87/Green 107 | Eric D. | | | | |
| aa-tRNA synthetase | Q7L3T8 | 2.100547869 | 1.948410565 | Y | PARS2 | 25973 | prolyl-tRNA synthetase 2, mitochondrial | | Ann. Rev. Genomics Hum. Genet. (2008) 9-87/Green 107 | Eric D. | | | | |
| aa-tRNA synthetase | Q5T160 | 1.918726725 | 1.874222036 | Y | RARS2 | 57038 | arginyl-tRNA synthetase 2, mitochondrial | | Ann. Rev. Genomics Hum. Genet. (2008) 9-87/Green 107 | Eric D. | | | | |
| aa-tRNA synthetase | Q9NP81 | 2.521240578 | 2.416928923 | Y | SARS2 | 54938 | seryl-tRNA synthetase 2, mitochondrial | | Ann. Rev. Genomics Hum. Genet. (2008) 9-87/Green 107 | Eric D. | | | | |
| aa-tRNA synthetase | Q9BW92 | 2.163985149 | 2.341593625 | Y | TARS2 | 80222 | threonyl-tRNA synthetase 2, mitochondrial | | Ann. Rev. Genomics Hum. Genet. (2008) 9-87/Green 107 | Eric D. | | | | |

FIG. 32 cont.

TABLE 4
Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| aa-tRNA synthetase | F5H323 | 2.180245549 | 2.112996331 | Y | VARS2 | 57176 | valyl-tRNA synthetase 2, mitochondrial | | Ann. Rev. Genomics Hum. Genet. (2008) 9:87/Green 107 | Eric D. | | | | |
| aa-tRNA synthetase | Q9UGM6 | 3.154677544 | 3.152347614 | Y | WARS2 | 10352 | tryptophanyl-tRNA synthetase 2, mitochondrial | | Ann. Rev. Genomics Hum. Genet. (2008) 9:87/Green 107 | Eric D. | | | | |
| aa-tRNA synthetase | Q9Y2Z4 | 1.949675626 | 1.993352396 | Y | YARS2 | 51067 | tyrosyl-tRNA synthetase 2, mitochondrial | | Ann. Rev. Genomics Hum. Genet. (2008) 9:87/Green 107 | Eric D. | | | | |
| aa-tRNA synthetase | P41250 | . | . | Y | GARS | 2617 | glycyl-tRNA synthetase, bifunctional | | Ann. Rev. Genomics Hum. Genet. (2008) 9:87/Green 107 | Eric D. | | | | |
| aa-tRNA synthetase | O15946 | . | . | Y | KARS | 3735 | lysyl-tRNA synthetase, bifunctional | | Ann. Rev. Genomics Hum. Genet. (2008) 9:87/Green 107 | Eric D. | | | | |
| aa-tRNA synthetase | P47897 | . | . | Y | QARS | 5859 | glutaminyl-tRNA synthetase, bifunctional | | Ann. Rev. Genomics Hum. Genet. (2008) 9:87/Green 107 | Eric D. | | | | |
| nucleoid-associated | Q00059 | 3.137153979 | 3.211005465 | Y | TFAM | 7019 | transcription factor A, mitochondrial | DNA replication, transcription, repair, recombination or packaging | J Biol Chem (2006) 281:25791-25802. | Daniel F. Bogenhagen | J Biochem (2005) 138:673-678 | Dongchon Kang | | |

FIG. 32 cont.

TABLE 4
Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| nucleic-acid associated | Q04837 | 2.867201942 | 2.820751472 | Y | SSBP1 | 6742 | mtSSb = mitochondrial ssDNA-binding protein | DNA replication, transcription, repair, recombination or packaging | J Biol Chem (2006) 281:25791-25802 | Daniel F. Bogenhagen | J Biochem (2005) 138:573-678 | Dongchon Kang | | |
| nucleic-acid associated | Q4G6F4 | 2.302739785 | 2.150876762 | Y | POLRMT | 5442 | DNA-directed RNA polymerase, mitochondrial | DNA replication, transcription, repair, recombination or packaging | J Biol Chem (2006) 281:25791-25802 | Daniel F. Bogenhagen | | | | |
| nucleic-acid associated | E5KNU5 | 2.199262875 | 2.055753305 | Y | POLG | 5428 | mitochondrial DNA polymerase gamma | DNA replication, transcription, repair, recombination or packaging | J Biol Chem (2006) 281:25791-25802 | Daniel F. Bogenhagen | | | | |
| nucleic-acid associated | Q9UHN1 | 2.985953897 | 2.740068165 | Y | POLG2 | 11232 | mitochondrial DNA polymerase gamma | DNA replication, transcription, repair, recombination or packaging | J Biol Chem (2006) 281:25791-25802 | Daniel F. Bogenhagen | | | | |
| nucleic-acid associated | Q9Y257 | 2.579827334 | 2.401776624 | Y | POLDIP2 | 26073 | polymerase delta-interacting protein 38 (PDIP38) | DNA replication, transcription, repair, recombination or packaging | J Biochem (2005) 138:573-678 | Dongchon Kang | | | | |

FIG. 32 cont.

TABLE 4
Mitochondrial matrix protein groups detected.

| Category | UniProt Accession | log2 Rep1 | log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| nucleoid-associated | Q3LR86 | | | Y | BRCA1 | 672 | breast cancer 1 | DNA replication, transcription, repair, recombination or packaging | Mol Biol Cell (2005) 16:997-1010 | David J. Vaux | | | | |
| nucleoid-associated | Q9H5Q4 | 2.350203131 | 2.094398811 | Y | TFB2M | 64216 | mitochondrial transcription factor B2 | DNA replication, transcription, repair, recombination or packaging | J Biol Chem (2006) 281:25791-25802 | Daniel F. Bogenhagen | | | | |
| nucleoid-associated | Q8HGV3 | 2.205327141 | 2.148535864 | Y | C16orf2 | 56652 | DNA helicase, twinkle | DNA replication, transcription, repair, recombination or packaging | J Biol Chem (2006) 281:25791-25802 | Daniel F. Bogenhagen | | | | |
| nucleoid-associated | Q8IYB8 | 3.066596321 | 2.750894146 | Y | SUPV3L1 | 6832 | SUV3-like helicase | DNA replication, transcription, repair, recombination or packaging | J Biol Chem (2006) 281:25791-25802 | Daniel F. Bogenhagen | | | | |
| nucleoid-associated | Q7L2E3 | | | Y | DHX30 | 22907 | Putative ATP-dependent RNA helicase | DNA replication, transcription, repair, recombination or packaging | J Biol Chem (2006) 281:25791-25802 | Daniel F. Bogenhagen | | | | |

FIG. 32 cont.

TABLE 4
Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| nucleoid-associated | P17096 | | | y | HMGA1 | 3159 | high-mobility group protein A1 | DNA replication, transcription, repair, recombination or packaging | Exp Cell Res (2005) 307:388-401 | Raymond Reeves | | | | |
| nucleoid-associated | E5KNV5 | 2.9760709586 | 2.8703514446 | y | LRPPRC | 10128 | leucine-rich protein 130 (LRP130) | DNA replication, transcription, repair, recombination or packaging | J Biol Chem (2006) 281:25791-25802 | Daniel F. Bogenhagen | J Biochem (2005) 138:673-678 | Dongchon Kang | | |
| nucleoid-associated | P36776 | 2.41223822 | 2.3969196639 | y | LONP1 | 9361 | lon protease | Heat shock proteins, proteases | J Biochem (2005) 138:673-678 | Dongchon Kang | | | | |
| nucleoid-associated | P10809 | 2.603199234 | 2.4943471717 | y | HSPD1 | 3329 | heat shock 60kDa protein 1 (chaperonin) | Heat shock proteins, proteases | J Biol Chem (2006) 281:25791-25802 | Daniel F. Bogenhagen | J Biochem (2005) 138:673-678 | Dongchon Kang | | |
| nucleoid-associated | O76031 | 2.7502885543 | 2.5941859976 | y | CLPX | 10845 | ATP-dependent Clp protease, mitochondrial | Heat shock proteins, proteases | J Biol Chem (2005) 138:673-678 | Dongchon Kang | | | | |
| nucleoid-associated | P38646 | 2.9289902 | 2.650033721 | y | HSPA9 | 3313 | stress-70 protein, mitochondrial (GRP75) | Heat shock proteins, proteases | J Biol Chem (2006) 281:25791-25802 | Daniel F. Bogenhagen | J Biochem (2005) 138:673-678 | Dongchon Kang | FEBS Letters 581 (2007) 3702-3710 | Marja Jaattela |
| nucleoid-associated | A8K401 | | | y | PHB | 5245 | prohibitin 1 | Heat shock proteins, proteases | J Biol Chem (2006) 281:25791-25802 | Daniel F. Bogenhagen | | | | |

FIG. 32 cont.

TABLE 4

Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| nucleoid-associated | Q99623 | - | - | Y | PHB2 | 11331 | prohibitin 2 | Heat shock proteins, proteases | J Biol Chem (2006) 281:25791-25802 | Daniel F. Bogenhagen | | | | |
| nucleoid-associated | Q99E88 | 2.517656306 | 2.482283146 | Y | DNAJA3 | 9093 | DnaJ (Hsp40) homolog, subfamily A, member 3 (TID1) | Heat shock proteins, proteases | J Biol Chem (2006) 281:13150-8 | Carolyn K. Suzuki | | | | |
| nucleoid-associated | P00505 | 3.152275101 | 3.056002298 | Y | GOT2 | 2806 | aspartate aminotransferase, mitochondrial | Metabolic enzymes | J Biochem (2005) 138:673-678 | Dongchon Kang | | | | |
| nucleoid-associated | P48047 | 2.211734931 | 2.131425961 | Y | ATP5O | 539 | ATPase O subunit | Metabolic enzymes | J Biochem (2005) 138:673-678 | Dongchon Kang | | | | |
| nucleoid-associated | Q6PEK7 | 2.069765389 | 2.077392295 | Y | CPS1 | 1373 | carbamoyl phosphate synthetase | Metabolic enzymes | J Biol Chem (2006) 281:25791-25802 | Daniel F. Bogenhagen | | | | |
| nucleoid-associated | Q16698 | 1.244115424 | 1.870475325 | Y | DECR1 | 1666 | 2,4-dienoyl-CoA reductase 1, mitochondrial | Metabolic enzymes | J Biochem (2005) 138:673-678 | Dongchon Kang | | | | |
| nucleoid-associated | P40939 | 2.735769022 | 2.458160459 | Y | HADHA | 3030 | hydroxyacyl-CoA dehydrogenase alpha subunit | Metabolic enzymes | J Biol Chem (2006) 281:25791-25802 | Daniel F. Bogenhagen | | | | |
| nucleoid-associated | P40926 | 2.836786773 | 2.814451131 | Y | MDH2 | 4191 | malate dehydrogenase 2, mitochondrial | Metabolic enzymes | J Biochem (2005) 138:673-678 | Dongchon Kang | | | | |

FIG. 32 cont.

TABLE 4

Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| nucleoid-associated | E9PH29 | 3.137243716 | 3.009737737 | Y | PRDX3 | 10935 | Thioredoxin-dependent peroxide reductase | Metabolic enzymes | J Biochem (2005) 138:573-678 | Dongchon Kang | J Biochem (1994) 115:648-654 | Nakazawa T. | | |
| nucleoid-associated | B4DJC3 | 2.868398318 | 2.79793254 | Y | SHMT2 | 6472 | serine hydroxymethyl transferase 2 | Metabolic enzymes | J Biol Chem (2006) 281:25791-25802 | Daniel F. Bogenhagen | | | | |
| nucleoid-associated | G3V1I6 | 2.494504386 | 2.26974623 | Y | ATAD3A | 55210 | ATPase family AAA domain-containing protein 3 | Others | J Biol Chem (2006) 281:25791-25802 | Daniel F. Bogenhagen | | | | |
| nucleoid-associated | Q5T9A4 | 1.970510715 | 1.391921471 | Y | ATAD3B | 83858 | ATPase family AAA domain-containing protein 3 | Others | J Biol Chem (2006) 281:25791-25802 | Daniel F. Bogenhagen | | | | |
| mitoribosome | Q9BYD6 | 3.310514404 | 3.115255216 | Y | MRPL1 | 65008 | 39S ribosomal protein | PDB: 2FTC, chain A; PDB: 1GIY, chain C | J. Biol. Chem. (2001) 276:43958-43969 | Linda L. Spremulli | J Mol Biol (2006) 358:193-212 | Stephen C. Harvey | Science (2001) 292:883-896 | Harry F. Noller |
| mitoribosome | Q5T653 | 3.070383368 | 2.912900076 | Y | MRPL2 | 51069 | 39S ribosomal protein | PDB: 2FTC, chain B; PDB: 1GIY, chain D | J. Biol. Chem. (2001) 276:43958-43969 | Linda L. Spremulli | J Mol Biol (2006) 358:193-212 | Stephen C. Harvey | Science (2001) 292:883-896 | Harry F. Noller |
| mitoribosome | P09001 | 2.968474653 | 2.892712888 | Y | MRPL3 | 11222 | 39S ribosomal protein | PDB: 2FTC, chain C; PDB: 1GIY, chain E | J. Biol. Chem. (2001) 276:43958-43969 | Linda L. Spremulli | J Mol Biol (2006) 358:193-212 | Stephen C. Harvey | Science (2001) 292:883-896 | Harry F. Noller |
| mitoribosome | Q9BYD3 | 3.829986666 | 2.808369854 | Y | MRPL4 | 51073 | 39S ribosomal protein | PDB: 2FTC, chain D; PDB: 1GIY, chain F | J. Biol. Chem. (2001) 276:43958-43969 | Linda L. Spremulli | J Mol Biol (2006) 358:193-212 | Stephen C. Harvey | Science (2001) 292:883-896 | Harry F. Noller |
| mitoribosome | Q9BYD2 | 3.243053049 | 3.029280453 | Y | MRPL9 | 65005 | 39S ribosomal protein | PDB: 1GIY, chain K | J. Biol. Chem. (2001) 276:43958-43969 | Linda L. Spremulli | | | Science (2001) 292:883-896 | Harry F. Noller |

FIG. 32 cont.

TABLE 4
Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| mitoribosome | Q7Z7H8 | 2.195827541 | 2.117267977 | Y | MRPL10 | 124995 | 39S ribosomal protein | | J. Biol. Chem. (2001) 276:43958-43969 | Linda L. Spremulli | | | | |
| mitoribosome | Q9Y3B7 | | | Y | MRPL11 | 65003 | 39S ribosomal protein | PDB: 2FTC, chain G; PDB: 1GIY, chain L | J. Biol. Chem. (2001) 276:43958-43969 | Linda L. Spremulli | J Mol Biol (2006) 358:193-212 | Stephen C. Harvey | Science (2001) 292:883-896 | Harry F. Noller |
| mitoribosome | P52815 | | | Y | MRPL12 | 6182 | 39S ribosomal protein | PDB: 2FTC, chain E, F; PDB: 1GIY, chain I, J | J. Biol. Chem. (2001) 276:43958-43969 | Linda L. Spremulli | J Mol Biol (2006) 358:193-212 | Stephen C. Harvey | Science (2001) 292:883-896 | Harry F. Noller |
| mitoribosome | Q9BYD1 | 2.944653784 | 2.891243303 | Y | MRPL13 | 28998 | 39S ribosomal protein | PDB: 2FTC, chain H; PDB: 1GIY, chain M | J. Biol. Chem. (2001) 276:43958-43969 | Linda L. Spremulli | J Mol Biol (2006) 358:193-212 | Stephen C. Harvey | Science (2001) 292:883-896 | Harry F. Noller |
| mitoribosome | Q6P1L8 | 1.911376336 | 1.791965434 | Y | MRPL14 | 64928 | 39S ribosomal protein | PDB: 1GIY, chain N | J. Biol. Chem. (2001) 276:43958-43969 | Linda L. Spremulli | | | Science (2001) 292:883-896 | Harry F. Noller |
| mitoribosome | Q9P015 | 3.068077887 | 2.636869077 | Y | MRPL15 | 29088 | 39S ribosomal protein | PDB: 1GIY, chain O | J. Biol. Chem. (2001) 276:43958-43969 | Linda L. Spremulli | | | | |
| mitoribosome | Q9NX20 | | | Y | MRPL16 | 54948 | 39S ribosomal protein | PDB: 2FTC, chain I; PDB: 1GIY, chain P | J. Biol. Chem. (2001) 276:43958-43969 | Linda L. Spremulli | J Mol Biol (2006) 358:193-212 | Stephen C. Harvey | Science (2001) 292:883-896 | Harry F. Noller |
| mitoribosome | Q9NRX2 | 3.026640481 | 2.789903761 | Y | MRPL17 | 63875 | 39S ribosomal protein | PDB: 2FTC, chain J | J. Biol. Chem. (2001) 276:43958-43969 | Linda L. Spremulli | J Mol Biol (2006) 358:193-212 | Stephen C. Harvey | | |
| mitoribosome | Q9H0U6 | 3.025218635 | 2.667712083 | Y | MRPL18 | 29074 | 39S ribosomal protein | PDB: 1GIY, chain Q | J. Biol. Chem. (2001) 276:43958-43969 | Linda L. Spremulli | J Mol Biol (2006) 358:193-212 | Stephen C. Harvey | | |
| mitoribosome | P49406 | 2.898398193 | 2.671890321 | Y | MRPL19 | 9801 | 39S ribosomal protein | PDB: 2FTC, chain K; PDB: 1GIY, chain R | J. Biol. Chem. (2001) 276:43958-43969 | Linda L. Spremulli | J Mol Biol (2006) 358:193-212 | Stephen C. Harvey | Science (2001) 292:883-896 | Harry F. Noller |
| mitoribosome | Q9BYC9 | 3.315687429 | 3.167737704 | Y | MRPL20 | 55052 | 39S ribosomal protein | PDB: 2FTC, chain L | J. Biol. Chem. (2001) 276:43958-43969 | Linda L. Spremulli | J Mol Biol (2006) 358:193-212 | Stephen C. Harvey | | |

FIG. 32 cont.

TABLE 4
Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| mitoribosome | Q7Z2W9 | 3.081722324 | 2.857068216 | Y | MRPL21 | 219927 | 39S ribosomal protein | | J. Biol. Chem. (2001) 276:43958-43969 | Linda L. Spremulli | | | | |
| mitoribosome | A6NG48 | 2.824341324 | 2.898011486 | Y | MRPL22 | 29093 | 39S ribosomal protein | PDB: 2FTC, chain M; PDB: 1GIY, chain S | J. Biol. Chem. (2001) 276:43958-43969 | Linda L. Spremulli | J Mol Biol (2006) 358:193-212 | Stephen C. Harvey | Science (2001) 292:883-896 | Harry F. Noller |
| mitoribosome | Q16540 | 2.895656564 | 2.819725373 | Y | MRPL23 | 6150 | 39S ribosomal protein | PDB: 1GIY, chain T | J. Biol. Chem. (2001) 276:43958-43969 | Linda L. Spremulli | J Mol Biol (2006) 358:193-212 | Stephen C. Harvey | Science (2001) 292:883-896 | Harry F. Noller |
| mitoribosome | Q96A35 | 3.116703440 | 2.861119189 | Y | MRPL24 | 79590 | 39S ribosomal protein | PDB: 2FTC, chain N; PDB: 1GIY, chain U | J. Biol. Chem. (2001) 276:43958-43969 | Linda L. Spremulli | J Mol Biol (2006) 358:193-212 | Stephen C. Harvey | Science (2001) 292:883-896 | Harry F. Noller |
| mitoribosome | Q9P0M9 | 2.940653361 | 2.794405673 | Y | MRPL27 | 51264 | 39S ribosomal protein | PDB: 2FTC, chain O | J. Biol. Chem. (2001) 276:43958-43969 | Linda L. Spremulli | J Mol Biol (2006) 358:193-212 | Stephen C. Harvey | | |
| mitoribosome | Q13084 | 3.304182028 | 3.159483309 | Y | MRPL28 | 10573 | 39S ribosomal protein | | J. Biol. Chem. (2001) 276:43958-43969 | Linda L. Spremulli | | | | |
| mitoribosome | Q8TCC3 | 3.251450483 | 3.134700778 | Y | MRPL30 | 51263 | 39S ribosomal protein | PDB: 1GIY, chain X | J. Biol. Chem. (2001) 276:43958-43969 | Linda L. Spremulli | | | Science (2001) 292:883-896 | Harry F. Noller |
| mitoribosome | Q9BYC8 | 3.475633168 | 3.248398601 | Y | MRPL32 | 64983 | 39S ribosomal protein | | J. Biol. Chem. (2001) 276:43958-43969 | Linda L. Spremulli | | | | |
| mitoribosome | O75394 | | | Y | MRPL33 | 9553 | 39S ribosomal protein | PDB: 2FTC, chain P | J. Biol. Chem. (2001) 276:43958-43969 | Linda L. Spremulli | J Mol Biol (2006) 358:193-212 | Stephen C. Harvey | | |
| mitoribosome | Q9BQ48 | 3.203205485 | 3.079908669 | Y | MRPL34 | 64981 | 39S ribosomal protein | PDB: 2FTC, chain Q | J. Biol. Chem. (2001) 276:43958-43969 | Linda L. Spremulli | J Mol Biol (2006) 358:193-212 | Stephen C. Harvey | | |
| mitoribosome | Q9NZE8 | 3.414407352 | 3.212123095 | Y | MRPL35 | 51318 | 39S ribosomal protein | | J. Biol. Chem. (2001) 276:43958-43969 | Linda L. Spremulli | | | | |

FIG. 32 cont.

TABLE 4

Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| mitoribosome | Q9P0M6 | | | Y | MRPL36 | 64979 | 39S ribosomal protein | | J. Biol. Chem. (2001) 276:43958-43969 | Linda L. Spremulli | | | | |
| mitoribosome | Q9NZE1 | 2.838955988 | 2.728652795 | Y | MRPL37 | 51253 | 39S ribosomal protein | | J. Biol. Chem. (2001) 276:43958-43969 | Linda L. Spremulli | | | | |
| mitoribosome | Q96DV4 | 2.979926434 | 2.768511975 | Y | MRPL38 | 64978 | 39S ribosomal protein | | J. Biol. Chem. (2001) 276:43958-43969 | Linda L. Spremulli | | | | |
| mitoribosome | Q9NYK5 | 2.753248208 | 2.620245478 | Y | MRPL39 | 54148 | 39S ribosomal protein | | J. Biol. Chem. (2001) 276:43958-43969 | Linda L. Spremulli | | | | |
| mitoribosome | Q9NQ50 | 3.420597778 | 3.233057201 | Y | MRPL40 | 64976 | 39S ribosomal protein | | J. Biol. Chem. (2001) 276:43958-43969 | Linda L. Spremulli | | | | |
| mitoribosome | Q8IXM3 | 3.192923898 | 3.080655644 | Y | MRPL41 | 64975 | 39S ribosomal protein | | J. Biol. Chem. (2001) 276:43958-43969 | Linda L. Spremulli | | | | |
| mitoribosome | Q9Y6G3 | 2.723460973 | 2.852006724 | Y | MRPL42 | 28977 | 39S ribosomal protein | | J. Biol. Chem. (2001) 276:43958-43969 | Linda L. Spremulli | | | | |
| mitoribosome | Q8N983 | | | Y | MRPL43 | 84545 | 39S ribosomal protein | | J. Biol. Chem. (2001) 276:43958-43969 | Linda L. Spremulli | | | | |
| mitoribosome | Q9H9J2 | 3.128367717 | 2.964661759 | Y | MRPL44 | 65080 | 39S ribosomal protein | | J. Biol. Chem. (2001) 276:43958-43969 | Linda L. Spremulli | | | | |
| mitoribosome | Q9BRJ2 | 2.812066043 | 2.638441759 | Y | MRPL45 | 84111 | 39S ribosomal protein | | J. Biol. Chem. (2001) 276:43958-43969 | Linda L. Spremulli | | | | |
| mitoribosome | Q9H2W6 | 3.321453384 | 3.094858451 | Y | MRPL46 | 26589 | 39S ribosomal protein | | J. Biol. Chem. (2001) 276:43958-43969 | Linda L. Spremulli | | | | |

FIG. 32 cont.

TABLE 4

Mitochondrial matrix protein groups detected.

| Category | UniProt Accession | log2 Rep1 | log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| mitoribosome | Q9HD33 | 3.050049852 | 3.092934176 | Y | MRPL47 | 57129 | 39S ribosomal protein | | J. Biol. Chem. (2001) 276:43958-43969 | Linda L. Spremulli | | | | |
| mitoribosome | Q96GC5 | 3.072950073 | 2.915029237 | Y | MRPL48 | 51642 | 39S ribosomal protein | | J. Biol. Chem. (2001) 276:43958-43969 | Linda L. Spremulli | | | | |
| mitoribosome | Q13405 | 3.223876581 | 3.037534342 | Y | MRPL49 | 740 | 39S ribosomal protein | | J. Biol. Chem. (2001) 276:43958-43969 | Linda L. Spremulli | | | | |
| mitoribosome | Q8N5N7 | 3.078938984 | 2.829533203 | Y | MRPL50 | 54534 | 39S ribosomal protein | | J. Biol. Chem. (2001) 276:43958-43969 | Linda L. Spremulli | | | | |
| mitoribosome | Q4U2R6 | 3.381910372 | 2.947407653 | Y | MRPL51 | 51258 | 39S ribosomal protein | | J. Biol. Chem. (2001) 276:43958-43969 | Linda L. Spremulli | | | | |
| mitoribosome | A6NMQ8 | 3.040736249 | 3.093251954 | Y | MRPL52 | 122704 | 39S ribosomal protein | | J. Biol. Chem. (2001) 276:43958-43969 | Linda L. Spremulli | | | | |
| mitoribosome | Q96EL3 | 2.279309198 | 2.294228335 | Y | MRPL53 | 116540 | 39S ribosomal protein | | J. Biol. Chem. (2001) 276:43958-43969 | Linda L. Spremulli | | | | |
| mitoribosome | Q6P161 | 2.128083731 | 2.487948174 | Y | MRPL54 | 116541 | 39S ribosomal protein | | J. Biol. Chem. (2001) 276:43958-43969 | Linda L. Spremulli | | | | |
| mitoribosome | Q7Z7F7 | 2.870294943 | 2.895004802 | Y | MRPL55 | 128308 | 39S ribosomal protein | | J. Biol. Chem. (2001) 276:43958-43969 | Linda L. Spremulli | | | | |
| mitoribosome | P83111 | . | . | Y | MRPL56 | 114294 | 39S ribosomal protein | | J. Biol. Chem. (2001) 276:43958-43969 | Linda L. Spremulli | | | | |
| mitoribosome | Q9Y399 | 1.190056005 | 1.355239659 | Y | MRPS2 | 51116 | 28S ribosomal protein | PDB ID: 1GIX, chain E | J. Biol. Chem. (2001) 276:19363-19374 | Linda L. Spremulli | Science (2001) 292:883-896 | Harry F. Noller | | |

FIG. 32 cont.

TABLE 4

Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| mitoribosome | P82675 | 1.149295144 | 1.294533865 | Y | MRPS5 | 64969 | 28S ribosomal protein | PDB ID: 1GIX, chain H | J. Biol. Chem. (2001) 276:19363-19374 | Linda L. Spremulli | Science (2001) 292:883-896 | Harry F. Noller | | |
| mitoribosome | P82932 | 2.442469876 | 2.012402528 | Y | MRPS6 | 64969 | 28S ribosomal protein | PDB ID: 1GIX, chain I | J. Biol. Chem. (2001) 276:19363-19374 | Linda L. Spremulli | Science (2001) 292:883-896 | Harry F. Noller | | |
| mitoribosome | Q9Y2R9 | 3.236078105 | 3.116283334 | Y | MRPS7 | 51081 | 28S ribosomal protein | PDB ID: 1GIX, chain J | J. Biol. Chem. (2001) 276:19363-19374 | Linda L. Spremulli | Science (2001) 292:883-896 | Harry F. Noller | | |
| mitoribosome | P82933 | 2.639391534 | 2.535529792 | Y | MRPS9 | 64965 | 28S ribosomal protein | PDB ID: 1GIX, chain L | J. Biol. Chem. (2001) 276:19363-19374 | Linda L. Spremulli | Science (2001) 292:883-896 | Harry F. Noller | | |
| mitoribosome | P82664 | 2.956491097 | 2.813774289 | Y | MRPS10 | 55173 | 28S ribosomal protein | PDB ID: 1GIX, chain M | J. Biol. Chem. (2001) 276:19363-19374 | Linda L. Spremulli | Science (2001) 292:883-896 | Harry F. Noller | | |
| mitoribosome | P82912 | | | Y | MRPS11 | 64963 | 28S ribosomal protein | PDB ID: 1GIX, chain N | J. Biol. Chem. (2001) 276:19363-19374 | Linda L. Spremulli | Science (2001) 292:883-896 | Harry F. Noller | | |
| mitoribosome | O15235 | | | Y | MRPS12 | 6183 | 28S ribosomal protein | PDB ID: 1GIX, chain O | J. Biol. Chem. (2001) 276:19363-19374 | Linda L. Spremulli | Science (2001) 292:883-896 | Harry F. Noller | | |
| mitoribosome | O60783 | 2.542934058 | 2.412341576 | Y | MRPS14 | 63931 | 28S ribosomal protein | PDB ID: 1GIX, chain Q | J. Biol. Chem. (2001) 276:19363-19374 | Linda L. Spremulli | Science (2001) 292:883-896 | Harry F. Noller | | |
| mitoribosome | P82914 | | | Y | MRPS15 | 64960 | 28S ribosomal protein | PDB ID: 1GIX, chain R | J. Biol. Chem. (2001) 276:19363-19374 | Linda L. Spremulli | Science (2001) 292:883-896 | Harry F. Noller | | |
| mitoribosome | Q9Y3D3 | 2.734057911 | 2.655252663 | Y | MRPS16 | 51021 | 28S ribosomal protein | PDB ID: 1GIX, chain S | J. Biol. Chem. (2001) 276:19363-19374 | Linda L. Spremulli | Science (2001) 292:883-896 | Harry F. Noller | | |
| mitoribosome | Q9Y2R5 | | | Y | MRPS17 | 51373 | 28S ribosomal protein | PDB ID: 1GIX, chain T | J. Biol. Chem. (2001) 276:19363-19374 | Linda L. Spremulli | Science (2001) 292:883-896 | Harry F. Noller | | |

FIG. 32 cont.

TABLE 4

Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| mitoribosome | Q9NWS2 | 2.757174851 | 2.710973209 | Y | MRPS18A | 55168 | 28S ribosomal protein | PDB ID: 1GIX, chain U | J. Biol. Chem. (2001) 276:19363-19374 | Linda L. Spremulli | Science (2001) 292:883-896 | Harry F. Noller | | |
| mitoribosome | B0S7P4 | 2.733315798 | 2.645428993 | Y | MRPS18B | 28973 | 28S ribosomal protein | PDB ID: 1GIX, chain U | J. Biol. Chem. (2001) 276:19363-19374 | Linda L. Spremulli | Science (2001) 292:883-896 | Harry F. Noller | | |
| mitoribosome | P82921 | | | Y | MRPS21 | 54460 | 28S ribosomal protein | | J. Biol. Chem. (2001) 276:19363-19374 | Linda L. Spremulli | | | | |
| mitoribosome | P82650 | 2.749808788 | 2.753122573 | Y | MRPS22 | 56945 | 28S ribosomal protein | | J. Biol. Chem. (2001) 276:19363-19374 | Linda L. Spremulli | | | | |
| mitoribosome | Q9Y3D9 | 2.806182209 | 2.597470122 | Y | MRPS23 | 51649 | 28S ribosomal protein | | J. Biol. Chem. (2001) 276:19363-19374 | Linda L. Spremulli | | | | |
| mitoribosome | Q96EL2 | 2.878579621 | 2.826017055 | Y | MRPS24 | 64951 | 28S ribosomal protein | | J. Biol. Chem. (2001) 276:19363-19374 | Linda L. Spremulli | | | | |
| mitoribosome | P82663 | 2.654996219 | 2.597395724 | Y | MRPS25 | 64432 | 28S ribosomal protein | | J. Biol. Chem. (2001) 276:19363-19374 | Linda L. Spremulli | | | | |
| mitoribosome | Q9BYN8 | 2.635633764 | 2.589592359 | Y | MRPS26 | 64949 | 28S ribosomal protein | | J. Biol. Chem. (2001) 276:19363-19374 | Linda L. Spremulli | | | | |
| mitoribosome | Q92552 | 2.549632043 | 2.274650851 | Y | MRPS27 | 23107 | 28S ribosomal protein | | J. Biol. Chem. (2001) 276:19363-19374 | Linda L. Spremulli | | | | |
| mitoribosome | Q9Y2Q9 | | | Y | MRPS28 | 28957 | 28S ribosomal protein | | J. Biol. Chem. (2001) 276:19363-19374 | Linda L. Spremulli | | | | |
| mitoribosome | E7EM60 | 3.010097996 | 2.765812577 | Y | MRPS29 | 7818 | 28S ribosomal protein (DAP3) | | J. Biol. Chem. (2001) 276:19363-19374 | Linda L. Spremulli | | | | |

FIG. 32 cont.

TABLE 4
Mitochondrial matrix protein groups detected.

| Category | UniProt Accession | Log2 Rep1 | Log2 Rep2 | matrix expressed | Gene Symbol | ENTREZ | DESCRIPTION | NOTE | REFERENCE | IP1 | REFERENCE2 | IP12 | REFERENCE2 | FIG |
|---|---|---|---|---|---|---|---|---|---|---|---|---|---|---|
| mitoribosome | Q9NP92 | 2.990943013329 | 2.882230624 | Y | MRPS30 | 10884 | 28S ribosomal protein | | J. Biol. Chem. (2001) 276:19363-19374 | Linda L. Spremulli | | | | |
| mitoribosome | Q92665 | 2.949306968 | 2.856337855 | Y | MRPS31 | 10240 | 28S ribosomal protein | | J. Biol. Chem. (2001) 276:19363-19374 | Linda L. Spremulli | | | | |
| mitoribosome | Q9Y6G3 | 2.723460673 | 2.852006724 | Y | MRPL42 | 28977 | 28S ribosomal protein | | J. Biol. Chem. (2001) 276:19363-19374 | Linda L. Spremulli | | | | |
| mitoribosome | A4D1T3 | | | Y | MRPS33 | 51650 | 28S ribosomal protein | | J. Biol. Chem. (2001) 276:19363-19374 | Linda L. Spremulli | | | | |
| mitoribosome | P82930 | 2.659213034 | 2.575028289 | Y | MRPS34 | 65993 | 28S ribosomal protein | | J. Biol. Chem. (2001) 276:19363-19374 | Linda L. Spremulli | | | | |
| mitoribosome | P82673 | 2.990738722 | 2.797523091 | Y | MRPS35 | 60488 | 28S ribosomal protein | | J. Biol. Chem. (2001) 276:19363-19374 | Linda L. Spremulli | | | | |
| mitoribosome | P82909 | 2.599163021 | 2.348470893 | Y | MRPS36 | 92259 | 28S ribosomal protein | | J. Biol. Chem. (2001) 276:19363-19374 | Linda L. Spremulli | | | | |
| mitoribosome | Q9BQC6 | 3.352862889 | 3.311537736 | Y | MRP63 | 78988 | 28S ribosomal protein | | J Biol Chem (2001)276:33181-95 | Kimitsuna Watanabe | | | | |
| mitoribosome | O75616 | 2.396082449 | 2.163642004 | Y | ERAL1 | 26284 | mito RNA chaperone | involved in the assembly of 28S small mitochondrial ribosomal subunit | Biochem. J. (2010) 430:551-558 | Robert N. Lightowlers | | | | |

FIG. 32 cont.

TABLE 4
Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| TCA cycle | O75390 | 3.03671631 | 2.9593862 | Y | CS | 1431 | citrate synthase | | http://en.wikipedia.org/wiki/Citric_acid_cycle | http://www.wikipathways.org/index.php/Pathway:WP78 | | | | |
| TCA cycle | Q99798 | 2.832440292 | 2.6984075 | Y | ACO2 | 50 | aconitase 2 | | http://en.wikipedia.org/wiki/Citric_acid_cycle | http://www.wikipathways.org/index.php/Pathway:WP78 | | | | |
| TCA cycle | P50213 | 2.466336085 | 2.334965593 | Y | IDH3A | 3419 | isocitrate dehydrogenase [NAD] subunit alpha | | http://en.wikipedia.org/wiki/Citric_acid_cycle | http://www.wikipathways.org/index.php/Pathway:WP78 | | | | |
| TCA cycle | O43837 | 2.010215822 | 1.9748375 | Y | IDH3B | 3420 | isocitrate dehydrogenase [NAD] subunit beta | | http://en.wikipedia.org/wiki/Citric_acid_cycle | http://www.wikipathways.org/index.php/Pathway:WP78 | | | | |

FIG. 32 cont.

TABLE 4

Mitochondrial matrix protein groups detected.

| Category | UniProt Accession | log2 Rep1 | log2 Rep2 | matrix exposed | Gene Symbol | ENTREZ | DESCRIPTION | NOTE | REFERENCE | P1 | REFERENCE2 | P12 | REFERENCE2 | P13 |
|---|---|---|---|---|---|---|---|---|---|---|---|---|---|---|
| TCA cycle | O15384 | 1.762386229 | 1.834315122 | Y | IDH3G | 3421 | Isocitrate dehydrogenase [NAD] subunit gamma | | http://en.wikipedia.org/wiki/Citric_acid_cycle | http://www.wikipathways.org/index.php/Pathway:WP78 | | | | |
| TCA cycle | P48735 | 2.377606885 | 2.164306181 | Y | IDH2 | 3418 | Isocitrate dehydrogenase [NADP], mitochondrial | | http://en.wikipedia.org/wiki/Citric_acid_cycle | http://www.wikipathways.org/index.php/Pathway:WP78 | | | | |
| TCA cycle | B4E3E9 | 2.790550342 | 2.828332939 | Y | OGDH | 4967 | 2-oxoglutarate dehydrogenase E1 component | | http://en.wikipedia.org/wiki/Citric_acid_cycle | http://www.wikipathways.org/index.php/Pathway:WP78 | | | | |
| TCA cycle | B7Z6J1 | 3.012853602 | 2.774330792 | Y | DLST | 1743 | Dihydrolipoyllysine-residue succinyltransferase component of 2-oxoglutarate dehydrogenase complex | | http://en.wikipedia.org/wiki/Citric_acid_cycle | http://www.wikipathways.org/index.php/Pathway:WP78 | | | | |

FIG. 32 cont.

TABLE 4

Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| TCA cycle | P09622 | 2.270953482 | 1.973717702 | Y | DLD | 1738 | Dihydrolipoamide dehydrogenase | | http://en.wikipedia.org/wiki/Citric_acid_cycle | http://www.wikipathways.org/index.php/Pathway:WP78 | | | | |
| TCA cycle | P53597 | | | Y | SUCLG1 | 8802 | succinate-CoA ligase, alpha subunit | | http://en.wikipedia.org/wiki/Citric_acid_cycle | http://www.wikipathways.org/index.php/Pathway:WP78 | | | | |
| TCA cycle | Q96I99 | 2.650138028 | 2.620655732 | Y | SUCLG2 | 8801 | succinate-CoA ligase, GDP-forming, beta subunit | | http://en.wikipedia.org/wiki/Citric_acid_cycle | http://www.wikipathways.org/index.php/Pathway:WP78 | | | | |
| TCA cycle | Q9P2R7 | 1.815557409 | 1.887014524 | Y | SUCLA2 | 8803 | succinate-CoA ligase, ADP-forming, beta subunit | | http://en.wikipedia.org/wiki/Citric_acid_cycle | http://www.wikipathways.org/index.php/Pathway:WP78 | | | | |

FIG. 32 cont.

TABLE 4

Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | P1 | REFERENCE2 | P12 | REFERENCE2 | P13 |
|---|---|---|---|---|---|---|---|---|---|---|---|---|---|---|
| TCA cycle | P07954 | 2.5026008848 | 2.3992275191 | Y | FH | 2271 | fumarase | | http://en.wikipedia.org/wiki/Citric_acid_cycle | http://www.wikipathways.org/index.php/Pathway:WP78 | | | | |
| TCA cycle | P40926 | 2.8307367773 | 2.8144513131 | Y | MDH2 | 4191 | malate dehydrogenase 2 | | http://en.wikipedia.org/wiki/Citric_acid_cycle | http://www.wikipathways.org/index.php/Pathway:WP78 | | | | |
| TCA cycle | P08559 | 1.6900774961 | 1.5490440731 | Y | PDHA1 | 5160 | Pyruvate dehydrogenase (lipoamide) alpha 1 | pyruvate dehydrogenase E1 component subunit alpha | http://en.wikipedia.org/wiki/Citric_acid_cycle | | | | | |
| TCA cycle | P11177 | 1.1626712771 | | Y | PDHB | 5162 | Pyruvate dehydrogenase (lipoamide) beta | pyruvate dehydrogenase E1 component subunit beta | http://en.wikipedia.org/wiki/Citric_acid_cycle | | | | | |
| TCA cycle | P10515 | 2.9583510181 | 2.5108487061 | Y | DLAT | 1737 | dihydrolipoamide S-acetyltransferase | pyruvate dehydrogenase E2 component | http://en.wikipedia.org/wiki/Citric_acid_cycle | | | | | |

FIG. 32 cont.

TABLE 4

Mitochondrial matrix protein groups detected.

| Category | UniProt Accession | Log2 Rep1 | Log2 Rep2 | matrix expressed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| TCA cycle | O00330 | 2.828249473 | 2.502112051 | Y | PDHX | 8050 | pyruvate dehydrogenase protein X component | pyruvate dehydrogenase E3 binding protein subunit | http://en.wikipedia.org/wiki/Citric_acid_cycle | | | | | |
| TCA cycle | Q15118 | 2.057001151 | 1.834351413 | Y | PDK1 | 5163 | Pyruvate dehydrogenase kinase isozyme 1 | | http://en.wikipedia.org/wiki/Citric_acid_cycle | | | | | |
| TCA cycle | Q15119 | 2.219990135 | 2.151139004 | Y | PDK2 | 5164 | Pyruvate dehydrogenase kinase isozyme 2 | | http://en.wikipedia.org/wiki/Citric_acid_cycle | | | | | |
| TCA cycle | Q15120 | 1.824796927 | 1.841591147 | Y | PDK3 | 5165 | Pyruvate dehydrogenase kinase isozyme 3 | | http://en.wikipedia.org/wiki/Citric_acid_cycle | | | | | |
| TCA cycle | A4D1H4 | | | Y | PDK4 | 5166 | Pyruvate dehydrogenase kinase isozyme 4 | | http://en.wikipedia.org/wiki/Citric_acid_cycle | | | | | |
| TCA cycle | Q9P0J1 | 2.695565857 | 2.575801349 | Y | PDP1 | 54704 | pyruvate dehydrogenase phosphatase catalytic subunit 1 | | http://en.wikipedia.org/wiki/Citric_acid_cycle | | | | | |
| TCA cycle | Q9P2J9 | 1.719315625 | 1.569552988 | Y | PDP2 | 57546 | pyruvate dehydrogenase phosphatase catalytic subunit 2 | | http://en.wikipedia.org/wiki/Citric_acid_cycle | | | | | |

FIG. 32 cont.

TABLE 4

Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| TCA cycle | Q9UI09 | 2.577597352 | 2.16051916 | Y | OGDHL | 55753 | 2-oxoglutarate dehydrogenase-like, mitochondrial | | UniProt | | | | | |
| amino acid metabolism | O14874 | 1.657890012 | 1.771718071 | Y | BCKDK | 10295 | | | UniProt | | | | | |
| amino acid metabolism | O15382 | 2.931948018 | 2.575462581 | Y | BCAT2 | 587 | | | UniProt | | | | | |
| amino acid metabolism | O43272 | . | 1.952341592 | Y | PRODH | 5625 | Proline dehydrogenase 1, mitochondrial (EC 1.5.99.8) (Proline oxidase) (Proline oxidase 2) (p53-induced gene 6 protein) | | UniProt | | | | | |
| amino acid metabolism | O95571 | 2.092379471 | 2.324694876 | Y | ETHE1 | 23474 | Protein ETHE1, mitochondrial (EC 3.-.-.-) (Ethylmalonic encephalopathy protein 1) (Hepatoma subtracted clone one protein) | | | | | | | |

FIG. 32 cont.

TABLE 4

Mitochondrial matrix protein groups detected.

| Category | UniProt Accession | Log2 Rep1 | Log2 Rep2 | matrix expressed | Gene Symbol | ENTREZ | DESCRIPTION | NOTE | REFERENCE | PI | REFERENCE2 | PI2 | REFERENCE.E2 | PI3 |
|---|---|---|---|---|---|---|---|---|---|---|---|---|---|---|
| amino acid metabolism | P00367 | 2.7865660995 | 2.7599218021 | Y | GLUD1 | 2746 | Glutamate dehydrogenase 1, mitochondrial (GDH 1) [EC 1.4.1.3] | | UniProt | | | | | |
| amino acid metabolism | P04181 | 2.3329751391 | 2.2534108938 | Y | OAT | 4942 | Ornithine aminotransferase, mitochondrial [EC 2.6.1.13] (Ornithine delta-aminotransferase) (Ornithine-oxo-acid aminotransferase) [Cleaved into: Ornithine aminotransferase, hepatic form; Ornithine aminotransferase, renal form] | | UniProt | | | | | |
| amino acid metabolism | P11182 | 3.2358967491 | 2.8152568821 | Y | DBT | 1629 | | | UniProt | | | | | |
| amino acid metabolism | P12694 | 2.3122893921 | 1.9998867192 | Y | BCKDHA | 593 | | | UniProt | | | | | |

FIG. 32 cont.

TABLE 4

Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| amino acid metabolism | P21549 | | | y | AGXT | 189 | Serine-pyruvate aminotransferase (SPT) (EC 2.6.1.51) (Alanine-glyoxylate aminotransferase) (AGT) (EC 2.6.1.44) | | UniProt | | | | | |
| amino acid metabolism | P21953 | 2.061238369 | 1.630731141 | Y | BCKDHB | 594 | | | UniProt | | | | | |
| amino acid metabolism | P24752 | 2.601579022 | 2.472338531 | Y | ACAT1 | 38 | | | UniProt | | | | | |
| amino acid metabolism | P26440 | 3.167644961 | 2.908563366 | Y | IVD | 3712 | | | UniProt | | | | | |
| amino acid metabolism | P30038 | 2.199837101 | 2.560381513 | Y | ALDH4A1 | 8659 | Delta-1-pyrroline-5-carboxylate dehydrogenase, mitochondrial (P5C dehydrogenase) (EC 1.5.1.12) (Aldehyde dehydrogenase family 4 member A1) | | UniProt | | | | | |
| amino acid metabolism | P31937 | 2.86498652 | 2.873304297 | Y | HIBADH | 11112 | | | UniProt | | | | | |

FIG. 32 cont.

TABLE 4
Mitochondrial matrix protein groups detected.

| Category | UniProt Accession | log2 Rep1 | log2 Rep2 | matrix exposed | Gene Symbol | ENTREZ | DESCRIPTION | NOTE | REFERENCE | IP1 | REFERENCE2 | IP2 | REFERENCE2 | IP3 |
|---|---|---|---|---|---|---|---|---|---|---|---|---|---|---|
| amino acid metabolism | P35914 | 2.833559341 | 2.790800724 | Y | HMGCL | 3155 | | | UniProt | | | | | |
| amino acid metabolism | P45954 | 1.868450313 | 1.853063861 | Y | ACADSB | 36 | | | UniProt | | | | | |
| amino acid metabolism | P49448 | | | Y | GLUD2 | 2747 | Glutamate dehydrogenase 2, mitochondrial (GDH 2) (EC 1.4.1.3) | | UniProt | | | | | |
| amino acid metabolism | Q02252 | 2.372848738 | 2.679098755 | Y | ALDH6A1 | 4329 | | | UniProt | | | | | |
| amino acid metabolism | Q16762 | 2.218930229 | 2.459346651 | Y | TMTR | 7263 | Thiosulfate sulfurtransferase (EC 2.8.1.1) (Rhodanese) | | | | | | | |
| amino acid metabolism | Q6NVY1 | 2.546285726 | 2.563427881 | Y | HIBCH | 26275 | | | UniProt | | | | | |
| amino acid metabolism | Q8NCN5 | 3.014169187 | 2.702747394 | Y | PDPR | 55066 | Pyruvate dehydrogenase phosphatase regulatory subunit, mitochondrial (PDPr) | | | | | | | |

FIG. 32 cont.

TABLE 4
Mitochondrial matrix protein groups detected.

| Category | UniProt Accession | log2 Rep1 | log2 Rep2 | matrix exposed | Gene Symbol | ENTREZ | DESCRIPTION | NOTE | REFERENCE | PI | REFERENCE2 | PI2 | REFERENCE3 | PI3 |
|---|---|---|---|---|---|---|---|---|---|---|---|---|---|---|
| amino acid metabolism | Q92947 | 2.027269375 | 2.019452242 | Y | GCDH | 2639 | Glutaryl-CoA dehydrogenase, mitochondrial (GCD) [EC 1.3.99.7] | | | | | | | |
| amino acid metabolism | Q96RQ3 | - | - | Y | MCCC1 | 56922 | | | UniProt | | | | | |
| amino acid metabolism | Q99714 | 2.709263882 | 2.549237214 | Y | HSD17B10 | 3028 | | | UniProt | | | | | |
| amino acid metabolism | Q9HCC0 | 1.08774201 | - | Y | MCCC2 | 64087 | | | | | | | | |
| amino acid metabolism | Q9JKU7 | 1.942877188 | 1.735411803 | Y | ACAD8 | 27034 | | | UniProt | | | | | |
| amino acid metabolism | Q9UI12 | - | - | Y | SARDH | 1757 | Sarcosine dehydrogenase, mitochondrial (SarDH) [EC 1.5.99.1] (BPR-2) | | | | | | | |
| amino acid metabolism | P48728 | #N/A | #N/A | Y | AMT | 275 | Aminomethyltransferase | glycine cleavage system T protein | glycine cleavage system Biochem J. 1988 Oct 1;255(1):169-78 | Douce R. | | | | |
| amino acid metabolism | P23378 | 2.846392281 | 2.726777251 | Y | GLDC | 2731 | Glycine dehydrogenase [decarboxylating] | glycine cleavage system P protein | glycine cleavage system Biochem J. 1988 Oct 1;255(1):169-78 | Douce R. | | | | |
| amino acid metabolism | P23434 | 3.433711593 | 3.220477689 | Y | GCSH | 2653 | Glycine cleavage system H protein | glycine cleavage system H protein | glycine cleavage system Biochem J. 1988 Oct 1;255(1):169-78 | Douce R. | | | | |

FIG. 32 cont.

TABLE 4
Mitochondrial matrix protein groups detected.

| Category | UniProt Accession | Log2 Rep1 | Log2 Rep2 | matrix exposed | Gene Symbol | ENTREZ | DESCRIPTION | NOTE | REFERENCE | PI | REFERENCE2 | PI2 | REFERENCE2 | PI3 |
|---|---|---|---|---|---|---|---|---|---|---|---|---|---|---|
| amino acid metabolism | P09622 | 2.27095452 | 1.97371702 | Y | DLD | 1738 | Dihydrolipoyl dehydrogenase | glycine cleavage system L protein | Biochem J. 1988 Oct 1;255(1):169-78 | Douce R. | | | | |

FIG. 33

TABLE 5
Inner mitochondrial membrane complexes detected.

| Category | UniProt Accession | Log2 Rep1 | Log2 Rep2 | matrix exposed | Gene Symbol | ENTREZ | DESCRIPTION | NOTE | REFERENCE |
|---|---|---|---|---|---|---|---|---|---|
| complex I | E7ENF3 | 2.825091653 | 2.674930224 | | NDUFS1 | 4719 | central subunit | lamda subcomplex | Annu Rev Biochem (2006) 75:69-92 |
| complex I | E5KNH5 | 2.601135605 | 2.527263424 | | NDUFV1 | 4723 | central subunit | lamda subcomplex | Annu Rev Biochem (2006) 75:69-92 |
| complex I | O75306 | 2.74151.4893 | 2.599256289 | | NDUFS2 | 4720 | central subunit | lamda subcomplex | Annu Rev Biochem (2006) 75:69-92 |
| complex I | O75489 | 2.953390655 | 2.721960049 | | NDUFS3 | 4722 | central subunit | lamda subcomplex | Annu Rev Biochem (2006) 75:69-92 |
| complex I | P19404 | 2.655029343 | 2.449278238 | | NDUFV2 | 4729 | central subunit | lamda subcomplex | Annu Rev Biochem (2006) 75:69-92 |
| complex I | O00217 | 2.553366401 | 2.460231404 | | NDUFS8 | 4728 | central subunit | lamda subcomplex | Annu Rev Biochem (2006) 75:69-92 |
| complex I | O75251 | 2.629975907 | 2.499562108 | | NDUFS7 | 374291 | central subunit | lamda subcomplex | Annu Rev Biochem (2006) 75:69-92 |
| complex I | P03886 | | | | ND1 | 4535 | central subunit | gamma subcomplex | Annu Rev Biochem (2006) 75:69-92 |
| complex I | P03891 | | | | ND2 | 4536 | central subunit | gamma subcomplex | Annu Rev Biochem (2006) 75:69-92 |
| complex I | Q76XZ5 | 2.423005876 | 2.085299263 | | ND3 | 4537 | central subunit | gamma subcomplex | Annu Rev Biochem (2006) 75:69-92 |
| complex I | Q85L09 | | | | ND4 | 4538 | central subunit | beta subcomplex | Annu Rev Biochem (2006) 75:69-92 |
| complex I | P03901 | | | | ND4L | 4539 | central subunit | gamma subcomplex | Annu Rev Biochem (2006) 75:69-92 |
| complex I | P03915 | 2.499515442 | 2.088619481 | | ND5 | 4540 | central subunit | beta subcomplex | Annu Rev Biochem (2006) 75:69-92 |
| complex I | Q76XZ1 | | | | ND6 | 4541 | central subunit | gamma subcomplex | Annu Rev Biochem (2006) 75:69-92 |

FIG. 33 cont.

TABLE 5
Inner mitochondrial membrane complexes detected.

| Category | UniProt Accession | Log2 Rep1 | Log2 Rep2 | matrix exposed | Gene Symbol | ENTREZ | DESCRIPTION | NOTE | REFERENCE |
|---|---|---|---|---|---|---|---|---|---|
| complex I | Q16795 | 2.617129412 | 2.451953381 | | NDUFA9 | 4704 | accessory subunits; short-chain dehydrogenase | gamma subcomplex | Annu Rev Biochem (2006) 75:69-92 |
| complex I | Q6IBA0 | . | . | | NDUFS5 | 4725 | accessory subunits; cysteine-rich motif | gamma subcomplex | Annu Rev Biochem (2006) 75:69-92 |
| complex I | O75380 | 2.844860922 | 2.643110579 | | NDUFS6 | 4726 | accessory subunits | lamda subcomplex | Annu Rev Biochem (2006) 75:69-92 |
| complex I | O43181 | 2.750286543 | 2.727773942 | | NDUFS4 | 4724 | accessory subunits; phosphorylation | lamda subcomplex | Annu Rev Biochem (2006) 75:69-92 |
| complex I | Q9NX14 | 2.895211775 | 3.084002609 | | NDUFB11 | 54539 | accessory subunits; phosphorylation | beta subcomplex; single transmembrane domain | Annu Rev Biochem (2006) 75:69-92 |
| complex I | O15239 | . | . | | NDUFA1 | 4694 | accessory subunits; phosphorylation | gamma subcomplex; single transmembrane domain | Annu Rev Biochem (2006) 75:69-92 |
| complex I | A6K761 | 2.347879939 | 2.609364975 | | NDUFB10 | 4716 | accessory subunits; cysteine-rich motif | beta subcomplex | Annu Rev Biochem (2006) 75:69-92 |
| complex I | P51970 | . | . | | NDUFA8 | 4702 | accessory subunits; cysteine-rich motif | gamma subcomplex | Annu Rev Biochem (2006) 75:69-92 |
| complex I | O14561 | 2.909909104 | 3.048638886 | | NDUFAB1 | 4706 | accessory subunits; acyl-carrier protein, phosphopantetheine | beta/gamma subcomplex | Annu Rev Biochem (2006) 75:69-92 |
| complex I | Q9Y6M9 | 2.833266341 | 2.758984547 | | NDUFB9 | 4715 | accessory subunits | beta subcomplex | Annu Rev Biochem (2006) 75:69-92 |
| complex I | P17568 | 2.789903023 | 2.667820035 | | NDUFB7 | 4713 | accessory subunits; cysteine-rich motif | beta subcomplex | Annu Rev Biochem (2006) 75:69-92 |
| complex I | Q9UI09 | 2.827333302 | 2.615726219 | | NDUFA12 | 55967 | accessory subunits; nitration | lamda subcomplex | Annu Rev Biochem (2006) 75:69-92 |
| complex I | Q9P0J0 | . | . | | NDUFA13 | 51079 | accessory subunits; proapoptotic factor | lamda subcomplex; single transmembrane domain | Annu Rev Biochem (2006) 75:69-92 |
| complex I | Q86Y39 | . | . | | NDUFA11 | 126328 | accessory subunits; TIM17/22 family | lamda subcomplex | Annu Rev Biochem (2006) 75:69-92 |
| complex I | P56556 | 2.606756745 | 2.537315239 | | NDUFA6 | 4700 | accessory subunits; nitration (CI-B14) | gamma subcomplex | Annu Rev Biochem (2006) 75:69-92 |
| complex I | Q16718 | 2.928884681 | 2.774633411 | | NDUFA5 | 4698 | accessory subunits | lamda subcomplex | Annu Rev Biochem (2006) 75:69-92 |
| complex I | Q6IB60 | 2.981489774 | 3.041410618 | | NDUFB3 | 4709 | accessory subunits | beta subcomplex; single transmembrane domain | Annu Rev Biochem (2006) 75:69-92 |

FIG. 33 cont.

TABLE 5

Inner mitochondrial membrane complexes detected.

| Category | UniProt Accession | Log2 Rep1 | Log2 Rep2 | matrix exposed | Gene Symbol | ENTREZ | DESCRIPTION | NOTE | REFERENCE |
|---|---|---|---|---|---|---|---|---|---|
| complex I | O43678 | 2.915861691 | 2.748219934 | | NDUFA2 | 4695 | accessory subunits; thioredoxin fold | lamda subcomplex | Annu Rev Biochem (2006) 75:69-92 |
| complex I | O95299 | . | . | | NDUFA10 | 4705 | accessory subunits; phosphorylation | gamma subcomplex | Annu Rev Biochem (2006) 75:69-92 |
| complex I | P56181 | 3.073198228 | 2.661208243 | | NDUFV3 | 4731 | accessory subunits | lamda subcomplex | Annu Rev Biochem (2006) 75:69-92 |
| complex I | O95178 | . | . | | NDUFB2 | 4708 | accessory subunits | beta subcomplex; single transmembrane domain | Annu Rev Biochem (2006) 75:69-92 |
| complex I | O95169 | 2.749215928 | 2.727480872 | | NDUFB8 | 4714 | accessory subunits | beta subcomplex; single transmembrane domain | Annu Rev Biochem (2006) 75:69-92 |
| complex I | O43677 | . | . | | NDUFC1 | 4717 | accessory subunits | gamma subcomplex; single transmembrane domain | Annu Rev Biochem (2006) 75:69-92 |
| complex I | O00483 | . | . | | NDUFA4 | 4697 | accessory subunits | beta/gamma subcomplex; single transmembrane domain | Annu Rev Biochem (2006) 75:69-92 |
| complex I | O75438 | . | . | | NDUFB1 | 4707 | accessory subunits | beta subcomplex; single transmembrane domain | Annu Rev Biochem (2006) 75:69-92 |
| complex I | O43674 | 2.420331799 | 2.373335789 | | NDUFB5 | 4711 | accessory subunits | beta subcomplex; single transmembrane domain | Annu Rev Biochem (2006) 75:69-92 |
| complex I | Q5VYT2 | 2.914490709 | 2.83259029 | | NDUFB6 | 4712 | accessory subunits | beta subcomplex; single transmembrane domain | Annu Rev Biochem (2006) 75:69-92 |
| complex I | O95168 | . | . | | NDUFB4 | 4710 | accessory subunits; nitration | beta/gamma subcomplex; single transmembrane domain | Annu Rev Biochem (2006) 75:69-92 |
| complex I | O95182 | 2.829959302 | 2.932628496 | | NDUFA7 | 4701 | accessory subunits | lamda subcomplex | Annu Rev Biochem (2006) 75:69-92 |
| complex I | E9PNU8 | . | . | | NDUFC2 | 4718 | accessory subunits | beta subcomplex; single transmembrane domain | Annu Rev Biochem (2006) 75:69-92 |

FIG. 33 cont.

TABLE 5
Inner mitochondrial membrane complexes detected.

| Category | UniProt Accession | log2 Rep1 | log2 Rep2 | matrix exposed | Gene Symbol | ENTREZ | DESCRIPTION | NOTE | REFERENCE |
|---|---|---|---|---|---|---|---|---|---|
| complex I | O95167 | - | - | | NDUFA3 | 4696 | accessory subunits | gamma subcomplex; single transmembrane domain | Annu Rev Biochem (2006) 75:69-92 |
| complex I assembly factor | Q9Y375 | 2.353810288 | 2.301518345 | mito matrix | NDUFAF1 | 51103 | assembly factors | | IUBMB Life (2011) 63:669-677 |
| complex I assembly factor | Q8NI83 | 3.065566459 | 2.981030074 | mito matrix | NDUFAF2 | 91942 | assembly factors | | IUBMB Life (2011) 63:669-677 |
| complex I assembly factor | Q9Y320 | - | 2.757301189 | IMM, matrix exposed | NDUFAF3 | 25915 | assembly factors | | IUBMB Life (2011) 63:669-677 |
| complex I assembly factor | Q9P032 | 3.222494125 | 2.857463251 | IMM, matrix exposed | NDUFAF4 | 29078 | assembly factors | | IUBMB Life (2011) 63:669-677 |
| complex I assembly factor | Q3TEU4 | 3.031106672 | 2.827638617 | | C20orf7 | 79133 | assembly factors | | IUBMB Life (2011) 63:669-677 |
| complex I assembly factor | B4DQ45 | 1.321358423 | - | | C8orf38 | 137682 | assembly factors | | IUBMB Life (2011) 63:669-677 |
| complex I assembly factor | Q8TB37 | - | - | mito matrix | NUBPL | 80224 | assembly factors | iron-sulfur protein required for NADH dehydrogenase | IUBMB Life (2011) 63:669-677 |

FIG. 33 cont.

TABLE 5
Inner mitochondrial membrane complexes detected.

| Category | UniProt Accession | Log2 Rep1 | Log2 Rep2 | matrix exposed | Gene Symbol | ENTREZ | DESCRIPTION | NOTE | REFERENCE |
|---|---|---|---|---|---|---|---|---|---|
| complex I assembly factor | Q96CU9 | 1.35217517 | - | | FOXRED1 | 55572 | assembly factors | | IUBMB Life (2011) 63:669-677 |
| complex I assembly factor | Q9H845 | 1.911215388 | 1.958181727 | | ACAD9 | 28976 | assembly factors | | IUBMB Life (2011) 63:669-677 |
| complex I assembly factor | A8K401 | - | - | | PHB | 5245 | assembly factors | | IUBMB Life (2011) 63:669-677 |
| complex I assembly factor | A4D273 | - | - | | PTCD1 | 26024 | assembly factors | | IUBMB Life (2011) 63:669-677 |
| complex I assembly factor | E9PAN9 | 2.089795034 | 2.125417641 | mito matrix | ECSIT | 51295 | assembly factors | | IUBMB Life (2011) 63:669-677 |
| complex II | P31040 | 2.700395905 | 2.644083939 | mito matrix | SDHA | 6389 | succinate dehydrogenase complex, subunit A, flavoprotein (fp) | | Cell (2005) 121:1043-1057 |
| complex II | P21912 | 2.914452219 | 2.837867221 | mito matrix | SDHB | 6390 | succinate dehydrogenase complex, subunit B, iron sulfur (Ip) | | Cell (2005) 121:1043-1057 |
| complex II | Q99643 | - | - | IMM, limited matrix access | SDHC | 6391 | succinate dehydrogenase complex, subunit C, integral membrane protein | | Cell (2005) 121:1043-1057 |
| complex II | O14521 | - | - | IMM, limited matrix access | SDHD | 6392 | succinate dehydrogenase complex, subunit D, integral membrane protein | | Cell (2005) 121:1043-1057 |

FIG. 33 cont.

TABLE 5
Inner mitochondrial membrane complexes detected.

| Category | UniProt Accession | Log2 Rep1 | Log2 Rep2 | matrix exposed | Gene Symbol | ENTREZ | DESCRIPTION | NOTE | REFERENCE |
|---|---|---|---|---|---|---|---|---|---|
| complex III | P31930 | 2.414859501 | 2.233827754 | mito matrix | UQCRC1 | 7384 | UBIQUINOL-CYTOCHROME C REDUCTASE COMPLEX CORE PROTEIN I | PDB: 1L0L, chain A | Biochemistry (2002) 41:11692-11702 |
| complex III | P22695 | 1.693662125 | 1.605904076 | mito matrix | UQCRC2 | 7385 | UBIQUINOL-CYTOCHROME C REDUCTASE COMPLEX CORE PROTEIN 2 | PDB: 1L0L, chain B | Biochemistry (2002) 41:11692-11702 |
| complex III | P00156 | | | IMM, limited matrix access | CYTB | 4519 | Cytochrome b | PDB: 1L0L, chain C | Biochemistry (2002) 41:11692-11702 |
| complex III | P08574 | 2.463722818 | 2.662985446 | IMM, matrix exposed | CYC1 | 1537 | Cytochrome c1 | PDB: 1L0L, chain D | Biochemistry (2002) 41:11692-11702 |
| complex III | P47985 | 2.464307776 | 2.119832442 | IMM, matrix exposed | UQCRFS1 | 7386 | UBIQUINOL-CYTOCHROME C REDUCTASE IRON-SULFUR SUBUNIT | PDB: 1L0L, chain E, I | Biochemistry (2002) 41:11692-11702 |
| complex III | E5RIU0 | 3.327877205 | 3.374534165 | mito matrix | UQCRB | 7381 | Ubiquinol-cytochrome C reductase complex 14 kDa protein | PDB: 1L0L, chain F | Biochemistry (2002) 41:11692-11702 |
| complex III | O14949 | 1.096035449 | | IMM, matrix exposed | UQCRQ | 27089 | Ubiquinol-cytochrome C reductase complex ubiquinone-binding protein QP-C | PDB: 1L0L, chain G | Biochemistry (2002) 41:11692-11702 |
| complex III | P07919 | | | IMS | UQCRH | 7388 | Ubiquinol-cytochrome C reductase complex 11 kDa protein | PDB: 1L0L, chain H | Biochemistry (2002) 41:11692-11702 |
| complex III | Q9UDW1 | | | IMM, limited matrix access | UQCR10 | 29796 | Ubiquinol-cytochrome C reductase complex 7.2 kDa protein | PDB: 1L0L, chain J | Biochemistry (2002) 41:11692-11702 |
| complex III | O14957 | | | IMM, limited matrix access | UQCR11 | 10975 | Ubiquinol-cytochrome C reductase complex 6.4 kDa protein | PDB: 1L0L, chain K | Biochemistry (2002) 41:11692-11702 |
| complex IV | P00395 | 1.833665674 | | IMM, limited matrix access | COX1 | 4512 | cytochrome c oxidase subunit I | PDB: 1OCC, chain A | Science (1996) 272:1136-1144 |

FIG. 33 cont.

TABLE 5
Inner mitochondrial membrane complexes detected.

| Category | UniProt Accession | log2 Rep1 | log2 Rep2 | matrix exposed | Gene Symbol | ENTREZ | DESCRIPTION | NOTE | REFERENCE |
|---|---|---|---|---|---|---|---|---|---|
| complex IV | P00403 | 1.336782995 | 1.497717465 | IMM, limited matrix access | COX2 | 4513 | cytochrome c oxidase subunit II | PDB: 1OCC, chain B | Science (1996) 272:1136-1144 |
| complex IV | Q7GIM7 | - | - | IMM, limited matrix access | COX3 | 4514 | cytochrome c oxidase subunit III | PDB: 1OCC, chain C | Science (1996) 272:1136-1144 |
| complex IV | P13073 | 3.169524144 | 2.908373768 | IMM, matrix exposed | COX4I1 | 1327 | cytochrome c oxidase subunit IV isoform 1 | PDB: 1OCC, chain D | Science (1996) 272:1136-1144 |
| complex IV | P20674 | 2.809495562 | 2.862312051 | mito matrix | COX5A | 9377 | cytochrome c oxidase, subunit Va | PDB: 1OCC, chain E | Science (1996) 272:1136-1144 |
| complex IV | P10606 | 3.113416569 | 2.793587765 | mito matrix | COX5B | 1329 | cytochrome c oxidase, subunit Vb | PDB: 1OCC, chain F | Science (1996) 272:1136-1144 |
| complex IV | H6SG15 | - | - | IMM, limited matrix access | COX6A1 | 1337 | cytochrome c oxidase, subunit VI a, polypeptide 1 | PDB: 1OCC, chain G | Science (1996) 272:1136-1144 |
| complex IV | P14854 | - | - | IMS | COX6B1 | 1340 | cytochrome c oxidase, subunit VIb polypeptide 1 | PDB: 1OCC, chain H | Science (1996) 272:1136-1144 |
| complex IV | P09669 | 3.260790019 | 3.067610438 | IMM, matrix exposed | COX6C | 1345 | cytochrome c oxidase, subunit VIc | PDB: 1OCC, chain I | Science (1996) 272:1136-1144 |
| complex IV | P24310 | - | - | IMM, limited matrix access | COX7A1 | 1346 | cytochrome c oxidase, subunit VIIa 1 | PDB: 1OCC, chain J | Science (1996) 272:1136-1144 |
| complex IV | P24311 | - | - | IMM, limited matrix access | COX7B | 1349 | cytochrome c oxidase subunit VIIb | PDB: 1OCC, chain K | Science (1996) 272:1136-1144 |
| complex IV | P15954 | - | - | IMM, limited matrix access | COX7C | 1350 | cytochrome c oxidase, subunit VIIc | PDB: 1OCC, chain L | Science (1996) 272:1136-1144 |
| ATP Synthase | P25705 | 2.374014971 | 2.398736579 | mito matrix | ATP5A1 | 498 | F1-ATP synthase alpha subunit | | Annu Rev Biochem (2009) 78:649-672 |

FIG. 33 cont.

TABLE 5
Inner mitochondrial membrane complexes detected.

| Category | UniProt Accession | Log2 Rep1 | Log2 Rep2 | matrix exposed | Gene Symbol | ENTREZ | DESCRIPTION | NOTE | REFERENCE |
|---|---|---|---|---|---|---|---|---|---|
| ATP synthase | P06576 | 2.212267631 | 2.268154046 | mito matrix | ATP5B | 506 | F1-ATP synthase beta subunit | | Annu Rev Biochem (2009) 78:649-672 |
| ATP synthase | P36542 | - | - | mito matrix | ATP5C1 | 509 | F1-ATP synthase gamma subunit | | Annu Rev Biochem (2009) 78:649-672 |
| ATP synthase | P30049 | 2.201699896 | 2.295520589 | mito matrix | ATP5D | 513 | F1-ATP synthase delta subunit | | Annu Rev Biochem (2009) 78:649-672 |
| ATP synthase | P56381 | - | - | mito matrix | ATP5E | 514 | F1-ATP synthase epsilon subunit | | Annu Rev Biochem (2009) 78:649-672 |
| ATP synthase | P00846 | - | - | IMM, limited matrix access | ATP6 | 4508 | F0-ATP synthase subunit A | | Annu Rev Biochem (2009) 78:649-672 |
| ATP synthase | Q08ET0 | 2.678528657 | 2.544431437 | IMM, matrix exposed | ATP5F1 | 515 | F0-ATP synthase subunit B | | Annu Rev Biochem (2009) 78:649-672 |
| ATP synthase | P05496 | - | - | IMM, limited matrix access | ATP5G1 | 516 | F0-ATP synthase subunit C | | Annu Rev Biochem (2009) 78:649-672 |
| ATP synthase | B7Z7D6 | 2.53437598 | 2.224221153 | mito matrix | ATPAF1 | 64756 | F1 complex assembly factor 1 | | Biochim Biophys Acta (2002) 1555:101-105 |
| ATP synthase | Q8N5M1 | 1.228076806 | - | mito matrix | ATPAF2 | 91647 | F1 complex assembly factor 2 | | Biochim Biophys Acta (2002) 1555:101-106 |
| ATP synthase | P48047 | 2.211734931 | 2.131425981 | mito matrix | ATP5O | 539 | F1-ATP synthase O subunit | | J Mol Biol (2005) 351:824-838 |
| ATP synthase | A0PJH2 | 2.872629621 | 2.787563569 | mito matrix | ATP5H | 10476 | F0-ATP synthase subunit D | | J Mol Biol (2005) 351:824-838 |

FIG. 33 cont.

TABLE 5
Inner mitochondrial membrane complexes detected.

| Category | UniProt Accession | log2 Rep1 | log2 Rep2 | matrix exposed | Gene Symbol | ENTREZ | DESCRIPTION | NOTE | REFERENCE |
|---|---|---|---|---|---|---|---|---|---|
| ATP synthase | Q6IB54 | - | - | mito matrix | ATP5J | 522 | F0-ATP synthase subunit F6 | | J Mol Biol (2005) 351:824-838 |
| ATP synthase | P56385 | - | 2.548175363 | IMM, limited matrix access | ATP5I | 521 | F0-ATP synthase subunit E | | Eukaryot Cell (2005) 4:346-355 |
| ATP synthase | Q8NB90 | - | - | IMM, limited matrix access | ATP8 | 4509 | F0-ATP synthase subunit 8 | | J Biol Chem (2003) 278:17867-17875 |
| ATP synthase | P56134 | 1.214396466 | - | | ATP5J2 | 9551 | F0-ATP synthase subunit F2 | | http://en.wikipedia.org/wiki/ATP_synthase |
| ATP synthase | O75964 | 2.673865274 | 2.276815555 | | ATP5L | 10632 | F0-ATP synthase subunit G | | http://en.wikipedia.org/wiki/ATP_synthase |
| ATP synthase | Q7Z4Y8 | - | - | | ATP5L2 | 267020 | F0-ATP synthase subunit G2 | | http://en.wikipedia.org/wiki/ATP_synthase |
| ATP synthase | Q99766 | 2.727135753 | 2.642737629 | | ATP5S | 27109 | F0-ATP synthase subunit S | | http://en.wikipedia.org/wiki/ATP_synthase |
| TIM22 complex | Q9Y5L4 | - | - | N | TIMM13 | 26517 | Subunit of Tim9-Tim10 chaperone complex and TIM22 complex | Chaperones of intermembrane space (small TIM proteins) | EMBO reports (2008) 9:42-49 |
| TIM22 complex | P62072 | - | - | N | TIMM10 | 26519 | Subunit of Tim9-Tim10 chaperone complex and TIM22 complex | Chaperones of intermembrane space (small TIM proteins) | Ann Rev Biochem (2007) 76:723-49 |
| TIM22 complex | Q9Y5J7 | - | - | N | TIMM9 | 26520 | Subunit of Tim9-Tim10 chaperone complex and TIM22 complex | Chaperones of intermembrane space (small TIM proteins) | Ann Rev Biochem (2007) 76:723-49 |
| TIM22 complex | Q9Y5J6 | - | - | | TIMM9B | 26515 | Mitochondrial import inner membrane translocase subunit Tim9 B | | |

FIG. 33 cont.

TABLE 5
Inner mitochondrial membrane complexes detected.

| Category | UniProt Accession | log2 Rep1 | log2 Rep2 | matrix exposed | Gene Symbol | ENTREZ | DESCRIPTION | NOTE | REFERENCE |
|---|---|---|---|---|---|---|---|---|---|
| TIM22 complex | O60220 | - | - | N | TIMM8A | 1678 | Subunit of Tim9-Tim10 chaperone complex and TIM22 complex | Chaperones of intermembrane space (small TIM proteins) | EMBO reports (2008) 9:42-49 |
| TIM22 complex | Q3XAN6 | - | - | N | TIMM8B | 26521 | Subunit of Tim9-Tim10 chaperone complex and TIM22 complex | Chaperones of intermembrane space (small TIM proteins) | EMBO reports (2008) 9:42-49 |
| MIA complex | Q8N4Q1 | - | - | N | CHCHD4 | 131474 | Mitochondrial intermembrane space import and assembly protein 40 (Coiled-coil-helix-coiled-coil-helix domain-containing protein 4) | Mitochondrial intermembrane space import and assembly machinery (MIA) | EMBO reports (2008) 9:42-49 |
| TIM23 complex | O14925 | - | - | N | TIMM23 | 100287932 | Channel-forming subunit of TIM23 complex | Presequence translocase of inner membrane (TIM23 complex) | Ann Rev Biochem (2007) 76:723-49 |
| TIM23 complex | Q99595 | - | - | N | TIMM17A | 10440 | Regulator of Tim23 channel, sorting of preproteins | Presequence translocase of inner membrane (TIM23 complex) | Ann Rev Biochem (2007) 76:723-49 |
| TIM23 complex | O60830 | - | - | N | TIMM17B | 10245 | Regulator of Tim23 channel, sorting of preproteins | Presequence translocase of inner membrane (TIM23 complex) | Ann Rev Biochem (2007) 76:723-49 |
| TIM22 complex | Q9Y584 | - | - | N | TIMM22 | 29928 | Central, channel-forming subunit of TIM22 complex | Carrier translocase of inner membrane (TIM22 complex) | Ann Rev Biochem (2007) 76:723-49 |
| TIM23 complex | Q13099 | - | - | N | TIMM50 | 92609 | Intermembrane space-exposed subunit of TIM23 complex | Presequence translocase of inner membrane (TIM23 complex) | Ann Rev Biochem (2007) 76:723-49 |
| TIM23 complex | A8K1K8 | - | - | N | TIMM21 | 29090 | Interacts with TOM complex and respiratory chain | Presequence translocase of inner membrane (TIM23 complex) | EMBO reports (2008) 9:42-49 |
| PAM complex | P10809 | 2.603199234 | 2.494347177 | | HSPD1 | 3329 | Molecular chaperone, core of PAM (mtHsp70, HSP60) | Presequence translocase-associated motor (PAM) | Trends Cell Biol (2007) 17:586-592 |
| PAM complex | Q9Y3D7 | 3.059007597 | 2.701096588 | | PAM16 | 51025 | J-related regulator of Pam18 | Presequence translocase-associated motor (PAM) | Ann.Rev.Biochem. (2007) 76:723-63 |

FIG. 33 cont.

TABLE 5
Inner mitochondrial membrane complexes detected.

| Category | UniProt Accession | Log2 Rep1 | Log2 Rep2 | matrix exposed | Gene Symbol | ENTREZ | DESCRIPTION | NOTE | REFERENCE |
|---|---|---|---|---|---|---|---|---|---|
| PAM complex | Q96DA6 | 2.869411893 | 2.356149876 | Y | DNAJC19 | 131118 | J-protein at inner membrane, complex with Pam16 (Pam18) | Presequence translocase-associated motor (PAM) | Ann.Rev.Biochem.(2007) 76:723–64 |
| PAM complex | O43615 | 2.518526193 | 2.361494845 | Y | TIMM44 | 10469 | Binding partner of mtHsp70 at inner membrane | Presequence translocase-associated motor (PAM) | Ann Rev Biochem (2007) 76:723–58 |
| TOM complex | O94826 | - | - | OMM | TOMM70A | 9868 | Tom70, receptor for non-cleavable precursor proteins | Surface receptor | Ann Rev Biochem (2007) 76:723–49 |
| TOM complex | O96008 | - | - | OMM | TOMM40 | 10452 | Tom40, general import pore | Translocation pore | Ann Rev Biochem (2007) 76:723–49 |
| TOM complex | Q969M1 | - | - | OMM | TOMM40L | 84134 | | Translocation pore | Ann Rev Biochem (2007) 76:723–49 |
| TOM complex | Q9Y5C5 | - | - | OMM | TOMM22 | 56993 | Tom22, central receptor | Surface receptor | Ann Rev Biochem (2007) 76:723–49 |
| TOM complex | Q15388 | - | - | OMM | TOMM20 | 9804 | Tom20, presequence receptor | Surface receptor | Ann Rev Biochem (2007) 76:723–49 |
| TOM complex | Q6UXN7 | - | - | OMM | TOMM20L | 387990 | TOMM20-like protein 1 | | Biochim Biophys Acta (2002) 1592:97–105 |
| TOM complex | Q7Z4R5 | - | - | OMM | TOMM7 | 54543 | Tom7, stability/assembly factor | Translocation pore | Ann Rev Biochem (2007) 76:723–49 |
| TOM complex | Q96B49 | - | - | OMM | TOMM6 | 100188893 | Tom6, stability/assembly factor | Translocation pore | Ann Rev Biochem (2007) 76:723–49 |
| TOM complex | Q8N4H5 | - | - | OMM | TOMM5 | 401505 | Tom5, preprotein transfer and assembly factor | Translocation pore | Ann Rev Biochem (2007) 76:723–49 |

FIG. 33 cont.

TABLE 5
Inner mitochondrial membrane complexes detected.

| Category | UniProt Accession | Log2 Rep1 | Log2 Rep2 | matrix exposed | Gene Symbol | ENTREZ | DESCRIPTION | NOTE | REFERENCE |
|---|---|---|---|---|---|---|---|---|---|
| TOM complex | Q13505 | - | - | OMM | MTX1 | 4580 | Metaxin-1 (Mitochondrial outer membrane import complex protein 1) | | Biochim Biophys Acta (2002) 1592:97-105 |
| TOM complex | O75431 | - | - | OMM | MTX2 | 10651 | Metaxin-2 (Mitochondrial outer membrane import complex protein 2) | | Biochim Biophys Acta (2002) 1592:97-105 |
| TOM complex | Q9Y2380 | - | - | OMM | MTX3 | 345778 | Metaxin-3 | | Biochim Biophys Acta (2002) 1592:97-105 |
| TOM complex | Q15785 | - | - | OMM | TOMM34 | 10953 | Mitochondrial import receptor subunit TOMM34 (hTom34) | | Biochim Biophys Acta (2002) 1592:97-105 |

FIG. 34

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| SAM complex | Q9Y512 | 2.544629673 | 2.319622704 | OMM | SAMM50 | 25813 | | Sorting and assembly machinery | Ann Rev Biochem (2007) 76:723-49 |
| FA metabolism | Q13057 | 1.371968777 | 1.292063197 | OMM | COASY | 80347 | bifunctional coenzyme A synthase (CoA synthase) | | J Biol Chem (2003) 278:50316-21 |
| FA metabolism | P50416 | - | - | OMM | CPT1A | 1374 | Carnitine O-palmitoyltransferase 1, liver isoform | | Biochim Biophys Acta (2000) 1486:1-17 |
| FA metabolism | Q92523 | - | - | OMM | CPT1B | 1375 | Carnitine O-palmitoyltransferase 1, muscle isoform | | Biochim Biophys Acta (2000) 1486:1-17 |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| FA metabolism | Q8TCG5 | - | - | OMM | CPT1C | 126129 | Carnitine O-palmitoyltransferase 1, brain isoform | | Biochim Biophys Acta (2000) 1486:1-17 |
| FA metabolism | A6XG93 | - | - | OMM | KMO | 8564 | Kynurenine 3-monooxygenase | | J Biochem (1998) 123:253-262 |
| FA metabolism | P21397 | - | - | OMM | MAOA | 4128 | monoamine oxidase A | | J Histochem Cytochem (2005) 53:1149-1158 |
| FA metabolism | P27338 | - | - | OMM | MAOB | 4129 | monoamine oxidase B | | J Histochem Cytochem (2005) 53:1149-1158 |
| FA metabolism | P33121 | - | - | OMM | ACSL1 | 2180 | Long-chain-fatty-acid--CoA ligase 1 | | J Biol Chem (1990) 265:8681-8685 |
| FA metabolism | O95573 | - | - | OMM | ACSL3 | 2181 | Long-chain-fatty-acid--CoA ligase 3 | | J Biol Chem (1990) 265:8681-8685 |
| FA metabolism | Q5JWB | - | - | OMM | ACSL4 | 2182 | Long-chain-fatty-acid--CoA ligase 4 | | J Biol Chem (1990) 265:8681-8685 |
| FA metabolism | Q9ULC5 | - | - | OMM | ACSL5 | 51703 | Long-chain-fatty-acid--CoA ligase 5 | | J Biol Chem (1990) 265:8681-8685 |
| FA metabolism | B4DFW3 | - | - | OMM | ACSL6 | 23305 | Long-chain-fatty-acid--CoA ligase 6 | | J Biol Chem (1990) 265:8681-8685 |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| FA metabolism | O14975 | - | - | OMM | SLC27A2 | 11001 | solute carrier family 27 (fatty acid transporter), member 2 | | J Biol Chem (1990) 265:8681-8685 |
| Transporter | B3KTS5 | - | - | OMM | VDAC1 | 7416 | | | Biochim Biophys Acta. 2012 Jun;1818(6):1457-65 |
| Transporter | P45880 | - | - | OMM | VDAC2 | 7417 | | | Biochim Biophys Acta. 2012 Jun;1818(6):1457-65 |
| Transporter | Q9Y277 | - | - | OMM | VDAC3 | 7419 | | | Biochim Biophys Acta. 2012 Jun;1818(6):1457-65 |
| Others | Q96GF1 | - | - | OMM | RNF185 | 91445 | E3 ubiquitin-protein ligase RNF185 (RING finger protein 185) | | PLoS One (2011) 6:e24367 |
| Others | Q12981 | - | - | OMM | BNIP1 | 662 | BCL2/adenovirus E1B 19kDa interacting protein 1 | | PLoS One (2011) 6:e24367 |
| Others | Q9NX47 | - | - | OMM | MARCH5 | 54708 | membrane-associated ring finger (C3HC4) 5 | | EMBO J (2006) 25:3618-3626 |
| Others | F5H6C8 | - | - | OMM | MAVS | 57506 | mitochondrial antiviral signaling protein | | Nature (2006) 431:573-7 |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| Others | Q86UT6 | 2.362820693 | 2.270499439 | OMM | NLRX1 | 79671 | NLR family member X1 (Caterpillar protein 11.3) (CLR11.3) (Nucleotide-binding oligomerization domain protein 26) (Nucleotide-binding oligomerization domain protein 5) (Nucleotide-binding oligomerization domain protein 9) | | Nature (2008) 451:573-7 |
| Mito fusion/fission | Q9Y3D6 | - | - | OMM | FIS1 | 51024 | Mitochondrial fission 1 protein | | Mol Biol Cell (2008) 19:2402-12 |
| Mito fusion/fission | Q9GZY8 | - | - | OMM | MFF | 56947 | Mitochondrial fission factor | | Mol Biol Cell (2008) 19:2402-12 |
| Mito fusion/fission | Q8IWA4 | - | - | OMM | MFN1 | 55669 | Mitofusin-1 | | J Cell Sci (2003) 116:2763-74 |
| Mito fusion/fission | O95140 | - | - | OMM | MFN2 | 9927 | Mitofusin-2 | | J Cell Sci (2003) 116:2763-74 |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| Apoptosis | Q6FHZ1 | - | - | OMM | BAD | 572 | Bcl2 antagonist of cell death (BAD) | | Int J Biochem Cell Biol (2009) 41:1884-9 |
| Apoptosis | Q16611 | - | - | OMM | BAK1 | 578 | Bcl-2 homologous antagonist/killer (Apoptosis regulator BAK) | | Int J Biochem Cell Biol (2009) 41:1884-9 |
| Apoptosis | Q07812 | - | - | OMM | BAX | 581 | Apoptosis regulator BAX | | Int J Biochem Cell Biol (2009) 41:1884-9 |
| Apoptosis | B2Z879 | - | - | OMM | BID | 637 | BH3-interacting domain death agonist (BID) | | Int J Biochem Cell Biol (2009) 41:1884-9 |
| Apoptosis | C9JHD5 | - | - | OMM | BCL2 | 596 | Apoptosis regulator Bcl-2 | | J Cell Biol. (2003) 160:53-64 |
| Apoptosis | Q07817 | - | - | OMM | BCL2L1 | 598 | Bcl-2-like protein 1 (Bcl2-L-1) (BCL-XL) | | J Cell Biol. (2003) 160:53-64 |
| Mito fusion/fission | Q59GN9 | - | - | OMM | DNM1L | 10059 | Dynamin-1-like protein (DRP1) | | Int J Biochem Cell Biol (2009) 41:1884-9 |
| Mitophagy | Q8IVP5 | - | - | OMM | FUNDC1 | 139341 | | | Nat Cell Biol (2012) 14:177-85 |
| HW OMM | Q9NP58 | - | - | | ABCB6 | 10058 | ATP-binding cassette sub-family B member 6, mitochondrial (Mitochondrial ABC transporter 3) (Mt-ABC transporter 3) (P-glycoprotein-related protein) (Ubiquitously-expressed mammalian ABC half transporter) | mitochondrial outer membrane | mitochondrial envelope | mitochondrion | integral to membrane | ATP-binding cassette (ABC) transporter complex | membrane | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | Q6BRQ8 | - | - | | AIFM2 | 84883 | Apoptosis-inducing factor 2 (EC 1.-.-.-) (Apoptosis-inducing factor homologous mitochondrion-associated inducer of death) (Apoptosis-inducing factor-like mitochondrion-associated inducer of death) (p53-responsive gene 3 protein) | cytosol \| mitochondrial outer membrane \| mitochondrion \| integral to membrane \| membrane \| cytoplasm | |
| HW OMM | B4DN86 | - | - | | AKAP1 | 8165 | A-kinase anchor protein 1, mitochondrial (A-kinase anchor protein 149 kDa) (AKAP 149) (Dual specificity A-kinase-anchoring protein 1) (D-AKAP-1) (Protein kinase A-anchoring protein 1) (PRKA1) (Spermatid A-kinase anchor protein 84) (S-AKAP84) | mitochondrion \| mitochondrial cristae \| cytoplasm \| mitochondrial outer membrane \| neuromuscular junction \| integral to membrane \| lipid particle \| postsynaptic membrane \| mitochondrial matrix | |
| HW OMM | Q9BPG3 | - | - | | BBC3 | 27113 | Bcl-2-binding component 3 (JFY-1) (p53 up-regulated modulator of apoptosis) | mitochondrion | |
| HW OMM | O43521 | - | - | | BCL2L11 | 10018 | Bcl-2-like protein 11 (Bcl2-L-11) (Bcl2-interacting mediator of cell death) | cytosol \| endomembrane system \| mitochondrion \| peripheral to membrane of membrane fraction \| plasma membrane \| membrane fraction \| cytoplasm | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | Q96LC9 | - | - | | BMF | 90427 | Bcl-2-modifying factor | cytosol \| acrosomal vesicle \| plasma membrane \| myosin complex \| cytoplasm | |
| HW OMM | Q12983 | - | - | | BNIP3 | 664 | BCL2/adenovirus E1B 19 kDa protein-interacting protein 3 | nucleoplasm \| mitochondrion \| nuclear envelope \| cytoplasm \| integral to membrane \| mitochondrial membrane \| integral to mitochondrial outer membrane \| nucleus \| membrane \| dendrite | |
| HW OMM | Q6IBV1 | - | | | BNIP3L | 665 | BCL2/adenovirus E1B 19 kDa protein-interacting protein 3-like (Adenovirus E1B19K-binding protein B5) (BCL2/adenovirus E1B 19 kDa protein-interacting protein 3A) (NIP3-like protein X) (NIP3L) | mitochondrion \| nuclear envelope \| endoplasmic reticulum \| mitochondrial envelope \| intrinsic to membrane \| integral to membrane \| nucleus \| membrane | |
| HW OMM | Q8WY22 | - | - | | BRI3BP | 140707 | BRI3-binding protein (I3-binding protein) (Cervical cancer 1 proto-oncogene-binding protein KG19) (HCCRBP-1) | integral to membrane \| membrane | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | Q14790 | - | - | | CASP8 | 841 | Caspase-8 (CASP-8) (EC 3.4.22.61) (Apoptotic cysteine protease) (Apoptotic protease Mch-5) (CAP4) (FADD-homologous ICE/ced-3-like protease) (FADD-like ICE) (FLICE) (ICE-like apoptotic protease 5) (MORT1-associated ced-3 homolog) (MACH) [Cleaved into: Caspase-8 subunit p18; Caspase-8 subunit p10] | cytosol | mitochondrial outer membrane | mitochondrion | membrane raft | cytoskeleton | nucleus | death-inducing signaling complex | Noc1p-Noc2p complex | cytoplasm | |
| HW OMM | Q9NZ45 | - | - | | CISD1 | 55847 | CDGSH iron-sulfur domain-containing protein 1 (MitoNEET) | mitochondrial outer membrane | mitochondrion | integral to membrane | membrane | |
| HW OMM | Q8N5K1 | - | - | | CISD2 | 493856 | CDGSH iron-sulfur domain-containing protein 2 [Endoplasmic reticulum intermembrane small protein] (MitoNEET-related 1 protein) (Miner1) (Nutrient-deprivation autophagy factor-1) (NAF-1) | mitochondrial outer membrane | mitochondrion | integral to membrane | endoplasmic reticulum | endoplasmic reticulum membrane | protein complex | membrane | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | P00167 | - | - | | CYB5A | 1528 | Cytochrome b5 (Microsomal cytochrome b5 type A) (MCB5) | mitochondrial outer membrane \| mitochondrion \| integral to membrane \| endoplasmic reticulum \| microsome \| endoplasmic reticulum membrane \| membrane \| cytoplasm | |
| HW OMM | O43169 | - | - | | CYB5B | 80777 | Cytochrome b5 type B (Cytochrome b5 outer mitochondrial membrane isoform) | mitochondrial outer membrane \| mitochondrion \| integral to membrane \| mitochondrial inner membrane \| microsome \| membrane | |
| HW OMM | P00387 | - | - | | CYB5R3 | 1727 | NADH-cytochrome b5 reductase 3 (B5R) (Cytochrome b5 reductase) (EC 1.6.2.2) (Diaphorase-1) [Cleaved into: NADH-cytochrome b5 reductase 3 membrane-bound form; NADH-cytochrome b5 reductase 3 soluble form] | mitochondrial outer membrane \| mitochondrion \| endoplasmic reticulum \| mitochondrial inner membrane \| endoplasmic reticulum membrane \| membrane \| hemoglobin complex \| cytoplasm | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | O15528 | - | - | | CYP27B1 | 1594 | 25-hydroxyvitamin D-1 alpha hydroxylase, mitochondrial (EC 1.14.13.13) (25-OHD-1 alpha-hydroxylase) (25-hydroxyvitamin D(3) 1-alpha-hydroxylase) (VD3 1A hydroxylase) (Calcidiol 1-monooxygenase) (Cytochrome P450 subfamily XXVIIB polypeptide 1) (Cytochrome P450C1 alpha) (Cytochrome P450VD1-alpha) (Cytochrome p450 27B1) | mitochondrion ; mitochondrial membrane ; membrane ; cytoplasm | |
| HW OMM | E5KRQ5 | - | - | | DMPK | 1760 | Myotonin-protein kinase (MT-PK) (EC 2.7.11.1) (DM-kinase) (DMK) (DM1 protein kinase) (DMPK) (Myotonic dystrophy protein kinase) | | 0 |
| HW OMM | Q9BF15 | - | - | | GIMAP5 | 55340 | GTPase IMAP family member 5 (Immunity-associated nucleotide 4-like 1 protein) (Immunity-associated nucleotide 5 protein) (IAN-5) (hIAN5) (Immunity-associated protein 3) | mitochondrial outer membrane ; integral to membrane ; membrane | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | P32189 | - | - | | GK | 2710 | Glycerol kinase (GK) (Glycerokinase) [EC 2.7.1.30] (ATP:glycerol 3-phosphotransferase) | | 0 |
| HW OMM | Q14410 | - | - | | GK2 | 2712 | Glycerol kinase 2 (GK 2) (Glycerokinase 2) [EC 2.7.1.30] (ATP:glycerol 3-phosphotransferase 2) (Glycerol kinase, testis specific 2) | mitochondrial outer membrane \| mitochondrion \| membrane \| cytoplasm | |
| HW OMM | Q9HCL2 | - | - | | GPAM | 57678 | Glycerol-3-phosphate acyltransferase 1, mitochondrial (GPAT-1) [EC 2.3.1.15] | cytosol \| mitochondrial outer membrane \| mitochondrion \| integral to membrane \| mitochondrial inner membrane \| membrane | |
| HW OMM | Q6NUI2 | - | - | | GPAT2 | 150763 | Glycerol-3-phosphate acyltransferase 2, mitochondrial (GPAT-2) [EC 2.3.1.15] (xGPAT1) | mitochondrial outer membrane \| mitochondrion \| integral to membrane \| membrane | |
| HW OMM | Q59FD4 | - | - | | HK1 | 3098 | Hexokinase-1 [EC 2.7.1.1] (Brain form hexokinase) (Hexokinase type I) (HK I) | mitochondrial outer membrane \| mitochondrion \| membrane | |
| HW OMM | P52789 | - | - | | HK2 | 3099 | Hexokinase-2 [EC 2.7.1.1] (Hexokinase type II) (HK II) (Muscle form hexokinase) | mitochondrial outer membrane \| mitochondrion \| membrane | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | A8K0H0 | - | - | | IFI27 | 3429 | Interferon alpha-inducible protein 27, mitochondrial (p27) (Interferon alpha-induced 11.5 kDa protein) (Interferon-stimulated gene 12a protein) (ISG12(a)) | mitochondrion | integral to membrane | membrane | |
| HW OMM | Q6P1Q0 | - | - | | LETMD1 | 25875 | LETM1 domain-containing protein 1 (Cervical cancer 1 proto-oncogene protein p40) (Cervical cancer proto-oncogene 2 protein) (HCCR-2) (HCRR-2) | integral to membrane | membrane | |
| HW OMM | Q17RV3 | - | - | | LRRK2 | 120892 | Leucine-rich repeat serine/threonine-protein kinase 2 [EC 2.7.11.1] (Dardarin) | axon | synaptosome | membrane raft | synaptic vesicle | intracellular | cytoplasm | trans-Golgi network | external side of mitochondrial outer membrane | plasma membrane | microsome | dendrite | membrane fraction | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | Q96Z23 | - | - | | MOSC2 | 54996 | MOSC domain-containing protein 2, mitochondrial (EC 1.-.-.-) (Mitochondrial amidoxime reducing component 2) (mARC2) (Moco sulfurase C-terminal domain-containing protein 2) (Molybdenum cofactor sulfurase C-terminal domain-containing protein 2) | mitochondrial outer membrane \| mitochondrion \| mitochondrial inner membrane \| membrane | |
| HW OMM | Q07820 | - | - | | MCL1 | 4170 | Induced myeloid leukemia cell differentiation protein Mcl-1 (Bcl-2-like protein 3) (Bcl2-L-3) (Bcl-2-related protein EAT/mcl1) (mcl1/EAT) | mitochondrial outer membrane \| nucleoplasm \| mitochondrion \| integral to membrane \| nucleus \| membrane \| cytoplasm | |
| HW OMM | P10620 | - | - | | MGST1 | 4257 | Microsomal glutathione S-transferase 1 (Microsomal GST-1) (EC 2.5.1.18) (Microsomal GST-i) | mitochondrion \| endoplasmic reticulum \| mitochondrial inner membrane \| apical part of cell \| mitochondrial outer membrane \| peroxisomal membrane \| nucleus \| microsome \| membrane | |
| HW OMM | Q9HAP2 | - | - | | MLXIP | 22877 | MLX-interacting protein (Class E basic helix-loop-helix protein 36) (bHLHe36) (Transcriptional activator MondoA) | mitochondrial outer membrane \| mitochondrion \| nucleus \| membrane \| cytoplasm | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | Q9BUK6 | - | - | | MSTO1 | 55154 | Protein misato homolog 1 | mitochondrial outer membrane \| mitochondrion \| protein complex \| membrane \| cytoplasm | |
| HW OMM | P42345 | - | - | | MTOR | 2475 | Serine/threonine-protein kinase mTOR (EC 2.7.11.1) (FKBP-binding protein 12-rapamycin complex-associated protein 1) (FKBP12-rapamycin complex-associated protein) (Mammalian target of rapamycin) (mTOR) (Mechanistic target of rapamycin) (Rapamycin and FKBP12 target 1) (Rapamycin target protein 1) | neuronal cell body \| endomembrane system \| phosphoinositide 3-kinase complex \| mitochondrion \| Golgi apparatus \| endoplasmic reticulum \| Golgi membrane \| cytoplasm \| TORC1 complex \| cytosol \| mitochondrial outer membrane \| TORC2 complex \| soluble fraction \| nucleus \| endoplasmic reticulum membrane \| dendrite \| membrane | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | Q969V5 | - | - | | MUL1 | 79594 | Mitochondrial ubiquitin ligase activator of NFKB 1 (EC 6.3.2.-) (E3 SUMO-protein ligase MUL1) (E3 ubiquitin-protein ligase MUL1) (Growth inhibition and death E3 ligase) (Mitochondrial-anchored protein ligase) (MAPL) (Putative NF-kappa-B-activating protein 266) (RING finger protein 218) | mitochondrial outer membrane \| mitochondrion \| integral to membrane \| integral to mitochondrial outer membrane \| peroxisome \| membrane | |
| HW OMM | B4E218 | - | - | | MYO19 | 80179 | Unconventional myosin-XIX (Myosin head domain-containing protein 1) | myosin complex \| cytoplasm | |
| HW OMM | Q9UBF8 | - | - | | PI4KB | 5298 | Phosphatidylinositol 4-kinase beta (PI4K-beta) (PI4Kbeta) (PtdIns 4-kinase beta) (EC 2.7.1.67) (NPIK) (PI4K92) | endosome \| endomembrane system \| mitochondrion \| Golgi apparatus \| endoplasmic reticulum \| perinuclear region of cytoplasm \| rough endoplasmic reticulum membrane \| cytoplasm \| mitochondrial outer membrane \| membrane | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | Q9BXM7 | . | . | | PINK1 | 65018 | Serine/threonine-protein kinase PINK1, mitochondrial (EC 2.7.11.1) (BRPK) (PTEN-induced putative kinase protein 1) | cytosol | mitochondrial outer membrane | mitochondrion | integral to membrane | mitochondrial inner membrane | membrane | |
| HW OMM | Q8N2A8 | . | . | | PLD6 | 201164 | Mitochondrial cardiolipin hydrolase (EC 3.1.4.-) (Choline phosphatase 6) (Mitochondrial phospholipase) (MitoPLD) (Phosphatidylcholine-hydrolyzing phospholipase D6) (Phospholipase D6) (PLD 6) (Protein zucchini homolog) | integral to membrane | membrane | |
| HW OMM | Q8N589 | . | . | | PMAIP1 | 5366 | Phorbol-12-myristate-13-acetate-induced protein 1 (PMA-induced protein 1) (Immediate-early-response protein APR) (Protein Noxa) | mitochondrion | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | G3V1A9 | - | - | | PPP2R2B | 5521 | Serine/threonine-protein phosphatase 2A 55 kDa regulatory subunit B beta isoform (PP2A subunit B isoform B55-beta) (PP2A subunit B isoform PR55-beta) (PP2A subunit B isoform R2-beta) (PP2A subunit B isoform beta) | mitochondrial outer membrane \| mitochondrion \| cytoskeleton \| membrane \| protein phosphatase type 2A complex \| cytoplasm | |
| HW OMM | Q9BXF6 | - | - | | RAB11FIP5 | 26056 | Rab11 family-interacting protein 5 (Rab11-FIP5) (Gamma-SNAP-associated factor 1) (Gaf-1) (Phosphoprotein pp75) (Rab11-interacting protein Rip11) | endosome \| mitochondrial outer membrane \| mitochondrion \| membrane \| recycling endosome membrane \| cytoplasm | |
| HW OMM | P04049 | - | - | | RAF1 | 5894 | RAF proto-oncogene serine/threonine-protein kinase (EC 2.7.11.1) (Proto-oncogene c-RAF) (cRaf) (Raf-1) | cytosol \| mitochondrial outer membrane \| plasma membrane | |
| HW OMM | H7BXZ6 | - | - | | RHOT1 | 55288 | Mitochondrial Rho GTPase 1 (MIRO-1) (hMiro-1) (EC 3.6.5.-) (Rac-GTP-binding protein-like protein) (Ras homolog gene family member T1) | mitochondrial outer membrane \| mitochondrion \| integral to membrane \| integral to mitochondrial outer membrane \| intracellular \| membrane | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | Q8IXI1 | - | - | | RHOT2 | 89941 | Mitochondrial Rho GTPase 2 (MIRO-2) (hMiro-2) (EC 3.6.5.-) (Ras homolog gene family member T2) | mitochondrial outer membrane | mitochondrion | integral to membrane | integral to mitochondrial outer membrane | intracellular | membrane | |
| HW OMM | P23443 | - | - | | RPS6KB1 | 6198 | Ribosomal protein S6 kinase beta-1 (S6K-beta-1) (S6K1) (EC 2.7.11.1) (70 kDa ribosomal protein S6 kinase 1) (P70S6K1) (p70-S6K 1) (Ribosomal protein S6 kinase I) (Serine/threonine-protein kinase 14A) (p70 ribosomal S6 kinase alpha) (p70 S6 kinase alpha) (p70 S6K-alpha) (p70 S6KA) | synaptosome | mitochondrion | perinuclear region of cytoplasm | cytoplasm | mitochondrial outer membrane | cytosol | synapse | cell junction | soluble fraction | nucleus | cell surface | membrane | |
| HW OMM | Q9Y371 | - | - | | SH3GLB1 | 51100 | Endophilin-B1 (Bax-interacting factor 1) (BIF-1) (SH3 domain-containing GRB2-like protein B1) | mitochondrial outer membrane | mitochondrion | Golgi apparatus | nucleus | membrane | Golgi membrane | cytoplasm | |
| HW OMM | Q8WWI5 | - | - | | SLC44A1 | 23446 | Choline transporter-like protein 1 (CDw92) (Solute carrier family 44 member 1) (CD antigen CD92) | mitochondrial outer membrane | mitochondrion | integral to membrane | plasma membrane | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | Q96C03 | - | - | | SMCR7 | 125170 | Mitochondrial dynamic protein MID49 (Mitochondrial dynamic protein of 49 kDa) (Smith-Magenis syndrome chromosomal region candidate gene 7 protein) | integral to membrane \| membrane | |
| HW OMM | Q9NQG6 | - | - | | SMCR7L | 54471 | Mitochondrial dynamic protein MID51 (Mitochondrial dynamic protein of 51 kDa) (Mitochondrial elongation factor 1) (Smith-Magenis syndrome chromosomal region candidate gene 7 protein-like) | mitochondrion \| integral to membrane \| membrane | |
| HW OMM | O75324 | - | - | | SNN | 8303 | Stannin (AG8_1) | mitochondrial outer membrane \| mitochondrion \| integral to membrane \| membrane | |
| HW OMM | Q8TC71 | - | - | | SPATA18 | 132671 | Mitochondria-eating protein (Spermatogenesis-associated protein 18) | cytoplasm | |
| HW OMM | Q7Z5L4 | - | - | | SPATA19 | 219938 | Spermatogenesis-associated protein 19, mitochondrial (Spermatogenic cell-specific gene 1 protein) (Spergen-1) | mitochondrial outer membrane \| mitochondrion \| membrane | |

FIG. 34 cont.

TABLE 5
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | Q86WV5 | - | - | | TMEM173 | 340061 | Transmembrane protein 173 (Endoplasmic reticulum interferon stimulator) (ERIS) (Mediator of IRF3 activation) (hMITA) (Stimulator of interferon genes protein) (hSTING) | mitochondrial outer membrane | integral to membrane | endoplasmic reticulum | plasma membrane | endoplasmic reticulum membrane | |
| HW OMM | P30536 | - | - | | TSPO | 706 | Translocator protein (Mitochondrial benzodiazepine receptor) (PKBS) (Peripheral-type benzodiazepine receptor) (PBR) | mitochondrial outer membrane | integral to membrane | membrane | |
| HW OMM | Q70CQ3 | - | - | | USP30 | 84749 | Ubiquitin carboxyl-terminal hydrolase 30 (EC 3.4.19.12) (Deubiquitinating enzyme 30) (Ubiquitin thioesterase 30) (Ubiquitin-specific-processing protease 30) (Ub-specific protease 30) | mitochondrial outer membrane | integral to membrane | membrane | |

FIG. 34 cont.

TABLE 6
Outer mitochondrial membrane proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW OMM | P23763 | - | - | | VAMP1 | 6843 | Vesicle-associated membrane protein 1 (VAMP-1) (Synaptobrevin-1) | cytoplasmic vesicle membrane \| synaptosome \| mitochondrion \| mitochondrial outer membrane \| cytoplasmic vesicle \| synapse \| synaptic vesicle membrane \| cell junction \| integral to plasma membrane \| membrane | |

FIG. 35

TABLE 7
Intermembrane space proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| Mito fusion/fission | E5KLJ5 | - | - | IMS | OPA1 | 4976 | dynamin-like 120 kDa protein (Optic atrophy protein 1) | | J Biol Chem (2004) 279:18792-18798 |
| Apoptosis | P54819 | - | 1.283263663 | IMS | AK2 | 204 | adenylate kinase 2 | | Proc Natl Acad Sci U S A. (2006) 103:11573-11578 |
| Apoptosis | Q2QKE4 | - | - | IMS | AIFM1 | 9131 | apoptosis-inducing factor, mitochondrion-associated, 1 | | Proc Natl Acad Sci U S A. (2006) 103:11573-11578 |

FIG. 35 cont.

TABLE 7
Intermembrane space proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| Apoptosis | P99999 | - | 2.042149217 | IMS | CYCS | 54205 | cytochrome c | | Proc Natl Acad Sci U S A. (2006) 103:11573-11578 |
| Apoptosis | Q9NR28 | - | - | IMS | DIABLO | 56616 | Diablo homolog, mitochondrial (Direct IAP-binding protein with low pI) (Smac) | | Proc Natl Acad Sci U S A. (2006) 103:11573-11578 |
| Apoptosis | O43464 | - | - | IMS | HTRA2 | 27429 | Serine protease HTRA2, mitochondrial (Serine proteinase OMI) | | Proc Natl Acad Sci U S A. (2006) 103:11573-11578 |
| HW IMS | Q9NRP4 | - | | | ACN9 | 57001 | Protein ACN9 homolog, mitochondrial | mitochondrion | mitochondrial intermembrane space | |
| HW IMS | Q53YD8 | - | | | ARL2 | 402 | ADP-ribosylation factor-like protein 2 | cytosol | Golgi apparatus | cytoskeleton | intracellular | microtubule organizing center | cytoplasm | |
| HW IMS | Q9Y2Y0 | - | | | ARL2BP | 23568 | ADP-ribosylation factor-like protein 2-binding protein (ARF-like 2-binding protein) (Binder of ARF2 protein 1) | mitochondrion | cytoskeleton | microtubule organizing center | mitochondrial intermembrane space | cytoplasm | |

FIG. 35 cont.

TABLE 7
Intermembrane space proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| aerobic respiration | P78537 | - | - | | BLOC1S1 | 2647 | Biogenesis of lysosome-related organelles complex 1 subunit 1 (BLOC-1 subunit 1) (GCN5-like protein 1) (Protein RT14) | BLOC-1 complex | |
| HW IMS | Q14061 | - | - | | COX17 | 10063 | Cytochrome c oxidase copper chaperone | mitochondrion | mitochondrial intermembrane space | cytoplasm | |
| HW IMS | Q6YFQ2 | - | - | | COX6B2 | 125965 | Cytochrome c oxidase subunit 6B2 (Cancer/testis antigen 59) (CT59) (Cytochrome c oxidase subunit VIb isoform 2) (COX VIb-2) (Cytochrome c oxidase subunit VIb, testis-specific isoform) | mitochondrion | mitochondrial crista | mitochondrial intermembrane space | |
| HW IMS | P09769 | | | | FGR | 2268 | Tyrosine-protein kinase Fgr (EC 2.7.10.2) (Gardner-Rasheed feline sarcoma viral (v-fgr) oncogene homolog) (Proto-oncogene c-Fgr) (p55-Fgr) (p58-Fgr) (p58c-Fgr) | cytosol | plasma membrane | |

FIG. 35 cont.

TABLE 7
Intermembrane space proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW IMS | P50440 | - | - | | GATM | 2628 | Glycine amidinotransferase, mitochondrial (EC 2.1.4.1) (L-arginine:glycine amidinotransferase) (Transamidinase) | mitochondrion | mitochondrial inner membrane | membrane | mitochondrial intermembrane space | cytoplasm | |
| HW IMS | P55789 | - | - | | GFER | 2671 | FAD-linked sulfhydryl oxidase ALR (EC 1.8.3.2) (Augmenter of liver regeneration) (hERV1) (Hepatopoietin) | mitochondrion | cellular_component | |
| HW IMS | Q9H4A6 | - | | | GOLPH3 | 64083 | Golgi phosphoprotein 3 (Coat protein GPP34) (Mitochondrial DNA absence factor) (MIDAS) | endosome | mitochondrion | Golgi apparatus | mitochondrial intermembrane space | cytoplasm | trans-Golgi network | cytosol | Golgi cisterna membrane | plasma membrane | |

FIG. 35 cont.

TABLE 7
Intermembrane space proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW IMS | P14060 | | | | HSD3B1 | 3283 | 3 beta-hydroxysteroid dehydrogenase/Delta 5-->4-isomerase type 1 (3 beta-hydroxysteroid dehydrogenase/Delta 5-->4-isomerase type I) (3-beta-HSD I) (Trophoblast antigen FDO161G) [Includes: 3-beta-hydroxy-Delta(5)-steroid dehydrogenase (EC 1.1.1.145) (3-beta-hydroxy-5-ene steroid dehydrogenase) (Progesterone reductase); Steroid Delta-isomerase (EC 5.3.3.1) (Delta-5-3-ketosteroid isomerase)] | smooth endoplasmic reticulum membrane | mitochondrion | endoplasmic reticulum | mitochondrial inner membrane | mitochondrial intermembrane space | integral to membrane | endoplasmic reticulum membrane | microsome | membrane | |

FIG. 35 cont.

TABLE 7
Intermembrane space proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW IMS | P26439 | . | . | | HSD3B2 | 3284 | 3 beta-hydroxysteroid dehydrogenase/Delta 5-->4-isomerase type 2 (3 beta-hydroxysteroid dehydrogenase/Delta 5-->4-isomerase type II) (3-beta-HSD II) (3-beta-HSD adrenal and gonadal type) [Includes: 3-beta-hydroxy-Delta(5)-steroid dehydrogenase (EC 1.1.1.145) (3-beta-hydroxy-5-ene steroid dehydrogenase) (Progesterone reductase); Steroid Delta-isomerase (EC 5.3.3.1) (Delta-5-3-ketosteroid isomerase)] | smooth endoplasmic reticulum membrane | mitochondrion | endoplasmic reticulum | mitochondrial inner membrane | mitochondrial intermembrane space | integral to membrane | mitochondrial membrane | endoplasmic reticulum membrane | microsome | membrane | |
| HW IMS | Q9BYT8 | 2.668679256 | 2.88738186 | | NLN | 57486 | Neurolysin, mitochondrial (EC 3.4.24.16) (Angiotensin-binding protein) (Microsomal endopeptidase) (MEP) (Mitochondrial oligopeptidase M) (Neurotensin endopeptidase) | mitochondrion | mitochondrial intermembrane space | cytoplasm | |

FIG. 35 cont.

TABLE 7
Intermembrane space proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| HW IMS | O00746 | 2.529517643 | 2.869783501 | | NME4 | 4833 | Nucleoside diphosphate kinase, mitochondrial (NDK) (NDP kinase, mitochondrial) [EC 2.7.4.6] (Nucleoside diphosphate kinase D) (NDPKD) (nm23-H4) | mitochondrion | mitochondrial intermembrane space | |
| HW IMS | Q6PIK9 | | | | PANK2 | 80025 | Pantothenate kinase 2, mitochondrial (hPanK2) [EC 2.7.1.33] (Pantothenic acid kinase 2) | mitochondrion | cytoplasm | |
| HW IMS | Q8TCS8 | 3.232345647 | 2.934644131 | | PNPT1 | 87178 | Polyribonucleotide nucleotidyltransferase 1, mitochondrial [EC 2.7.7.8] [3'-5' RNA exonuclease OLD35] (PNPase old-35) (Polynucleotide phosphorylase 1) (PNPase 1) (Polynucleotide phosphorylase-like protein) | | |

FIG. 35 cont.

TABLE 7
Intermembrane space proteins detected.

| CLASS | UniProt Accession | Log2 Rep1 | Log2 Rep2 | LOCALIZATION | SYM | ENTREZ | DESCRIPTION | NOTE | REFERENCE |
|---|---|---|---|---|---|---|---|---|---|
| H/W IMS | Q6IBK0 | - | - | | STAR | 6770 | Steroidogenic acute regulatory protein, mitochondrial (StAR) (START domain-containing protein 1) (StARD1) | cytosol \| mitochondrion \| mitochondrial intermembrane space | |
| Sulfide oxidation | P51687 | - | - | | SUOX | 6821 | Sulfite oxidase, mitochondrial (EC 1.8.3.1) | cytosol \| mitochondrion \| mitochondrial intermembrane space | |

IN VIVO PROTEOMIC MAPPING

RELATED APPLICATION

This application claims priority under 35 U.S.C. §119(e) to U.S. provisional patent application, U.S. Ser. No. 61/497,155, filed Jun. 15, 2011, and entitled In Vivo Proteomics/Live Cell Proteomics, the entire contents of which are incorporated herein by reference.

GOVERNMENT SUPPORT

This invention was made with U.S. Government support under grant GM105381 awarded by the National Institutes of Health. The U.S. Government has certain rights in the invention.

BACKGROUND OF THE INVENTION

One of the greatest challenges in biology is to determine the complete molecular composition of cells and their sub-compartments. Currently, the state-of-the-art for tackling this problem is to purify compartments or macromolecular complexes of interest, and determine their components (e.g., proteins) by mass spectrometry. Such conventional proteomics methods are not capable to provide a comprehensive assessment of the proteome of living cells or of substructures within living cells, such as organelles, or macromolecular complexes. While some conventional approaches to proteomic analysis, e.g., based on mass spectrometry (MS) allow for the unbiased identification of nearly all proteins in a complex sample, they are limited by the fact that they cannot be performed on living cells. Sample preparation for current proteomics assays requires lysis of biological material, and, therefore, spatial and dynamic information cannot be analyzed.

Currently used approaches to solve this problem rely on the purification of spatially-defined components of interest from cells after lysis. For example, mitochondria, ER, and other organelles are purified by repeated centrifugation and fractionation steps, while macromolecular complexes are purified using antibodies or affinity tags. However, these purifications have drawbacks. For example, current purification methods typically lead to numerous false positives and false negatives, and many subcellular structures of live cells are not amenable to purification. For example, in neurons, it would be transformative to know the complete molecular composition of the synaptic cleft, but this structure cannot be purified. Likewise, although the mitochondrial proteome has been characterized, it would be illuminating to separately map the proteomes of the mitochondrial inter-membrane space, outer mitochondrial membrane, and contact sites between mitochondria and the endoplasmic reticulum. However, these proteomes are currently unknown because they cannot be purified.

SUMMARY OF THE INVENTION

Some aspects of this disclosure provide strategies, methods, reagents, systems, and kits for in vivo proteomics, allowing for the assessment of the proteome of cells and subcellular structures. The strategies for live cell proteomics described herein obviate the need for sample purification, and instead label the relevant proteome of interest within living cells. This is accomplished, for instance, through the use of promiscuous tagging enzymes that can be genetically targeted to any subcellular region of interest. The enzymes used catalyze reactions that lead to covalent labeling of nearby endogenous proteins. Because the methods for live cell proteomics provided herein do not rely on the purification of subcellular structures, problems and artifacts associated with organelle or macromolecular complex purification are avoided. Any subcellular region that can be accessed via genetic targeting is amenable to proteomic mapping using the strategies, methods, reagents, systems, and kits provided herein. The labeled proteome can be analyzed with any suitable downstream proteomic analysis technology, including, but not limited to mass spectrometry (MS) proteomics.

Some aspects of the invention relate to methods, materials, and compositions for tagging and analyzing molecules, e.g., proteins, in vivo. For example, some embodiments of this invention provide methods, materials, and compositions for tagging proteins in cells or in subcellular compartments, e.g., in living cells or subcellular compartments of living cells. In some embodiments, the tagged proteins are subsequently isolated and analyzed (e.g., identified). Aspects of the invention can be used to determine the proteomic composition of specific cells, cellular compartments, or macromolecular structures (e.g., protein complexes) under in vivo (e.g., physiological or perturbed) conditions. Aspects of this invention can be used to identify protein interaction partners, to map the proteome of subcellular compartments, and to map the proteome of specific cells or cell types in complex tissues or animals. Using aspects of this invention in personalized proteomics and for drug screening applications is also contemplated.

In some aspects the invention provides a method for proteomic mapping by contacting a living cell with a tagging enzyme under conditions suitable for the tagging enzyme to catalyze a reaction with a tagging substrate resulting in the tagging of proteins within the vicinity of the tagging enzyme, and isolating and analyzing the tagged proteins to create a first proteome map. In some embodiments the method further comprises contacting the living cell with a tagging substrate. In other embodiments the tagging enzyme that is contacted with the cell is a genetic construct encoding a protein tagging enzyme. The living cell may be exposed to a condition, such as exposure to a therapeutic agent, prior to or during the step of contacting with a tagging enzyme in some embodiments.

In other embodiments the method further comprises contacting a second living cell exposed to a second condition with a tagging enzyme under conditions suitable for the tagging enzyme to catalyze a reaction with a tagging substrate resulting in the tagging of proteins in the second living cell within the vicinity of the tagging enzyme, and isolating and analyzing the tagged proteins from the second living cell to create a second proteome map. In some embodiments the first and second proteome maps are compared.

Some aspects of this invention provide methods for protein tagging in live cells. In some embodiments, the method comprises contacting a living cell with a tagging enzyme and a tagging substrate under conditions suitable for the enzyme to catalyze a reaction resulting in the tagging of molecules within the vicinity of the enzyme. In some embodiments, the tagged molecules comprise protein molecules. In some embodiments, the enzyme is a peroxidase. In some embodiments, the conditions comprise the presence of a substrate of the enzyme within the subcellular compartment. In some embodiments, the substrate is a tyramide. In some embodiments, the substrate is a labeled tyramide. In some embodiments, the substrate is a biotinylated tyramide. In some embodiments, the method further comprises isolating the tagged molecules. In some embodiments, the method further comprises analyzing the isolated molecules. In some embodiments, the analyzing comprises identifying the molecules. In some embodiments, the analyzing comprises determining the amino acid sequence of the tagged proteins. In some embodiments, the analyzing is performed by mass spectrometry analysis. In some embodiments, the tagging enzyme is targeted to a subcellular compartment. In some embodiments, the subcellular compartment is endoplasmatic reticulum, golgi apparatus, synaptic plaques, nucleus, mitochondria. In some embodiments, the contacting comprises expressing the enzyme in the cell. In some embodiments, the enzyme comprises a localization signal or targeting sequences that targets the enzyme to a specific subcellular domain. In some embodiments, the localization signal is a peptide sequence, for example, a nuclear localization signal (NLS) peptide, fused to the enzyme. In some embodiments, the enzyme is expressed in the cell under the control of a cell-type specific promoter limiting expression of the enzyme to specific cell types. In some embodiments, the enzyme is expressed as a fusion to a signal peptide targeting the enzyme to a particular subcellular compartment and wherein expression of the enzyme is controlled by a cell type-specific promoter.

Some aspects of this invention provide methods for live cell protein tagging that, comprise contacting a living cell with a peroxidase under conditions suitable for the peroxidase to convert a substrate into a reactive, short-lived intermediate that covalently binds to a molecule in the vicinity of the peroxidase. In some embodiments, the substrate comprises a tag. In some embodiments, the tag is a binding agent, for example, biotin. In some embodiments, the substrate comprises a tyramide moiety. In some embodiments, the peroxidase is horse radish peroxidase. In some embodiments, the peroxidase is soybean peroxidase. In some embodiments, the peroxidase is ascorbate peroxidase. In some embodiments, the peroxidase is targeted to be localized in a specific subcellular compartment. In some embodiments, the subcellular compartment is endoplasmatic reticulum, golgi apparatus, synaptic plaques, nucleus, mitochondria, or synaptic cleft. In some embodiments, the method further comprises isolating the tagged molecules. In some embodiments, the method further comprises analyzing the isolated molecules. In some embodiments, the analyzing comprises identifying the molecules. In some embodiments, the analyzing is performed by Mass Spectrometry. In some embodiments, the contacting comprises expressing the enzyme in the cell.

Some aspects of this invention provide cells expressing a tagging enzyme fused to a localization signal targeting the tagging enzyme to a subcellular compartment. In some embodiments, the cell is contacted with a substrate of the tagging enzyme. In some embodiments, the tagging enzyme is a peroxidase. In some embodiments, the tagging enzyme is not horse radish peroxidase. In some embodiments, the tagging enzyme is soy bean peroxidase. In some embodiments, the substrate comprises a tyramide moiety. In some embodiments, the substrate is biotin tyramide. In some embodiments, the tagging enzyme is expressed from an expression construct comprising a tissue-specific promoter.

Some aspects of this invention provide methods for protein tagging that comprise (i) expressing a tagging enzyme comprising a subcellular localization signal in a living cell; (ii) contacting the subcellular compartment with a substrate of the tagging enzyme; (iii) isolating a population of tagged proteins from the cell; and (iv) characterizing the isolated protein population. In some embodiments, the characterizing comprises determining the identity of a protein in the isolated protein population. In some embodiments, the protein identity is determined by performing mass spectrometry. In some embodiments, the tagging enzyme is a peroxidase. In some embodiments, the tagging enzyme is contacted with the substrate in the presence of $H_2O_2$. In some embodiments, the substrate is a tagged tyramide. In some embodiments, the substrate is alkyne-tyramide. In some embodiments, the tagging enzyme is expressed as a fusion with a signaling peptide targeting the enzyme to a particular subcellular compartment. In some embodiments, the tagging enzyme is expressed from a tissue-specific promoter. In some embodiments, the tagging enzyme is selected from the group consisting of horseradish peroxidase, soybean peroxidase, and ascorbate peroxidase.

Some aspects of this invention provide isolated, monomeric peroxidases that mutants of a wild type peroxidases. In some embodiments, the mutant peroxidase is an ascorbate peroxidase mutant and exhibits peroxidase activity towards a substrate of a wild type ascorbate peroxidase (APX). In some embodiments, the substrate is 3,3'-diaminobenzidine. In some embodiments, the peroxidase exhibits activity towards the substrate at a level similar to or higher than the activity level of wild type APX. In some embodiments, the peroxidase is a mutant pea APX. In some embodiments, the peroxidase comprises a K17N, a K20A, and/or a R21L mutation.

Some aspects of this invention provide kits for protein tagging. In some embodiments, the kit comprises an expression construct encoding a tagging enzyme, for example, a peroxidase. In some embodiments, the kit comprises an expression construct comprising a subcellular localization signal. In some embodiments, the subcellular localization signal is a signal targeting a protein comprising the signal to the endoplasmatic reticulum, golgi apparatus, synaptic plaques, nucleus, mitochondria, or the synaptic cleft. In some embodiments, the kit includes an expression construct into which a desired tagging enzyme or localization signal can be cloned to generate a nucleic acid encoding a tagging enzyme fused to a localization signal. In some embodiments, the kit comprises an enzyme substrate. In some embodiments, the enzyme substrate comprises or is conjugated to an agent, for example, a detectable label or a reactive handle. In some embodiments, the tagging enzyme is a peroxidase. In some embodiments, the tagging enzyme is selected from the group consisting of horseradish peroxidase, ascorbate peroxidase, and soybean peroxidase. In some embodiments, the peroxidase is an engineered, mutant peroxidase. In some embodiments, the peroxidase is a mutant pea ascorbate peroxidase. In some embodiments, the peroxidase comprises a K17N, a K20A, and/or a R21L mutation. In some embodiments, the substrate comprises a tyramide moiety. In some embodiments, the substrate comprises a binding agent. In some embodiments, the substrate is biotin tyramide. In some embodiments, the kit further comprises $H_2O_2$. In some embodiments, the expression construct encodes a protein targeting signal as a fusion to the tagging enzyme.

Other advantages, features, and uses of the invention will be apparent from the Detailed Description of certain Embodiments; the Drawings, the Examples section, and the Claims.

BRIEF DESCRIPTION OF THE DRAWINGS

FIG. 4. Properties of previous proteomic datasets for the endoplasmic reticulum, highlighting in particular how all these were obtained by complex subcellular fractionation protocols.

FIG. 10. Example of a gel analysis of biotinylated proteins.

FIG. 11. Non-limiting example of a mass-spectrometry-based analysis of biotinylated proteins.

FIG. 12. A subset of proteins associated with the ER. Compared to this dataset, 21 out of 25 of these proteins were identified in the experiment described herein, and a few hundred additional ones as well.

FIG. 21. Proposed approach to mapping the proteomes of biologically important membrane-membrane contact sites, using peroxidase-mediated biotinylation of endogenous proteins.

FIG. 22. Large-scale mapping of membrane protein topology using promiscuous biotinylation.

FIG. 28. Determination of the cut-off point for our mitochondrial matrix proteome. (A) SILAC labeling scheme. (B) Table of # of enriched proteins (C) Histogram (D) Likelihood ratio plot.

FIG. 29. Table 1: Mitochondrial matrix proteome (495 proteins), ranked from most enriched to least enriched (H/L ratio from Rep1)

FIG. 30. Table 2: Mitochondrial orphans (31 proteins), ranked from most enriched to least enriched (H/L ratio from Rep1)

FIG. 31. Table 3: Biotinylated peptides detected (88 unique peptides, derived from 63 unique enriched proteins), grouped by protein FIG. 32. Table 4: Mitochondrial matrix protein groups detected.

FIG. 33. Table 5: Inner mitochondrial membrane complexes detected.

FIG. 34. Table 6: Outer mitochondrial membrane proteins detected.

FIG. 35. Table 7: Intermembrane space proteins detected.

DETAILED DESCRIPTION OF THE INVENTION

Figure 1:
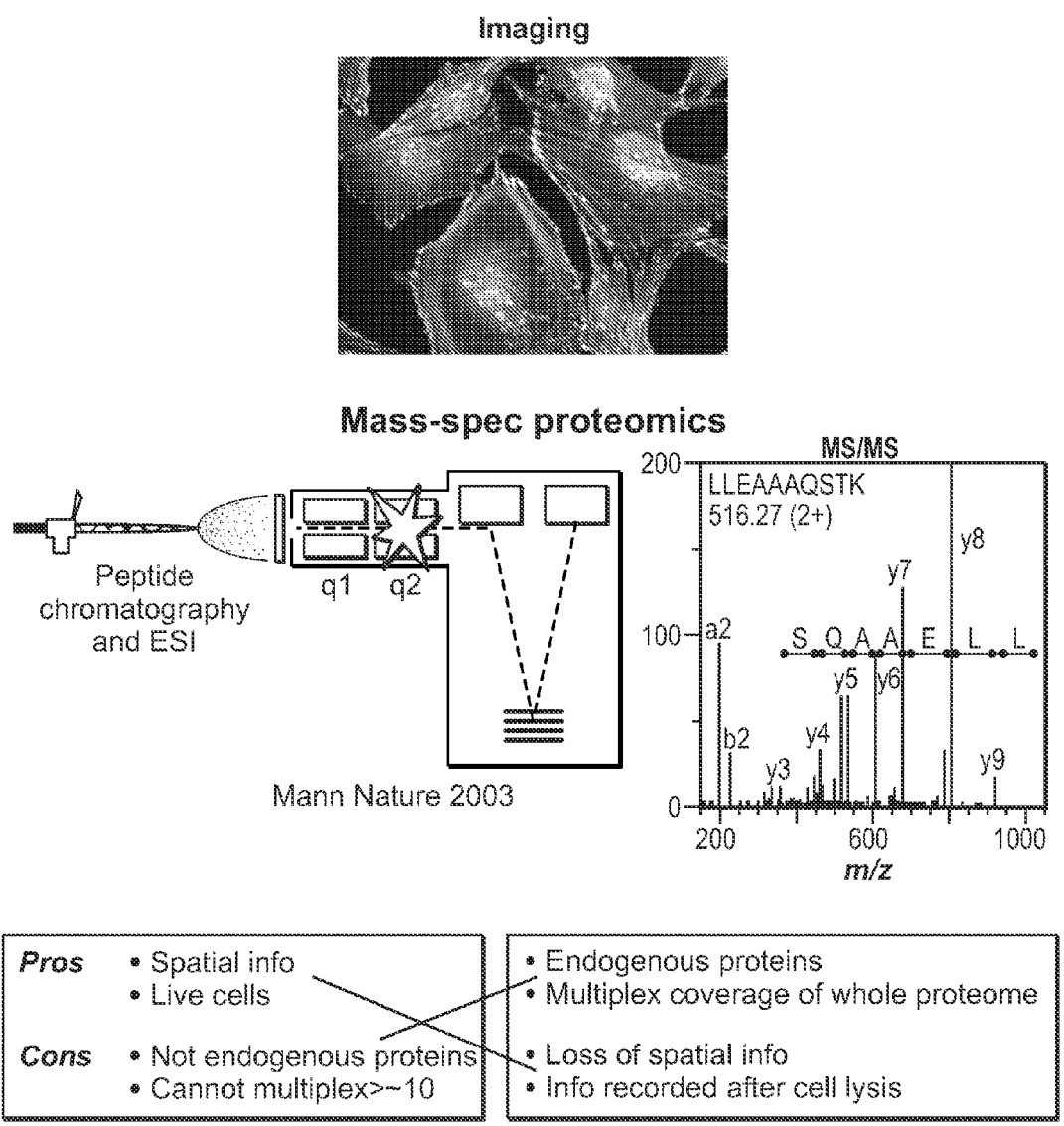
FIG. 1. Limitations of imaging and mass-spectrometry based analyses.

Some aspects of the present invention are based on the development of a protein tagging strategy using a promiscuous tagging enzyme that tags a proteome of interest, with spatial and temporal control, and that can be used to label molecules, e.g., proteins, within living cells or subcellular components, or multi protein complexes. This process may be referred to as proteome mapping. The approach described herein has not previously been explored for mapping cellular and sub-cellular proteomes, and allows for the tagging and subsequent analysis of live cell proteomes, for example, of proteomes associated with subcellular structures. An important advantage of the methods of the invention is that they permit both spatial and temporal control of labeling in live cells.

Some aspects of this invention relate to the surprising discovery that promiscuous labeling of proteins can be used in the context of living cells to tag proteins of cells or subcellular structures. This is surprising in that the interior of living cells comprises highly complex environments and compartments that were not previously thought to be accessible to promiscuous labeling methodologies. A proteome may be a set of proteins expressed by a genome, cell, subcellular compartment, a multi-protein complex, tissue or organism. In some embodiments, a proteome is the entire set of proteins expressed by a genome, subcellular compartment, multi-protein complex, tissue or organism, in some embodiments, a proteome is the set of expressed proteins expressed in a given type of cells, subcellular compartment or an organism at a given time under defined conditions.

The methods of the invention allow, for the first time, the ability to analyze proteomes in an accurate and high throughput manner. As such, proteome maps can be developed not only for different cells, subcellular compartments or organisms but also for cells or organisms exposed to different conditions or environments. For example, proteomes of cells or organisms exposed to different therapeutic agents, different concentrations of therapeutic agents, and/or combinations of therapeutic agents may be mapped and analyzed independently or compared against one another to examine changes occurring within a cell or organism. Additionally, changes in cells or organisms over time in diseased states or normal states may be examined at the proteome level. The wealth of information that can be extracted from the methods of the invention is enormous.

In general, the methods and strategies for protein tagging in living cells employ a tagging enzyme (a promiscuous bond-forming enzyme), alternatively, in some instances, simply referred to as an enzyme or promiscuous enzyme, e.g., a ligase, such as a biotin ligase, to catalyze a reaction resulting in tagging proteins in the vicinity of the enzyme. A tagging enzyme may be used, for instance, that utilizes a substrate to create and release a reactive moiety, e.g., an activated adenylate ester-biotin-AMP in the case of biotin ligase, that attaches to and thus labels nearby proteins[9]. When it is desirable to achieve sufficient spatial resolution of labeling, or spatial restriction of the cloud of reactive moieties generated by the tagging enzyme, reactive moieties with a sufficiently short half-life may be chosen. For example, because adenylate esters generated by biotin ligase persist for many minutes, using such tagging enzymes results in insufficient spatial resolution in cells for certain applications, since biotin-AMP would diffuse across the entire cell before becoming quenched. Some methods and strategies provided herein utilize reactive moieties that have a shorter half-life, and thus a restricted labeling radius, allowing for proteome tagging at a resolution of subcellular structures, such as organelles or protein complexes. The strategies provided herein further do not rely on toxic labels, such as ruthenium and nickel complexes which catalyze photo-oxidation of tyrosine and tryptophan side chains, leading to protein-protein crosslinking[10, 11]. Such toxic chemistry is incompatible with the cell interior due to its requirement for cytotoxic ammonium persulfate as a co-oxidant.

In some aspects, this disclosure provides methods for labeling the endogenous proteome of defined subcellular compartments or macromolecular complexes, with nanometer spatial resolution in living cells. Proteins thus labeled, for example with a binding agent, such as biotin, can be isolated using affinity-based methods (e.g., streptavidin beads) and analyzed by any suitable downstream assay (e.g., mass spectrometry). Some of the methods for labeling the endogenous proteome of subcellular compartments rely on tagging enzymes that can be genetically targeted to a cellular region of interest. The methods provided herein, accordingly, allow for the analysis of the molecular composition of cells and their sub-compartments. The strategies and methods provided herein are useful in the context of proteomics research as well as in the context of the diagnosis of disease, e.g., as they allow for the generation of patient-specific proteomes of subcellular structures implicated in disease.

Tagging methods and techniques described herein can be used for different applications. In some embodiments, proteins within a specific subcellular compartment or region (e.g., the nucleus, endoplasmic reticulum, Golgi, mitochondria, mitochondria outer membrane, mitochondria inner membrane, mitochondria matrix space, chloroplasts, synaptic cleft, presynaptic membrane, postsynaptic membrane, dendritic spines, transport vesicles, regions of contact between mitochondria and endoplasmic reticulum, nuclear membrane, etc.) can be specifically tagged. In some embodiments, proteins within particular cell types (e.g., astrocytes, dendrocytes, stem cells, etc.) can be specifically tagged, for example, proteins within a specific cell type within a complex tissue, animal, or cell population. In some embodiments, proteins within particular macromolecular complexes (e.g., protein complexes such as ribosomes, replisome, transcription complex, spliceosome, DNA repair complex, fatty acid synthase, polyketide synthase, non-ribosomal peptide synthase, glutamate receptor signaling complex, neurexin-neuroligin signaling complex, etc.) can be tagged. In each context, the tagged proteins can be analyzed (e.g., isolated and identified) to determine the proteomic content of the specific cells, cellular compartments or regions, or macromolecular complexes of interest. This information can be used for research, diagnostic, therapeutic, and other applications. In some embodiments, the proteomic content of patient cells may be determined. For example, cells may be isolated from a patient, amplified or differentiated using IPS cell technology (induced pluripotent stem cell), contacted with a vector (e.g., a viral vector) that expresses a tagging enzyme, for example, a tagging enzyme fused to a localization signal effecting localization of the tagging enzyme in a specific subcellular compartment, labeling can be performed in the living cells, and the resulting tagged proteins can be analyzed, for example, to identify patient specific proteomic information that can be useful to assist in diagnostic, prognostic, and/or therapeutic decisions, and in drug screening assays.

Thus, in some aspects the invention is a method for proteomic mapping, which involves contacting a living cell with a tagging enzyme under conditions suitable for the tagging enzyme to catalyze a reaction with a tagging substrate resulting in the tagging of proteins within the vicinity of the tagging enzyme, and isolating and analyzing the tagged proteins to create a first proteome map.

A living cell, as used herein, refers to an intact cell naturally occurring or modified isolated from other cells, mixed with other cells in a culture, within a tissue (partial or intact) or within an organism. In some embodiments, the living cell is a cell engineered to express a tagging enzyme, for example, a peroxidase. In some embodiments, the living cell expresses a tagging enzyme that is targeted to a subcellular compartment or structure, for example, via a localization signal comprised in or fused to the tagging enzyme.

In some embodiments, the living cell is contacted with a tagging enzyme. The term contacting as used herein refers to exposure of the cell to the enzyme in such a manner that the tagging enzyme is delivered to the cell interior or exterior, depending on which region of the cell will be analyzed. In some embodiments the tagging enzyme is delivered to the interior or the cell and in some instances to specific subcellular compartments. The term contacting may refer to expression of the tagging enzyme in the cell, e.g., from the cellular genome or from an exogenous nucleic acid (e.g., a viral genome, a plasmid, an artificial chromosome). The term may also refer to delivering the tagging enzyme to the cell, e.g., by administering a tagging enzyme to a tissue.

The term tagging enzyme refers to an enzyme that catalyzes a reaction which leads to the conjugation of a tag to a set of molecules, for example, proteins, carbohydrates, or lipids. In some embodiments, a tagging enzyme catalyzes a reaction that results in promiscuous labeling of molecules, e.g., proteins, in the vicinity of the enzyme. A tagging enzyme may catalyze a reaction in which a substrate, also referred to herein as a tagging substrate, is converted into a reactive form, e.g., a radical, which reacts with and attaches to a molecule, e.g., a protein, in the vicinity of the enzyme. In some embodiments, the reactive form of the tagging substrate attaches to the molecule via the formation of a covalent bond between the tagging substrate and the molecule. The half-life of the reactive form of the tagging substrate determines how far the reactive form can travel from its point of generation before reacting with a molecule. Accordingly, the half-life of the reactive form of the tagging substrate determines the labeling radius. For example, in some embodiments, the tagging enzyme is a biotin ligase, catalyzing the addition of a biotin tag to a protein. In some embodiments, the tagging enzyme catalyzes a reaction converting a tagging substrate into a reactive form by creating a reactive moiety on the tagging substrate that is able to react with a protein, for example, able to form a covalent bond with a protein, e.g., a moiety on the peptide backbone or a moiety on an amino acid side chain of the protein. In some embodiments, the tagging enzyme, for example, a peroxidase, is engineered to be expressed and targeted to particular cells, subcellular compartments, and/or macromolecular complexes in vivo. In some embodiments, a tagging enzyme is engineered to have a novel activity towards a substrate of interest. In some embodiments, a cell contacted with a tagging enzyme is contacted with a tagging substrate under conditions suitable for the tagging enzyme to convert the tagging substrate into a reactive form that can react with and attach to molecules in the vicinity of the tagging enzyme.

In some embodiments, the tagging enzyme is a peroxidase (e.g., horseradish peroxidase, soybean peroxidase, or ascorbate peroxidase). The discovery that peroxidases can be used as efficient tagging enzymes in living cells, as disclosed herein, was surprising, in that, while horseradish peroxidase (HRP) targeted to cell surface proteins via antibodies has been reported to convert an aryl azide into a nitrene, which labeled nearby proteins[12], the use of peroxidases for protein labeling in the interior of cells has not been deemed possible before, for example, since it has been reported that HRP is inactive in the cytosol because its four essential disulfide bonds have become reduced[13].

Some exemplary peroxidases suitable as tagging enzyme in embodiments of this invention are described herein. In some embodiments, the tagging enzyme is a wild type peroxidase. In some embodiments, the tagging enzyme is an engineered peroxidase, for example, a peroxidase engineered to be expressed and/or active only within a subcellular compartment or structure of interest. In some embodiments, the tagging enzyme is a mutant peroxidase, e.g., a peroxidase comprising one or more mutations that enhances the catalytic activity of the peroxidase towards a tagging substrate in a subcellular compartment or structure of interest.

Representative sequences of some exemplary suitable tagging enzymes are provided below:

wild-type Horseradish peroxidase
(SEQ ID NO: 1)
QLTPTFYDNSCPNVSNIVRDTIVNELRSDPRIAASILRLHFHDCFVNGCD

ASILLDNTTSFRTEKDAFGNANSARGFPVIDRMKAAVESACPRTVSCADL

LTIAAQQSVTLAGGPSWRVPLGRRDSLQAFLDLANANLPAPFFTLPQLKD

-continued
SFRNVGLNRSSDLVALSGGHTFGKNQCRFIMDRLYNFSNTGLPDPTLNTT

YLQTLRGLCPLNGNLSALVDFDLRTPTIFDNKYYVNLEEQKGLIQSDQEL

FSSPNATDTIPLVRSFANSTQTFFNAFVEAMDRMGNITPLTGTQGQIRLN

CRVVNSNS wild-type cytochrome c peroxidase sequence
(SEQ ID NO: 2)
TTPLVHVASVEKGRSYEDFQKVYNAIALKLREDDEYDNYIGYGPVLVRLA

WHTSGTWDKHDNTGGSYGGTYRFKKEFNDPSNAGLQNGFKFLEPIHKEFP

WISSGDLFSLGGVTAVQEMQGPKIPWRCGRVDTPEDTTPDNGRLPDADKD

ADYVRTFFQRLNMNDREVVALMGAHALGKTHLKNSGYEGPWGAANNVFTN

EFYLNLLNEDWKLEKNDANNEQWDSKSGYMMLPTDYSLIQDPKYLSIVKE

YANDQDKFFKDFSKAFEKLLENGITFPKDAPSPFIFKTLEEQGL wild-type soybean APX
(SEQ ID NO: 3)
GKSYPTVSADYQKAVEKAKKKLRGFIAEKRCAPLMLRLAWHSAGTFDKGT

KTGGPFGTIKHPAELAHSANNGLDIAVRLLEPLKAEFPILSYADFYQLAG

VVAVEVTGGPEVPFHPGREDKPEPPPEGRLPDATKGSDHLRDVFGKAMGL

TDQDIVALSGGHTIGAAHKERSGFEGPWTSNPLIFDNSYFTELLSGEKEG

LLQLPSDKALLSDPVFRPLVDKYAADEDAFFADYAEAHQKLSELGFADA soybean APX K14D, W41F, E112K (monomeric soybean
APX with an enhanced-activity mutation)
(SEQ ID NO: 4)
GKSYPTVSADYQDAVEKAKKKLRGFIAEKRCAPLMLRLAFHSAGTFDKGT

KTGGPFGTIKHPAELAHSANNGLDIAVRLLEPLKAEFPILSYADFYQLAG

VVAVEVTGGPKVPFHPGREDKPEPPPEGRLPDATKGSDHLRDVFGKAMGL

TDQDIVALSGGHTIGAAHKERSGFEGPWTSNPLIFDNSYFTELLSGEKEG

LLQLPSDKALLSDPVFRPLVDKYAADEDAFFADYAEAHQKLSELGFADA (mutations are underlined)

Additional suitable tagging enzymes will be apparent to those of skill in the art based on this disclosure. The application is not limited in this respect.

The methods of labeling, or tagging, molecules, e.g., proteins, in living cells provided herein typically include the use of a tagging substrate. A tagging substrate is a substrate of a tagging enzyme. A tagging substrate is typically provided in an inert, stable, or non-reactive form, e.g., a form that does not readily react with other molecules in living cells. Once in contact with an active tagging enzyme, the tagging substrate is converted from its stable form into a short-lived reactive form, for e.g., via generation of a reactive moiety, such as a radical, on the tagging substrate by the tagging enzyme. Some tagging substrates are, accordingly, also referred to as radical precursors. The reactive form of the tagging substrate then reacts with and attaches to a molecule, e.g., a protein, in the vicinity of the tagging enzyme. Accordingly, in some embodiments, a tagging substrate comprises an inert or stable moiety that can be converted by the tagging enzyme into a reactive moiety. The reaction of the tagging substrate with a molecule, e.g., a protein in the vicinity of the tagging enzyme, results in the tagging, or labeling, of the molecule. Typically, a tagging substrate comprises a tag, which is a functional moiety or structure that can be used to detect, identify, or isolate a molecule comprising the tag, e.g., a protein that has been tagged by reacting with a tagging substrate. Suitable tags include, but are not limited to, for example, a detectable label, a binding agent, such as biotin, or a fluorescent probe, a click chemistry handle, an azide, alkyne, phosphine, trans-cyclooctene, or a tetrazine moiety. In some embodiments, the reaction of the reactive form of the tagging substrate with a molecule, e.g., a protein, may lead to changes in the molecule, e.g., oxygenation, that can be exploited for detecting and/or isolating the changed molecules. Non-limiting examples of such tagging substrates are chromophores, e.g., resorufin, malachite green, KillerRed, Ru(bpy)$_3^{2+}$, and miniSOG[31], which can generate reactive oxygen species that oxidize molecules in the vicinity of the respective tagging enzyme. The oxidation can be used to isolate and/or identify the oxidized molecules. In some embodiments, the reactive form of the tagging substrate crosses cell membranes, while in other embodiments membranes are impermeable to the reactive form of the tagging substrate.

A tag may be, in some embodiments, a detectable label. In some embodiments, a tag may be a functional moiety or structure that can be used to detect, isolate, or identify molecules comprising the tag. A tag may also be created as a result of a reactive form of a tagging substrate reacting with a molecule, e.g., the creation of oxidative damage on a protein by a reactive oxygen species may be a tag. In some embodiments, the tag is a biotin-based tag and the tagging enzyme, e.g., a peroxidase, generates a reactive biotin moiety that binds to proteins within the vicinity of the tagging enzyme. In some embodiments, the biotin-based tags are biotin tyramide molecules. In some embodiments, the tagging substrate is a peroxidase substrate. Structures of some exemplary tagging substrates (radical precursors) of peroxidase enzymes that are useful in some of the methods provided herein are provided below:

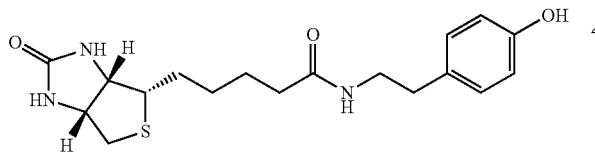
biotin-tyramide

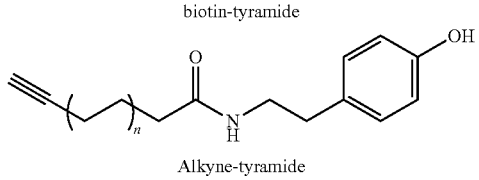
Alkyne-tyramide

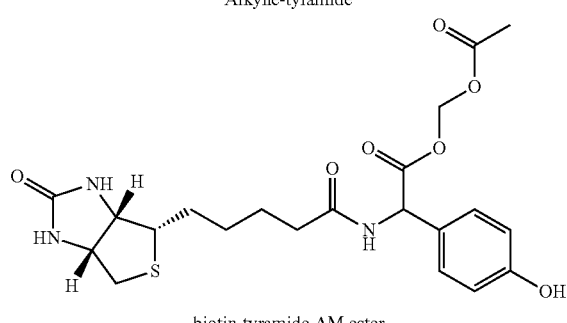
biotin-tyramide AM ester

Additional exemplary peroxidase substrates (radical precursors) are provided below:

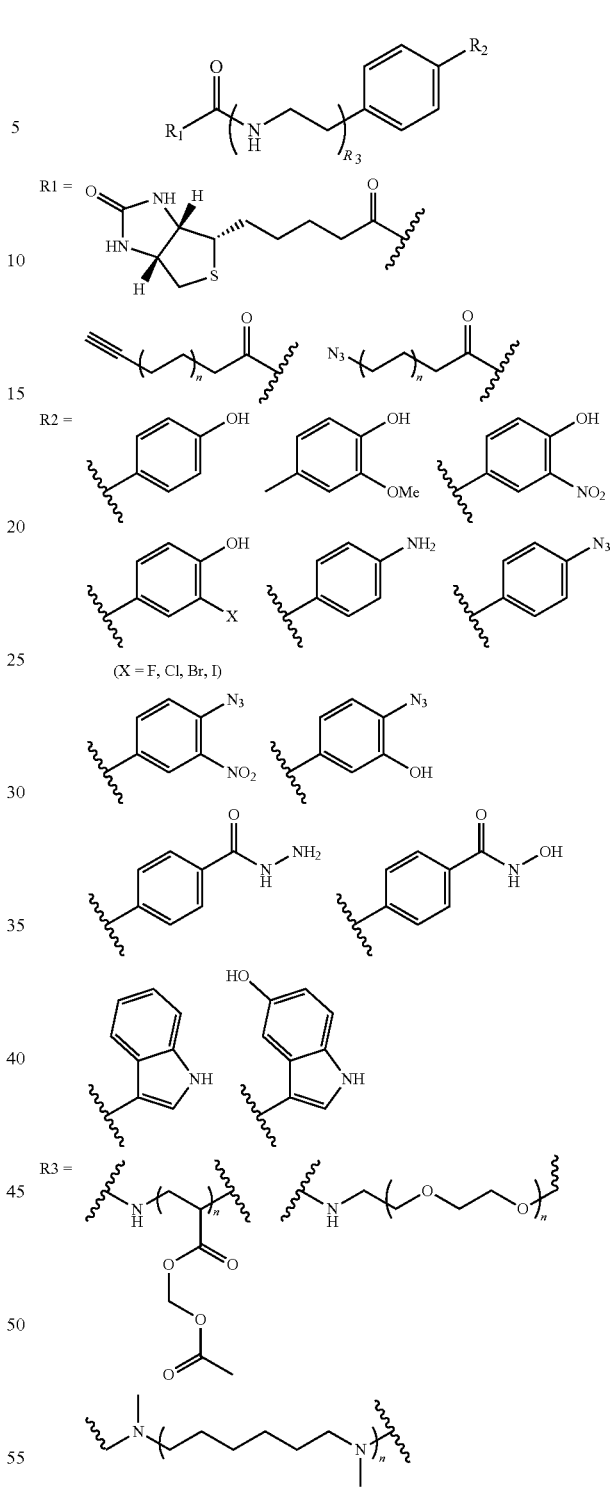

Additional suitable tagging substrates will be apparent to those of skill in the art, and the invention is not limited in this respect. In some embodiments, the tag is an alkyne tyramide and the peroxidase generates a reactive moiety that binds to proteins within the vicinity of the peroxidase. The alkyne subsequently can be modified, for example, by a click chemistry reaction to attach a tag (e.g., a biotin tag). The tag can then be used for further analysis (e.g., isolation and identification). It should be noted that the invention is not limited to alkyne tyramide, but that any functional group that can be chemoselectively derivatized can be used. Some examples are: azide or alkyne or phosphine, or trans-cyclooctene, or tetrazine, or cyclooctyne, or ketone, or hydrazide, or aldehyde, or hydrazine.

In some embodiments, a tagging substrate for peroxidase, for example, a biotinylated tyramide, is administered, applied, or contacted to the cells or tissue in vivo, and proteins that are located within the vicinity of the expressed peroxidase are tagged, i.e., the biotin tyramide is converted into a reactive form by the tagging enzyme, here the peroxidase, and the reactive form reacts with and attaches to proteins in the vicinity of the peroxidase, resulting in biotin-tagging of the respective proteins. In the presence of peroxide (e.g., $H_2O_2$), the peroxidase converts the substrate into a short-lived, reactive intermediate, for example, a reactive tyramide radical, that can form a covalent bond with a protein. In some embodiments, the reactive intermediate, once created, reacts with (labels) proteins that are within the vicinity of the peroxidase enzyme molecule. The term "within the vicinity" refers to the special location around the enzyme and/or substrate. In some instances it may refer to a region of the cell such as a sub-cellular region, a membrane or protein complex. Alternatively it can be defined in terms of distance from the enzyme or substrate or a region i.e., as a diameter, circumference or linear distance. For example, in some embodiments, a molecule within the vicinity of a tagging enzyme is a molecule that is positioned less than about less than about 900 nm, less than about 800 nm, less than about 700 nm, less than about 600 nm, less than about 500 nm, less than about 400 nm, less than about 300 nm, less than about 200 nm, less than about 100 nm, less than about 90 nm, less than about 80 nm, less than about 70 nm, less than about 60 nm, less than about 50 nm, less than about 40 nm, less than about 30 nm, less than about 20 nm, or less than about 10 nm away from the active site of the tagging enzyme. In some embodiments, proteins that are not within the vicinity of the enzyme are not exposed to the reactive intermediate and hence not labeled. In some embodiments, expression or targeting of the tagging enzyme to a subcellular compartment results in quantitative tagging of virtually all proteins within that compartment.

In addition to improving promiscuous labeling via peroxidase reaction engineering, the invention also includes but it is not limited to other non-peroxidase strategies for labeling, including the use of other enzymes, light-triggered labeling, and cascade reactions. For example, KatG (a mycobacterial catalase-peroxidase enzyme), CueO (a multi-copper oxidase), and bilirubin oxidase are three suitable tagging enzymes. Like peroxidases, all of these enzymes convert stable small molecule substrates into short-lived reactive species. Their advantage, however, is that they utilize $O_2$, and not $H_2O_2$, to catalyze their respective reactions, which may be advantageous in embodiments involving cells, subcellular compartments, or structures that are sensitive to $H_2O_2$ toxicity, KatG from *M. tuberculosis* is believed to oxidize the anti-tuberculosis drug isoniazid (an aryl hydrazide) into an acyl radical, which then diffuses out of the KatG active site to label the NADH moiety of InhA reductase[30]. CueO and bilirubin oxidase convert phenols into phenoxyl radicals at physiological pH. They also lack disulfides, and have solved crystal structures, which facilitates engineering.

Photo-oxidation reactions may also be used in the methods of the invention. Chromophores such as resorufin, malachite green, KillerRed, $Ru(bpy)_3^{2+}$, and miniSOG[31] can be used as tagging substrates, as they generate reactive oxygen species, which diffuse very short distances (40 Å for singlet oxygen and 15 Å for hydroxyl radical[32]) before oxidizing cellular molecules and thereby damaging them. These chromophores are the basis of Chromophore Assisted Light Inactivation, or CALI, which has been applied to cellular proteins. Common products of oxidative damage to proteins are aldehydes and ketones[33], which provide a handle for selective protein pull-down by hydrazine- or hydroxylamine-biotin conjugates. If photo-oxidation is performed in the presence of reducing substrates, such as phenols or anilines (e.g., diaminobenzidine, used for electron microscopy), organic radicals will be generated, which can be exploited for covalent protein labeling. An advantage of this photo-oxidation approach compared to peroxidase-mediated labeling is the use of $O_2$ instead of $H_2O_2$. In addition, hydroxyl radicals generated in type I photo-oxidation (by chromophores such as malachite green) are much more reactive than peroxidase-generated aryloxyl radicals (BDE 119 versus 88 kcal/mol[18]), which should lead to greater depth of coverage.

An additional type of tagging enzyme is based on a cascade reaction for covalent labeling in cells. Enediyne antibiotic prodrugs such as calicheamicin are activated inside cells to generate highly reactive 1,4-benzenoid diradicals. The structure of these prodrugs may be modified to make them activatable instead by orthogonal enzymes such as esterases or proteases, and, thus, useful as tagging substrates. N-nitrosoamides, which are converted by proteases via a cascade mechanism into reactive carbocations (with departure of $N_2$)[34] may also be used as tagging substrates. Originally designed as protease suicide inhibitors, the carbocations were found to diffuse too rapidly from the site of generation and label neighboring molecules, making them particularly well suited for use as tagging substrates.

Thus, exemplary tagging enzymes include but are not limited to peroxidases, KatG, CueO, and bilirubin oxidases. Exemplary tagging substrates include but are not limited to peroxidase substrates, such as tyramides, chromophores such as resorufin, malachite green, KillerRed, Ru(bpy)32+, and miniSOG (EKSFVITDPRLPDNPIIFASDGFLELTEY-SREEILGRNGRFLQGPETDQATVQKI RDAIRDQREIT-VQLINYTKSGKKFWNLLHLQPMRDQKGELQY-FIGVQLDG, SEQ ID NO: 5), and enediyne antibiotic prodrugs such as calicheamicin.

Some embodiments of this invention allow in vivo protein tagging mediated by a tagging enzyme which can be genetically targeted to any part of a living cell. In some embodiments, the tagging enzyme is present and/or active in all regions of the cell. In some embodiments, the tagging enzyme is present and/or active only in a subcellular compartment of the cell. In some embodiments, the tagging substrate is an exogenous small-molecule substrate that can be added or uncaged for the desired window of time, to permit precise temporal control of labeling. In some embodiments, the tagging substrate is conjugated to a binding agent, e.g., biotin (or other purification handle), for subsequent capture, e.g., by streptavidin-coated beads. In some embodiments, the tagging enzyme converts the substrate into a highly reactive species that has the potential to label any endogenous protein, in order to achieve high depth-of-coverage, e.g., in an MS experiment. In some embodiments, the reactive species has a short half-life on that its diffusion radius before quenching is less than ~100 nm, to ensure high specificity. In some embodiments, it is preferable for the reactive species not to cross cell membranes, to allow mapping of the proteomes of membrane-bounded structures.

In some embodiments, a tagging enzyme is engineered to be expressed and/or targeted in vivo or in situ to specific cells, cellular compartments (e.g., endoplasmic reticulum, Golgi apparatus, mitochondria, nucleus, the synaptic cleft, transport vesicles, etc.), and/or macromolecular complexes (e.g., protein complexes such as ribosomes, nuclear pore complex, fatty acid synthases) of interest. In some embodiments, a tagging enzyme is engineered to tag proteins that are located within a limited distance of the tagging enzyme. As a result, in some embodiments, proteins that are located within the targeted cell, cellular compartment, and/or macromolecular complex (e.g., protein complex) are specifically tagged relative to other proteins that are not located near the tagging enzyme. It should be appreciated that the tagging process itself does not need to be protein specific. For example, in some embodiments, it is the specific localization of the tagging enzyme that results in the specific tagging of a subset of proteins of interest. In some embodiments, proteins that are present within the vicinity of the tagging enzyme may be tagged for further analysis. In some embodiments, all proteins present within the vicinity of the tagging enzyme may be tagged. Various versions of the methodology offer a range of labeling radii, from ~500 nm to less than 10 nm, e.g., tagging radii of about 500 nm, about 400 nm, about 300 nm, about 250 nm, about 200 nm, about 100 nm, about 90 nm, about 80 nm, about 70 nm, about 60 nm, about 50 nm, about 40 nm, about 30 nm, about 20 nm, about 10 nm, about 5 nm, about 2.5 nm, or about 1 nm.

In some embodiments, the reactive moiety produced by the tagging enzyme, e.g., the peroxidase, can be inactivated by contacting it with a quenching agent, e.g., with water. As a result, the reactive moiety can have a short half-life and only modify proteins that are located within a short distance of the site of production (the peroxidase) before being inactivated. Accordingly, the zone of tagging can be limited by the diffusion rate of the reactive form of the tagging substrate, or the activated tagging moiety, and the half-life of the reactive form of the tagging substrate, or the activated tagging moiety.

In some embodiments, only proteins that are located within about 10 nm of the tagging enzyme are tagged. For example, in some embodiments using a peroxidase and a biotinylated peroxidase tagging substrate, e.g., a biotinylated tyramide, only proteins that are located within about 10 nm of the peroxidase are biotinylated. However, it should be appreciated that the zone of biotinylation may be altered depending on the enzyme and/or substrate structure used for tagging. Thus the labeling range can be adjusted from about 500 nm to <10 nm.

While the methods for protein tagging and the related reagents, materials and compositions described herein are well suited for use in living cells and tissues, it should be appreciated that their use is not so limited, but that they can also be applied to fixed cells and tissues, for example, to fixed cells and tissues obtained from a subject, e.g., in a clinical setting.

In some embodiments, only proteins that are located within about 10 nm of the peroxidase are biotinylated. However, it should be appreciated that the zone of biotinylation may be altered depending on the enzyme and/or substrate structure used for tagging. Thus the labeling range can be adjusted from about 500 nm to <10 nm.

While the methods for protein tagging and the related reagents, materials and compositions described herein are well suited for use in living cells and tissues, it should be appreciated that their use is not so limited, but that they can also be applied to fixed cells and tissues, for example, to fixed cells and tissues obtained from a subject, e.g., in a clinical setting.

The methods of the invention are particularly useful for analyzing proteins. The terms "protein," "peptide" and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a lipid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

The term "amino acid," as used herein, includes any naturally occurring and non-naturally occurring amino acid. There are many known non-natural amino acids any of which may be included in the polypeptides or proteins described herein. See, for example, S. Hunt, The Non-Protein Amino Acids: In Chemistry and Biochemistry of the Amino Acids, edited by G. C. Barrett, Chapman and Hall, 1985. Some non-limiting examples of non-natural amino acids are 4-hydroxyproline, desmosine, gamma-aminobutyric acid, beta-cyanoalanine, norvaline, 4-(E)-butenyl-4 (R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C6H5; —CF3; —CN; -halo; —NO2; —CH3), disubstituted phenylalanines, substituted tyrosines (e.g., further substituted with —C(=O)C6H5; —CF3; —CN; -halo; —NO2; —CH3), and statine. In the context of amino acid sequences, "X" or "Xaa" represents any amino acid residue, e.g., any naturally occurring and/or any non-naturally occurring amino acid residue.

Some methods described herein are useful to identify and characterize the proteomes of defined subcellular zones (organelles, synapses, macromolecular complexes) of living cells. In some embodiments, in vivo analysis of localized proteomes combines the advantages of imaging (spatial and temporal resolution, compatibility with live cells) with those of mass spectrometry-based proteomics (multiplexed detection of endogenous proteins) without their respective limitations (limited multiplexing and not endogenous proteins, for imaging—and loss of spatial information and information recorded after cell lysis for mass spectrometry) as illustrated in FIG. 1.

Existing methods for analyzing the subcellular localization of proteins involve subcellular fractionation. However, this approach is messy and prone to contamination (for example, proteins get lost during purification, or contaminating proteins get included in the analysis). In addition, the biochemistry changes during long purification processes making it difficult to analyze dynamic states. Furthermore, fractionation methods require a lot of material making it difficult to analyze patient-derived samples. It also should be appreciated that certain cellular regions or zones just cannot be purified (e.g., synapses).

Figure 2:
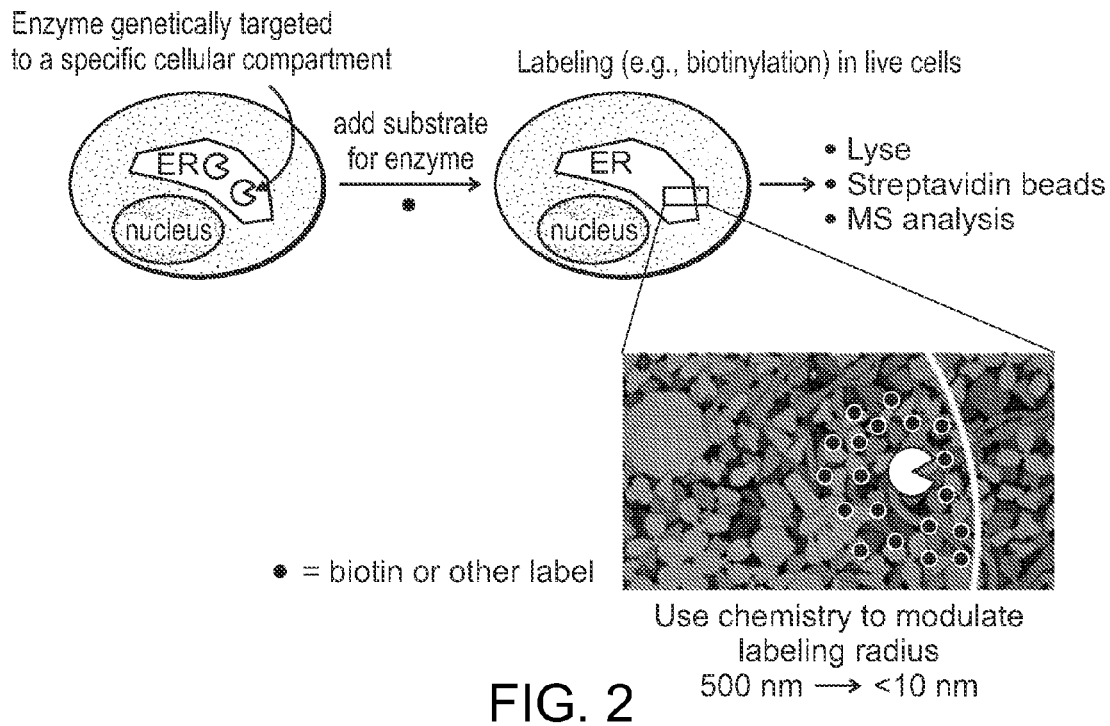
FIG. 2. Non-limiting example of spatially restricted labeling of endogenous proteins using an ER-targeted biotinylating enzyme.

In contrast, methods described herein allow for rapid in vivo tagging (e.g., in living cells or tissues), starting from small amounts of cells. Because in some embodiments, labeling is performed on living, intact cells, subcellular compartments are intact and undisrupted, reducing the possibility of contamination or loss of protein components. In some embodiments, promiscuous enzymes are used in live cells to biotinylate endogenous proteins in a spatially-defined manner. See FIG. 2. Biotin can be used as a handle to purify proteins after cell lysis for further analysis, for example, identification (e.g., using mass spectrometry). In some embodiments, peroxidases are used to perform the live cell labeling. In some embodiments, aspects of the invention allow proteins within specific zones to be identified, as illustrated for the synaptic region in FIG. 3.

Figure 3:
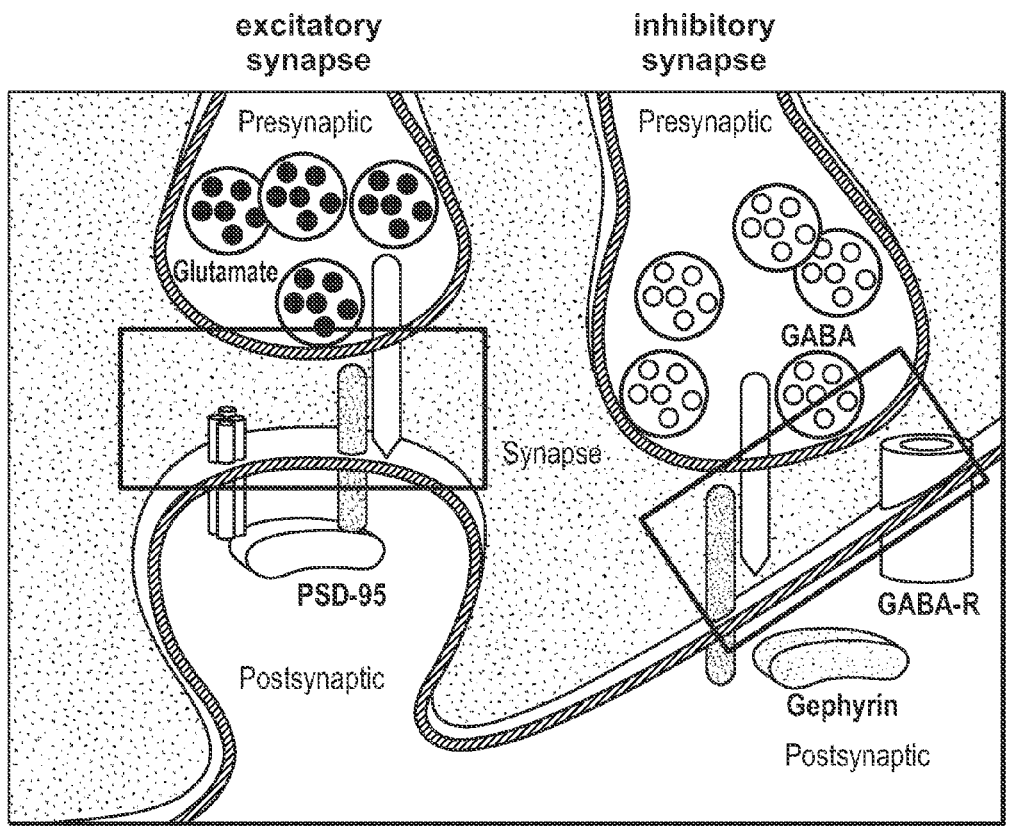
FIG. 3. Potential applications of the methodology to mapping subcellular proteomes, determining the composition of macromolecular complexes, and defining the proteome of specific cell types in tissue or animals. In addition, it illustrates how the proteomic composition of the synaptic cleft could be obtained.
Figure 5:
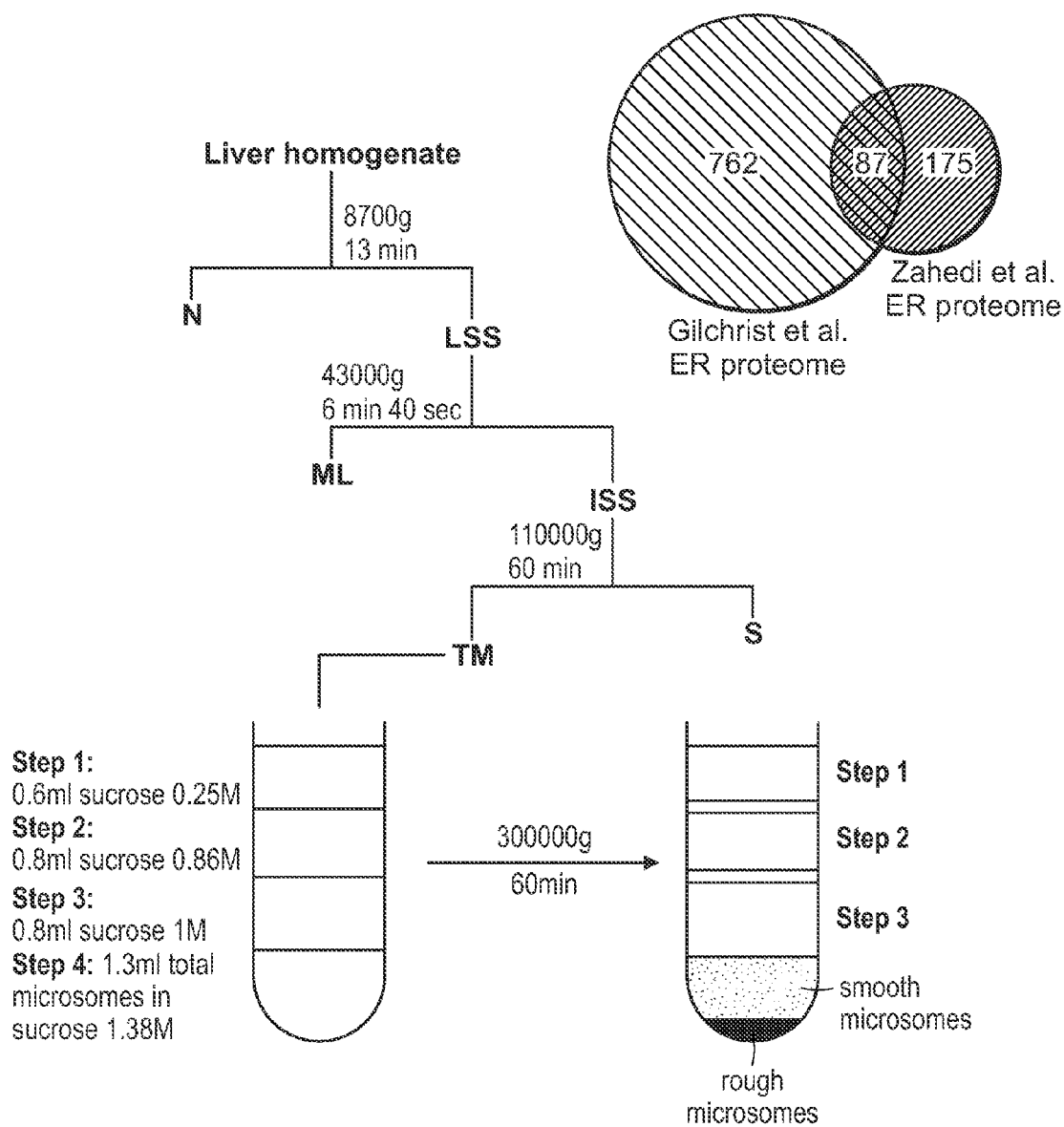
FIG. 5. A protocol for subcellular fractionation to purify microsomes derived from endoplasmic reticulum membranes. Such preparations were used for obtaining the previous endoplasmic reticulum proteomic datasets.
Figure 6:
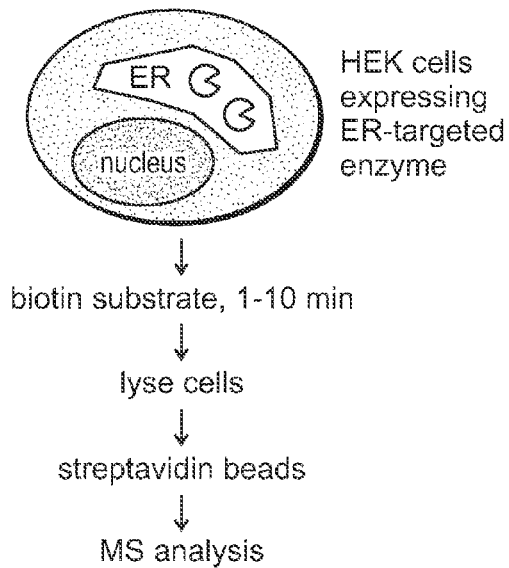
FIG. 6. Non-limiting embodiment of a live cell localized tagging method for organelle proteome identification.
Figure 7:
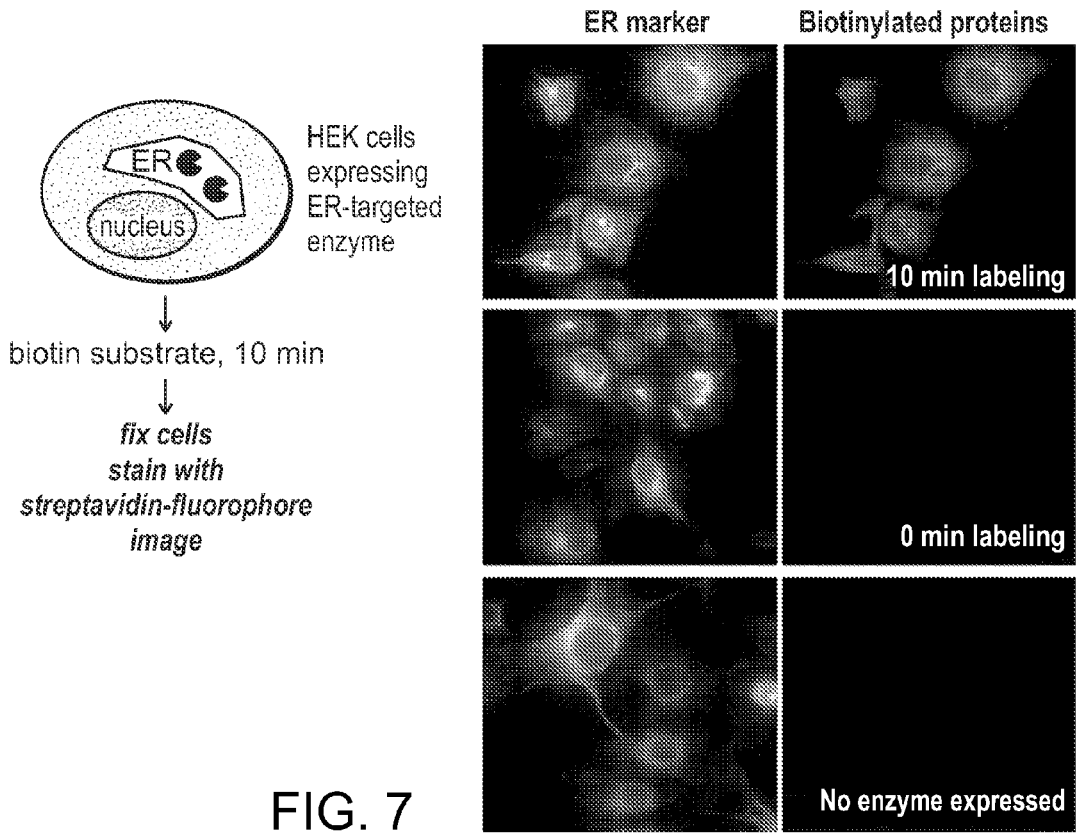
FIG. 7. Imaging analysis to assess tagging specificity.
Figure 8:
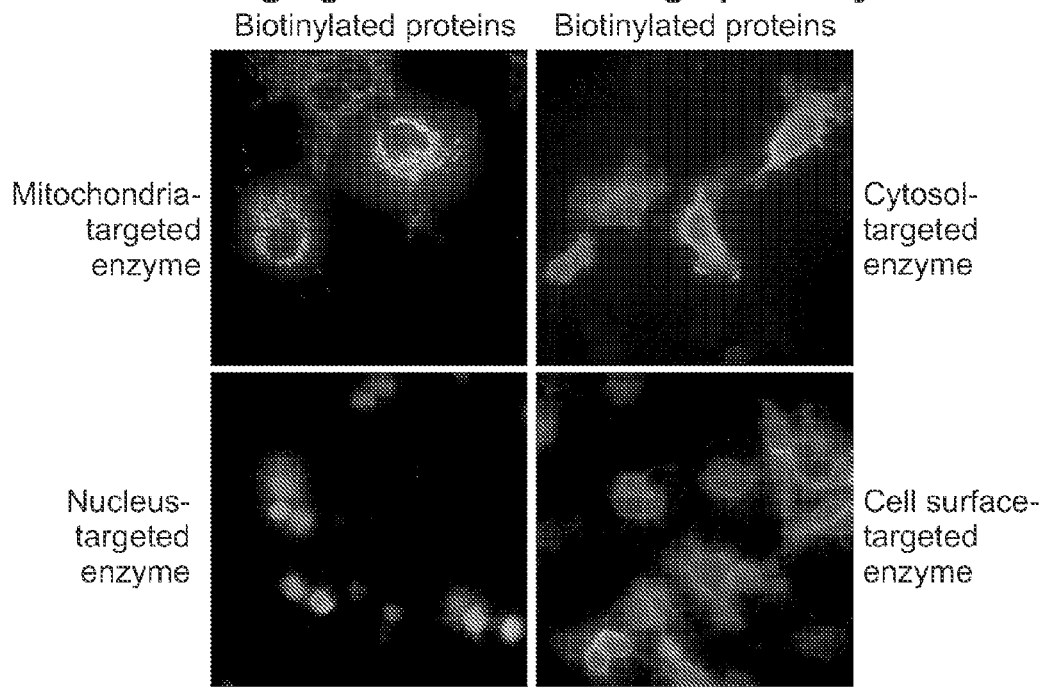
FIG. 8. Imaging examples of proteins that are expressed in specific cellular regions.
Figure 9:
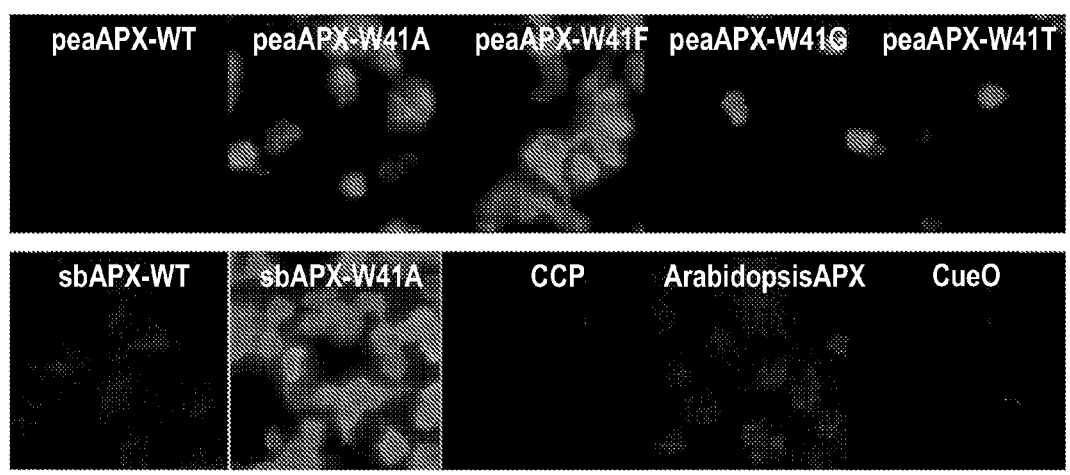
FIG. 9. Examples using different tagging enzyme mutants with variable levels of activity.
Figure 13:
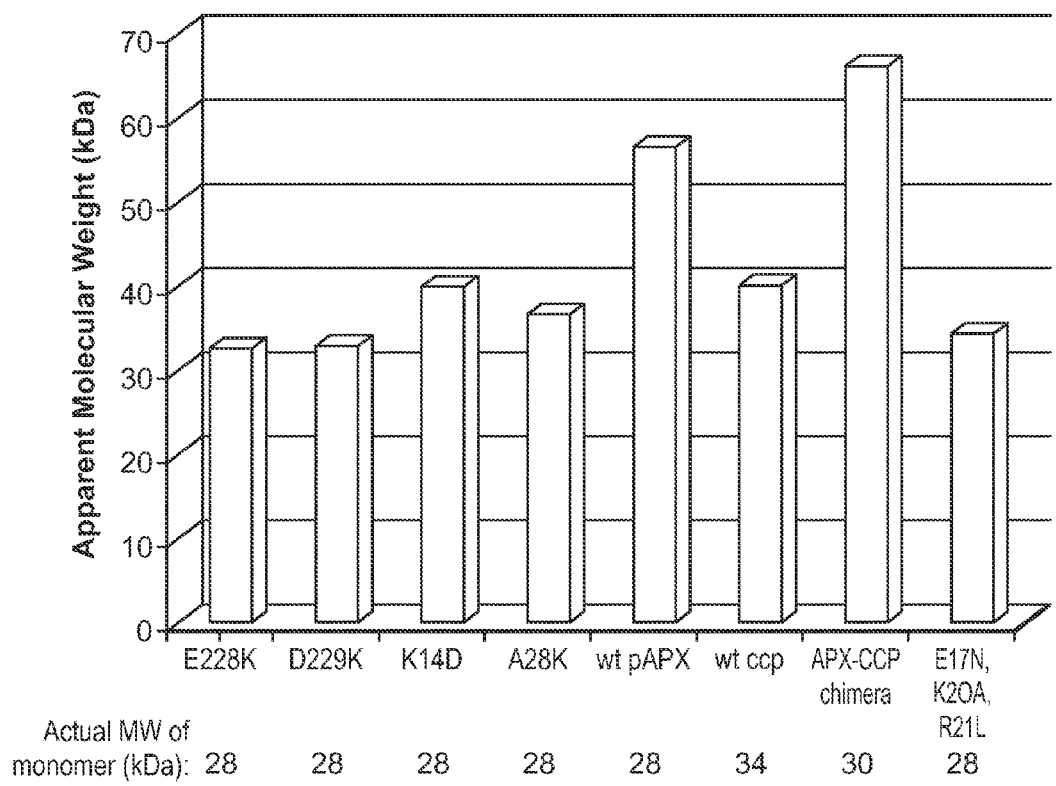
FIG. 13. Apparent MW of APX and CCP variants determined by gel filtration. 20 µM enzyme for all. All mutants are pAPX (peaAPX).

FIG. 3 illustrates an exemplary strategy for determining the proteome of organelles without subcellular fractionation. Examples for suitable organelles that can be assessed with methods described herein include, without limitation, golgi, mitochondria, nucleus, endosome, peroxisome, endoplasmatic reticulum (ER), ER membrane facing cytosol, ER membrane facing lumen, P-bodies, transport vesicles, COPII vesicles, and synaptic vesicles. In analyzing the synaptic cleft, the methods provided herein allow for a determination of the proteome of the cleft in different synapses and in synapses of different stages, e.g., in an excitatory and inhibitory synapses, and in synapses showing basal activity as well as in stimulated synapses.

The methods provided herein can also be used to discover endogenous components of macromolecular complexes, for example, of replisomes, ribosomes, transcription complexes, spliceosomes, and DNA repair complexes, complexes for fatty acid synthesis or for non-ribosomal peptide synthesis, neurexin-neuroligin signaling complexes, and glutamate receptor signaling complexes.

The methods provided herein can also be used to determine the proteome of specific cell types within complex tissues or heterogeneous cell populations, or of specific subcellular structures or organelles within specific cells in complex tissues or populations. For example, the methods provided herein can be used to assess the proteome of specific cell types in the brain, such as astrocytes, or of adult stem cells. The methods are particularly useful for analyzing the proteome of rare cells within complex cell populations.

Some aspects of the invention relate to an in vivo method of localizing protein tagging in order to analyze the proteins within a particular cell, cellular region or compartment, and/or macromolecular complex. Accordingly, some aspects of the invention are useful to identify specific proteomes associated with particular cells, cellular regions or compartments, and/or macromolecular complexes Some embodiments of this invention use a peroxidase targeted to a specific cell type or subcellular structure and utilizes a tyramide substrate to label proteins within its immediate vicinity. For example, in some embodiments, horseradish peroxidase (HRP) is directed to a cell or subcellular compartment, and an HRP substrate, biotin-tyramide, is added along with $H_2O_2$. HRP oxidizes biotin-tyramide, which reacts locally and covalently with proteins in the vicinity of the enzyme. Deposited biotin can then be visualized by staining with fluorophore-conjugated streptavidin or biotin-labeled proteins can be isolated and further analyzed.

Those of skill in the art will appreciate that any peroxidase exhibiting peroxidase activity within the cell, cell type, or subcellular compartment or structure of interest can be used in embodiments of this invention. As described in more detail in the Examples section, specific peroxidases, e.g., HRP, soybean peroxidase, and ascorbate peroxidase, as well as mutant peroxidases, can be used in living cells for spatially-restricted biotinylation of endogenous proteins. These peroxidases were used in connection with some methods provided herein to obtain preliminary proteomes of the endoplasmic reticulum (ER) and mitochondrial matrix in living mammalian cells.

Additional exemplary protein tagging methods and results obtained by using such methods are described in more detail in the Examples section and in FIGS. 4-14.

The term "agent," as used herein, refers to any molecule, entity, or moiety that can be conjugated to a protein, peptide, carbohydrate, lipid, or other biomolecule. For example, an agent may be a protein, an amino acid, a peptide, a polynucleotide, a carbohydrate, a detectable label, a binding agent, a tag, a metal atom, a contrast agent, a catalyst, a non-polypeptide polymer, a synthetic polymer, a recognition element, a lipid, a linker, or chemical compound, such as a small molecule. In some embodiments, the agent is a binding agent, for example, a ligand or a ligand-binding molecule, streptavidin, biotin, an antibody or an antibody fragment. In some such embodiments, the agent is a lipid, a carbohydrate, or a small molecule. Additional agents suitable for use in embodiments of the present invention will be apparent to the skilled artisan. The invention is not limited in this respect.

Figure 17:
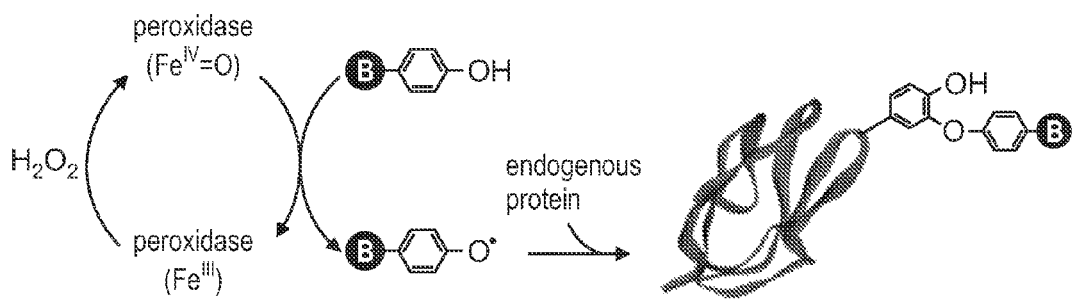
FIG. 17. Peroxidase-catalyzed conversion of biotin-phenol into a highly reactive biotin-phenoxyl radical.

Peroxidases are enzymes that catalyze the one-electron oxidation of phenol-type substrates into highly-reactive phenoxyl radicals (FIG. 17). Some aspects of this invention are based on the recognition that although phenoxyl radicals have not been fully characterized in the biological context, they exhibit a combination of half-life range and reactivity towards proteins suitable for the protein tagging methods and strategies provided herein. For instance, peroxidase-catalyzed oxidation of a biotin-phenol conjugate has been used to generate local polymer deposits on fixed cells, which are subsequently stained with uranyl acetate to give electron microscopy contrast[14]. Some aspects of this invention are based on the recognition that the high resolution (~20 nm) of these images suggests that the phenoxyl radical does not diffuse far before reacting with cellular material. Some aspects of this invention are based on the recognition that phenoxyl radicals can couple to amino acid side chains via aromatic homolytic substitution, or radical abstraction followed by diradical coupling[10, 11, 15-17]. Some aspects of this invention are based on the recognition that glutathione, which is present at a concentration of about 5 mM in the cytoplasm and has an S—H bond dissociation energy (BDE) of 87 kcal/mol, is an efficient phenoxyl radical quencher (phenol O—H BDE 88 kcal/mol) that can be exploited to limit its labeling radius[18].

Peroxidases cannot readily be exploited for intracellular protein labeling because of their expression in mammalian cells and because of their lack of activity sufficient to achieve effective labeling. For example, Horseradish peroxidase (HRP), the most widely used peroxidase in biotechnology, has been successfully expressed and shown to be active in the secretory pathway of mammalian cells[13]. However, HRP has four structurally essential disulfide bonds that are reduced in the cytosol, destroying its activity. Some aspects of this invention address the problem of peroxidase expression and activity in mammalian cells, for example, by using different peroxidases, e.g., ascorbate peroxidase (APX), that lacks disulfide bonds. APX exhibits high activity in the mammalian cytosol with a range of substrates, including biotin-phenol (FIG. 4). Some embodiments provide APX enzymes with improved utility, for example, APX enzymes engineered to be active as a monomer (instead of the wild type dimer), and APX enzymes comprising mutations, e.g., in the active site, that boost APX activity toward aromatic substrates such as phenol. The engineered APX enzymes provided herein are the first recombinant peroxidases with demonstrated activity in the mammalian cytosol.

The term "antibody", as used herein, refers to a protein belonging to the immunoglobulin superfamily. The terms antibody and immunoglobulin are used interchangeably. With some exceptions, mammalian antibodies are typically made of basic structural units each with two large heavy chains and two small light chains. There are several different types of antibody heavy chains, and several different kinds of antibodies, which are grouped into different isotypes based on which heavy chain they possess. Five different antibody isotypes are known in mammals, IgG, IgA, IgE, IgD, and IgM, which perform different roles, and help direct the appropriate immune response for each different type of foreign object they encounter. In some embodiments, an antibody is an IgG antibody, e.g., an antibody of the IgG1, 2, 3, or 4 human subclass. Antibodies from mammalian species (e.g., human, mouse, rat, goat, pig, horse, cattle, camel) are within the scope of the term, as are antibodies from non-mammalian species (e.g., from birds, reptiles, amphibia) are also within the scope of the term, e.g., IgY antibodies.

Only part of an antibody is involved in the binding of the antigen, and antigen-binding antibody fragments, their preparation and use, are well known to those of skill in the art. As is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). Suitable antibodies and antibody fragments for use in the context of some embodiments of the present invention include, for example, human antibodies, humanized antibodies, domain antibodies, F(ab'), F(ab')2, Fab, Fv, Fc, and Fd fragments, antibodies in which the Fc and/or FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; and antibodies in which the FR and/or CDR1 and/or CDR2 regions have been replaced by homologous human or non-human sequences. In some embodiments, so-called single chain antibodies (e.g., ScFv), (single) domain antibodies, and other intracellular antibodies may be used in the context of the present invention. Domain antibodies, camelid and camelized antibodies and fragments thereof, for example, VHH domains, or nanobodies are also encompassed in the term antibody. Further, chimeric antibodies, e.g., antibodies comprising two antigen-binding domains that bind to different antigens, are also suitable for use in the context of some embodiments of the present invention.

The term "antigen-binding antibody fragment," as used herein, refers to a fragment of an antibody that comprises the paratope, or a fragment of the antibody that binds to the antigen the antibody binds to, with similar specificity and affinity as the intact antibody. Antibodies, e.g., fully human monoclonal antibodies, may be identified using phage display (or other display methods such as yeast display, ribosome display, bacterial display). Display libraries, e.g., phage display libraries, are available (and/or can be generated by one of ordinary skill in the art) that can be screened to identify an antibody that binds to an antigen of interest, e.g., using panning. See, e.g., Sidhu, S. (ed.) Phage Display in Biotechnology and Drug Discovery (Drug Discovery Series; CRC Press; 1st ed., 2005; Aitken, R. (ed.) Antibody Phage Display: Methods and Protocols (Methods in Molecular Biology) Humana Press; 2nd ed., 2009.

The term "binding agent," as used herein refers to any molecule that binds another molecule with high affinity. In some embodiments, a binding agent binds its binding partner with high specificity. Examples for binding agents include, without limitation, antibodies, antibody fragments, receptors, ligands, aptamers, and adnectins.

The term "click chemistry" refers to a chemical philosophy introduced by K. Barry Sharpless of The Scripps Research Institute, describing chemistry tailored to generate covalent bonds quickly and reliably by joining small units comprising reactive groups together (see H. C. Kolb, M. G. Finn and K. B. Sharpless (2001). Click Chemistry: Diverse Chemical Function from a Few Good Reactions. Angewandte Chemie International Edition 40 (11): 2004-2021). Click chemistry does not refer to a specific reaction, but to a concept including, but not limited to, reactions that mimic reactions found in nature. In some embodiments, click chemistry reactions are modular, wide in scope, give high chemical yields, generate inoffensive byproducts, are stereospecific, exhibit a large thermodynamic driving force>84 kJ/mol to favor a reaction with a single reaction product, and/or can be carried out under physiological conditions. In some embodiments, a click chemistry reaction exhibits high atom economy, can be carried out under simple reaction conditions, use readily available starting materials and reagents, uses no toxic solvents or use a solvent that is benign or easily removed (preferably water), and/or provides simple product isolation by non-chromatographic methods (crystallisation or distillation).

The term "click chemistry handle," as used herein, refers to a reactant, or a reactive group, that can partake in a click chemistry reaction. In some embodiments, a reactive handle is a click chemistry handle. For example, a strained alkyne, e.g., a cyclooctyne, is a click chemistry handle, since it can partake in a strain-promoted cycloaddition. In general, click chemistry reactions require at least two molecules comprising click chemistry handles that can react with each other. Such click chemistry handle pairs that are reactive with each other are sometimes referred to herein as partner click chemistry handles. For example, an azide is a partner click chemistry handle to a cyclooctyne or any other alkyne. Exemplary click chemistry handles suitable for use according to some aspects of this invention are described herein. Other suitable click chemistry handles are known to those of skill in the art. For two molecules to be conjugated via click chemistry, the click chemistry handles of the molecules have to be reactive with each other, for example, in that the reactive moiety of one of the click chemistry handles can react with the reactive moiety of the second click chemistry handle to form a covalent bond. Such reactive pairs of click chemistry handles are well known to those of skill in the art and include, but are not limited to, those described in Becer, Hoogenboom, and Schubert, Click Chemistry beyond Metal-Catalyzed Cycloaddition, *Angewandte Chemie International Edition* (2009) 48: 4900-4908; and H. C. Kolb, M. G. Finn and K. B. Sharpless (2001). Click Chemistry: Diverse Chemical Function from a Few Good Reactions. Angewandte Chemie International Edition 40 (11): 2004-2021, the entire contents of each of which are incorporated herein by reference.

The term "conjugated" or "conjugation" refers to an association of two molecules, for example, two proteins or a protein and an agent, e.g., a small molecule, with one another in a way that they are linked by a direct or indirect covalent or non-covalent interaction. In certain embodiments, the association is covalent, and the entities are said to be "conjugated" to one another. In some embodiments, a protein is post-translationally conjugated to another molecule, for example, a second protein, a small molecule, a detectable label, a click chemistry handle, or a binding agent, by forming a covalent bond between the protein and the other molecule after the protein has been formed, and, in some embodiments, after the protein has been isolated. In some embodiments, two molecules are conjugated via a linker connecting both molecules. For example, in some embodiments where two proteins are conjugated to each other to form a protein fusion, the two proteins may be conjugated via a polypeptide linker, e.g., an amino acid sequence connecting the C-terminus of one protein to the N-terminus of the other protein. In some embodiments, two proteins are conjugated at their respective C-termini, generating a C—C conjugated chimeric protein. In some embodiments, two proteins are conjugated at their respective N-termini, generating an N—N conjugated chimeric protein.

The term "detectable label" refers to a moiety that has at least one element, isotope, or functional group incorporated into the moiety which enables detection of the molecule, e.g., a protein or peptide, or other entity, to which the label is attached. Labels can be directly attached (i.e., via a bond) or can be attached by a linker (such as, for example, an optionally substituted alkylene; an optionally substituted alkenylene; an optionally substituted alkynylene; an optionally substituted heteroalkylene; an optionally substituted heteroalkenylene; an optionally substituted heteroalkynylene; an optionally substituted arylene; an optionally substituted heteroarylene; or an optionally substituted acylene, or any combination thereof, which can make up a linker). It will be appreciated that the label may be attached to or incorporated into a molecule, for example, a protein, polypeptide, or other entity, at any position. In general, a detectable label can fall into any one (or more) of five classes: a) a label which contains isotopic moieties, which may be radioactive or heavy isotopes, including, but not limited to, $^{2}H$, $^{3}H$, $^{13}C$, $^{14}C$, $^{15}N$, $^{18}F$, $^{31}P$, $^{32}P$, $^{35}S$, $^{67}Ga$, $^{76}Br$, $^{99m}Tc$ (Tc-$^{99}m$) $^{111}In$, $^{123}I$, $^{125}I$, $^{131}I$, $^{153}Gd$, $^{169}Yb$, and $^{186}Re$; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label fluorescein-isothiocyanate (FITC); d) a label which has one or more photo affinity moieties; and e) a label which is a ligand for one or more known binding partners (e.g., biotin-streptavidin, FK506-FKBP). In certain embodiments, a label comprises a radioactive isotope, preferably an isotope which emits detectable particles, such as β particles. In certain embodiments, the label comprises a fluorescent moiety. In certain embodiments, the label is the fluorescent label fluorescein-isothiocyanate (FITC). In certain embodiments, the label comprises a ligand moiety with one or more known binding partners. In certain embodiments, the label comprises biotin. In some embodiments, a label is a fluorescent polypeptide (e.g., GFP or a derivative thereof such as enhanced GFP (EGFP)) or a luciferase (e.g., a firefly, Renilla, or Gaussia luciferase). It will be appreciated that, in certain embodiments, a label may react with a suitable substrate (e.g., a luciferin) to generate a detectable signal. Non-limiting examples of fluorescent proteins include GFP and derivatives thereof, proteins comprising fluorophores that emit light of different colors such as red, yellow, and cyan fluorescent proteins. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M. and Kain, S R (eds.) Green fluorescent protein: properties, applications, and protocols Methods of biochemical analysis, v. 47 Wiley-Interscience, Hoboken, N.J., 2006; and Chudakov, D M, et al., Physiol Rev. 90(3):1103-63, 2010, for discussion of GFP and numerous other fluorescent or luminescent proteins. In some embodiments, a label comprises a dark quencher, e.g., a substance that absorbs excitation energy from a fluorophore and dissipates the energy as heat.

The term "linker," as used herein, refers to a chemical group or molecule covalently linked to a molecule, for example, a protein, and a chemical group or moiety, for example, a click chemistry handle. In some embodiments, the linker is positioned between, or flanked by, two groups, molecules, or moieties and connected to each one via a covalent bond, thus connecting the two.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties, groups, and reactivities, are as described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987; the entire contents of each of which are incorporated herein by reference.

The term "alkyne," used herein interchangeably with the term "alynyl,", refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms (C2-20alkynyl). In some embodiments, the alkynyl group employed in the invention contains 2-15 carbon atoms (C2-15alkynyl). In another embodiment, the alkynyl group employed contains 2-10 carbon atoms (C2-10alkynyl). In still other embodiments, the alkynyl group contains 2-8 carbon atoms (C2-8alkynyl). In still other embodiments, the alkynyl group contains 2-6 carbon atoms (C2-6alkynyl). In still other embodiments, the alkynyl group contains 2-5 carbon atoms (C2-5alkynyl). In still other embodiments, the alkynyl group contains 2-4 carbon atoms (C2-4alkynyl). In still other embodiments, the alkynyl group contains 2-3 carbon atoms (C2-3alkynyl). In still other embodiments, the alkynyl group contains 2 carbon atoms (C2alkynyl). Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety. The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety.

The term "amino," as used herein, refers to a group of the formula (—NH2). A "substituted amino" refers either to a mono-substituted amine (—NHRh) of a disubstituted amine (—NRh2), wherein the Rh substituent is any substituent as described herein that results in the formation of a stable moiety (e.g., an amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the Rh substituents of the di-substituted amino group (—NRh2) form a 5- to 6-membered heterocyclic ring.

The term "azide" or "azido," as used herein, refers to a group of the formula (—N3).

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Example 1

Endoplasmic Reticulum (ER) Analysis

A non-limiting study of the ER proteome was performed as illustrated in FIGS. 4-12. Certain potential technical challenges needed to be considered (including $H_2O_2$ toxicity, endogenous peroxidase activity in the mitochondria, depth of coverage limited by radical reactivity (peroxidase-generated radicals prefer Trp, Tyr, Cys), peroxidase dimerization, speed of labeling, membrane permeability of radical cloud, etc.). However, methods described herein were surprisingly effective. For example, extensive labeling was obtained in approximately 1 minute and only 10 $cm^2$ of cultured cells were required to generate enough material for proteomics analyses.

Example 2

Preferred Peroxidase/Substrate Combinations

Various peroxidase/substrate combinations were evaluated for use in the provided methods of in vivo proteomics. The following assays were used to measure the performance of the different combinations: In vitro generation of dityramide fluorescence; Cellular peroxidase activity assay with Amplex Red; Cellular peroxidase activity assay with streptavidin-fluorophore staining.

Peroxidases evaluated included Horse Radish Peroxidase (HRP), HRP mutants, soy bean ascorbate peroxidase (sbAPX), sbAPX mutants, peaAPX, peaAPX point mutants, *Arabidopsis* APX, maize APX, cytochrome C peroxidase, laccase, tyrosinase. All of the above listed peroxidases are useful in some aspects of this invention.

Substrates evaluated included: biotin-tyramide, biotin-linker-tyramide, biotin-dopamide, biotin-methoxytyramide, biotin-nitrotyramide, alkyne-tyramide, alkyne-linker-tyramide. All of these substrates are useful in some aspects of this invention.

In some embodiments, the preferred peroxidase/substrate combination is sbAPX, for example, sbAPX W41A mutant in combination with a tyramide substrate, for example, alkyne-tyramide.

Further, wild-type HRP in combination with biotin tyramide, and sbAPX(W41A) in combination with hexy-tyramide are preferred tagging enzyme/substrate combinations in some embodiments.

Example 3

Characterization of the Chemical Properties of Preferred Peroxidase/Substrate Pairs In some embodiments, mass spectrometry is used to analyze tagged molecules, for example, tagged proteins. In some embodiments, heavy/light-biotin-tyramide substrate is used in combination with mass spec.

In some embodiments, the tagging methods and reagents provided herein are also useful for applications involving fixed cells. For example, in some embodiments, STORM imaging has been successfully performed, e.g., imaging of vimentin on fixed cells. In some embodiments, AP-myc-vimentin was used in combination with SA-HRP or vimentin-APX.

It should be appreciated that the labeling radius may be affected by the half-life of the reactive moiety created by the tagging enzyme. For example, different substrates create different reactive moieties with different half-life, and thus different labeling radii. Further, endogenous factors may influence half-life and labeling radius, for example, endogenous GSH, ascorbate, beta-carotene, etc., may shorten tyramide radical half-life and, thus, the labeling radius of tyramide-based reactive moieties, thus creating a more focused labeling hot spot.

Example 4

Use of Tagging Enzyme Fusions to Identify Protein Interaction Partner

In some embodiments, a protein of interest is fused to a tagging enzyme. For example, in some embodiments, a peroxidase useful in aspects of this invention is fused to a protein of interest to identify a molecule (e.g., a protein) that the protein of interest interacts with (e.g., binds to). In some embodiments, the protein of interest is fused to the protein of interest, e.g., expressed in a cell from a recombinant expression construct encoding the enzyme/protein of interest fusion. The cell is then contacted with a suitable substrate, for example, a tyramide substrate described herein, and labeled proteins, which are proteins in the vicinity of the enzyme, and, thus, of the protein of interest, are identified according to methods described herein.

Example 5

Characterization of the Cellular Properties of Preferred Peroxidase/Substrate Pairs In some embodiments, HRP is functional in the ER and/or Golgi, but not in other subcellular compartments. Accordingly, in some embodiments HRP is not functional when targeted with a nuclear localization signal (NLS), nuclear export signal (NES), or mitochondrial localization sequence. Some aspects of this invention provide that soybean peroxidase, for example, a soybean peroxidase described herein, is active and can be used according to aspects of this invention in subcellular compartments in which HRP is inactive.

Example 6

Application to Proteome Mapping

The ER proteome was analyzed using a peroxidase targeted to the ER. A SILAC experiment was performed using HRP-ER+biotin-tyramide, and 279 proteins were isolated and identified that are enriched in +HRP-ER cells compared to untransfected negative control cells. For these 279 proteins, 67% are classified as "ER" by the Gene Ontology Cell Component (GOCC) database. This indicates that the technique described herein is characterized by a high specificity in identifying bona fide ER proteins. For comparison, of the entire human proteome, 7% of proteins are classified as "ER" according to GOCC. For comparison, the best previously available ER proteomic database (Gilchrist Cell 2006), 16% are classified as "ER" according to GOCC.

It was also investigated how many known ER proteins were captured in the above experiment. Compared to a list of 25 bona fide ER proteins analyzed by Rapoport et al. (Cell 2010), 21 were detected with the above methodology. Further, peroxidase was targeted to the mitochondria, and activity according to cellular peroxidase activity assays was detected in mitochondria.

In some embodiments, the methods provided herein can be used to analyze mitochondrial proteomes. In some embodiments, the localization of mito-APX is determined, for example, as compared to mitotracker+/− $H_2O_2$ and tyramide. In some embodiments, endogenous peroxidase activity is controlled for under labeling conditions described herein. In some embodiments, a SILAC experiment is performed, comparing cells with and without mito-APX expression In some embodiments, the mitochondrial matrix proteome for cells from healthy versus diseased subjects is compared. For example, the proteome from healthy subjects is compared to subjects diagnosed with MDS patient (mito DNA depletion syndrome). In some embodiments, such comparisons are used in the evaluation of drug treatments, in the screening of drugs, or in the monitoring of the efficacy of a specific treatment schedule in a patient undergoing such treatment.

In some embodiments, sub-proteomes of subcellular compartments are analyzed, for example, mitochondrial sub-proteomes, such as the mitochondrial outer membrane (OM) proteome, both facing cytosol and facing inside. In conventional proteomic analyses of mitochondrial proteomes (e.g. mitocarta), outer membrane proteins were depleted and likely missed.

Example 7

Use of Monomeric Peroxidases

Wild-type (wt) aspartate peroxidase (APX), for example, soybean APX, is dimeric. This property makes it disadvantageous as a reporter enzyme for some applications since dimeric tags can perturb the trafficking of the endogenous proteins to which they are appended. To address this disadvantage, mutants of APX were engineered that are monomeric, as confirmed by gel filtration chromatography (GFC, FIG. 13). The experiment was performed on a Superdex S75 10/300 column on a medium pressure chromatography system. The most promising mutants have apparent molecular weights close to 28 kDa, indicating they are predominantly monomeric. Cytochrome C peroxidase (CCP), a 34 kDa enzyme known to be monomeric, is included as a control.

Figure 14:
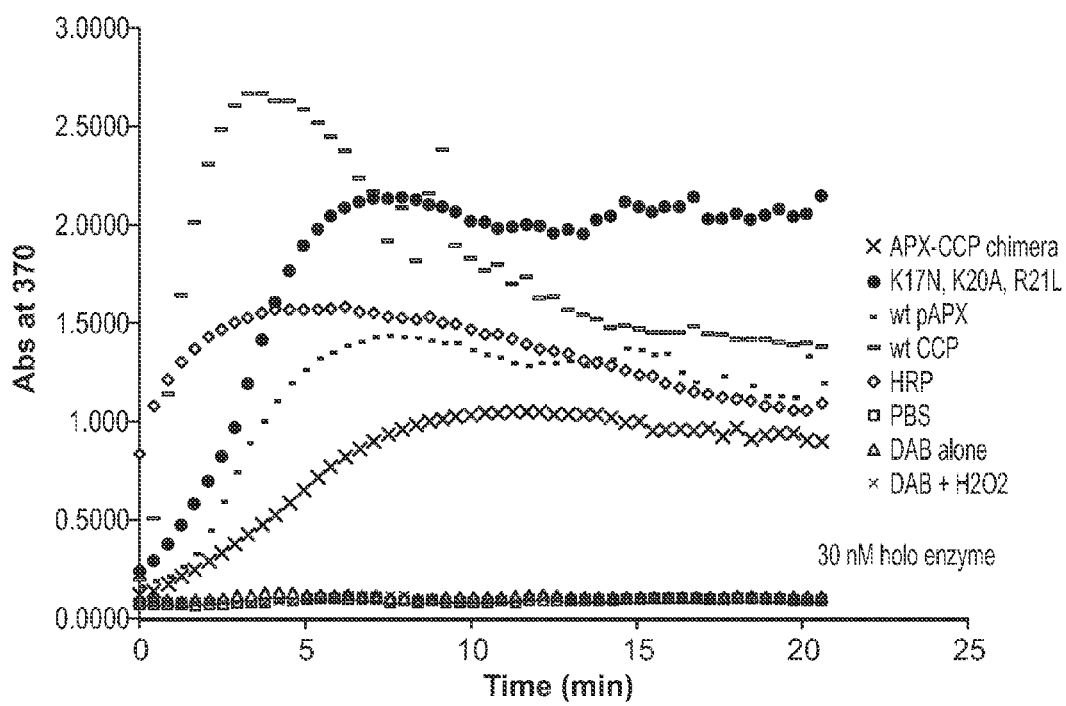
FIG. 14. Results of an in vitro assay for activity toward 3,3'-diaminobenzidine.

FIG. 14 shows the activity of some monomeric APX enzymes. In this assay, the APX variants are incubated with 3,3'-diaminobenzidine and $H_2O_2$. APX catalyzes the formation of a dense polymer with absorbance at 370 nm. The monomeric variants of APX displayed activity comparable to that of wild-type APX. In some embodiments, the monomeric APX is derived from pAPX.

Some aspects of this invention provide for engineered monomeric APX enzymes that are useful in the proteomics methods described herein. Methods using such engineered monomeric enzymes are also provided.

Example 8

Mapping Proteomes of Living Cells Using Peroxidases

Figure 15:
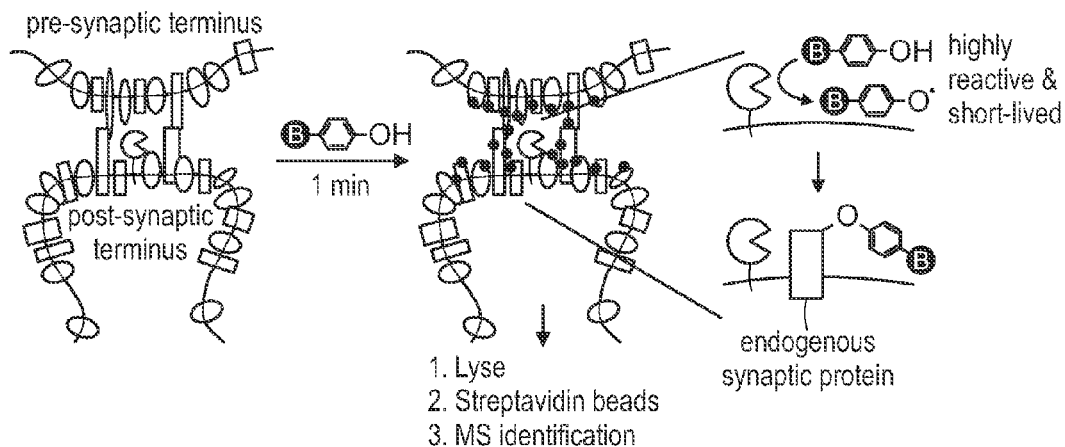
FIG. 15. Proposed method for mapping proteomes of living cells via spatially-restricted biotinylation of endogenous proteins.
Figure 16:
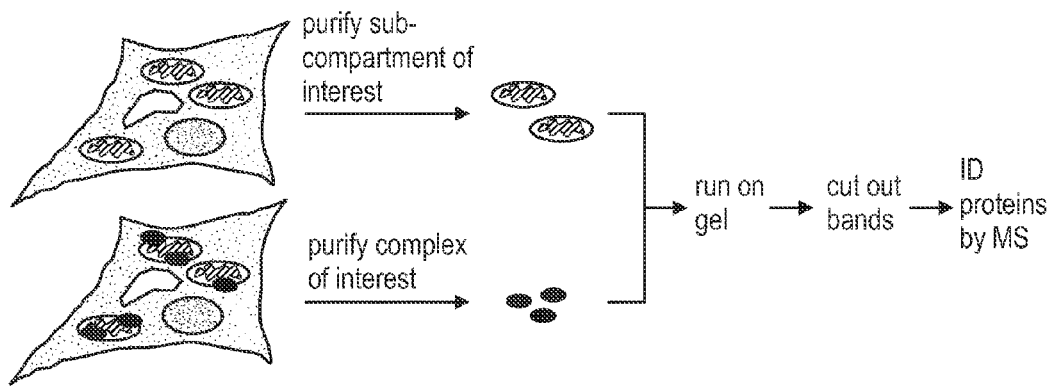
FIG. 16. Traditional mass-spectrometric (MS) proteomics.

Several experiments were performed to determine the suitability of HRP and APX and mutants of these enzymes for in vivo protein tagging, for example, in exemplary protein tagging strategies as provided herein, e.g., as illustrated in FIGS. 15-17.

FIG. 15 shows the mapping of the synaptic cleftome. A promiscuous tagging enzyme (such as a peroxidase, in green) is genetically targeted to the synaptic cleft, by fusion to a known synaptic protein such as neuroligin-1. To initiate labeling, a biotinylated substrate for the enzyme is added (such as a biotin-phenol conjugate; biotin is represented as "B"). The enzyme converts this substrate into a highly reactive radical species that covalently biotinylates neighboring proteins. Due to the short lifetime of this radical, labeling is restricted to an area within 1400 nm of the promiscuous enzyme; hence proteins outside the synaptic cleft are not labeled. In this example, intracellular proteins are also not labeled because the biotin-phenol substrate is charged and cannot cross membranes. After labeling is performed on live cells, biotinylated proteins are enriched with streptavidin beads and identified by mass spectrometry.

FIG. 16 illustrates the drawbacks of traditional MS technology as compared to the instantly provided technology. Organelles or macromolecular complexes are purified from cells after lysis. Purified samples are then identified by mass spectrometry. The purification step introduces artifacts due to contamination and protein loss, leading to false positives and false negatives. Furthermore, many subcellular regions of interest, such as the synaptic cleft, are impossible to purify. The technology provided herein, e.g., as illustrated in the exemplary embodiment described in FIG. 15, obviates the need for purification altogether by tagging the relevant proteome.

FIG. 17 illustrates the enzyme-mediated generation of a highly reactive biotin-phenoxyl radical. In the catalytic cycle, $H_2O_2$ first oxidizes the heme center of the peroxidase to Fe(IV)=O. This oxidized form of the enzyme then catalyzes one-electron oxidation of biotin-phenol into a biotin-phenoxyl radical[19]. The radical diffuses from the peroxidase active site and covalently reacts with electron-rich amino acid side chains such as tyrosine, tryptophan, and cysteine[11, 15-17] on nearby endogenous proteins, before becoming quenched by cellular glutathione and other species.

It was observed that (1) APX expresses well in all cell compartments tested (cytosol, nucleus, ER, mitochondria, cell surface), and HRP expresses well in the secretory pathway (ER, Golgi, cell surface), as has previously been shown[13]. (2) Both peroxidases catalyze covalent biotinylation when biotin-phenol and 1 mM $H_2O_2$ are added to live cells for 1 minute (FIG. 18). Streptavidin blotting of cell lysate showed that numerous endogenous proteins are tagged with biotin, in addition to the peroxidase itself. (3) Confocal and super-resolution imaging (by Stochastic Optical Reconstruction Microscopy, or STORM[21]) showed that labeling is restricted to the immediate vicinity of the peroxidase (200 nm or 22 nm, for confocal and STORM (FIG. 19), respectively). (4) Intracellular labeling with plasma membrane-anchored, cytosol-facing APX failed to produce biotinylated extracellular proteins that can be detected with a membrane-impermeant streptavidin-fluorophore conjugate, suggesting that the biotin-phenoxyl radical does not cross membranes. (5) MS/MS analysis of peptides derived from biotinylated proteins detected labeling on tyrosine side chains, with the expected molecular weight change for covalent coupling to the biotin phenoxyl radical. (6) One minute $H_2O_2$ treatment did not alter cell or mitochondrial morphology, suggesting that toxicity is limited in this time window.

Figure 18A:
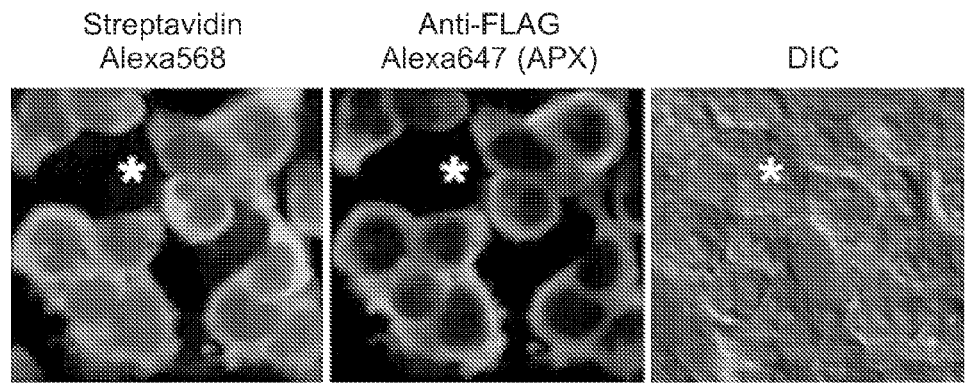
FIG. 18. Engineered ascorbate peroxidase (APX) is active in the mammalian cytosol.
Figure 18B:
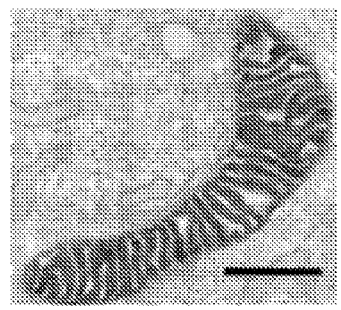

FIG. 18 demonstrates that an engineered version of APX is useful for in vivo proteomics according to some aspects of this invention. Unlike HRP, APX lacks disulfide bonds[20], and we have engineered it to be monomeric and highly active toward aromatic substrates like biotin-phenol. FIG. 18(A) illustrates imaging of HEK cells expressing cytosolic APX, labeled live with biotin-phenol. After fixation, biotinylated sites were detected by staining with streptavidin-Alexa568. APX was detected by anti-FLAG immunofluorescence (Alexa647 channel). Untransfected cells (starred) display negligible biotinylation, showing that endogenous peroxidases do not cross-react with biotin-phenol to a significant degree. FIG. 18(B) illustrates that engineered APX can be used as a reporter for electron microscopy (EM). Here, APX was genetically targeted to the mitochondrial matrix, and EM contrast was generated by APX-catalyzed oxidative polymerization of diaminobenzidine, followed by $OsO_4$ staining. Dark regions show the localization of APX in the mitochondrial matrix. Using APX instead of HRP has the advantage that APX is not inactivated after translation in the cytosol, before import into the mitochondria. Scale bar, 500 nm.

Figure 19:
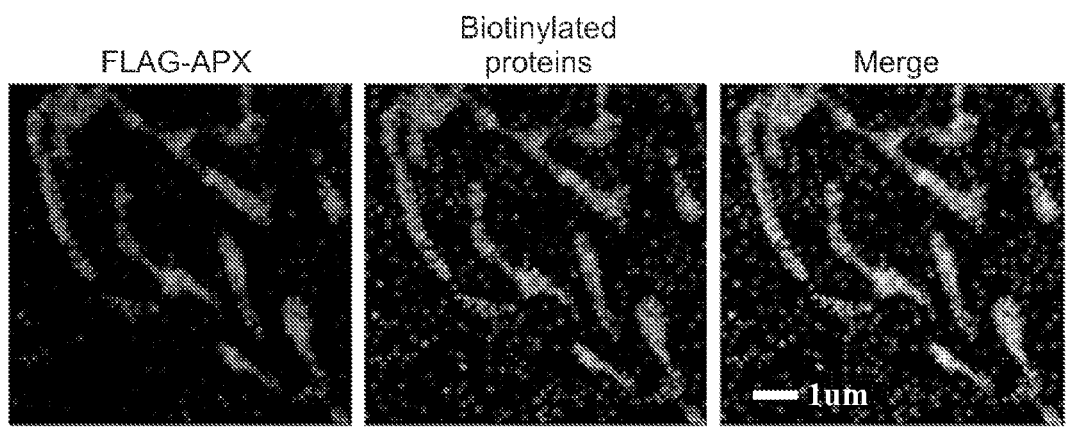
FIG. 19. Super-resolution imaging to characterize the APX labeling radius in cells.

FIG. 19 illustrates COS cells expressing mitochondrial matrix-localized FLAG-APX that were labeled for 1 minute with biotin-phenol and $H_2O_2$. Cells were then fixed and biotinylation sites were detected by staining with streptavidin-AlexaFluors 405/647. APX was detected by anti-FLAG immunofluorescence staining (AlexaFluors 568/647). Two-color STORM super-resolution imaging (resolution 22 nm, about 10-fold higher than confocal imaging resolution) showed high co-localization between APX and biotinylated proteins.

Example 9

Labeling the ER and Mitochondrial Proteomes in Living Cells

Based on the promising characteristics of peroxidase-mediated biotinylation described above, proteomics experiments were conducted. We targeted the ER proteome because although many attempts have been made to map its proteome via subcellular fractionation[3], and published datasets are inconsistent, likely due to high rates of false positives and false negatives in ER-derived microsomes. We also targeted the proteome of the mitochondrial matrix, which has only been mapped crudely by mitochondrial fractionation followed by hypotonic lysis to remove the outer mitochondrial membrane[22].

APX was fused to a mitochondrial matrix targeting sequence, and HRP (because it has higher activity in the ER than APX) was fused to a KDEL tag to induce retention in the ER. Both constructs were introduced into HEK cells with lipofectamine, and labeling was performed by pre-loading the cells for 30 min with biotin-phenol, then adding 1 mM $H_2O_2$ for 1 min to allow biotinylation. Thereafter, cells were lysed, with simultaneous quenching of peroxidase activity. Negative controls with $H_2O_2$, biotin-phenol, or peroxidase omitted did not show labeling, demonstrating that endogenous mammalian peroxidases do not contribute to background under our labeling conditions[23]. We used SILAC labeling of untransfected control samples to subtract back round due to non-specific bead binding.

FIG. 20 summarizes the features of our resulting ER and mitochondrial matrix MS datasets. We evaluated specificity by checking each hit for previous ER or mitochondrial annotation. For instance, 83% of our top 300 labeled mitochondrial proteins can be found in MitoCarta, the most comprehensive database of human mitochondrial proteins[1]. We have started to evaluate depth-of-coverage by calculating the fraction of well-established ER or mitochondrial proteins (gold standards) that are found in our datasets. For instance, 28 of 45 (62%) complex I subunits are seen in our mitochondrial dataset. 21 of 25 (84%) abundant ER membrane proteins characterized by Rapoport et al.[5] are found in our ER dataset.

Figure 20A:
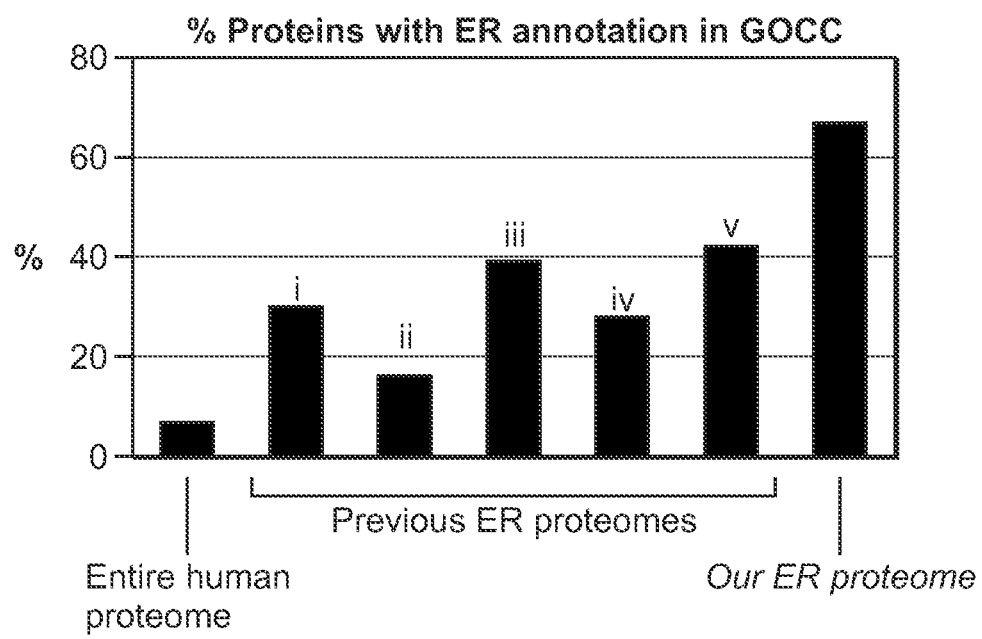
FIG. 20. Preliminary determination of ER and mitochondrial matrix proteomes.
Figure 20B:
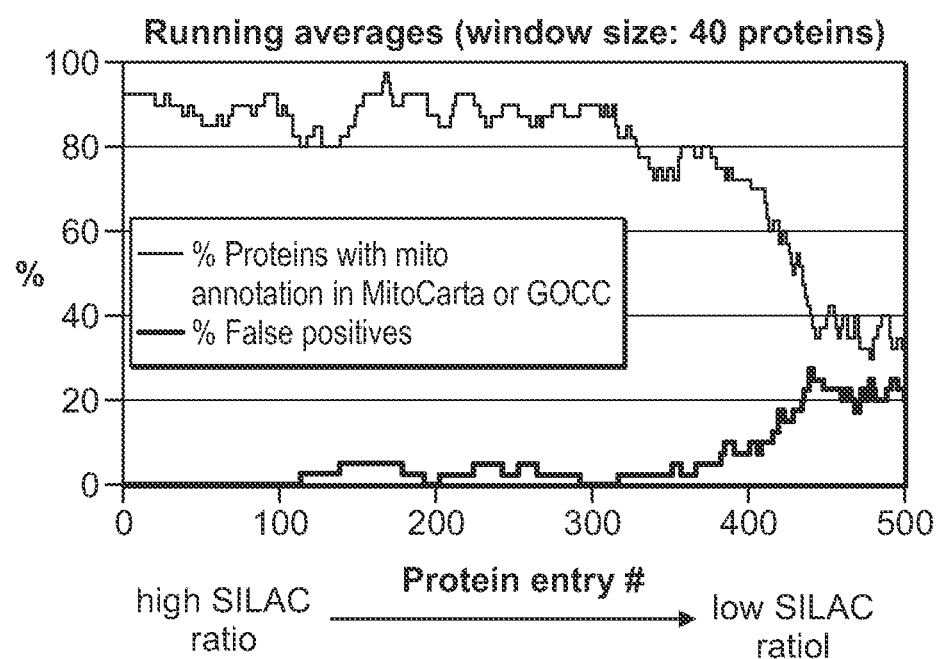

Living HEK cells expressing ER-targeted HRP or mitochondrial matrix-targeted APX were labeled with biotin-phenol and $H_2O_2$, before lysis and analysis of biotinylated proteins by MS (FIG. 20). Analysis of the specificity of our ER proteomic dataset (279 proteins) by comparison to the Gene Ontology Cellular Component (GOCC) database is illustrated in FIG. 20(A). For comparison, five previous ER proteomic datasets[3], obtained by microsome purification, are analyzed in a similar fashion. i, ER from rat pancreas (428 proteins); ii, rat liver, non-overlapping with COPI (849 proteins); iii, rat liver, overlapping with COPI (431 proteins); iv, mouse liver (153 proteins); v, canine pancreas (262 proteins). Analysis of the specificity of our mitochondrial proteome is illustrated in FIG. 20(B). 500 proteins in our dataset are listed along the x axis, from high to low SILAC ratio. High SILAC ratio indicates high abundance of that protein in APX-expressing cells compared to untransfected control cells. Running averages were calculated for the percentage of proteins with previous mitochondrial annotation. False positive rates were calculated using previous methods[24]. For example, this graph shows that for the 40 proteins centered around protein #300, 34 (85%) have mito annotation in MitoCarta or GOCC, and none appear in a list of >2000 known non-mitochondrial proteins (0% false positives).

These experiments demonstrated that peroxidases can be used in living cells to biotinylate endogenous proteomes for MS identification. Preliminary characterization suggests that specificity is high for these membrane-bounded compartments, although depth-of-coverage could be improved.

Example 10

Mapping Proteomes of Membrane-Membrane Contact Sites

The data presented herein demonstrate that the peroxidase-mediated protein tagging strategies provided herein are applicable to proteomic mapping experiments in some subcellular compartments. The successful labeling of the endoplasmic reticulum (ER) and mitochondrial matrix proteomes as described herein represent a critical step towards the proteomic mapping of subcellular regions that are impossible to purify and hence inaccessible to any current technology. Similar to these two subcellular compartments, the contact sites between biological membranes are impossible to purify with conventional methods. In some embodiments, the technology provided herein is applied to three such contact sites (FIG. 21): the synaptic cleft, contact sites between mitochondrial and ER membranes, and the intermembrane space (IMS) between the mitochondrial outer and inner membranes.

Mapping of the synaptic cleftome with synapse-targeted ascorbate peroxidase (APX) is illustrated in FIG. 21(A). Mapping of the mitochondrial intermembrane space (IMS) with APX fused to the 59-amino acid targeting sequence of the IMS protein Smac/Diablo is illustrated in FIG. 21(B). Mapping of the proteome at mitochondria-ER junctions, either using APX fused to a known junction protein (mitofusin-2 or Mff), or using a split peroxidase strategy, in which one peroxidase fragment is expressed on the mitochondrial outer membrane, and the other peroxidase fragment is expressed on the ER membrane is illustrated in FIG. 21(C). Reconstituted, active peroxidase is found only at mitochondria-ER junctions.

Mapping the Synaptic Cleftome.

The synaptic cleft is responsible for electrical coupling between neurons in the brain, and undergoes differentiation and remodeling in response to developmental state, environment, and activity/usage. Only a couple dozen synaptic cleft proteins are known, and these have mostly been discovered in a slow, labor-intensive, one-by-one manner. The methods and strategies provided herein are applied to tag and identify the complete inventory of endogenous proteins in the synaptic cleft by fusing either HRP or APX peroxidase to the extracellular domains of well-characterized synaptically-localized transmembrane proteins such as neurexin and neuroligin. A recent study targeted fragments of GFP to the synaptic cleft via fusions to these same proteins[25]. Whereas a peroxidase-neuroligin-1 fusion will traffic to excitatory synapses, a neuroligin-2 fusion will traffic to inhibitory synapses, allowing us to compare their proteomes.

In some embodiments, each type of synaptic cleft is analyzed before and after neurotransmitter stimulation, and at earlier versus later stages of development.

To enhance labeling specificity, a membrane impermeant biotin-phenol conjugate is used, such as a carboxylated variant bearing a permanent negative charge, that will react with surface pools of the peroxidase fusion construct, but not intracellular pools in the ER or Golgi. Initially labeling is performed on cultures of dissociated rat cortical neurons, transfected with HSV virus. Subsequently, tissue from transgenic mice expressing the peroxidase fusion construct will be analyzed.

The delivery of biotin-phenol and $H_2O_2$ into some tissues presents a challenge. Some aspects of this invention provide strategies that address this problem by partially homogenizing the transgenic tissue, as if performing a synaptosome preparation[7], and then adding the labeling reagents. To eliminate background from ER and Golgi pools of peroxidase that would be exposed by this protocol, a "split peroxidase" reporter is used in some embodiments, that reconstitutes across synaptic membranes and therefore gives activity only in the cleft, similar to the mGRASP split-GFP reporter[25]. A split HRP was engineered and it has been confirmed to reconstitute its fragments in the ER of live cells. In addition to identifying synaptic proteins, studies using the strategies provided herein provide information about the topology of membrane proteins in the synapse. The results obtained so far show that the biotin phenoxyl radical does not cross membranes, so surface-exposed/extracellular amino acids should be labeled, while intracellular amino acids should not (FIG. 22).

Membrane-anchored APX peroxidase, facing the extracellular space, will label only surface-exposed amino acids of endogenous membrane proteins, because the phenoxyl radical does not cross membranes (FIG. 22). After proteolytic digestion, directly biotinylated peptides can be purified and sequenced by MS/MS. Not only should we be able to identify which peptides contact the extracellular space, we can also determine the specific labeled amino acids. Analogously, residues facing the intracellular side can be mapped using APX anchored to the inner leaflet of the plasma membrane. For this experiment, we would use a neutral biotin-phenol that crosses membranes (such as that used in FIG. 4A), but becomes converted by APX into a membrane-impermeant biotin phenoxyl radical. This general approach can be extended to intracellular membrane proteins as well, such as proteins within the mitochondrial inner and outer membranes.

In some embodiments, biotinylated peptides and proteins are isolate and sequence directly, for example, by affinity purification and subsequent MS analysis. The information thus obtained is used, in some embodiments, to infer which regions of synaptic proteins face into the cleft.

Mapping the Proteome of Mitochondria-ER Contact Sites.

The methods and strategies for protein tagging provided herein are, in some embodiments, used to map the proteome of contact sites between mitochondria and ER. A handful of proteins—Mff, Drp1, and mitofusin-2—have been discovered at these sites in mammalian cells, and shed light on the diverse possible roles of mitochondria-ER junctions in the regulation of mitochondrial division[26], calcium and phospholipid exchange, and protein import into mitochondria[8].

Three different approaches are contemplated: (1) fuse APX to proteins already known to be present at these junctions; (2) separately map the proteomes of the mitochondrial outer membrane and the ER membrane, and then intersect these two lists (3) develop and use a split-APX reporter, in which half of APX will be targeted to the outer mitochondrial membrane, and the other half of APX will be targeted to the ER membrane (facing cytosol) (FIG. 21C). APX reconstitution is believed to occur only at mitochondria-ER contact sites. It is further believed that use of a split APX reporter system will be suitable in this context.

Mapping the Proteome of the Mitochondrial Inter-membrane Space.

In some embodiments, the in vivo proteomics methodology provided herein is employed to analyze the proteome of the mitochondrial inter-membrane space (IMS). During apoptosis, the mitochondrial outer membrane undergoes a permeability transition, and contents of the IMS, including caspases, Smac/Diablo, and cytochrome c, release into the cytosol[27]. We have targeted our APX peroxidase to the IMS using a localization sequence from Smac/Diablo. By mapping the IMS proteome, it is possible to gain insight into how mitochondria control programmed cell death. Furthermore, proteins embedded in the mitochondrial inner and outer membranes can be detected that function in protein translocation, calcium exchange, and oxidative phosphorylation.

Example 11

Proximity Labeling for Mapping of Macromolecular Complexes and Proteomes of Specific Cell Types In addition to proteomic mapping of spatially-defined zones of cells, the strategies and methods for in vivo protein tagging can be used to uncover the molecular composition of macromolecular complexes, in their intact state within living cells. In this context, it is preferable to use enzyme/substrate: pairs with a labeling radius that is relatively small, e.g., less than 5-10 nm.

In some embodiments, a peroxidase, e.g., APX, is fused to a known protein component of a macromolecular complex (e.g., similar to GFP-tagging), and then promiscuous, spatially-restricted biotinylation is exploited to tag and identify the unknown protein members of the macromolecular complex. The strategies provided herein can be used to map protein and other components of, for example, ribosomes, the neurexin-neuroligin trans-synaptic adhesion complex, the calcium channel complex, and other macromolecular complexes.

Another class of applications for which this technology is suitable is proteomic mapping of specific cell types within complex tissue. For example, the astrocyte proteome has been elusive because pure astrocyte cultures are not physiological, and astrocyte dissociation and purification from brain tissue greatly disrupts its physiology. According to some aspects of this invention, it is preferable to determine the proteome of healthy astrocytes embedded in their native context—the brain—and clearly distinguish this proteome from that of the surrounding neurons. To this end, transgenic mice that express cytosolic APX under control of an astrocyte-specific promoter, such as the GLT-1 promoter are used.

Example 12

Modulating the Labeling Process

Labeling specificity is determined by the labeling radius, which in turn is determined by radical half-life. In some embodiments, the labeling radius is modulated by the presence or sequestration of radical quenchers, such as ascorbate and trolox, which are non-toxic membrane-permeable radical scavengers. Such radical quenchers can be added at different concentrations to cells being subjected to an in vivo protein tagging procedure as described herein. Changes in labeling radius can be measured by super-resolution STORM imaging of biotinylated proteins after cell fixation, as in FIG. 19, or electron microscopy for even higher resolution. Alternatively, labeling radius can be assessed by targeting APX to well-Characterized cellular structures, such as the centrosome, and then using MS readout of resulting biotinylation patterns as a molecular ruler.

Another approach to reducing radical lifetime is to explore other peroxidase substrate structures. Aside from phenols, peroxidases are known to oxidize and generate radical species from anilines, hydrazines, hydroxamic acids, indoles, amines, beta-diketones, and other compounds, each with different half-life, reaction efficiency, and, thus, labeling radius. Furthermore, since phenoxyl radicals are electron-deficient, electron withdrawing groups such as nitro, perchloro, or cyano further destabilize them, thus further decreasing the labeling radius. In some embodiments, the use of alternate peroxidase substrate structures may necessitate the use of peroxidases with higher oxidizing power than APX, such as myeloperoxidase or engineered peroxidases with enhanced activity. Such enhanced peroxidases are provided herein and additional enhanced peroxidases will be apparent to the skilled artisan or can be generated by the skilled artisan without more than routine experimentation. For example, enhanced peroxidases can be created using yeast display evolution, previously employed to engineer the enantioselectivity of HRP[29].

To improve specificity, it may be preferable in some embodiments to reduce the toxicity of labeling conditions. For example, in some embodiments, cells are treated with 1 mM $H_2O$ for 1 minute to initiate peroxidase labeling. In some cell types, this treatment may initiate early apoptotic events that might alter proteomic compositions within the cells. In some embodiments, this problem is addressed by using glucose, oxygen, and transfected glucose oxidase to generate $H_2O_2$ only locally in the compartments of interest.

To improve the sensitivity, or depth of coverage, of the technology provided herein, it is preferable in some embodiments to maximize the phenoxyl radical conjugation yield, and expand the scope of the reaction to amino acid side chains besides tyrosine, tryptophan, and cysteine. The more reactive radical products described herein can be employed to achieve this goal. In addition, tuning enzyme kinetics, and hence the rate of radical generation from the enzyme active site, can be exploited to modulate labeling yields.

Example 13

The Mitochondrial Matrix Proteome Labeled in Living Cells

Figure 23A:
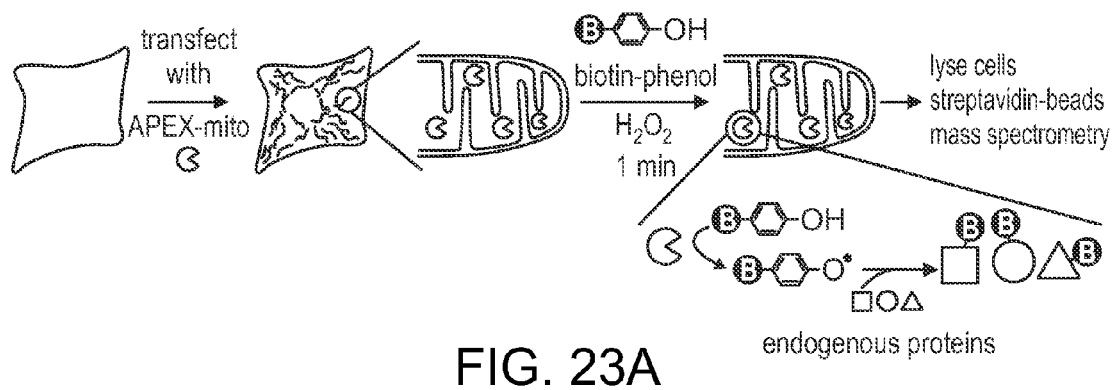
FIG. 23(A) is a schematic depicting the method of mitochondrial matrix proteome labeling in living cells. A gel showing the results of the described methods is shown in FIG. 23(D). Electron microscopy was performed on the cells by APEX-catalyzed diaminobenzidine polymerization as shown in 23(B). The biotinylated proteins were also examined by fluorescence imaging 23(C).
Figure 23B:
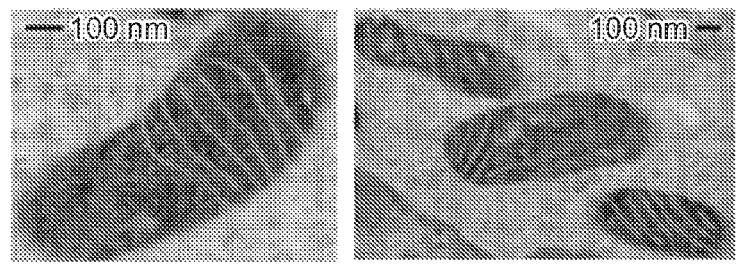
FIG. 23. Labeling the mitochondrial matrix proteome in living cells.
Figure 23C:
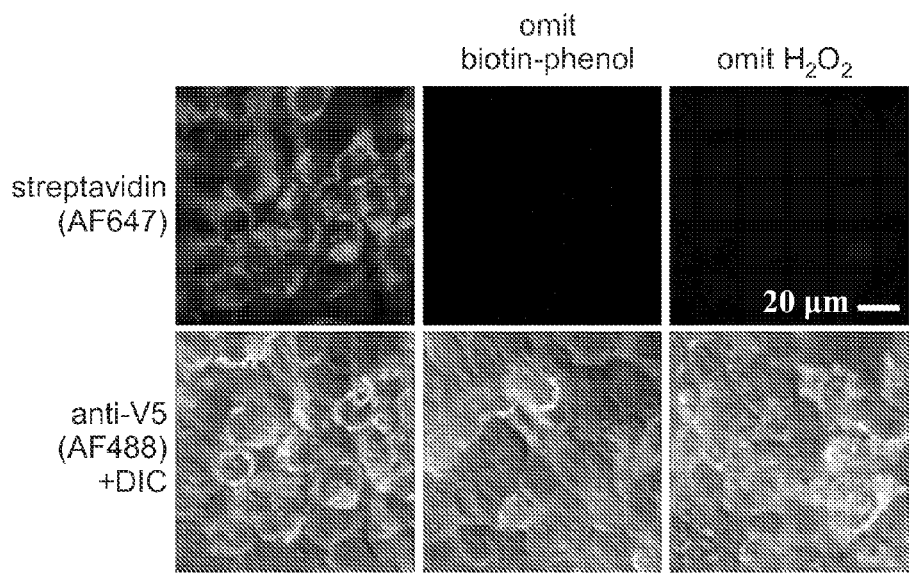

The methods were performed as shown in FIG. 23(A). The peroxidase (APEX or HRP) was genetically targeted to the cellular compartment of interest. Labeling was initiated by addition of biotin-phenol and H2O2 to live cells for 1 minute. The cells were then lysed and biotinylated proteins were recovered with streptavidin-coated beads, eluted, separated on a gel, and identified by mass spectrometry.

Electron microscopy was performed on the cells by APEX-catalyzed diaminobenzidine polymerization, followed by OsO4 staining 23(B). It was determined based on the electron micrographs that APEX-mito was localized in the mitochondrial matrix of HEK cells.

Figure 23D:
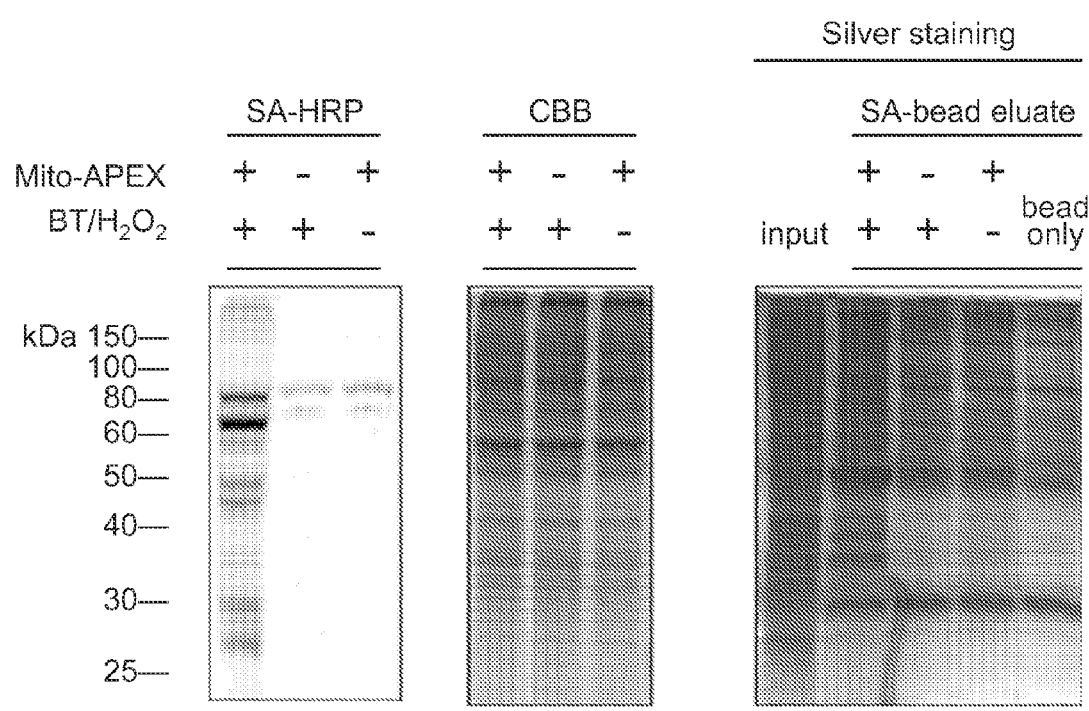

The biotinylated proteins were also examined by fluorescence imaging 23(C). Mitochondrial matrix-targeted APEX in HEK was visualized by anti-V5 staining. Proteins biotinylated by APEX were stained with streptavidin. Super-resolution STORM images showed streptavidin and APEX localization patterns in cells. A gel showing the results of the described methods is shown in FIG. 23(D).

Figure 24A:
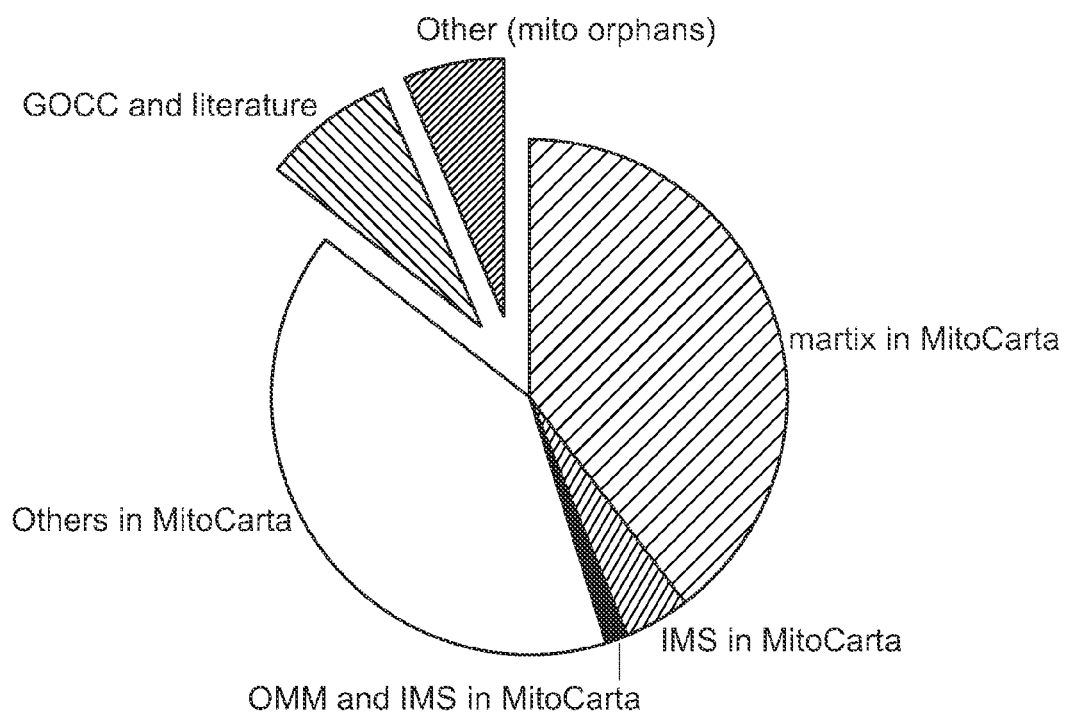
FIG. 24. Specificity and depth of coverage of the mitochondrial matrix proteome. 24(A) is a pie chart depicting the mitochondrial matrix proteins labeled in the methods. 24(B) is a graph providing the amount of microsomal proteins detected in the methods versus the total number. 24(C) is a schematic showing the membrane complexes.
Figure 24B:
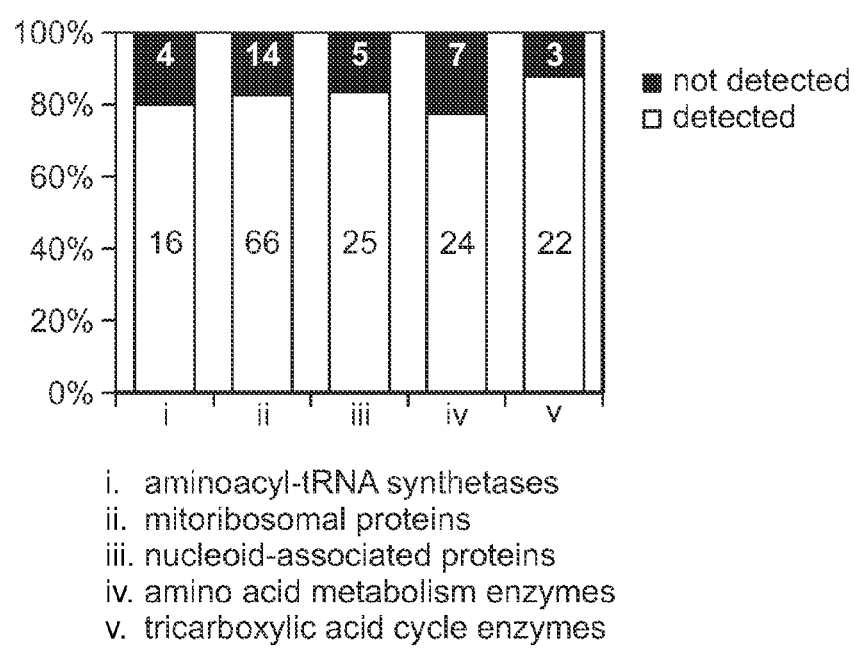
Figure 24C:
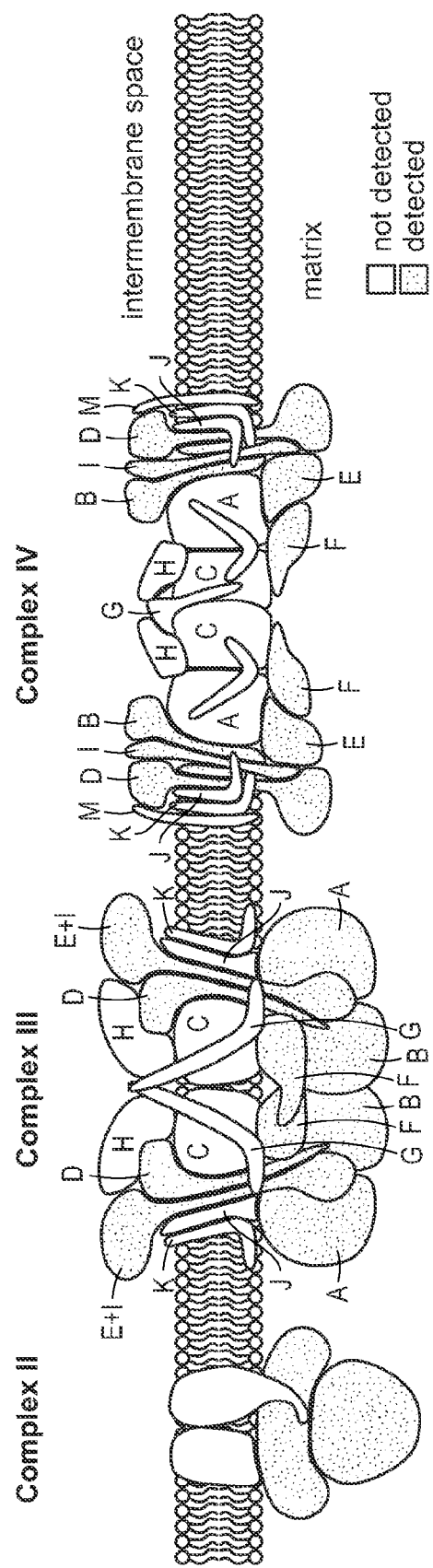

FIG. 24 is a set of schematics showing the results of the mitochondrial matrix labeling. The mitochondrial matrix proteins labeled in the methods is shown in pie chart form in FIG. 24(A). 24(B) is a graph depicting schematically the amount of microsomal proteins detected in the methods versus the total number of proteins. The membrane complexes are shown in FIG. 24(C).

Example 14

Analysis of Multiple Substrates in Proteomal Labeling Methods in Living Cells

Figure 25A:
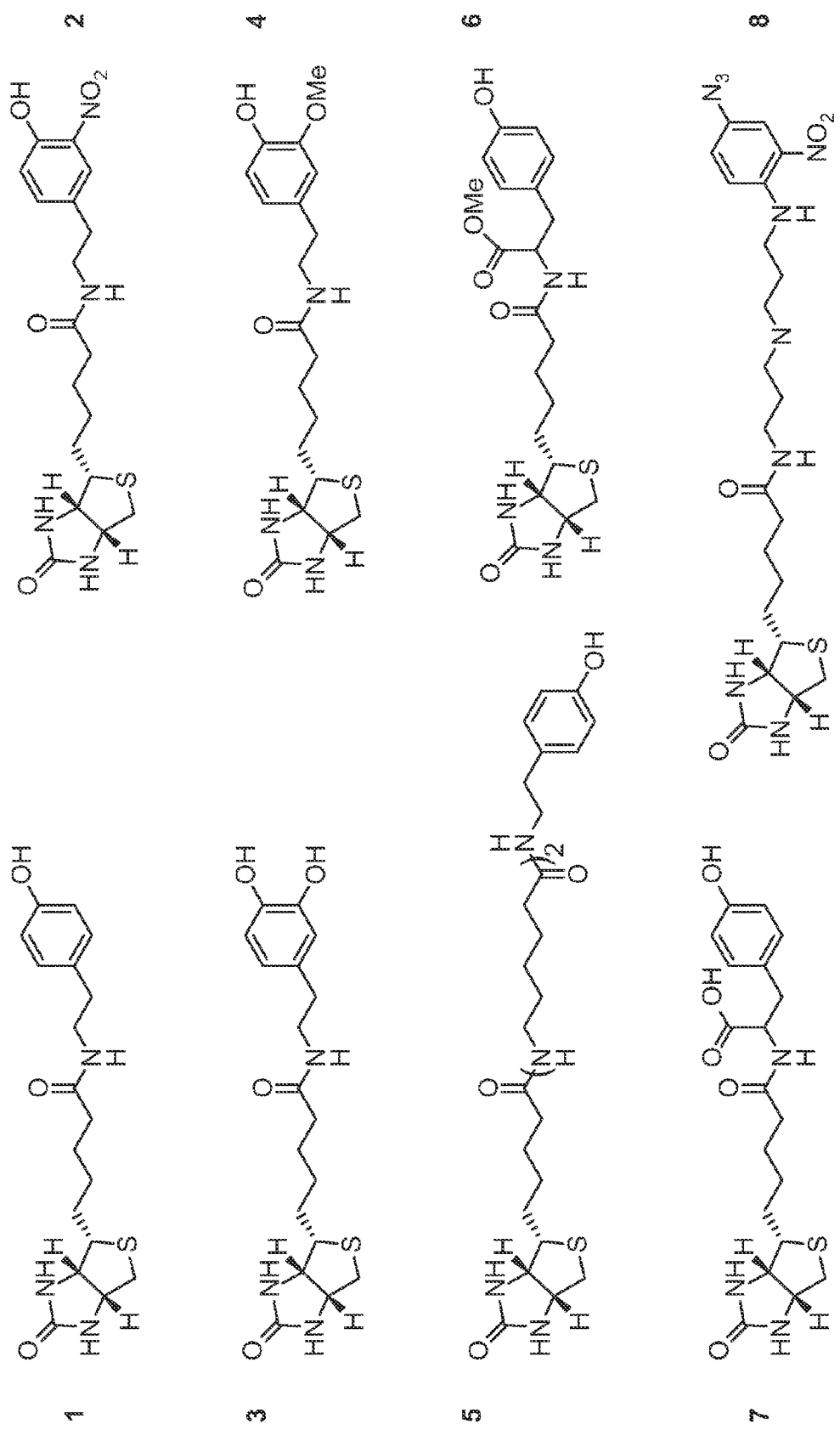
FIG. 25. Comparison of 8 different biotin substrate structures with APX and HRP. 25(A): structures of biotin conjugates tested. 25(B): Imaging results with HEK cells expressing cytosolic Flag-W41FAPX-NES (top row) or cell surface HRP-myc-TM (bottom row).
Figure 25B:
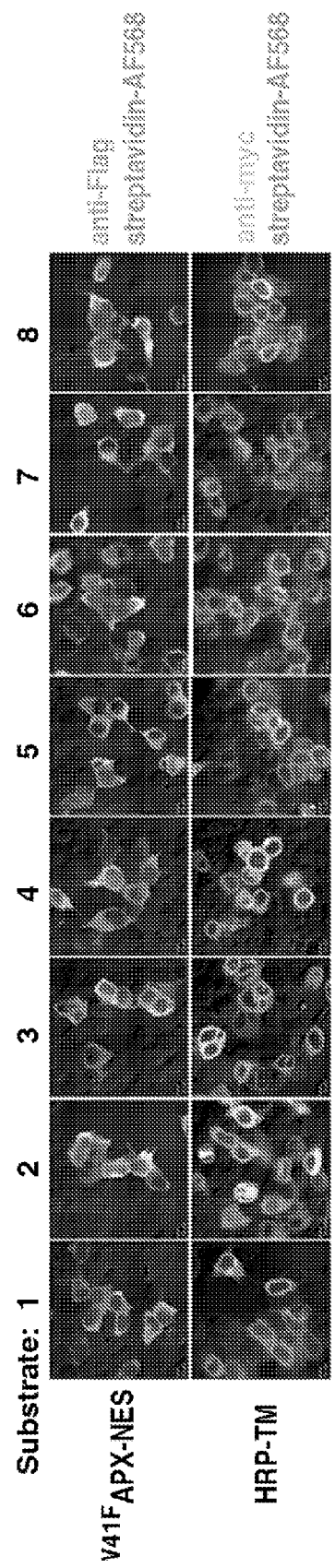

Eight different biotin substrate structures were tested in the methods of the invention using APX (25(B) top row) and HRP (25(B) bottom row) as enzymes. The structures for the tested biotin substrates are shown in FIG. 25(A). The imaging results with HEK cells expressing cytosolic Flag-W41FAPX-NES (top row) or cell surface HRP-myc-TM (bottom row) are shown in FIG. 25(B). For APX, labeling was performed by incubating cells with 500 µM of the indicated substrate for 30 min, then adding 1 mM H2O2 for 1 min to initiate biotinylation. Cells were then fixed and stained. For HRP, 100 µM of the indicated substrate was added for 10 min, then 1 mM H2O2 was added for 1 min to initiate labeling. Cells were then fixed and stained. Scale bars, 10 um.

Example 15

Figure 26:
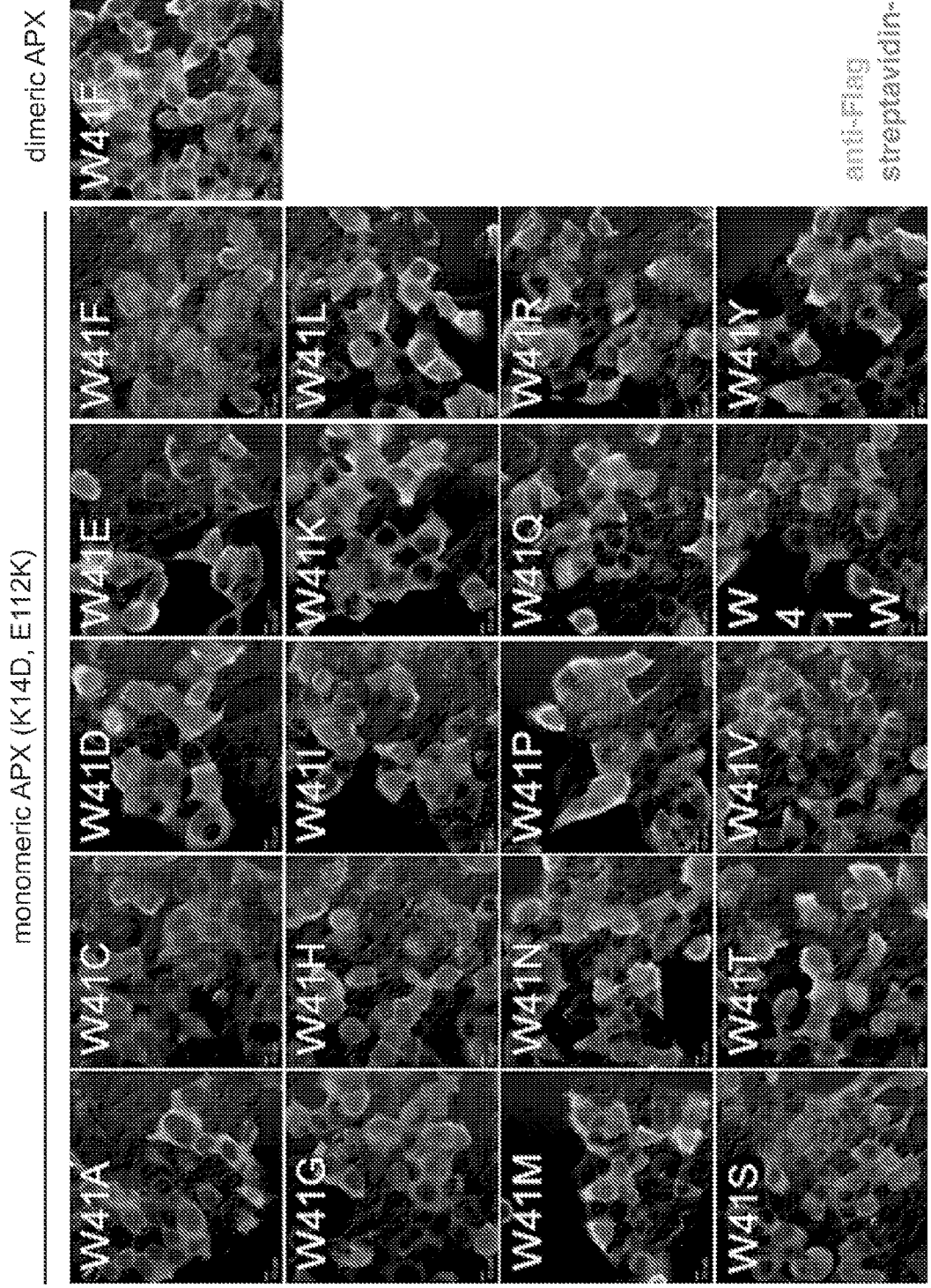
FIG. 26. Imaging results of W41 mutants of monomeric APX having increased intracellular activity.

Imaging Results of W41 Mutants of Monomeric APX Having Increased Intracellular Activity W41 mutants of monomeric APX having increased intracellular activity were examined and the imaging results are shown in FIG. 26. A scan was performed on all possible W41 mutations on the monomeric APX template (NES-tagged for cytosolic localization). Labeling was performed by incubating cells for 30 min with biotin-phenol, then adding $H_2O_2$ for 1 min. After fixation, cells were stained with anti-Flag antibody to visualize APX expression level, and streptavidin-AF568 to visualize biotinylated proteins. For comparison, W41FAPX-NES (dimeric) was characterized in parallel.

Example 16

The Biotin-Phenoxyl Radical Does Not Cross the Plasma Membrane

Figure 27A:
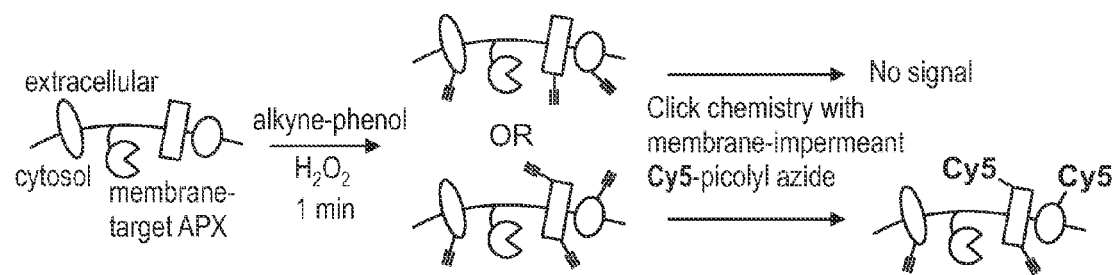
FIG. 27. The biotin-phenoxyl radical does not cross the plasma membrane. 27(A) Assay scheme. 27(B) Images with W41AAPX-CAAX (left) and W41AAPX-NES (right).
Figure 27B:
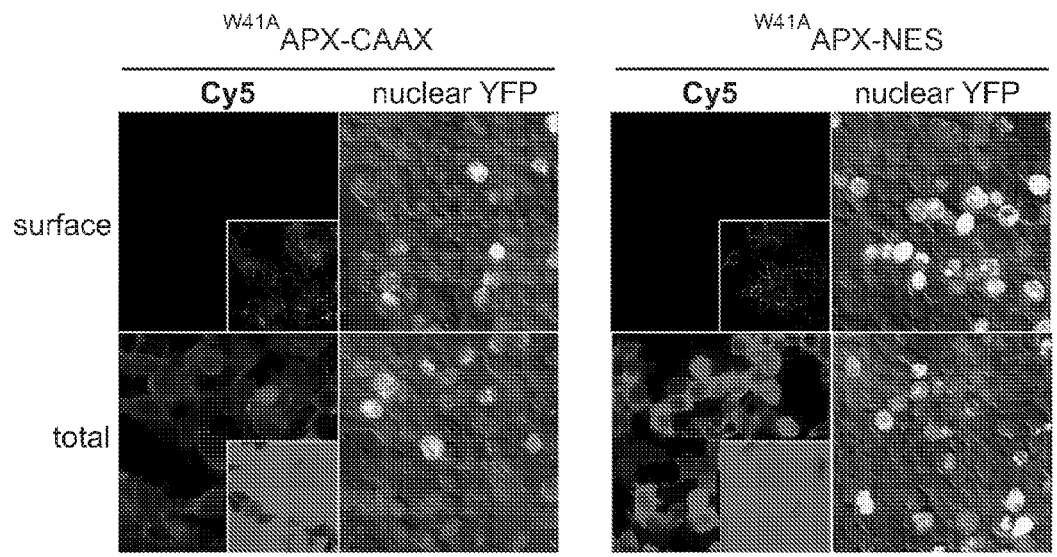

An assay scheme of the method performed is shown in FIG. 27(A). HEK293T cells are transfected with W41AAPX targeted to the cytosol (NES) or inner leaflet of the plasma membrane (CAAX). Labeling is performed with alkyne-phenol and H2O2 for 1 min. Thereafter Click chemistry is performed at the cell surface with membrane-impermeant Cy5-picolyl azide conjugate. Only if the phenoxyl radical can cross the plasma membrane will alkyne be present at the cell surface and detectable by the Cy5 reagent. The images with W41AAPX-CAAX (left) and W41AAPX-NES (right) are shown in FIG. 27(B). Nuclear-localized YFP was a transfection marker. As a control (bottom rows labeled "total"), cells were fixed and permeabilized prior to Click chemistry to detect intracellular alkyne-phenol labeling. Insets show the same fields of view with 50-fold greater contrast.

Example 17

Determination of the Cut-Off Point for Our Mitochondrial Matrix Proteome

A SILAC labeling scheme, as shown in FIG. 28A was used to label a mitochondrial matrix proteome. Determination of the cut-off point for our mitochondrial matrix proteome. (A) SILAC labeling scheme. The results are shown graphically in FIGS. 28C and D. FIG. 28(C) is a histogram showing the number of proteins previously identified in the mitochondria which were detected by the methods. FIG. 28(D) is a likelihood ratio plot.

Example 18

Detection of Mitochondrial Proteomes

Members of mitochondrial proteomes were identified using the methods provided herein. FIG. 29 (Table 1) illustrates an exemplary mitochondrial matrix proteome (495 proteins), ranked from most enriched to least enriched (H/L ratio from Rep1). FIG. 30 (Table 2) identifies mitochondrial orphans (31 newly discovered mitochondrial proteins), ranked from most enriched to least enriched (H/L ratio from Rep1). FIG. 31 (Table 3) described biotinylated peptides detected (88 unique peptides, derived from 63 unique enriched proteins), grouped by protein. FIG. 32 (Table 4) describes mitochondrial matrix protein groups detected. FIG. 33 (Table 5) describes inner mitochondrial membrane complexes detected. FIG. 34 (Table 6) describes outer mitochondrial membrane proteins detected. FIG. 35 (Table 7) describes intermembrane space proteins detected.

REFERENCES (1) Pagliarini, D. J.; Calvo, S. E.; Chang, B.; Sheth, S. A.; Vafai, S. B.; Ong, S. E.; Walford, G. A.; Sugiana, C.; Boneh, A.; Chen, W. K.; Hill, D. E.; Vidal, M.; Evans, J. G.; Thorburn, D. R.; Carr, S. A.; Mootha, V. K. *Cell* 2008, 134, 112.
(2) Siddiqui, T. J.; Craig, A. M. *Curr Opin Neurobiol* 2011, 21, 132.
(3) Chen, X.; Karnovsky, A.; Sans, M. D.; Andrews, P. C.; Williams, J. A. *Proteomics* 2010, 10, 4040.
(4) Brunner, Y.; Schvartz, D.; Coute, Y.; Sanchez, J. C. *Mass Spectrom Rev* 2009, 28, 844.
(5) Shibata, Y.; Shemesh, T.; Prinz, W. A.; Palazzo, A. F.; Kozlov, M. M.; Rapoport, T. A. *Cell* 2010, 143, 774.
(6) Cusick, M. E.; Klitgord, N.; Vidal, M.; Hill, D. E. *Hum Mol Genet* 2005, 14 Spec No. 2, R171.
(7) Bai, F.; Witzmann, F. A. *Subcell Biochem* 2007, 43, 77.
(8) Kornmann, B.; Walter, P. *J Cell Sci* 2010, 123, 1389.
(9) Choi-Rhee, E.; Schulman, H.; Cronan, J. E. *Protein Sci* 2004, 13, 3043.
(10) Fancy, D. A.; Kodadek, T. *Proc Natl Acad Sci USA* 1999, 96, 6020.
(11) Kodadek, T.; Duroux-Richard, I.; Bonnafous, J. C. *Trends Pharmacol Sci* 2005, 26, 210.

(12) Kotani, N.; Gu, J.; Isaji, T.; Udaka, K.; Taniguchi, N.; Honke, K. *Proc Natl Acad Sci USA* 2008, 105, 7405.
(13) Connolly, C. N.; Futter, C. E.; Gibson, A.; Hopkins, C. R.; Cutler, D. F. *J Cell Biol* 1994, 127, 641.
(14) Mayer, G.; Bendayan, M. *J Histochem Cytochem* 1997, 45, 1449.
(15) Bhaskar, B.; Immoos, C. E.; Shimizu, H.; Sulc, F.; Farmer, P. J.; Poulos, T. L. *J Mol Biol* 2003, 328, 157.
(16) Rogers, M. S.; Hurtado-Guerrero, R.; Firbank, S. J.; Halcrow, M. A.; Dooley, D. M.; Phillips, S. E.; Knowles, P. F.; McPherson, M. J. *Biochemistry* 2008, 47, 10428.
(17) Minamihata, K.; Goto, M.; Kamiya, N. *Bioconjug Chem* 2011, 22, 74.
(18) Luo, Y.-R. *Handbook of bond dissociation energies in organic compounds*; CRC Press: Boca Raton, Fla., 2003.
(19) Veitch, N. C. *Phytochemistry* 2004, 65, 249.
(20) Patterson, W. R.; Poulos, T. L. *Biochemistry* 1995, 34, 4331.
(21) Huang, B.; Bates, M.; Zhuang, X. *Annu Rev Biochem* 2009, 78, 993.
(22) Forner, F.; Foster, L. J.; Campanaro, S.; Valle, G.; Mann, M. *Mol Cell Proteomics* 2006, 5, 608.
(23) Epp, O.; Ladenstein, R.; Wendel, A. *Eur J Biochem* 1983, 133, 51.
(24) Calvo, S.; Jain, M.; Xie, X.; Sheth, S. A.; Chang, B.; Goldberger, O. A.; Spinazzola, A.; Zeviani, M.; Carr, S. A.; Mootha, V. K. *Nat Genet* 2006, 38, 576.
(25) Kim, J.; Zhao, T.; Petralia, R. S.; Yu, Y.; Peng, H.; Myers, E.; Magee, J. C. *Nat Methods* 2011.
(26) Friedman, J. R.; Lackner, L. L.; West, M.; DiBenedetto, J. R.; Nunnari, J.; Voeltz, G. K. *Science* 2011, 334, 358.
(27) Patterson, S. D.; Spahr, C. S.; Daugas, E.; Susin, S. A.; Irinopoulou, T.; Koehler, C.; Kroemer, G. *Cell Death Differ* 2000, 7, 137.
(28) Baughman, J. M.; Perocchi, F.; Girgis, H. S.; Plovanich, M.; Belcher-Timme, C. A.; Sancak, Y.; Bao, X. R.; Strittmatter, L.; Goldberger, O.; Bogorad, R. L.; Koteliansky, V.; Mootha, V. K. *Nature* 2011, 476, 341.
(29) Lipovsek, D.; Antipov, E.; Armstrong, K. A.; Olsen, M. J.; Klibanov, A. M.; Tidor, B.; Wittrup, K. D. *Chem Biol* 2007, 14, 1176.
(30) Nguyen, M.; Claparols, C.; Bernadou, J.; Meunier, B. *Chembiochem* 2001, 2, 877.
(31) Shu, X.; Lev-Ram, V.; Deerinck, T. J.; Qi, Y.; Ramko, E. B.; Davidson, M. W.; Jin, Y.; Ellisman, M. H.; Tsien, R. Y. *PLoS Biol* 2011, 9, e1001041.
(32) Beck, S.; Sakurai, T.; Eustace, B. K.; Beste, G.; Schier, R.; Rudert, F.; Jay, D. G. *Proteomics* 2002, 2, 247.
(33) Shacter, E. *Drug Metab Rev* 2000, 32, 307.
(34) Li, M.; Luo, W.; White, E. H. *Arch Biochem Biophys* 1995, 320, 135.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A method for proteomic mapping of a living cell comprising:
    contacting a living cell with a tagging enzyme under physiological conditions wherein the tagging enzyme catalyzes a reaction with a tagging substrate resulting in the tagging of proteins within an intracellular spatial location around the enzyme and/or substrate;
    wherein the tagging enzyme is genetically targeted or is targeted using a targeting sequence such as antibody to a subcellular region; and
    isolating and analyzing the tagged proteins to create a first proteome map.

2. The method of claim 1, further comprising contacting the living cell with a tagging substrate.

3. The method of claim 1, wherein a nucleic acid construct encoding the tagging enzyme is delivered to the cell.

4. The method of claim 1, wherein the living cell is exposed to a therapeutic agent prior to or during the step of contacting with a tagging enzyme.

5. The method of claim 4, further comprising contacting a second living cell exposed to a second therapeutic agent with a tagging enzyme under physiological conditions wherein the tagging enzyme catalyzes a reaction with a tagging substrate resulting in the tagging of proteins within an intracellular spatial location around the enzyme and/or substrate;
    wherein the tagging enzyme is genetically targeted to a subcellular region; and
    isolating and analyzing the tagged proteins to create a second proteomic map.

6. The method of claim 5, wherein the first and second proteome maps are compared.

7. A method of mapping the proteome of a living cells comprising:
    contacting a living cell with a tagging enzyme and a tagging substrate in order to catalyze a reaction resulting in the production of a tagged protein within the spatial location around the tagging enzyme and/or substrate of the tagging enzyme, and further comprising generating a proteome map based on the tagged proteins;
    wherein the tagging enzyme is genetically targeted to a subcellular region.

8. The method of claim 1, wherein the tagging enzyme is a peroxidase.

9. The method of claim 1, wherein the tagging enzyme is HRP.

10. The method of claim 1, wherein the tagging substrate is a tyramide.

11. The method of claim 1, wherein the tagging substrate is a labeled tyramide.

12. The method of claim 1, wherein the tagging substrate is a biotinylated tyramide.

13. The method of claim 7, further comprising isolating the tagged proteins.

14. The method of claim 13, further comprising analyzing the isolated proteins.

15. A method for proteomic mapping, comprising
    contacting a living cell with a tagging enzyme under physiological conditions wherein the tagging enzyme is targeted to a spatial location of the cell and catalyzes a reaction with a tagging substrate resulting in the tagging of proteins within the spatial location around the tagging enzyme and/or substrate of the tagging enzyme, and
    isolating and analyzing the tagged proteins to create a first proteome map, wherein the proteome map is a map of a proteome which is a set of expressed proteins expressed in a cell, a subcellular compartment or an organism under a set of conditions.

16. The method of claim 15, wherein a nucleic acid construct encoding the tagging enzyme is delivered to the cell.

* * * * *